United States Patent
Hunziker et al.

(10) Patent No.: US 8,268,820 B2
(45) Date of Patent: Sep. 18, 2012

(54) 2,3-DIARYL- OR HETEROARYL-SUBSTITUTED 1,1,1-TRIFLUORO-2-HYDROXYPROPYL COMPOUNDS

(75) Inventors: Daniel Hunziker, Moehlin (CH); Chrisitan Lerner, Binningen (CH); Werner Mueller, Aesch BL (CH); Ulrike Obst Sander, Reinach BL (CH); Philippe Pflieger, Schwoben (FR); Pius Waldmeier, Wegenstetten (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 250 days.

(21) Appl. No.: 12/727,271

(22) Filed: Mar. 19, 2010

(65) Prior Publication Data

US 2010/0249124 A1    Sep. 30, 2010

(30) Foreign Application Priority Data

Mar. 26, 2009 (EP) .................... 09156267

(51) Int. Cl.
*C07D 265/36* (2006.01)
*A61K 31/536* (2006.01)

(52) U.S. Cl. .................... 514/230.5; 544/105
(58) Field of Classification Search .................. 544/105; 514/230.5
See application file for complete search history.

(56) References Cited

U.S. PATENT DOCUMENTS

| | | | |
|---|---|---|---|
| 4,678,790 | A | 7/1987 | Dorn et al. |
| 4,699,652 | A | 10/1987 | Zehnder |
| 2005/0090559 | A1 | 4/2005 | Berger et al. |

FOREIGN PATENT DOCUMENTS

| | | |
|---|---|---|
| DE | 10346939 | 5/2005 |
| EP | 117485 | 9/1984 |
| EP | 137456 | 4/1985 |
| EP | 209854 | 1/1987 |
| EP | 1930320 | 6/2008 |
| WO | 0058293 | 10/2000 |
| WO | 03/082787 | 10/2003 |
| WO | 2005030213 | 4/2005 |
| WO | 2006135826 | 12/2006 |

OTHER PUBLICATIONS

Chiodini et al, Eur. J. Endocrinol. 2005, vol. 153, pp. 837-844.
Young, Stress 2004, vol. 7 (4), pp. 205-208.
Flores et al, Neuropsychopharmacology 2006, vol. 31, pp. 628-636.
Chu et al, J. Clin. Endocrinol. Metab. 2001, vol. 86, pp. 3568-3573.
Von Geldern et al, J. Med. Chem. 2004, vol. 47 (17), pp. 4213-4230.
Hu et al, Drug Develop. Res. 2006, vol. 67, pp. 871-883.
Andrews, Handbook of the stress and the brain 2005, vol. 15, pp. 437-450.
Zinker et al, Meta. Clin. Exp. 2007, vol. 57, pp. 380-387.
Delauney et al, J. Clin. Invest. 1997, vol. (100, pp. 2094-2098.
DeFronzo, Med. Clin. N. Am. 2004, vol. 88 pp. 787-835.
Garrel et al, J. Clin. Endocrinol. Metab. 1995, vol. 80 (2), pp. 379-385.
Nieman et al, J. Clin. Endocrinol. Metab. 1985, vol. 61 (3), pp. 536-540.
Gettys et al, Int. J. Obes. 1997, vol. 21, pp. 865-873.
Friedman et al, J. Biol. Chem. 1997, vol. 272 (50) pp. 31475-31481.
Opherk et al, Mol. Endocrinol. 2004, vol. 18 (6), pp. 1346-1353.
Gaillard et al, Pro. Natl, Acad. Sci. 1984, vol. 81, pp. 3879-3882.
Sitruk-Ware et al, 2003, Contraception, vol. 68, pp. 409-420.
English language abstract corresponding to EP117485, Apr. 21, 2005.

*Primary Examiner* — Kahsay T Habte
(74) *Attorney, Agent, or Firm* — George W. Johnston; Patricia S. Rocha-Tramaloni; Gene J. Yao

(57) ABSTRACT

The present invention relates to compounds of formula I

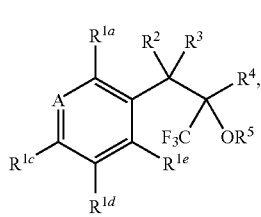

wherein $R^{1a}$ to $R^{1e}$, $R^2$, $R^3$ and $R^5$ are as defined in the description and claims and $R^4$ signifies a bicyclic heteroaryl group or a cyanophenyl group, as well as pharmaceutically acceptable salts thereof. The compounds are glucocorticoid receptor antagonists useful for the treatment and/or prevention of diseases such as diabetes, dyslipidemia, obesity, hypertension, cardiovascular diseases, adrenal imbalance or depression.

24 Claims, No Drawings

2,3-DIARYL- OR HETEROARYL-SUBSTITUTED 1,1,1-TRIFLUORO-2-HYDROXYPROPYL COMPOUNDS

PRIORITY TO RELATED APPLICATIONS(S)

This application claims the benefit of European Patent Application No. 09156267.8 filed Mar. 26, 2009, which is hereby incorporated by reference in its entirety.

BACKGROUND OF THE INVENTION

The present invention relates to novel 2,3-diaryl- or heteroaryl-substituted 1,1,1-trifluoro-2-hydroxypropyl compounds, their manufacture, pharmaceutical compositions containing them and their use as medicaments. The active compounds of the present invention are acting as modulators of the glucocorticoid receptor, preferably antagonists, and are useful in treating diabetes and other disorders such as dyslipidemia, obesity, hypertension, cardiovascular diseases, adrenal imbalance or depression.

Glucocorticoids are responsible for several physiological functions including answer to stress, immune and inflammatory responses as well as stimulation of hepatic gluconeogenesis and glucose utilization at the periphery. Glucocorticoids act via an intracellular glucocorticoid receptor (GR) belonging to the family of the nuclear steroidal receptors. The non-activated GR is located in the cellular cytoplasm and is associated with several chaperone proteins. When a ligand activates the receptor, the complex is translocated in the cell nucleus and interacts with the glucocorticoid response element which is located in several gene promoters. The receptor could act in the cell nucleus as an homodimer or an heterodimer Moreover several associated co-activators or co-repressors could also interact with the complex. This large range of possible combinations leads to several GR conformations and several possible physiological answers.

Pathologies like diabetes, Cushing's syndrome or depression have been associated with moderate to severe hypercortisolism (Chiodini et al, *Eur. J. Endocrinol.* 2005, Vol. 153, pp 837-844; Young, *Stress* 2004, Vol. 7 (4), pp 205-208). GR antagonist administration has been proven to be clinically active in depression (Flores et al, *Neuropsychopharmacology* 2006, Vol. 31, pp 628-636) or in Cushing's syndrome (Chu et al, *J. Clin. Endocrinol. Metab.* 2001, Vol. 86, pp 3568-3573). These clinical evidences illustrate the potential clinical value of a potent and selective GR antagonist in many indications like diabetes, dyslipidemia, obesity, hypertension, cardiovascular diseases or depression (Von Geldern et al, *J. Med. Chem.* 2004, Vol 47 (17), pp 4213-4230; Hu et al, *Drug Develop. Res.* 2006, Vol. 67, pp 871-883; Andrews, *Handbook of the stress and the brain* 2005, Vol. 15, pp 437-450). This approach might also improve peripheral insulin sensitivity (Zinker et al, *Meta. Clin. Exp.* 2007, Vol. 57, pp 380-387) and protect pancreatic beta cells (Delauney et al, *J. Clin. Invest.* 1997, Vol. (100, pp 2094-2098).

Diabetic patients have an increased level of fasting blood glucose which has been correlated in clinic with an impaired control of gluconeogenesis (DeFronzo, *Med. Clin. N. Am.* 2004, Vol. 88 pp 787-835). The hepatic gluconeogenesis process is under the control of glucocorticoids. Clinical administration of a non-specific GR antagonist (RU486/mifepristone) leads acutely to a decrease of fasting plasma glucose in normal volunteers (Garrel et al, *J. Clin. Endocrinol. Metab.* 1995, Vol. 80 (2), pp 379-385) and chronically to a decrease of plasmatic HbA1c in Cushing's patients (Nieman et al, *J. Clin. Endocrinol. Metab.* 1985, Vol. 61 (3), pp 536-540). Moreover, this drug given to leptin deficient animals normalizes fasting plasma glucose (ob/ob mice, Gettys et al, *Int. J. Obes.* 1997, Vol. 21, pp 865-873) as well as the activity of gluconeogenic enzymes (db/db mice, Friedman et al, *J. Biol. Chem.* 1997, Vol. 272 (50) pp 31475-31481). Liver-specific knockout mice have been produced and these animals display a moderate hypoglycemia when they are fasted for 48 h excluding the risk of severe hypoglycemia (Opherk et al, *Mol. Endocrinol.* 2004, Vol. 18 (6), pp 1346-1353).

Mifepristone is also known to stimulate the Hypothalamus-Pituitary gland-Adrenal gland (HPA) axis via the activation of a feed-back mechanism which leads to an increase of endogenous corticosteroids circulating in the blood (Gaillard et al, *Pro. Natl. Acad. Sci.* 1984, Vol. 81, pp 3879-3882). Mifepristone also induces some adrenal insufficiency symptoms after long term treatment (up to 1 year, for review see: Sitruk-Ware et al, 2003, *Contraception*, Vol. 68, pp 409-420).

For GR modulators to be used in indications such as diabetes, dyslipidemia, obesity, hypertension and cardiovascular diseases it is necessary to limit the risk to activate or inhibit the HPA axis. Several strategies can be used to achieve this goal like to have a drug with a moderate to high liver selectivity or to get a drug which would not penetrate brain. Liver selectivity can be obtained by introducing liver targeting vectors in the molecule or by limiting the volume of distribution of the substance in the body. On the opposite for GR modulators to be used in indications such as adrenal/HPA imbalance, insomnia or depression it will be necessary to obtain a drug with a moderate to high brain selectivity.

It is therefore an object of the present invention to provide potent and highly selective modulators of the glucocorticoid receptor (GR), preferably GR antagonists, with various tissue selectivities. Such GR modulators are useful as therapeutically active substances, particularly in the treatment and/or prevention of diseases which are associated with modulation of the glucocorticoid receptors.

SUMMARY OF THE INVENTION

The present invention relates to compounds of formula I,

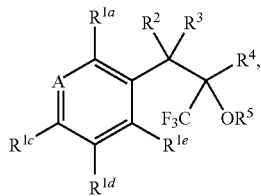

wherein
A is C—$R^{1b}$ or N;
$R^{1a}$, $R^{1b}$, $R^{1c}$, $R^{1d}$ and $R^{1e}$ independently from each other are selected from the group consisting of
hydrogen, $C_{1-7}$-alkyl, $C_{2-7}$-alkenyl, $C_{3-7}$-cycloalkyl-$C_{1-7}$-alkyl, halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl- $C_{1-7}$-alkoxy, di-$C_{1-7}$-alkylamino, di-$C_{2-7}$-alkenylamino, $C_{1-7}$-alkylsulfonyl-amino, carboxyl-$C_{1-7}$-alkylaminocarbonyl, phenyl, said phenyl being substituted by a group selected from carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy;

phenyloxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, heteroaryl selected from the group consisting of pyridyl, pyridazinyl, pyrimidinyl and pyrazinyl, said heteroaryl being unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

heteroaryloxy, wherein heteroaryl is selected from the group consisting of pyridyl, pyridazinyl, pyrimidinyl and pyrazinyl, and is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, phenyl-$C_{1-7}$-alkoxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkyl, hydroxy, cyano, $C_{1-7}$-alkylsulfonyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxy-carbonyl, $C_{1-7}$-alkoxycarbonyl-$C_{1-7}$-alkyl and $C_{1-7}$-alkoxycarbonyl-$C_{1-7}$-alkoxy; and heterocyclyl or heterocyclylcarbonyl, wherein heterocyclyl is selected from the group consisting of pyrrolidine, piperidine and azepine and is substituted by carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy;

$R^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;

$R^3$ is hydrogen or $C_{1-7}$-alkyl;

or $R^2$ and $R^3$ together with the carbon atom they are attached to form a $C_3$-$C_5$-cycloalkyl ring;

$R^4$ is a heteroaryl ring selected from the group consisting of 3-oxo-3,4-dihydro-2H-benzo[1,4]oxazinyl, 3,4-dihydro-2H-benzo[1,4]oxazinyl, 2-oxo-2,3-dihydro-1H-pyrido[2,3-b][1,4]oxazinyl, 4-oxo-4H-quinolizinyl, 2-oxo-2,3-dihydro-1H-benzoimidazoyl, 2-oxo-2,3-dihydrobenzooxazolyl, benzo[1,3]dioxolyl, 2-oxo-1,2-dihydroquinolinyl and 1,3-dimethyl-2,2-dioxo-2,3-dihydro-1H-2λ6-benzo[1,2,5]thiadiazolyl, said heteroaryl ring being unsubstituted or substituted by one, two or three substituents selected from the group consisting of $C_{1-7}$-alkyl, $C_{2-7}$-alkenyl and halogen, or $R^4$ is phenyl substituted by cyano and, in addition, optionally substituted by one or two substituents selected from the group consisting of halogen, halogen-$C_{1-7}$-alkyl, $C_{1-7}$-alkyl, $C_{1-7}$-alkoxy and halogen-$C_{1-7}$-alkoxy; and $R^5$ is hydrogen or methyl.

The present invention also relates to pharmaceutically acceptable salts of such compounds.

A further aspect of the present invention is a pharmaceutical composition comprising such a compound, or a pharmaceutically acceptable salt thereof, and a pharmaceutically acceptable carrier and/or adjuvant.

The compounds of formula I are glucocorticoid receptor (GR) antagonists.

DETAILED DESCRIPTION OF THE INVENTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "lower alkenyl" or "$C_{2-7}$-alkenyl" signifies a straight-chain or branched chain hydrocarbon residue comprising an olefinic bond and 1 to 7, preferably 1 to 6, particularly preferred 1 to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by cycloalkyl. A preferred example is cyclopropylmethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy and most preferred ethoxy.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by another alkoxy group. Also included are groups wherein the second alkoxy group is substituted by a further alkoxy group. Among the preferred lower alkoxyalkoxy groups are 1-methoxymethoxy, 2-methoxyethoxy, 3-methoxypropyloxy and 2-(2-methoxyethoxy)-ethoxy.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the preferred lower hydroxyalkyl groups are hydroxymethyl or hydroxyethyl.

The term "lower hydroxyalkoxy" or "hydroxy-$C_{1-7}$-alkoxy" means a lower alkoxy group as defined herein before wherein at least one of the hydrogen atoms of the lower alkoxy group is replaced by a hydroxy group. A preferred lower hydroxyalkoxy group is 2-hydroxyethoxy.

The term "lower aminoalkoxy" or "amino-$C_{1-7}$-alkoxy" means a lower alkoxy group as defined herein before wherein at least one of the hydrogen atoms of the lower alkoxy group is replaced by an amino group. A preferred lower aminoalkoxy group is 2-aminoethoxy.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkoxy groups are trifluoromethoxy, difluoromethoxy, fluormethoxy and chloromethoxy, with trifluoromethoxy being especially preferred.

The term "lower alkoxycarbonyl" or "$C_{1-7}$-alkoxycarbonyl" refers to the group —CO—OR' wherein R' is lower alkyl and the term "lower alkyl" has the previously given significance. Preferred lower alkoxycarbonyl groups are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A preferred lower alkoxycarbonylalkyl group is —$CH_2$—$COOCH_3$.

The term "lower alkoxycarbonylalkoxy" or "$C_{1-7}$-alkoxycarbonyl-$C_{1-7}$-alkoxy" refers to lower alkoxy groups as defined above wherein one of the hydrogen atoms of the lower alkoxy group is replaced by $C_{1-7}$-alkoxycarbonyl. A preferred lower alkoxycarbonylalkoxy group is t-butoxycarbonylmethoxy (—O—$CH_2$—COOO—$C(CH_3)_3$).

The term "lower alkoxycarbonylaminoalkoxy" or "$C_{1-7}$-alkoxycarbonylamino-$C_{1-7}$-alkoxy" refers to lower alkoxy groups as defined above wherein one of the hydrogen atoms of the lower alkoxy group is replaced by $C_{1-7}$-alkoxycarbonylamino. A preferred lower alkoxycarbonylaminoalkoxy group is —O—$CH_2$—$CH_2$—NH—COO—$C(CH_3)_3$.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the preferred lower carboxyl alkyl groups are carboxylmethyl (—$CH_2$—COOH) and carboxylethyl (—$CH_2$—$CH_2$—COOH), with carboxylmethyl being especially preferred.

The term "lower carboxylalkoxy" or "carboxyl-$C_{1-7}$-alkoxy" refers to lower alkoxy groups as defined above wherein at least one of the hydrogen atoms of the lower alkoxy group is replaced by a carboxyl group. Preferred lower carboxylalkoxy group is carboxylmethoxy (—O—$CH_2$—COOH).

The term "aminocarbonyl" means the group —CO—$NH_2$.

The term "aminocarbonylalkoxy" or "aminocarbonyl-$C_{1-7}$-alkoxy" refers to lower alkoxy groups as defined above wherein one of the hydrogen atoms of the lower alkoxy group is replaced by aminocarbonyl. A preferred aminocarbonylalkoxy group is the group —O—$CH_2$—CO—$NH_2$.

The term "lower carboxylalkylaminocarbonyl" or "carboxyl-$C_{1-7}$-alkylaminocarbonyl" refers to the group —C(O)—NH—$R^x$, wherein $R^x$ is a carboxyl-$C_{1-7}$-alkyl group as defined above.

The term "di-$C_{1-7}$-alkylamino" signifies the group —NR'R", wherein R' and R" are lower alkyl as defined above.

The term "di-$C_{1-7}$-alkenylamino" signifies the group —NR'R", wherein R' and R" are lower alkenyl groups as defined above. A preferred dialkenylamino group is diallylamino.

The term "$C_{1-7}$-alkylsulfonyl" means the group —$S(O)_2$—R, wherein R is lower alkyl as defined above.

The term "$C_{1-7}$-alkylsulfonylamino" refers to the group —NH—$S(O)_2$—R, wherein R is lower alkyl as defined above.

The term "halogen-$C_{1-7}$-alkyl-sulfonyloxy" means the group —O—$S(O)_2$—R", wherein R" is lower halogenalkyl as defined above. Preferred halogenalkylsulfonyloxy is trifluoromethanesulfonyloxy.

The term "phenyloxy" refers to the group —O-phenyl.

The term "lower phenylalkyl" or "phenyl-$C_{1-7}$-alkyl" refers to lower alkyl groups as defined above wherein at least one of the hydrogen atoms of the lower alkyl group is replaced by a phenyl group. The phenyl group may be further substituted. Preferred lower phenylalkyl groups are benzyl or phenethyl.

The term "lower phenylalkoxy" or "phenyl-$C_{1-7}$-alkoxy" refers to lower alkoxy groups as defined above wherein at least one of the hydrogen atoms of the lower alkoxy group is replaced by a phenyl group. The phenyl group may be further substituted. Preferred lower phenylalkoxy group is benzyloxy.

The term "heteroaryl" in general refers to an aromatic or partly unsaturated 5- or 6-membered ring which comprises one, two or three atoms selected from nitrogen, oxygen and/or sulphur, such as pyridyl, pyrazinyl, pyrimidinyl, pyridazinyl, 2-oxo-1,2-dihydropyridinyl, oxazolyl, oxadiazolyl, isoxazolyl, thiadiazolyl, tetrazolyl, pyrazolyl, imidazolyl, thiazolyl and thienyl. The term "heteroaryl" further refers to bicyclic aromatic or partly unsaturated groups comprising two 5- or 6-membered rings, in which one or both rings can contain one, two or three atoms selected from nitrogen, oxygen or sulphur, such as 3-oxo-3,4-dihydro-2H-benzo[1,4]oxazinyl, 3,4-dihydro-2H-benzo[1,4]oxazinyl, 2-oxo-2,3-dihydro-1H-pyrido[2,3-b][1,4]oxazinyl, 4-oxo-4H-quinolizinyl, 2-oxo-2,3-dihydro-1H-benzoimidazoyl, 2-oxo-2,3-dihydro-benzooxazolyl, benzo[1,3]dioxolyl, 2-oxo-1,2-dihydroquinolinyl and 1,3-dimethyl-2,2-dioxo-2,3-dihydro-1H-2λ6-benzo[1,2,5]thiadiazolyl. Preferred heteroaryl groups are pyridyl, pyridazinyl, pyrmidinyl and pyrazinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compounds of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I or II (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of 0.1 mg to 5 g, preferably from about 0.1 mg to 1 g, more preferably from 0.5 mg to 500 mg, and most preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The present invention relates to compounds of formula I,

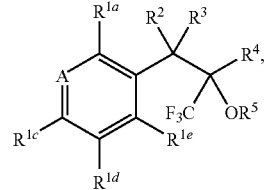

wherein
A is $C-R^{1b}$ or N;
$R^{1a}$, $R^{1b}$, $R^{1c}$, $R^{1d}$ and $R^{1e}$ independently from each other are selected from the group consisting of hydrogen; $C_{1-7}$-alkyl; $C_{2-7}$-alkenyl; $C_{3-7}$-cycloalkyl-$C_{1-7}$-alkyl; halogen; halogen-$C_{1-7}$-alkyl; halogen-$C_{1-7}$-alkoxy; halogen-$C_{1-7}$-alkyl-sulfonyloxy; hydroxy; hydroxy-$C_{1-7}$-alkyl; $C_{1-7}$-alkoxy; $C_{1-7}$-alkoxy-$C_{1-7}$-alkoxy; hydroxy-$C_{1-7}$-alkoxy; amino-$C_{1-7}$-alkoxy; cyano; carboxyl; carboxyl-$C_{1-7}$-alkyl; carboxyl-$C_{1-7}$-alkoxy; $C_{1-7}$-alkoxycarbonyl; $C_{1-7}$-alkoxycarbonyl-$C_{1-7}$-alkoxy; $C_{1-7}$-alkoxycarbonylamino-$C_{1-7}$-alkoxy; $C_{1-7}$-alkylcarbonyloxy-$C_{1-7}$-alkoxy; aminocarbonyl-$C_{1-7}$-alkoxy; di-$C_{1-7}$-alkylamino; di-$C_{2-7}$-alkenylamino; $C_{1-7}$-alkylsulfonyl-amino; carboxyl-$C_{1-7}$-alkylaminocarbonyl;

phenyl, said phenyl being substituted by a group selected from carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy;

phenyloxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

heteroaryl selected from the group consisting of pyridyl, pyridazinyl, pyrimidinyl and pyrazinyl, said heteroaryl being unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

heteroaryloxy, wherein heteroaryl is selected from the group consisting of pyridyl, pyridazinyl, pyrimidinyl and pyrazinyl, and is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$- alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

phenyl-$C_{1-7}$-alkoxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkyl, hydroxy, cyano, $C_{1-7}$-alkylsulfonyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxy-carbonyl, $C_{1-7}$-alkoxycarbonyl-$C_{1-7}$-alkyl and $C_{1-7}$-alkoxycarbonyl-$C_{1-7}$-alkoxy; and heterocyclyl or heterocyclylcarbonyl, wherein heterocyclyl is selected from the group consisting of pyrrolidine, piperidine and azepine and is substituted by carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy;

$R^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;

$R^3$ is hydrogen or $C_{1-2}$-alkyl;

or $R^2$ and $R^3$ together with the carbon atom they are attached to form a $C_3$-$C_5$-cycloalkyl ring;

$R^4$ is a heteroaryl ring selected from the group consisting of 3-oxo-3,4-dihydro-2H-benzo[1,4]oxazinyl, 3,4-dihydro-2H-benzo[1,4]oxazinyl, 2-oxo-2,3-dihydro-1H-pyrido[2,3-b][1,4]oxazinyl, 4-oxo-4H-quinolizinyl, 2-oxo-2,3-dihydro-1H-benzoimidazoyl, 2-oxo-2,3-dihydrobenzooxazolyl, benzo[1,3]dioxolyl, 2-oxo-1,2-dihydroquinolinyl and 1,3-dimethyl-2,2-dioxo-2,3-dihydro-1H-2λ6-benzo[1,2,5]thiadiazolyl, said heteroaryl ring being unsubstituted or substituted by one, two or three substituents selected from the group consisting of $C_{1-7}$-alkyl, $C_{2-7}$-alkenyl and halogen, or $R^4$ is phenyl substituted by cyano and, in addition, optionally substituted by one or two substituents selected from the group consisting of halogen, halogen-$C_{1-7}$-alkyl, $C_{1-7}$-alkyl, $C_{1-7}$-alkoxy and halogen-$C_{1-7}$-alkoxy; and $R^5$ is hydrogen or methyl.

The present invention also relates to pharmaceutically acceptable salts of such compounds.

Preferred compounds of formula I of the invention are those, wherein A is C—$R^{1b}$, meaning these are compounds having the formula I-A,

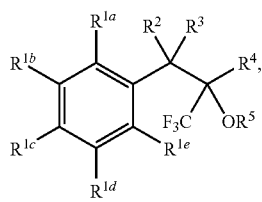

I-A wherein $R^{1a}$, $R^{1b}$, $R^{1c}$, $R^{1d}$, $R^{1e}$, $R^2$, $R^3$, $R^4$ and $R^5$ are as defined herein before.

Furthermore, compounds of formula I according to the invention are preferred, wherein one of $R^{1c}$ and $R^{1d}$ is selected from the group consisting of phenyl, said phenyl being substituted by a group selected from carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy;

phenyloxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, heteroaryl selected from the group consisting of pyridyl, pyridazinyl, pyrimidinyl and pyrazinyl, said heteroaryl being unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

heteroaryloxy, wherein heteroaryl is selected from the group consisting of pyridyl, pyridazinyl, pyrimidinyl and pyrazinyl, and is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, phenyl-$C_{1-7}$-alkoxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkyl, hydroxy, cyano, $C_{1-7}$-alkylsulfonyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxy-carbonyl, $C_{1-7}$-alkoxycarbonyl-$C_{1-7}$-alkyl and $C_{1-7}$-alkoxycarbonyl-$C_{1-7}$-alkoxy; and heterocyclyl or heterocyclylcarbonyl, wherein heterocyclyl is selected from the group consisting of pyrrolidine, piperidine and azepine and is substituted by carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy.

Within this group compounds of formula I are more preferred, wherein one of $R^{1c}$ and $R^{1d}$ is selected from the group consisting of phenyl, said phenyl being substituted by a group selected from carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy;

phenyloxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and phenyl-$C_{1-7}$-alkoxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkyl, hydroxy, cyano, $C_{1-7}$-alkylsulfonyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxy-carbonyl, $C_{1-7}$-alkoxycarbonyl-$C_{1-7}$-alkyl and $C_{1-7}$-alkoxycarbonyl-$C_{1-7}$-alkoxy.

Especially preferred are for example compounds of formula I, wherein one of $R^{1c}$ and $R^{1d}$ is phenyl, said phenyl being substituted by a group selected from carboxyl, carboxyl-$C_{1-7}$-alkyl, carboxyl-$C_{1-7}$-alkoxy, $C_{1-7}$-alkoxycarbonyl and $C_{1-7}$-alkoxycarbonyl-$C_{1-7}$-alkoxy, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy, more preferably selected from halogen or $C_{1-7}$-alkoxy.

Also especially preferred are compounds of formula I, wherein one of $R^{1c}$ and $R^{1d}$ is phenyloxy, wherein the phenyl ring is unsubstituted or substituted by one, two or three substituents selected from the group consisting of halogen, halogen-$C_{1-7}$-alkyl, carboxyl, carboxyl-$C_{1-7}$-alkyl, and $C_{1-7}$-alkoxycarbonyl.

Further especially preferred are compounds of formula I, wherein one of $R^{1c}$ and $R^{1d}$ is phenyl-$C_{1-7}$-alkoxy, wherein the phenyl ring is unsubstituted or substituted by one, two or three substituents selected from the group consisting of $C_{1-7}$-alkoxy, carboxyl, carboxyl-$C_{1-7}$-alkyl, carboxyl-$C_{1-7}$-alkoxy and $C_{1-7}$-alkoxy-carbonyl.

Furthermore, compounds of formula I according to the present invention are preferred, wherein one of $R^{1c}$ and $R^{1d}$ is selected from the group consisting of heteroaryl selected from the group consisting of pyridyl, pyridazinyl, pyrimidinyl and pyrazinyl, said heteroaryl being unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

heteroaryloxy, wherein heteroaryl is selected from the group consisting of pyridyl, pyridazinyl, pyrimidinyl and pyrazinyl, and is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and heterocyclyl or heterocyclylcarbonyl, wherein heterocyclyl is selected from the group consisting of pyrrolidine, piperidine and azepine and is substituted by carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy.

Especially preferred are for example compounds of formula I, wherein one of $R^{1c}$ and $R^{1d}$ is heteroaryl selected from the group consisting of pyridyl, pyridazinyl, pyrimidinyl and pyrazinyl, said heteroaryl being substituted by a group selected from carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy. Most preferably, one of $R^{1c}$ and $R^{1d}$ is heteroaryl selected from the group consisting of pyridyl, pyridazinyl, pyrimidinyl and pyrazinyl, said heteroaryl being substituted by carboxyl or $C_{1-7}$-alkoxycarbonyl, and, in addition, optionally substituted by one or two substituents selected from halogen or halogen-$C_{1-7}$-alkyl.

Also especially preferred are compounds of formula I, wherein one of $R^{1c}$ and $R^{1d}$ is heteroaryloxy, wherein heteroaryl is selected from the group consisting of pyridyl, pyridazinyl, pyrimidinyl and pyrazinyl, and is unsubstituted or substituted by one, two or three substituents selected from the group consisting of halogen, halogen-$C_{1-7}$-alkyl and carboxyl.

Further especially preferred are compounds of formula I, wherein one of $R^{1c}$ and $R^{1d}$ is heterocyclyl or heterocyclylcarbonyl, wherein heterocyclyl is selected from the group consisting of pyrrolidine, piperidine and azepine and is substituted by carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy. Preferred heterocyclyl is piperidine, substituted by carboxyl-$C_{1-7}$-alkyl, $C_{1-7}$-alkoxycarbonyl or $C_{1-7}$-alkoxycarbonyl-$C_{1-7}$-alkyl.

In addition, compounds of formula I according to the present invention are preferred, wherein one of $R^{1c}$ and $R^{1d}$ is selected from the group consisting of hydroxy, $C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy and carboxyl-$C_{1-7}$-alkylaminocarbonyl.

Especially preferred are compounds of formula I, wherein $R^{1a}$ is halogen or halogen-$C_{1-7}$-alkyl, more preferably $R^{1a}$ is halogen, most preferably chloro.

Also preferred are compounds of formula I according to the invention are those, wherein three of $R^{1a}$, $R^{1b}$, $R^{1c}$, $R^{1d}$ and $R^{1e}$ are hydrogen.

In addition, compounds of formula I according to the present invention are preferred, wherein $R^2$ is $C_{1-7}$-alkyl. Most preferably, $R^2$ is methyl.

Preferred are the compounds of formula I according to the present invention, wherein $R^3$ is hydrogen. Most preferred are compounds of formula I, wherein $R^2$ is methyl and $R^3$ is hydrogen.

Furthermore, compounds of formula I according to the present invention are preferred, wherein $R^4$ is a heteroaryl ring selected from the group consisting of 3-oxo-3,4-dihydro-2H-benzo[1,4]oxazinyl, 3,4-dihydro-2H-benzo[1,4]oxazinyl, 2-oxo-2,3-dihydro-1H-pyrido[2,3-b][1,4]oxazinyl, 4-oxo-4H-quinolizinyl, 2-oxo-2,3-dihydro-1H-benzoimidazoyl, 2-oxo-2,3-dihydro-benzooxazolyl, benzo[1,3]dioxolyl, 2-oxo-1,2-dihydro-quinolinyl and 1,3-dimethyl-2,2-dioxo-2,3-dihydro-1H-2λ6-benzo[1,2,5]thiadiazolyl, said heteroaryl ring being unsubstituted or substituted by one, two or three substituents selected from the group consisting of $C_{1-7}$-alkyl, $C_{2-7}$-alkenyl and halogen.

Within this group, compounds of formula I according to the invention are preferred, wherein $R^4$ is a heteroaryl ring selected from 3-oxo-3,4-dihydro-2H-benzo[1,4]oxazinyl and 3,4-dihydro-2H-benzo[1,4]oxazinyl, said heteroaryl ring being unsubstituted or substituted by one, two or three substituents selected from the group consisting of $C_{1-7}$-alkyl, $C_{2-7}$-alkenyl and halogen.

Especially preferred are compounds of formula I according to the invention having the formula

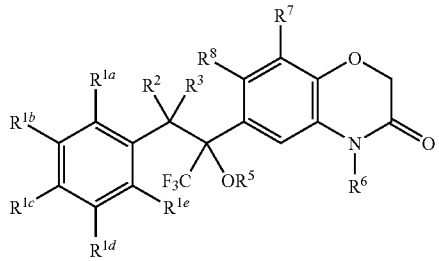

I-B wherein $R^{1a}$ to $R^{1e}$, $R^2$, $R^3$ and $R^5$ are as defined herein before,
$R^6$ is selected from the group consisting of hydrogen, $C_{1-7}$-alkyl and $C_{2-7}$-alkenyl, and $R^7$ and $R^8$ independently from each other are selected from hydrogen or halogen, or pharmaceutically salts thereof.

Further preferred compounds of formula I according to invention are those, wherein $R^4$ is a heteroaryl ring selected from 2-oxo-2,3-dihydro-1H-benzoimidazoyl and 2-oxo-2,3-dihydro-benzooxazolyl, said heteroaryl ring being unsubstituted or substituted by one, two or three substituents selected from the group consisting of $C_{1-7}$-alkyl, $C_{2-7}$-alkenyl and halogen.

Especially preferred are compounds of formula I according to the invention having the formula

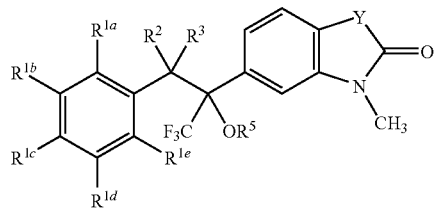

I-C wherein $R^{1a}$ to $R^{1e}$, $R^2$, $R^3$ and $R^5$ are as defined herein before and Y is $N(CH_3)$ or O,
or pharmaceutically acceptable salts thereof.

Further preferred are compounds of formula I, wherein $R^4$ is 1,3-dimethyl-2,2-dioxo-2,3-dihydro-1H-2λ6-benzo[1,2,5]thiadiazolyl, meaning compounds having the formula

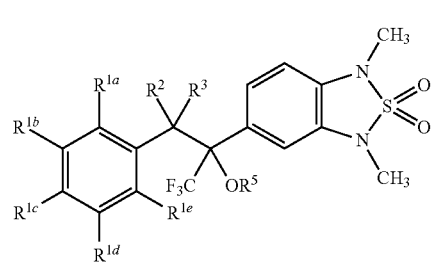

I-D wherein $R^{1a}$ to $R^{1e}$, $R^2$, $R^3$ and $R^5$ are as defined herein before, or pharmaceutically acceptable salts thereof.

Furthermore, compounds of formula I according to the present invention are preferred, wherein $R^4$ is phenyl substituted by cyano and, in addition, optionally substituted by one or two substituents selected from the group consisting of halogen, halogen-$C_{1-7}$-alkyl, $C_{1-7}$-alkyl, $C_{1-7}$-alkoxy and halogen-$C_{1-7}$-alkoxy.

More preferred are compounds of formula I according to the invention having the formula

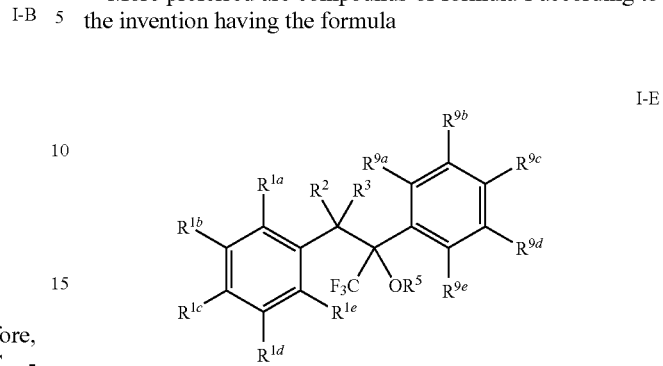

I-E wherein $R^{1a}$ to $R^{1e}$, $R^2$, $R^3$ and $R^5$ are as defined herein before, one of $R^{9e}$ or $R^{9d}$ is cyano and the other ones of $R^{9a}$, $R^{9b}$, $R^{9e}$, $R^{9d}$ and $R^{9e}$ are selected from the
group consisting of hydrogen, halogen, halogen-$C_{1-7}$-alkyl, $C_{1-7}$-alkyl, $C_{1-7}$-alkoxy and halogen-$C_{1-7}$-alkoxy,
or pharmaceutically acceptable salts thereof.

Especially preferred are compounds of formula I, wherein $R^4$ is selected from the group consisting of 4-cyano-3,5-dimethylphenyl, 4-cyanophenyl and 3-cyanophenyl.

Preferred are furthermore compounds of formula I according to the invention, wherein $R^5$ is hydrogen.

The following are preferred compounds of formula I of the present invention:
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxymethyl}-benzoic acid ethyl ester,
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxymethyl}-benzoic acid,
{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-acetic acid ethyl ester,
{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-acetic acid,
3-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid ethyl ester,
3-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester,
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
2-chloro-4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester,
2-chloro-4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid, (3-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid,
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid methyl ester,
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid,
2-chloro-5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-3-fluoro-benzoic acid,
4'-chloro-3'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid,
4'-chloro-3'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid,
(1-{4-chloro-3-[3,3,3-trifluoro-2-hydroxy-1-methyl-2-(4-methyl-3-oxo-3,4-dihydro-2H-benzo[1,4]oxazin-6-yl)-propyl]-benzoyl}-piperidin-4-yl)-acetic acid methyl ester,
(1-{4-chloro-3-[3,3,3-trifluoro-2-hydroxy-1-methyl-2-(4-methyl-3-oxo-3,4-dihydro-2H-benzo[1,4]oxazin-6-yl)-propyl]-benzoyl}-piperidin-4-yl)-acetic acid,
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-benzoylamino}-butyric acid,
3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid,
3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid,
3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-2-carboxylic acid,
3'-chloro-3-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester,
3'-chloro-3-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid,
3'-chloro-3-fluoro-4'-[(1S,2S)-3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid or (1R,2R) enantiomer,
3'-chloro-3-fluoro-4'-[(1R,2R)-3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid or (1S,2S) enantiomer,
3-{3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-propionic acid,
3,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester,
3,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid,
3'-chloro-4-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid,
3'-chloro-2-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester,
3'-chloro-2-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid,
3'-chloro-3-methoxy-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester,
3'-chloro-3-methoxy-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid,
{3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-acetic acid,
3'-chloro-6-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid,
4,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid ethyl ester,
4,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid,
{3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-yl}-acetic acid,
1-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenyl}-piperidine-4-carboxylic acid ethyl ester,
3-chloro-4-[3,3,3-trifluoro-2-hydroxy-1-methyl-2-(4-methyl-3-oxo-3,4-dihydro-2H-benzo[1,4]oxazin-6-yl)-propyl]-benzoic acid,
(4-{3-chloro-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid,
3'-chloro-3-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-4-carboxylic acid methyl ester,
3'-chloro-3-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-4-carboxylic acid,
{3'-chloro-4-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-3-yloxy}-acetic acid ethyl ester,
{3'-chloro-4-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-3-yloxy}-acetic acid,
3'-chloro-3-fluoro-4'-[3,3,3-trifluoro-2-hydroxy-1-methyl-2-(4-oxo-4H-quinolizin-1-yl)-propyl]-biphenyl-4-carboxylic acid methyl ester,
3'-chloro-3-fluoro-4'-[3,3,3-trifluoro-2-hydroxy-1-methyl-2-(4-oxo-4H-quinolizin-1-yl)-propyl]-biphenyl-4-carboxylic acid,
3'-chloro-3-fluoro-4'-[3,3,3-trifluoro-2-hydroxy-1-methyl-2-(1-methyl-2-oxo-2,3-dihydro-1H-pyrido[2,3-b][1,4]oxazin-7-yl)-propyl]-biphenyl-4-carboxylic acid methyl ester,
3'-chloro-3-fluoro-4'-[3,3,3-trifluoro-2-hydroxy-1-methyl-2-(1-methyl-2-oxo-2,3-dihydro-1H-pyrido[2,3-b][1,4]oxazin-7-yl)-propyl]-biphenyl-4-carboxylic acid,
3'-chloro-3-fluoro-4'-[3,3,3-trifluoro-2-hydroxy-1-methyl-2-(4-methyl-3-oxo-3,4-dihydro-2H-benzo[1,4]oxazin-8-yl)-propyl]-biphenyl-4-carboxylic acid methyl ester, 3'-chloro-3-fluoro-4'-[3,3,3-trifluoro-2-hydroxy-1-methyl-2-(4-methyl-3-oxo-3,4-dihydro-2H-benzo[1,4]oxazin-8-yl)-propyl]-biphenyl-4-carboxylic acid, 5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid, 4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid, 2-chloro-5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid, 2-chloro-4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid, 4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid, 3-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid, 6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-4-trifluoromethyl-nicotinic acid, 2-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid, 3,3'-dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-4-carboxylic acid, 3'-chloro-4'-[2-(4-ethyl-3-oxo-3,4-dihydro-2H-benzo[1,4]oxazin-6-yl)-3,3,3-trifluoro-2-hydroxy-1-methyl-propyl]-3-fluoro-biphenyl-4-carboxylic acid, 4,3'-dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-3-carboxylic acid, 3'-chloro-4'-[2-(4-ethyl-3-oxo-3,4-dihydro-2H-benzo[1,4]oxazin-6-yl)-3,3,3-trifluoro-2-hydroxy-1-methyl-propyl]-4-fluoro-biphenyl-3-carboxylic acid, 6-{3-chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-4-trifluoromethyl-nicotinic acid, 2-chloro-6-{3-chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-nicotinic acid, 4'-[2-(4-allyl-3-oxo-3,4-dihydro-2H-benzo[1,4]oxazin-6-yl)-3,3,3-trifluoro-2-hydroxy-1-methyl-propyl]-3'-chloro-3-fluoro-biphenyl-4-carboxylic acid methyl ester, 3'-chloro-3-fluoro-4'-[3,3,3-trifluoro-2-hydroxy-1-methyl-2-(3-oxo-3,4-dihydro-2H-benzo[1,4]oxazin-6-yl)-propyl]-biphenyl-4-carboxylic acid methyl ester, 3'-chloro-3-fluoro-4'-[3,3,3-trifluoro-2-hydroxy-1-methyl-2-(3-oxo-3,4-dihydro-2H-benzo[1,4]oxazin-6-yl)-propyl]-biphenyl-4-carboxylic acid, 3'-chloro-4'-[2-(1,3-dimethyl-2-oxo-2,3-dihydro-1H-benzoimidazol-5-yl)-3,3,3-trifluoro-2-hydroxy-1-methyl-propyl]-3-fluoro-biphenyl-4-carboxylic acid, 3'-chloro-4'-[2-(1,3-dimethyl-2-oxo-2,3-dihydro-1H-benzoimidazol-5-yl)-3,3,3-trifluoro-2-hydroxy-1-methyl-propyl]-4-fluoro-biphenyl-3-carboxylic acid, {3'-chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-yloxy}-acetic acid, 3,3'-dichloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-carboxylic acid, 3'-chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-carboxylic acid, 3'-chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-3-carboxylic acid, 4,3'-dichloro-4'-[2-(1,3-dimethyl-2-oxo-2,3-dihydro-1H-benzoimidazol-5-yl)-3,3,3-trifluoro-2-hydroxy-1-methyl-propyl]-biphenyl-3-carboxylic acid, 3'-chloro-4'-[2-(1,3-dimethyl-2-oxo-2,3-dihydro-1H-benzoimidazol-5-yl)-3,3,3-trifluoro-2-hydroxy-1-methyl-propyl]-3-methoxy-biphenyl-4-carboxylic acid, 2,3'-dichloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-carboxylic acid, {3'-chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-yl}-acetic acid, {3'-chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-3-yl}-acetic acid, 5-{3-chloro-4-[2-(1,3-dimethyl-2-oxo-2,3-dihydro-1H-benzoimidazol-5-yl)-3,3,3-trifluoro-2-hydroxy-1-methyl-propyl]-phenyl}-pyridine-2-carboxylic acid, 5-[2-(2-chloro-4-hydroxy-phenyl)-1-hydroxy-1-trifluoromethyl-propyl]-1,3-dimethyl-1,3-dihydro-benzoimidazol-2-one, 4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-3-fluoro-benzoic acid, 3-chloro-4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid, 4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-fluoro-benzoic acid, (4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenyl)-acetic acid, 2-chloro-4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid, 5-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-fluoro-benzoic acid, 2-chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid, (4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenoxy)-acetic acid, (3-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenoxy)-acetic acid, 5-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-pyridine-2-carboxylic acid, 2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid, 4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-methoxy-benzoic acid, 4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid, 3-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid, 5-chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid, 6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid, 6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-4-trifluoromethyl-nicotinic acid, 4-[4-(2-benzo[1,3]dioxol-5-yl-3,3,3-trifluoro-2-hydroxy-1-methyl-propyl)-3-chloro-phenoxy]-2-chloro-benzoic acid, 5-chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid, 2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid, 5-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-pyrazine-2-carboxylic acid, 5-chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid, 6-chloro-4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid, 4-chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid, 2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-5-trifluoromethyl-isonicotinic acid, 2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-6-trifluoromethyl-nicotinic acid, 6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-3-trifluoromethyl-pyridine-2-carboxylic acid, 2-chloro-3-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-isonicotinic acid, 3'-chloro-3-fluoro-4'-[3,3,3-trifluoro-2-hydroxy-1-methyl-2-(2-oxo-2,3-dihydro-1H-benzoimidazol-5-yl)-propyl]-biphenyl-4-carboxylic acid, 6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-trifluoromethyl-nicotinic acid, 5-[2-(4-bromo-2-chloro-phenyl)-1-hydroxy-1-trifluoromethyl-propyl]-3-methyl-3H-benzooxazol-2-one, 3'-chloro-3-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester, 3'-chloro-3-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid, 3'-chloro-3-fluoro-4'-[(1S,2S)-3,3,3-trifluoro-2-hydroxy-1-methyl-2-(3-methyl-2-oxo-2,3-dihydro-benzooxazol-5-yl)-propyl]-biphenyl-4-carboxylic acid or (1R,2R)enantiomer, 3'-chloro-3-fluoro-4'-[(1R,2R)-3,3,3-trifluoro-2-hydroxy-1-methyl-2-(3-methyl-2-oxo-2,3-dihydro-benzooxazol-5-yl)-propyl]-biphenyl-4-carboxylic acid or (1S,2S) enantiomer, 3'-chloro-4-fluoro-4'-[3,3,3-trifluoro-2-hydroxy-1-methyl-2-(3-methyl-2-oxo-2,3-dihydro-benzooxazol-5-yl)-propyl]-biphenyl-3-carboxylic acid ethyl ester, 3'-chloro-4-fluoro-4'-[3,3,3-trifluoro-2-hydroxy-1-methyl-2-(3-methyl-2-oxo-2,3-dihydro-benzooxazol-5-yl)-propyl]-biphenyl-3-carboxylic acid, 3,3'-dichloro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester, 3,3'-dichloro-4'-[3,3,3-trifluoro-2-hydroxy-1-methyl-2-(3-methyl-2-oxo-2,3-dihydro-benzooxazol-5-yl)-propyl]-biphenyl-4-carboxylic acid, 3'-chloro-2-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester, 3'-chloro-2-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid, 6-{3-chloro-4-[3,3,3-trifluoro-2-hydroxy-1-methyl-2-(3-methyl-2-oxo-2,3-dihydro-benzooxazol-5-yl)-propyl]-phenyl}-nicotinic acid methyl ester, 6-{3-chloro-4-[3,3,3-trifluoro-2-hydroxy-1-methyl-2-(3-methyl-2-oxo-2,3-dihydro-benzooxazol-5-yl)-propyl]-phenyl}-nicotinic acid, {3'-chloro-4'-[3,3,3-trifluoro-2-hydroxy-1-methyl-2-(3-methyl-2-oxo-2,3-dihydro-benzooxazol-5-yl)-propyl]-biphenyl-4-yloxy}-acetic acid ethyl ester, {3'-chloro-4'-[3,3,3-trifluoro-2-hydroxy-1-methyl-2-(3-methyl-2-oxo-2,3-dihydro-benzooxazol-5-yl)-propyl]-biphenyl-4-yloxy}-acetic acid, 3'-chloro-3-methoxy-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester, 3'-chloro-3-methoxy-4'-[3,3,3-trifluoro-2-hydroxy-1-methyl-2-(3-methyl-2-oxo-2,3-dihydro-benzooxazol-5-yl)-propyl]-biphenyl-4-carboxylic acid, 6-[2-(4-bromo-2-chloro-phenyl)-1-hydroxy-1-trifluoromethyl-propyl]-3-methyl-3H-benzooxazol-2-one, 3'-chloro-3-fluoro-4'-[3,3,3-trifluoro-2-hydroxy-1-methyl-2-(3-methyl-2-oxo-2,3-dihydro-benzooxazol-6-yl)-propyl]-biphenyl-4-carboxylic acid, 3,3'-dichloro-4'-[3,3,3-trifluoro-2-hydroxy-1-methyl-2-(3-methyl-2-oxo-2,3-dihydro-benzooxazol-6-yl)-propyl]-biphenyl-4-carboxylic acid, 3'-chloro-3-fluoro-4'-[3,3,3-trifluoro-2-(7-fluoro-4-methyl-3-oxo-3,4-dihydro-2H-benzo[1,4]oxazin-6-yl)-2-hydroxy-1-methyl-propyl]-biphenyl-4-carboxylic acid methyl ester, 3'-chloro-3-fluoro-4'-[3,3,3-trifluoro-2-(7-fluoro-4-methyl-3-oxo-3,4-dihydro-2H-benzo[1,4]oxazin-6-yl)-2-hydroxy-1-methyl-propyl]-biphenyl-4-carboxylic acid, 2-chloro-4-{3-chloro-4-[3,3,3-trifluoro-2-(7-fluoro-4-methyl-3-oxo-3,4-dihydro-2H-benzo[1,4]oxazin-6-yl)-2-hydroxy-1-methyl-propyl]-phenoxy}-benzoic acid methyl ester, 2-chloro-4-{3-chloro-4-[3,3,3-trifluoro-2-(7-fluoro-4-methyl-3-oxo-3,4-dihydro-2H-benzo[1,4]oxazin-6-yl)-2-hydroxy-1-methyl-propyl]-phenoxy}-benzoic acid, 2-chloro-4-{3-chloro-4-[3,3,3-trifluoro-2-hydroxy-1-methyl-2-(2-oxo-4-trifluoromethyl-1,2-dihydro-quinolin-6-yl)-propyl]-phenoxy}-benzoic acid, 4-{3-chloro-4-[2-(4-cyano-3,5-dimethyl-phenyl)-3,3,3-trifluoro-2-hydroxy-1-methyl-propyl]-phenoxy}-2-fluoro-benzoic acid methyl ester,
4-{3-chloro-4-[2-(4-cyano-3,5-dimethyl-phenyl)-3,3,3-trifluoro-2-hydroxy-1-methyl-propyl]-phenoxy}-2-fluoro-benzoic acid,
2-chloro-4-{3-chloro-4-[2-(4-cyano-3,5-dimethyl-phenyl)-3,3,3-trifluoro-2-hydroxy-1-methyl-propyl]-phenoxy}-benzoic acid methyl ester,
2-chloro-4-{3-chloro-4-[2-(4-cyano-3,5-dimethyl-phenyl)-3,3,3-trifluoro-2-hydroxy-1-methyl-propyl]-phenoxy}-benzoic acid,
6-{3-chloro-4-[2-(4-cyano-3,5-dimethyl-phenyl)-3,3,3-trifluoro-2-hydroxy-1-methyl-propyl]-phenoxy}-4-trifluoromethyl-nicotinic acid methyl ester,
6-{3-chloro-4-[2-(4-cyano-3,5-dimethyl-phenyl)-3,3,3-trifluoro-2-hydroxy-1-methyl-propyl]-phenoxy}-4-trifluoromethyl-nicotinic acid,
6-{3-chloro-4-[2-(4-cyano-3,5-dimethyl-phenyl)-3,3,3-trifluoro-2-hydroxy-1-methyl-propyl]-phenoxy}-nicotinic acid methyl ester,
6-{3-chloro-4-[2-(4-cyano-3,5-dimethyl-phenyl)-3,3,3-trifluoro-2-hydroxy-1-methyl-propyl]-phenoxy}-nicotinic acid,
5-chloro-6-{3-chloro-4-[2-(4-cyano-3,5-dimethyl-phenyl)-3,3,3-trifluoro-2-hydroxy-1-methyl-propyl]-phenoxy}-nicotinic acid methyl ester,
5-chloro-6-{3-chloro-4-[2-(4-cyano-3,5-dimethyl-phenyl)-3,3,3-trifluoro-2-hydroxy-1-methyl-propyl]-phenoxy}-nicotinic acid,
3'-chloro-4'-[2-(4-cyano-phenyl)-3,3,3-trifluoro-2-hydroxy-1-methyl-propyl]-4-fluoro-biphenyl-3-carboxylic acid,
3'-chloro-4'-[2-(4-cyano-phenyl)-3,3,3-trifluoro-2-hydroxy-1-methyl-propyl]-3-fluoro-biphenyl-4-carboxylic acid,
3'-chloro-4'-[2-(3-cyano-phenyl)-3,3,3-trifluoro-2-hydroxy-1-methyl-propyl]-3-fluoro-biphenyl-4-carboxylic acid,
3'-chloro-4'-[2-(3-cyano-phenyl)-3,3,3-trifluoro-2-hydroxy-1-methyl-propyl]-4-fluoro-biphenyl-3-carboxylic acid,
5-chloro-6-{3-chloro-4-[2-(4-cyano-phenyl)-3,3,3-trifluoro-2-hydroxy-1-methyl-propyl]-phenoxy}-nicotinic acid,
2-chloro-4-{3-chloro-4-[2-(4-cyano-phenyl)-3,3,3-trifluoro-2-hydroxy-1-methyl-propyl]-phenoxy}-benzoic acid,
6-{3-chloro-4-[2-(4-cyano-phenyl)-3,3,3-trifluoro-2-hydroxy-1-methyl-propyl]-phenoxy}-nicotinic acid,
2-chloro-6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid,
2-chloro-6-{3-chloro-4-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-phenoxy}-nicotinic acid,
2-chloro-4-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-benzoic acid,
2-chloro-4-{3-chloro-4-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-phenoxy}-benzoic acid,
3'-chloro-4'-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-4-fluoro-biphenyl-3-carboxylic acid,
3'-chloro-4'-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-3-fluoro-biphenyl-4-carboxylic acid,
3'-chloro-3-fluoro-4'-[3,3,3-trifluoro-2-hydroxy-1-methyl-2-(4-methyl-3-oxo-3,4-dihydro-2H-benzo[1,4]oxazin-7-yl)-propyl]-biphenyl-4-carboxylic acid,
5-chloro-6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid,
4-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-2-fluoro-benzoic acid,
5-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-2-fluoro-benzoic acid,
3'-chloro-3-fluoro-4'-[3,3,3-trifluoro-2-hydroxy-1-methyl-2-(2,2,4-trimethyl-3-oxo-3,4-dihydro-2H-benzo[1,4]oxazin-6-yl)-propyl]-biphenyl-4-carboxylic acid,
6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid,
3'-chloro-3-fluoro-4'-[3,3,3-trifluoro-2-hydroxy-1-methyl-2-(4-methyl-3,4-dihydro-2H-benzo[1,4]oxazin-6-yl)-propyl]-biphenyl-4-carboxylic acid,
5-[2-(2-chloro-4-methoxy-phenyl)-1-hydroxy-1-trifluoromethyl-propyl]-3-methyl-3H-benzooxazol-2-one,
5-[2-(2-chloro-4-hydroxy-phenyl)-1-hydroxy-1-trifluoromethyl-propyl]-3-methyl-3H-benzooxazol-2-one,
2-chloro-4-{3-chloro-4-[3,3,3-trifluoro-2-hydroxy-1-methyl-2-(3-methyl-2-oxo-2,3-dihydro-benzooxazol-5-yl)-propyl]-phenoxy}-benzoic acid,
6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester,
5-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester,
4-{3-chloro-4-[3,3,3-trifluoro-2-hydroxy-1-methyl-2-(3-methyl-2-oxo-2,3-dihydro-benzooxazol-5-yl)-propyl]-phenoxy}-2-fluoro-benzoic acid methyl ester,
4-{3-chloro-4-[3,3,3-trifluoro-2-hydroxy-1-methyl-2-(3-methyl-2-oxo-2,3-dihydro-benzooxazol-5-yl)-propyl]-phenoxy}-2-fluoro-benzoic acid,
3'-chloro-4-fluoro-4'-[3,3,3-trifluoro-2-hydroxy-1-methyl-2-(3-methyl-2-oxo-2,3-dihydro-benzooxazol-6-yl)-propyl]-biphenyl-3-carboxylic acid,
3'-chloro-4'-[3,3,3-trifluoro-2-hydroxy-1-methyl-2-(3-methyl-2-oxo-2,3-dihydro-benzooxazol-6-yl)-propyl]-biphenyl-3-carboxylic acid,
5-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid,
6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid,
2-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester,
4-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester,
2-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid,
4-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid,
5-{3-chloro-4-[3,3,3-trifluoro-2-hydroxy-1-methyl-2-(3-methyl-2-oxo-2,3-dihydro-benzooxazol-5-yl)-propyl]-phenyl}-nicotinic acid methyl ester, 5-{3-chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid methyl ester,
6-{3-chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid ethyl ester,
5-{3-chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid,
6-{3-chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid,
5-{3-chloro-4-[3,3,3-trifluoro-2-hydroxy-1-methyl-2-(3-methyl-2-oxo-2,3-dihydro-benzooxazol-5-yl)-propyl]-phenyl}-nicotinic acid,
5-[2-(2-chloro-5-methoxy-phenyl)-1-hydroxy-1-trifluoromethyl-propyl]-3-methyl-3H-benzooxazol-2-one,
5-[2-(4-bromo-2-trifluoromethyl-phenyl)-1-hydroxy-1-trifluoromethyl-propyl]-3-methyl-3H-benzooxazol-2-one,
5-[2-(2-chloro-4-pyrimidin-5-yl-phenyl)-1-hydroxy-1-trifluoromethyl-propyl]-3-methyl-3H-benzooxazol-2-one,
5-[2-(2-chloro-4-pyridazin-4-yl-phenyl)-1-hydroxy-1-trifluoromethyl-propyl]-3-methyl-3H-benzooxazol-2-one,
5-{2-[2-chloro-4-(pyrimidin-2-yloxy)-phenyl]-1-hydroxy-1-trifluoromethyl-propyl}-3-methyl-3H-benzooxazol-2-one,
5-[2-(2-chloro-5-hydroxy-phenyl)-1-hydroxy-1-trifluoromethyl-propyl]-3-methyl-3H-benzooxazol-2-one,
3-fluoro-4'-[3,3,3-trifluoro-2-hydroxy-1-methyl-2-(3-methyl-2-oxo-2,3-dihydro-benzooxazol-5-yl)-propyl]-3'-trifluoromethyl-biphenyl-4-carboxylic acid methyl ester,
6-{3-chloro-4-[3,3,3-trifluoro-2-hydroxy-1-methyl-2-(3-methyl-2-oxo-2,3-dihydro-benzooxazol-5-yl)-propyl]-phenoxy}-pyridazine-3-carboxylic acid methyl ester,
3-fluoro-4'-[3,3,3-trifluoro-2-hydroxy-1-methyl-2-(3-methyl-2-oxo-2,3-dihydro-benzooxazol-5-yl)-propyl]-3'-trifluoromethyl-biphenyl-4-carboxylic acid,
6-{3-chloro-4-[3,3,3-trifluoro-2-hydroxy-1-methyl-2-(3-methyl-2-oxo-2,3-dihydro-benzooxazol-5-yl)-propyl]-phenoxy}-pyridazine-3-carboxylic acid,
2-{3-chloro-4-[3,3,3-trifluoro-2-hydroxy-1-methyl-2-(3-methyl-2-oxo-2,3-dihydro-benzooxazol-5-yl)-propyl]-phenoxy}-pyrimidine-5-carboxylic acid methyl ester,
2-{3-chloro-4-[3,3,3-trifluoro-2-hydroxy-1-methyl-2-(3-methyl-2-oxo-2,3-dihydro-benzooxazol-5-yl)-propyl]-phenoxy}-pyrimidine-5-carboxylic acid,
6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester,
6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
2-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-methyl-propionic acid ethyl ester,
2-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-methyl-propionic acid,
2-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester,
2-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
4-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester,
4-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
5-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester,
5-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
6-{3-chloro-4-[3,3,3-trifluoro-2-hydroxy-1-methyl-2-(4-methyl-3-oxo-3,4-dihydro-2H!-benzo[1,4]oxazin-6-yl)-propyl]-phenoxy}-2-trifluoromethyl-nicotinic acid ethyl ester,
6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-nicotinic acid,
2-chloro-4-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester or (1S,2S)enantiomer,
2-chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester or (1R,2R)enantiomer,
2-chloro-4-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid or (1S,2S) enantiomer,
2-chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid or (1R,2R) enantiomer,
4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-benzoic acid,
5-chloro-6-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester or (1S,2S)enantiomer,
5-chloro-6-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester or (1R,2R)enantiomer,
5-chloro-6-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid or (1S,2S) enantiomer,
5-chloro-6-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid or (1R,2R) enantiomer,
2-{3-chloro-4-[,3,3-trifluoro-2-hydroxy-1-methyl-2-(4-methyl-3-oxo-3,4-dihydro-2H-benzo[1,4]oxazin-6-yl)-propyl]-phenoxy}-4-trifluoromethyl-pyrimidine-5-carboxylic acid methyl ester,
2-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrimidine-5-carboxylic acid methyl ester,
5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrazine-2-carboxylic acid methyl ester,
5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrazine-2-carboxylic acid, 2-{3-chloro-4-[3,3,3-trifluoro-2-hydroxy-1-methyl-2-(3-methyl-2-oxo-2,3-dihydro-benzooxazol-5-yl)-propyl]-phenoxy}-2-methyl-propionic acid ethyl ester,
2-{3-chloro-4-[3,3,3-trifluoro-2-hydroxy-1-methyl-2-(3-methyl-2-oxo-2,3-dihydro-benzooxazol-5-yl)-propyl]-phenoxy}-2-methyl-propionic acid,
{3-chloro-4-[3,3,3-trifluoro-2-hydroxy-1-methyl-2-(3-methyl-2-oxo-2,3-dihydrobenzooxazol-5-yl)-propyl]-benzoylamino}-acetic acid tert-butyl ester,
{3-chloro-4-[3,3,3-trifluoro-2-hydroxy-1-methyl-2-(3-methyl-2-oxo-2,3-dihydrobenzooxazol-5-yl)-propyl]-benzoylamino}-acetic acid,
and pharmaceutically acceptable salts thereof.

Especially preferred compounds of formula I of the present invention are the following:
4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid,
3'-chloro-3-fluoro-4'-[(1R,2R)-3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid or (1S,2S)enantiomer,
3,3'-dichloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-carboxylic acid,
3'-chloro-3-fluoro-4'-[(1S,2S)-3,3,3-trifluoro-2-hydroxy-1-methyl-2-(3-methyl-2-oxo-2,3-dihydro-benzooxazol-5-yl)-propyl]-biphenyl-4-carboxylic acid or (1R,2R)enantiomer,
3'-chloro-4-fluoro-4'-[3,3,3-trifluoro-2-hydroxy-1-methyl-2-(3-methyl-2-oxo-2,3-dihydro-benzooxazol-5-yl)-propyl]-biphenyl-3-carboxylic acid,
4-{3-chloro-4-[2-(4-cyano-3,5-dimethyl-phenyl)-3,3,3-trifluoro-2-hydroxy-1-methyl-propyl]-phenoxy}-2-fluoro-benzoic acid,
2-chloro-4-{3-chloro-4-[2-(4-cyano-3,5-dimethyl-phenyl)-3,3,3-trifluoro-2-hydroxy-1-methyl-propyl]-phenoxy}-benzoic acid,
6-{3-chloro-4-[2-(4-cyano-3,5-dimethyl-phenyl)-3,3,3-trifluoro-2-hydroxy-1-methyl-propyl]-phenoxy}-nicotinic acid,
5-chloro-6-{3-chloro-4-[2-(4-cyano-3,5-dimethyl-phenyl)-3,3,3-trifluoro-2-hydroxy-1-methyl-propyl]-phenoxy}-nicotinic acid,
2-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid,
4-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid,
2-chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid or (1R,2R) enantiomer,
and pharmaceutically acceptable salts thereof.

Furthermore, the pharmaceutically acceptable salts of the compounds of formula I constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms. The compounds of formula I as optically pure diastereomers constitute a preferred embodiment of the invention.

It will be appreciated that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises treating a compound of the formula II

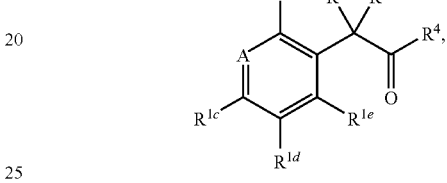

wherein A, $R^{1a}$ to $R^{1e}$, $R^2$, $R^3$ and $R^4$ are as defined herein before, with trifluoromethyltrimethylsilane and a suitable fluoride,
to obtain a compound of the formula Ia

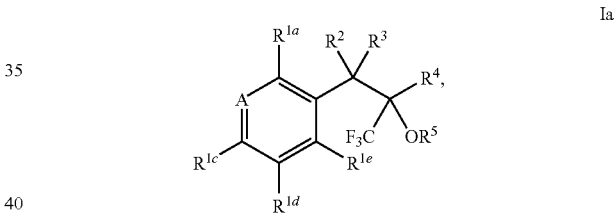

wherein $R^5$ is hydrogen, and, if desired, alkylating the compound of formula Ia with methyliodide in the presence of a base such as NaH to obtain a compound of formula Ib

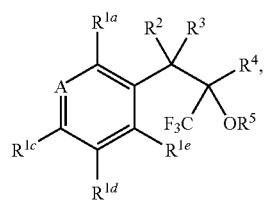

wherein $R^5$ is methyl, and, if desired, converting the compound obtained into a pharmaceutically acceptable salt.

The compounds of formula I can be manufactured by the methods given below, by the methods given in the examples or by analogous methods. Appropriate reaction conditions for the individual reaction steps are known to a person skilled in the art. General approaches for the synthesis of compounds with the general formula I are outlined in the following section. Several different synthetic approaches had to be used in order to generate the different sub-sets of the compounds of formula I described in this patent application. Scheme 1 describes the first possible approach with a Negishi type reaction as a synthetic key step to provide a key intermediate of formula A9 towards the synthesis of compounds with the general formula I. Note that $R^1$ is one or several groups taken from $R^{1a-e}$ as defined previously which may be present or absent, FG is a group taken from $R^{1a-e}$ as defined previously which can be modified to perform further functionalization and $R^2$, $R^3$, $R^4$ and $R^5$ are groups as defined previously. Other R-groups such as R', R", R* and R and R are $R^{6-10}$ defined in the schemes below or can be taken, for example, from the groups of peripheral substituents as defined previously.

ment of A1 with carbon monoxide in the presence of a suitable palladium catalyst which itself is generated by addition of the appropriate palladium derivative such as palladium acetate or palladium chloride or the like and the appropriate ligand such as for example 1,3-bis(diphenylphosphino)-propane (DPPP). Many other ligands are known and available and can potentially be used in this reaction step. The choice of the solvent and solvent additives will determine whether esters of formula A2 or free acids of formula A3 are formed. For example the use of DMSO as a base solvent with methanol or ethanol as a an additive will provide the corresponding carboxylic acid esters of formula A2 (step (a)), whereas the

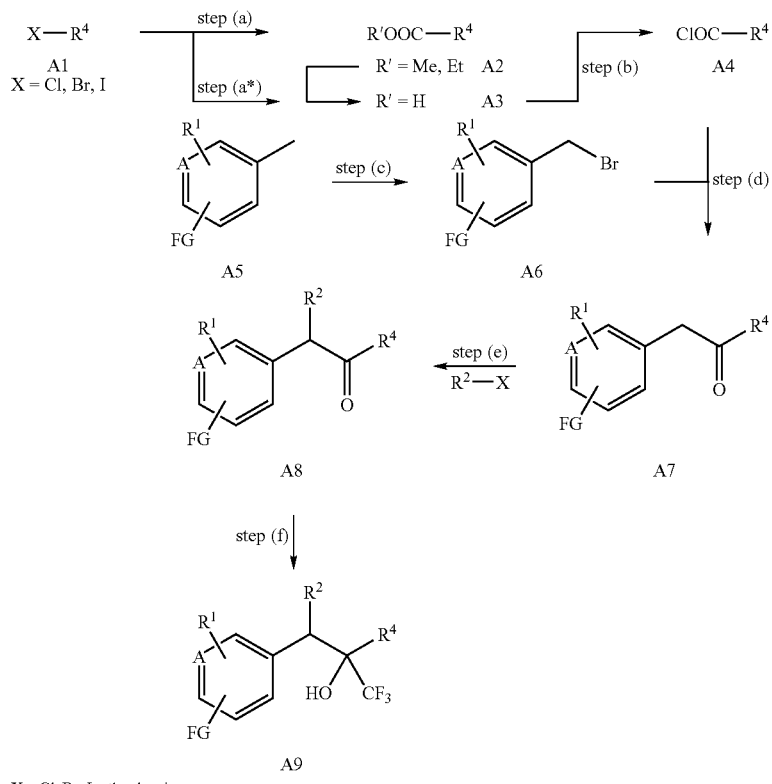

Scheme 1

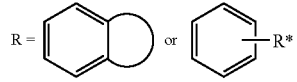

R* = one or several substituents chosen from e.g.: CN, Me
FG = functional group, suitable for further modification
$R^1$ = one or several substituents chosen from $R^{1a-e}$ Suitable starting materials for this synthetic approach are for example fused heterocycles of formula A1 such as benzoimidazolones, benzooxazolones and benzooxazinones or the like with suitable functional groups such as halogens (chlorine, bromine, iodine) in the appropriate positions. Starting materials of formula A1 are commercially available or can be made according to known procedures described in the literature. Other key intermediates of the synthesis are the corresponding carboxylic acid derivatives (free carboxylic acids or the corresponding carboxylic acid esters) of formula A2 or A3, respectively. Again, some of these compounds are commercially available; but access is also easily possible e.g. from halides A1 by a standard carbonylation reaction (step (a)). Suitable conditions for step (a) are for example: treatment of use of DMSO with water as an additive will lead to free carboxylic acids of formula A3 directly (step (a*)). Alternatively, carboxylic acids of formula A3 are easily accessible from the esters of formula A2 either by saponification with a base such as NaOH or KOH or the like or by treatment with strong aqueous mineral acid such as HCl, HBr or $H_2SO_4$ or similar at various temperatures.

A first prerequisite for the Negishi type coupling step (step (d)) is the formation of a suitable acid chloride of formula A4. Acid chlorides can be made in a standard fashion for example by treatment of a free carboxylic acid A3 with oxalyl chloride in the presence of a catalytic amount of DMF or by treatment with $SOCl_2$ (step (b)). The acid chloride A4 can be made in situ or can be isolated.

Another prerequisite for the Negishi coupling is the availability of a suitable benzylic halide of formula A6, for example a benzylic bromide. Benzylic bromides of formula A6 are either commercially available or can be made easily from the appropriate toluene derivatives of formula A5 by treatment with e.g. N-bromosuccinimide as the most popular bromination reagent (step (c)). Other approaches for the synthesis of A6 such as treatment of a suitable benzylic alcohol with HBr are also possible, but are not shown in scheme 1.

For the Negishi coupling itself, the suitable acid chloride A4 is treated with zinc powder and an appropriate palladium catalyst such as tetrakis(triphenylphosphine)palladium(0), followed by the benzyl bromide component A6 to give a ketone of formula A7 as the main coupling product. Again, other known catalyst systems can potentially be used in this reaction and conditions such as temperatures and solvents can be widely varied.

Further elaboration of ketone A7 towards the synthesis of GRA antagonist of formula I includes alkylation of A7 with an appropriate alkyl halide $R^2$—X (X=Cl, Br, I) in the presence of a suitable base such as LDA, tert-BuOK, NaH, LiHMDS or the like at temperatures ranging from −78 to 100° C. in an appropriate solvent such as DMF, THF, DCM or the like to provide alkyl ketone intermediates of formula A8 (step (e)). Ketones A8 are then converted to the key trifluoromethyl alcohols A9 by treatment with Ruppert's reagent and a suitable fluoride source such as tetrabutylammonium fluoride or tetramethylammonium fluoride or the like in an appropriate solvent such as DCM, THF, ether or the like at suitable temperatures ranging from −50° C. to 50° C. (step (f)).

Key intermediates of formula A9 are usually showing high activities in the GR assay, however further modifications are usually needed to introduce some important additional properties such as liver tissue selectivity. Several approaches can be used to provide, for example, carboxylic acid derivatives of general formula (I).

Scheme 2

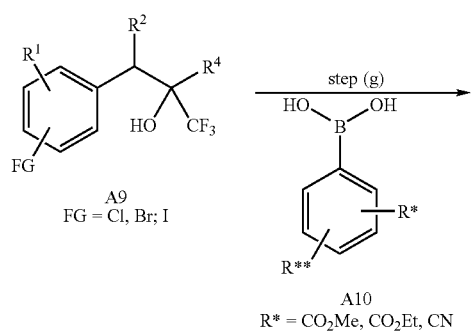

A10
$R^* = CO_2Me, CO_2Et, CN$

-continued

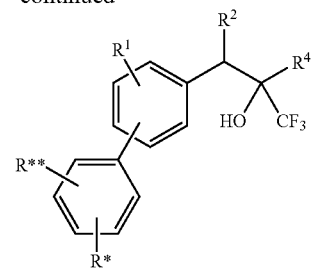

step (h) $R^* = CO_2Me, CO_2Et$ (A11); CN (A12)
$R^* = CO_2H$ A13

For example, if FG in intermediate A9 is a halogen such as chlorine or preferentially bromine or iodine, A9 can be further modified by palladium catalyzed coupling with suitable boronic acids or boronic acid esters bearing a masked carboxylic acid function A10 (usually as the corresponding ester or nitrile, see Scheme 2) in the presence of a suitable catalyst to give the masked carboxylic acid derivatives A11 or A12 (step (g)). Again, many different catalyst systems can potentially be used in this reaction, however the use of dichloro(1,1'-bis(diphenylphosphino)ferrocene)palladium(II)dichloromethane adduct has proven to be particularly beneficial. Coupling products bearing ester groups (A11) can then be converted to the free carboxylic acid derivatives A13 either by saponification under basic conditions with dilute bases such as LiOH, NaOH, KOH or the like in suitable solvents in solvent systems (water, alcohols, mixtures between solvents mentioned before and aprotic solvents such as THF, dioxane, DMF or the like) at temperatures ranging from −20° C. to 120° C. (step (h)). Coupling products bearing nitriles of formula A12 can also be converted to carboxylic acids of formula A13 by conversion to the corresponding iminoethers by addition of alcoholic solutions of acids such as HCl, HBr or the like at various temperatures, preferably ranging from 0 to 100° C., followed by hydrolysis of the iminoether to the corresponding ester and hydrolysis of the ester as described above. Other methods known in the art for hydrolysis of nitriles can be used, for example treatment with aqueous KOH, NaOH or the like with or without addition of a suitable organic solvent or solvent mixture such as dioxane, MeOH, THF or the like at various temperatures, preferentially ranging from −20° C. to reflux temperature of the solvent. The carboxylic acids are either attached directly or via diverse linkers such as alkyl or alkoxy chains to the aromatic ring. Starting materials of formula A10 are either commercially available, described in the literature or can be prepared by methods well known in the art.

Another approach for modification of the key intermediates A9 can be used if FG in intermediate A9 is a methoxy group as shown in scheme 3. In this case, the methoxy group can be easily converted to a free phenol A14 either by treatment with strong mineral acids such as HBr, HCl or the like at elevated temperatures ranging from 20 to 150° C. or alternatively under much milder conditions using for example $BBr_3$ in aprotic solvents such as DCM, THF or the like at temperatures ranging from −50° C. to 50° C. (step (i)).

Scheme 3

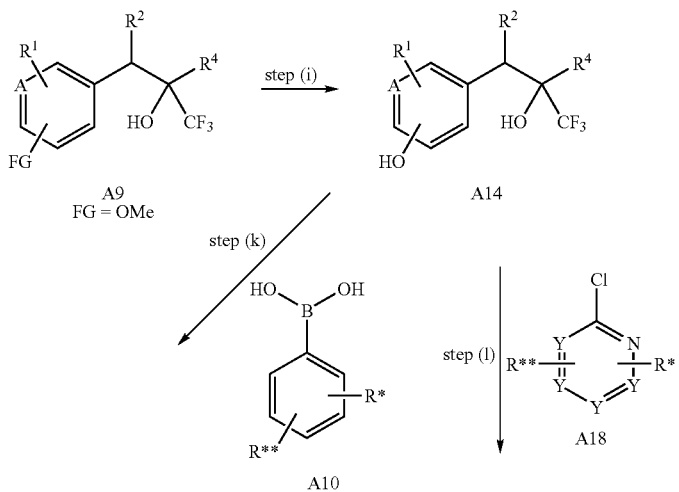

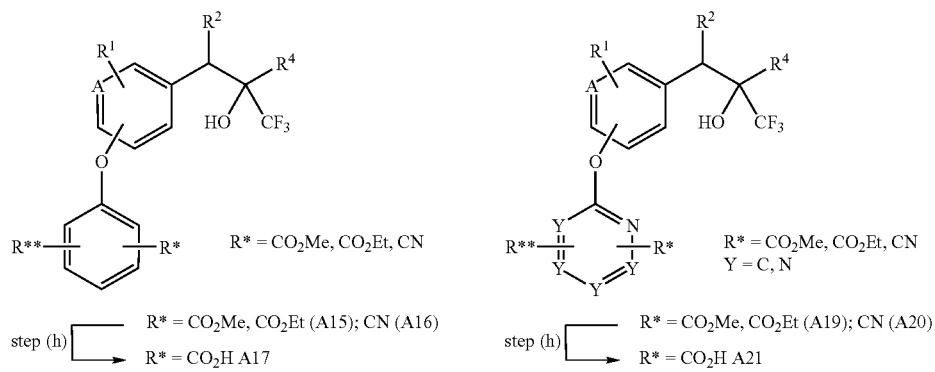

Free phenol A14 itself is suitable for various coupling reactions. On one hand, it can be used for example in a copper(II) mediated coupling with suitably substituted boronic acids A10 (or the corresponding pinacol esters) in the presence of pyridine, DMAP or triethylamine or the like in aprotic solvents such as DCM, ACN or the like to provide protected diphenylethers carrying either esters (A15) or nitriles (A16) (Chan-Lam coupling, step (k)). Again, ester A15 or nitrile A16, respectively, can be converted to the free carboxylic acid A17 under conditions that have been described previously for compounds A11 and A12, respectively (see description in scheme 2, step (h)).

On the other hand, various heteroarylphenylethers A21 can be made in two other ways (scheme 3, step (l)). First, phenol A14 can be coupled with a suitably functionalized chloropyridine A18 by treatment with DABCO and another amine base such as triethylamine, diisopropylamine or the like in a polar solvent such as DMF to provide heteroaryl-phenylether A19 or A20, respectively. Second, if A18 is a chloropyrazine or chloropyrimidine derivative or the like, it is advantageous to use other conditions for step (l). In this case, phenol A14 is simply treated with a base such as NaH, tert-BuOK or the like in an appropriate solvent such as DMF, THF or similar followed by addition of A18 to provide heteroaryl-phenylethers A19 and A20, respectively.

Similar as before, if the coupling product is containing a carboxylic acid ester function (A19) or nitrile function (A20), it can be converted to the free carboxylic acid A21 as described previously in Scheme 2, step (h).

Scheme 4

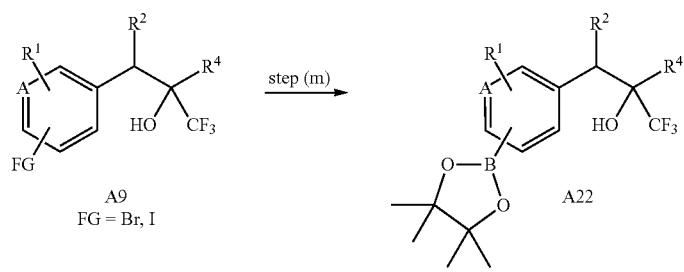

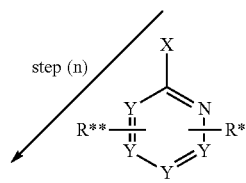

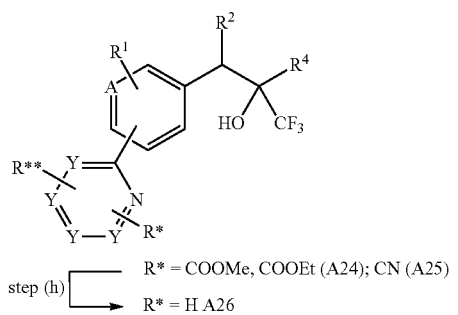

Yet another option for modification of intermediate A9 if FG is bromine or iodine is outlined in scheme 4. In this approach, A9 is converted to a borolane A22, for example by treatment with bis-(pinacolato)-diboron and a suitable palladium catalyst such as bis-(triphenylphosphine)-palladium dichloride or the like and potassium acetate in dioxane or DMF or the like at elevated temperatures ranging from 50° C. to 130° C. (step (m)). Borolane A22 can be isolated or can be made in situ. Borolane A22 can then be used in subsequent palladium catalyzed cross coupling reactions, similar to the ones described in scheme 2. However, in this case a broader variety of aryl and heteroaryl-halides A23 (which are often commercially available) can be used for step (n). Thus, treatment of borolane A22 with an aryl- or heteroaryl halide A23 and a suitable palladium catalyst such as dichloro(1,1'-bis(diphenylphosphino)ferrocene)palladium(II)dichloromethane adduct and a base such as $Na_2CO_3$ or $K_2CO_3$ or the like in dioxane or other suitable solvents at temperatures ranging from 25° C. to 100° C. will provide coupling products carrying esters A24 or nitriles A25. Again, a number of different palladium catalysts can potentially be screened and used in reaction step (n).

Similar as before A24 containing a carboxylic acid ester function or A25 carrying a nitrile can be converted to the free carboxylic acid A26 as outlined in Scheme 2, step (h).

Another possible approach for the synthesis of intermediates A8 and A9 consists of a Grignard type reaction, followed by oxidation of the resulting alcohol as synthetic key steps as shown in Scheme 5.

Scheme 5

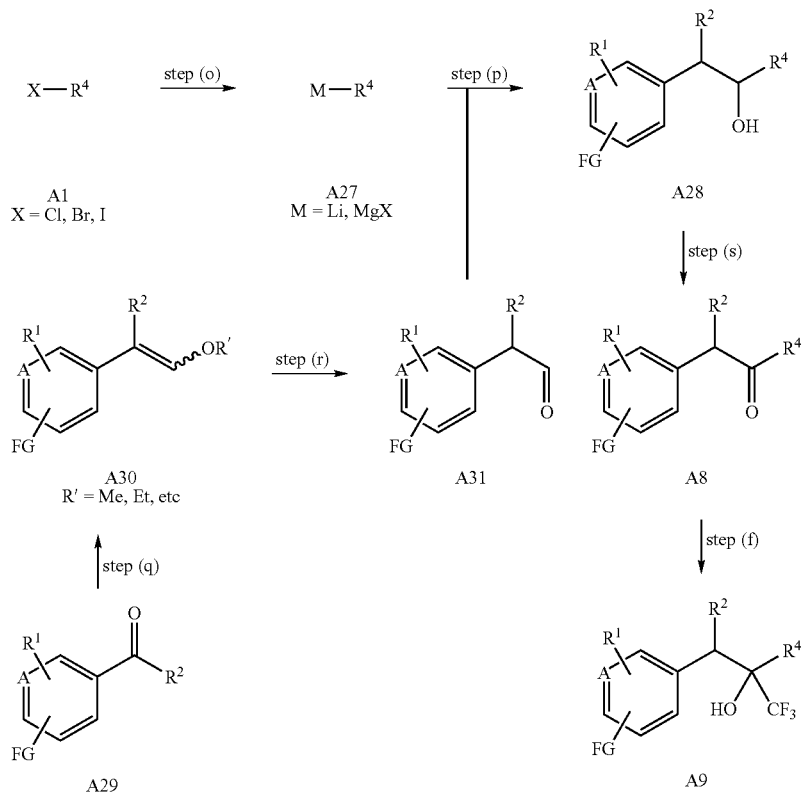

Suitable starting materials for this synthetic approach are for example fused heterocycles of formula A1 such as benzoimidazolones, benzooxazolones and benzooxazinones or the like with suitable functional groups such as halogens (chlorine, bromine, iodine) in the appropriate positions. Starting materials of formula A1 are commercially available or can be made according to known procedures described in the literature. Exchange of the halogen atom X of A1 by a metal atom such as lithium or magnesium using reagents such as n-butyllithium, isopropylmagnesium chloride or elementary metals such as magnesium or lithium, preferably at temperatures ranging from −78 to 100° C. in an appropriate solvent such as THF, MTBE, diethyl ether, dioxane or the like, gives metallated intermediates A27 (step (o)) to which aldehyde intermediates A31 are added to give alcohols A28 (step (p)). Aldehydes of formula A31 are either commercially available, described in the literature or can be prepared by methods well known in the art. One possibility to prepare aldehydes A31 is to convert an appropriate ketone of formula A29 in a Wittig reaction, for example by treatment with (methoxymethyl)-triphenylphosphonium chloride and a suitable base such as potassium tert-butoxide, LDA, LHMDS, or the like, in an appropriate solvent such as THF, MTBE, diethyl ether, dioxane or the like at an appropriate temperature, preferably ranging from −78° C. to 100° C., to give an enol ether A30 (step (q)). A30 is then hydrolyzed by treatment with aqueous solutions of acids such as HCl, HBr or $H_2SO_4$ or the like at various temperatures, preferably ranging from 0° C. to 100° C. to give aldehyde A31 (step (r)). Starting materials of formula A29 are either commercially available, described in the literature or can be prepared by methods well known in the art. Alcohol A28 is oxidized to a ketone of formula A8 by treatment with an appropriate oxidizing agent such as 4-methyl-morpholine-4-oxide and tetrapropylammonium perruthenate or Dess-Martin periodinane or the like in a suitable solvent such as DCM or acetonitrile or the like at various temperatures, preferably ranging from 0° C. to reflux temperature of the solvent (step (s)). Many other oxidizing methods are described in the literature and can be used for oxidation of alcohol A28. Ketones A8 are then converted to key intermediates of formula A9 as described in Scheme 1, step (f).

Another approach for the synthesis of intermediates of formula A7 and A9 consists of a Friedel-Crafts type reaction as outlined in Scheme 6.

Scheme 6

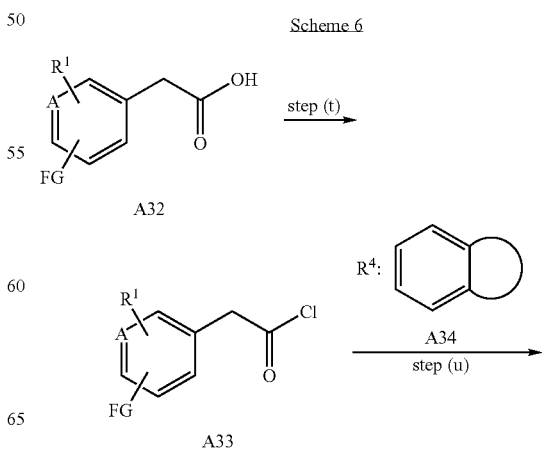

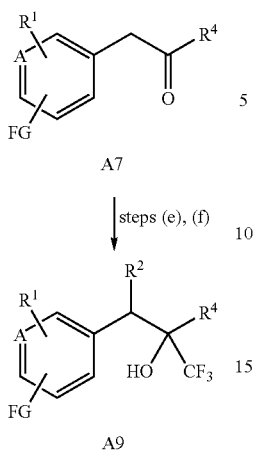

A7

↓ steps (e), (f)

A9

A phenylacetic acid of formula A32 is converted to the corresponding acid chloride of formula A33 (step (t)). Acid chlorides can be made in a standard fashion for example by treatment of carboxylic acid A32 with oxalyl chloride in the presence of a catalytic amount of DMF or by treatment with $SOCl_2$. The acid chloride A33 can be made in situ or can be isolated. Treatment of A33 with suitable fused heterocycles of formula A34 such as benzoimidazolones, benzooxazolones and benzooxazinones or the like in presence of a lewis acid such as $AlCl_3$ or the like in a suitable solvent such as DCM, DCE, $CS_2$ or the like at various temperatures, preferentially ranging from −20° C. to the reflux temperature of the solvent, gives ketones of formula A7, which are then converted to intermediates of formula A9 in steps (e) and (f) as described above in Scheme 1. Starting materials of formula A32, A33, and A34 are either commercially available, are described in the literature or can be prepared according to methods well known in the art.

Another possibility for the synthesis of diaryl ethers of formula A15 and/or A16 (see Scheme 7) is to react phenols of formula A14 with a suitable aryl halide, preferentially an aryl fluoride, of formula A35 using a suitable base such as cesium carbonate, sodium hydride, potassium carbonate or the like in a suitable solvent such as DMF, DMSO, DMA or the like at various temperatures, preferentially ranging from room temperature to reflux temperature of the solvent (Scheme 7, step (v)). The masked carboxylic acids are either attached directly or via diverse linkers such as alkyl or alkoxy chains to the aromatic ring. Starting materials of formula A35 are either commercially available, described in the literature or can be prepared by methods well known in the art. Intermediates of formula A15 or A16 can then be further processed as shown above (see for example Scheme 3, step (h)).

Scheme 7

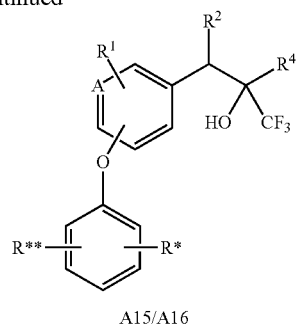

A15/A16

Yet another way to produce diaryl ethers of formula A15/A16 is shown in Scheme 8.

Scheme 8

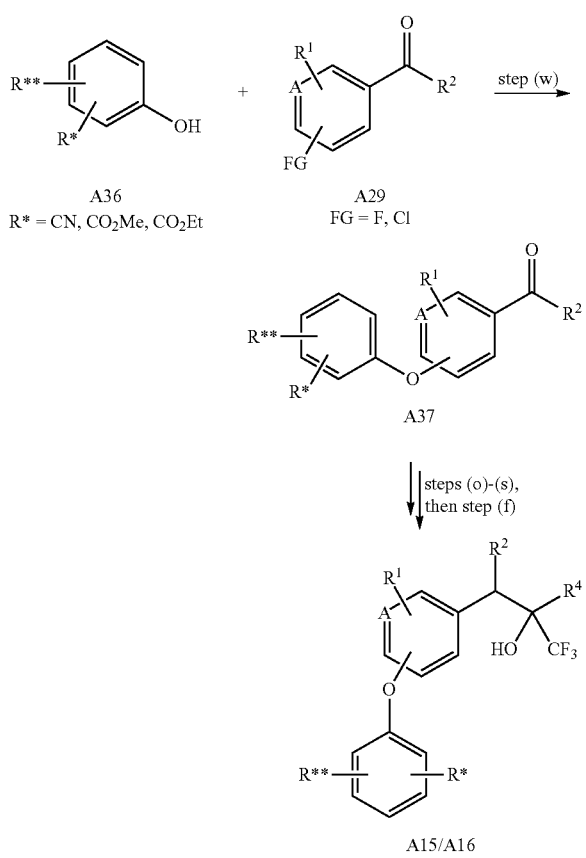

If FG in intermediate A29 is a halogen atom such as chlorine or preferentially fluorine in a suitable position, A29 can be reacted with a phenol of formula A36 using a suitable base such as cesium carbonate, sodium hydride, potassium carbonate or the like in a suitable solvent such as DMF, DMSO, DMA or the like at various temperatures, preferentially ranging from room temperature to reflux temperature of the solvent (step (w)). Starting materials of formula A36 and A29 are either commercially available, described in the literature or can be prepared by methods well known in the art. Intermediates of formula A37 are then converted to intermediates of formula A15/A16 as outlined in Scheme 5, steps (o)-(s) and step (f). Intermediates of formula A15/A16 can then be further processed as shown above (see Scheme 3, step (h)).

Another possibility for modifying phenols of formula A14 is outlined in Scheme 9: Phenol A14 can be treated with a base such as sodium hydride, potassium tert-butylate, potassium carbonate, cesium carbonate, silver carbonate or the like followed by treatment with an alkylating agent A38 in suitable solvents such as THF, DMF or the like at various temperatures to provide alkylated compounds of formula A39. Ethers A39 bearing a carboxylic acid precursor (e.g. a nitrile or an ester group) can then be converted to the corresponding carboxylic acids using standard conditions.

peratures, preferentially ranging from room temperature to the reflux temperature of the solvent in a suitable solvent such as DCM, DCE, dioxane, THF, DMF, DMA or the like. Many others of the various known methods for amide bond formation can be used. Amides A42 bearing a carboxylic acid precursor (e.g. a nitrile or an ester group) can then be converted to the corresponding carboxylic acids using standard conditions as described previously.

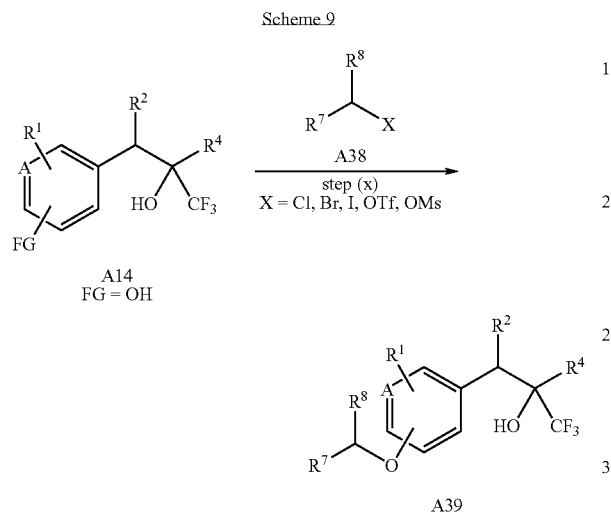

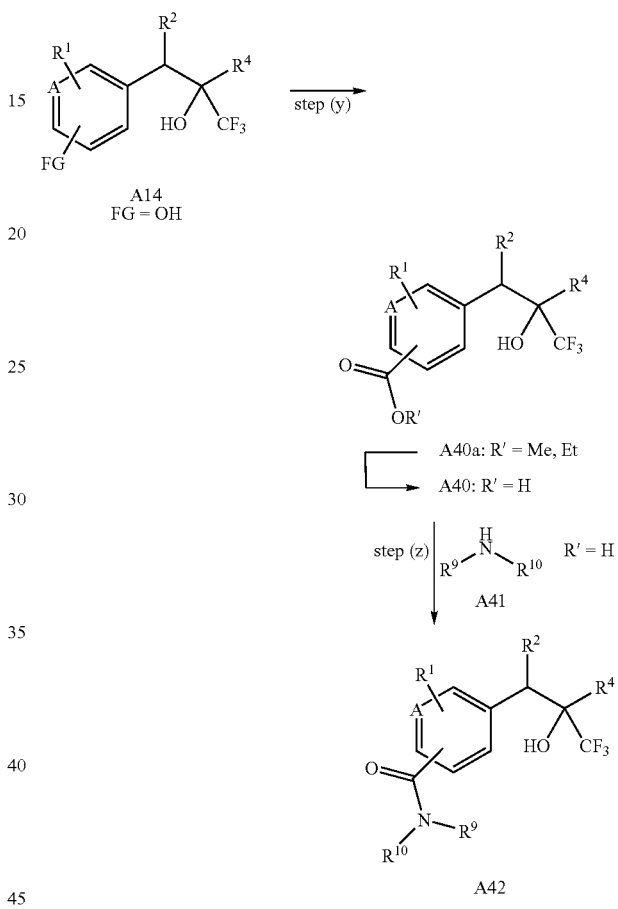

Yet another possibility for modifying phenols of formula A14 is outlined in Scheme 10: Phenols of formula A14 can be transformed into triflates or similar followed by a palladium catalyzed carbonylation reaction (step (y)) to provide carboxylic acids A40 or the corresponding esters of formula A40a. Suitable catalysts and ligands for this transformation are for example palladium(II)acetate and a bi-dentate 1,3-bis(diphenylphosphino)propane in an appropriate solvent such as DMF or DMSO; however other suitable components can also be screened and potentially be used in that reaction. Carboxylic acid esters A40a (R'=Me, Et) can be hydrolyzed using standard conditions to provide free carboxylic acids A40 (R'=H). Carboxylic acids A40 can be converted to amides of formula A42 by reaction with amines A41 in presence of a suitable coupling agent such as HBTU, HATU, DCC, EDC or the like with a suitable base such as triethyl amine, N,N-diisopropylethylamine or the like at various tem- An alternative method to synthesize ketones of formula A7 is outlined in Scheme 11. This approach is based on a Claisen type condensation of suitable precursors as a key reaction step.

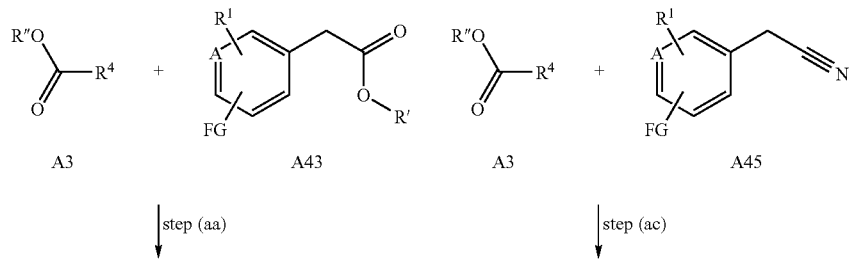

-continued

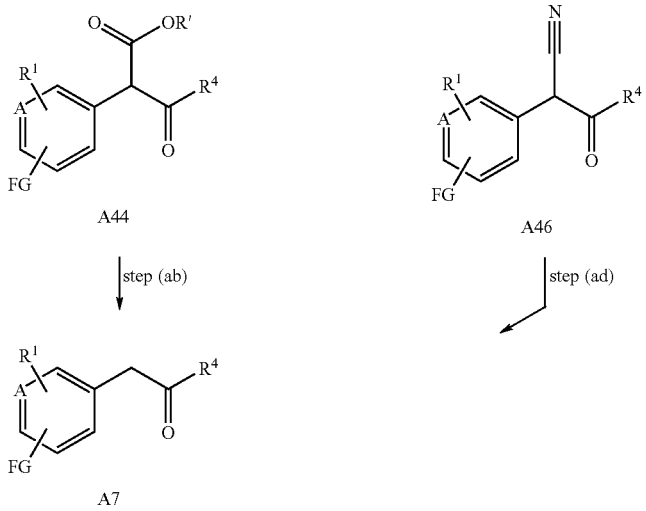

R' = Me, Et, H
R" = H, Me, Et

A carboxylic acid A3 (R"=H) is suitably activated, e.g. by reaction with 1,1'-carbonyldiimidazole and reacted with a phenyl-acetic acid ester A43 (R' is e.g. Me, Et), which is deprotonated in situ by a suitable base, such as NaH or potassium tert-butylate or the like, to give the compound of formula A44 (step (aa)). The reaction is carried out at a temperature of −10° C. to 0° C. in a suitable solvent such as DMF or THF. Compound A44 is then saponified and decarboxylated, e.g. by heating of A44 in a mixture of DMSO, water and NaCl to a temperature of 140° C. to give the ketone A7 (step (ab). In some cases it is also possible to deprotonate a carboxylic acid of formula A43 (R'=H) twice using an excess (>2 equivalents) of a strong base such as tert-butylmagnesium chloride, LHMDS, LDA, NaH or the like in a suitable solvent such as THF, diethyl ether, dioxane, DMF or the like, preferentially at temperatures ranging from −20° C. to 100° C., and to treat the resulting mixture with an ester of formula A3 (R"=Me, Et or the like), to give after acidification and usually spontaneous decarboxylation ketones of formula A7.

Alternatively, ketone A7 can be obtained as outlined in Scheme 11 via steps (ac) and (ad): A phenyl-acetonitrile A45 is deprotonated with a suitable base, such as potassium tert-pentylate, sodium hydride, potassium tert-butylate or the like, in a suitable solvent such as THF or DMF and reacted with an ester A3 (R"=Me, Et or the like) to give a compound of formula A46 (step (ac)). The nitrile of formula A46 is then hydrolyzed followed by decarboxylation, e.g. by heating a mixture of A46 with concentrated hydrobromic acid to reflux followed by addition of a base such as NaHCO₃, to give a ketone of formula A7 (step (ad)).

All starting materials are either commercially available, have been described in the literature, or can be prepared by methods well known in the art.

Compounds of formula I contain stereocenters and can optionally be separated into optically pure enantiomers or diastereomers by methods well known in the art, e.g. by chromatography on a chiral HPLC column.

As described above, the compounds of formula I of the present invention can be used as medicaments for the treatment and/or prevention of diseases which are associated with glucocorticoid receptor (GR) modulation.

In this context, the expression 'diseases which are associated with glucocorticoid receptor (GR) modulation' means diseases which can be treated and/or prevented by glucocorticoid receptor (GR) modulation, i.e. preferably by treatment with a glucocorticoid receptor antagonist. Such diseases encompass, but are not limited to, diabetes, preferably type 2 diabetes, dyslipidemia, obesity, metabolic syndrome, hypertension, adrenal imbalance, cardiovascular diseases, Cushing's syndrome, stress-related immunosuppression and neurological disorders such as depression.

In a preferable aspect, the expression 'diseases which are associated with glucocorticoid receptor modulation' relates to diabetes, preferably type 2 diabetes, dyslipidemia, obesity, hypertension, adrenal imbalance, cardiovascular diseases and depression. More preferably, the expression 'diseases which are associated with glucocorticoid receptor modulation' relates to diabetes, preferably type 2 diabetes.

Exceptionally, the compounds of the present invention can also be useful in treating immune, autoimmune and inflammatory diseases when they are selectively activating the glucocorticoid receptor.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with glucocorticoid receptor modulation.

In another embodiment, the invention relates to a method for the treatment and/or prevention of diseases which are associated with glucocorticoid receptor modulation, which method comprises administering a therapeutically active amount of a compound of formula I to a human being or animal. A method for the treatment and/or prevention of diabetes is preferred.

The invention further relates to the use of compounds of formula I as defined above for the treatment and/or prevention of diseases which are associated with glucocorticoid receptor modulation.

In addition, the invention relates to the use of compounds of formula I as defined above for the preparation of medicaments for the treatment and/or prevention of diseases which are associated with glucocorticoid receptor modulation. The use of compounds of formula I as defined above for the preparation of medicaments for the treatment and/or prevention of diabetes is preferred.

The compounds of the present invention can also be used in combination therapy with other antidiabetic drugs. Suitable antidiabetic drugs for use in combination with the compounds of the present invention include, but are not limited to insulin and insulin analogs (e.g. LysPro insulin, inhaled formulations comprising insulin); sulfonylureas and analogs (e.g. chlorpropamide, glibenclamide, tolbutamide, tolazamide, acetohexamide, glypizide, glyburide, glimepiride); biguanides (e.g. metformin hydrochloride, phenformin, buformin); alpha-glucosidase inhibitors (acarbose, epalrestat, miglitol, voglibose), alpha2-antagonists and imidazolines (e.g. midaglizole, isaglidole, deriglidole, idazoxan, efaroxan, fluparoxan); thiazolidinediones and PPAR-gamma agonists (e.g. ciglitazone, pioglitazone hydrochloride, troglitazone, rosiglitazone maleate, balaglitazone); PPAR-alpha agonists (e.g. fenofibrate, gemfibrozil); PPAR alpha/gamma dual agonists (e.g. muraglitazar, aleglitazar, peliglitazar); dipeptidyl peptidase-IV (DPP-4) inhibitors (e.g. saxagliptin, sitagliptin, vildagliptin, alogliptin and denagliptin); glucagon like peptide-1 (GLP-1) receptor agonists (e.g. Exenatide (Byetta™) NN2211 (Liraglutide), GLP-1(7-36) amide and its analogs, GLP-1(7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4: PC-DAC™); insulin secretagogues (e.g. linogliride, nateglinide, repaglinide, mitiglinide calcium hydrate, meglitinide); SGLT-2 inhibitors (e.g. dapagliflozin (BMS), sergliflozin (Kissei), AVE 2268 (Sanofi-Aventis)); Angiotensin AT1 antagonists (e.g. irbesartan, valsartan); amylin agonists (e.g. pramlintide, AC-137) and Glucokinase activators such as the compounds disclosed in e.g. WO 00/58293 A1.

As described above, the compounds of formula I and their pharmaceutically acceptable salts possess valuable pharmacological properties. Specifically, it has been found that compounds of the present invention are excellent glucocorticoid receptor antagonists.

The following tests were carried out in order to determine the activity of the compounds of formula I.

Glucocorticoid Receptor Binding Assay

The ability of the substances to bind to the glucocorticoid receptor was determined with the help of a commercial Glucocorticoid Receptor Competitor Assay far red kit provided by Panvera/Invitrogen (PV4302). This kit is used as provided by the supplier. It contains some partially purified full length human recombinant glucocorticoid receptor, a coactivator related GR stabilizing peptide, a tight-binding fluorescent GR ligand Fluormone™ GS Far Red as labeled tracer and a screening buffer. All reagents are prepared and the assay is run according to the recommendations of the kit manufacturer.

Briefly, the GR stabilizing peptide and the human recombinant glucocorticoid receptor are both diluted with the screening buffer (pH 7.4) and are gently mixed (no vortexing) just before the assay and kept on ice until use. The fluorescent-labeled ligand is also diluted with the screening buffer just before the assay and kept on ice until use. The substances to test are pre-diluted in pure DMSO then some water is added to get an intermediate 4.2% DMSO stock solution. Ten microliter of the intermediate stock solution is gently mixed with 5 µl of diluted fluorescent-labeled ligand and 5 µl of diluted human recombinant glucocorticoid receptor in a 384-well plate (low volume, ultraclear, glass plate from Greiner ref 788896). The plate is centrifuged, sealed and incubated for 3 hours at 22° C. in the dark. The polarized fluorescence is measured with a Zeiss-HTS reader or any equivalent equipment (610-660 nm).

All compounds were tested to determine $IC_{50}$ in a serial dilution experiment. The concentration at which 50% inhibition of the fluorescent GR ligand Fluormone™ GS Far Red is obtained (the $IC_{50}$) is determined after fitting with a sigmoidal dose-response model of a plot of the logarithm of the concentration versus percent inhibition measured for the different concentrations. $K_i$'s were calculated from $IC_{50}$ based on Cheng-Prusoff equation (Cheng, Y, Prusoff, W H (1973) Biochem Pharmacol 22, 3099-3108): $K_i=IC_{50}/[1+D/Kd]$ wherein D is the concentration of the fluorescent ligand and Kd is the binding constant for the fluorescent ligand binding to the receptor under the conditions used in the competition experiment.

The compounds of the present invention exhibit $K_i$ values within the range of about 1 nM to about 5000 nM, preferably of about 1 nM to about 1000 nM, and more preferably of about 1 nM to about 30 nM, most preferably of about 1 nM to about 10 nM. The following table shows measured values for some selected compounds of the present invention.

| Example | $K_i$ (µM) |
| --- | --- |
| 1 | 0.0097 |
| 2 | 0.002 |
| 3 | 0.0092 |
| 4 | 0.4262 |
| 5 | 0.0075 |
| 6 | 0.0048 |
| 7 | 0.0111 |
| 8 | 0.0108 |
| 9 | 0.0089 |
| 10 | 0.0037 |
| 11 | 0.0024 |
| 12 | 0.008 |
| 13 | 0.0054 |
| 14 | 0.0039 |
| 15 | 0.0037 |
| 16 | 0.0025 |
| 17 | 0.0556 |
| 18 | 0.6094 |
| 19 | 0.2143 |
| 22 | 0.0029 |
| 23 | 0.0013 |
| 24 | 0.0196 |
| 25 | 0.0028 |
| 26 | 0.0035 |
| 27 | 0.0406 |
| 28 | 0.0013 |
| 29 | 0.0075 |
| 30 | 0.002 |
| 31 | 0.0031 |
| 32 | 0.0013 |
| 33 | 0.0173 |
| 34 | 0.0078 |
| 35 | 0.0026 |
| 36 | 0.0065 |
| 37 | 0.0066 |
| 38 | 0.0018 |
| 39 | 0.0007 |
| 40 | 0.0015 |
| 41 | 0.0015 |
| 42 | 0.004 |
| 43 | 0.261 |
| 44 | 0.0032 |
| 45 | 0.0021 |
| 46 | 0.0109 |
| 47 | 0.002 |
| 48 | 0.0013 |
| 49 | 0.016 |

| Example | $K_i$ (μM) |
|---|---|
| 50 | 0.0487 |
| 51 | 0.0208 |
| 52 | 0.1218 |
| 53 | 0.0661 |
| 54 | 0.2811 |
| 56 | 0.0003 |
| 57 | 0.0013 |
| 58 | 0.0003 |
| 59 | 0.001 |
| 60 | 0.0023 |
| 61 | 0.001 |
| 62 | 0.0021 |
| 63 | 0.0008 |
| 64 | 0.0979 |
| 65 | 0.1275 |
| 66 | 0.1914 |
| 67 | 0.0402 |
| 68 | 0.0598 |
| 69 | 0.0359 |
| 70 | 0.2782 |
| 71 | 0.0281 |
| 72 | 0.2223 |
| 73 | 0.0073 |
| 74 | 0.0017 |
| 75 | 0.0019 |
| 76 | 0.001 |
| 77 | 0.0024 |
| 78 | 0.0013 |
| 79 | 0.001 |
| 80 | 0.0136 |
| 81 | 0.0014 |
| 82 | 0.007 |
| 83 | 0.0022 |
| 84 | 0.0119 |
| 85 | 0.0008 |
| 86 | 0.0027 |
| 87 | 0.0037 |
| 88 | 0.0007 |
| 89 | 0.0011 |
| 90 | 0.0004 |
| 91 | 0.0003 |
| 92 | 0.0006 |
| 93 | 0.0003 |
| 94 | 0.0003 |
| 95 | 0.0053 |
| 96 | 0.0024 |
| 97 | 0.005 |
| 98 | 0.0016 |
| 99 | 0.0012 |
| 100 | 0.0019 |
| 101 | 0.0011 |
| 102 | 0.0005 |
| 103 | 0.0231 |
| 104 | 0.0016 |
| 105 | 0.0148 |
| 106 | 0.0052 |
| 107 | 0.0004 |
| 108 | 0.0104 |
| 109 | 0.0011 |
| 110 | 0.0021 |
| 111 | 0.036 |
| 112 | 0.0264 |
| 113 | 0.0062 |
| 114 | 0.354 |
| 115 | 0.0011 |
| 116 | 0.001 |
| 117 | 0.0022 |
| 118 | 0.001 |
| 119 | 0.0003 |
| 120 | 0.046 |
| 121 | 0.0016 |
| 122 | 0.0005 |
| 123 | 0.0011 |
| 124 | 0.0003 |
| 125 | 0.001 |
| 126 | 0.0005 |
| 127 | 0.0007 |
| 128 | 0.0017 |
| 129 | 0.0011 |
| 130 | 0.0005 |
| 131 | 0.0012 |
| 132 | 0.003 |
| 133 | 0.0016 |
| 134 | 0.109 |
| 135 | 0.154 |
| 136 | 0.0013 |
| 137 | 0.02 |
| 138 | 0.0006 |
| 139 | 0.0027 |
| 140 | 0.022 |
| 141 | 0.0018 |
| 142 | 0.0021 |
| 143 | 0.0017 |
| 144 | 0.0025 |
| 145 | 0.0031 |
| 146 | 0.0014 |
| 147 | 0.0028 |
| 148 | 0.0016 |
| 149 | 0.0017 |
| 150 | 0.0013 |
| 151 | 0.0185 |
| 152 | 0.0462 |
| 153 | 0.0232 |
| 154 | 0.0337 |
| 155 | 0.0089 |
| 156 | 0.1921 |
| 157 | 0.0198 |
| 158 | 0.0022 |
| 159 | 0.0021 |
| 160 | 0.0013 |
| 161 | 0.0036 |
| 162 | 0.0108 |
| 163 | 0.0351 |
| 164 | 0.0075 |
| 165 | 0.0009 |
| 166 | 0.0027 |
| 167 | 0.0031 |
| 168 | 0.6095 |
| 169 | 0.0282 |
| 170 | 0.2104 |
| 171 | 0.0004 |
| 172 | 0.0006 |
| 173 | 0.0011 |
| 174 | 0.002 |
| 175 | 0.0018 |
| 176 | 0.0017 |
| 177 | 0.0013 |
| 178 | 0.1142 |
| 179 | 0.0133 |
| 180 | 0.001 |
| 181 | 0.0005 |
| 182 | 0.0033 |
| 183 | 0.003 |
| 184 | 0.0008 |
| 185 | 0.0007 |
| 186 | 0.0014 |
| 187 | 0.0021 |
| 188 | 0.0022 |
| 189 | 0.0066 |
| 190 | 0.003 |
| 191 | 0.0014 |
| 192 | 0.0008 |
| 193 | 0.0009 |
| 194 | 0.0007 |
| 195 | 0.0008 |
| 196 | 0.0016 |
| 197 | 0.0058 |
| 198 | 0.0017 |
| 199 | 0.0021 |
| 200 | 0.0045 |
| 201 | 0.0039 |
| 202 | 0.0018 |
| 203 | 0.0018 |
| 204 | 0.0035 |
| 205 | 0.0025 |
| 206 | 0.0062 |

-continued

| Example | $K_i$ (μM) |
|---|---|
| 207 | 0.37 |
| 209 | 0.0008 |
| 210 | 0.0015 |
| 211 | 0.0012 |
| 212 | 0.001 |
| 213 | 0.0017 |
| 214 | 0.0041 |
| 215 | 0.0014 |
| 216 | 0.0602 |
| 217 | 0.001 |
| 218 | 0.1185 |
| 219 | 0.0008 |
| 220 | 0.0011 |
| 222 | 0.0016 |
| 223 | 0.5521 |
| 224 | 0.0008 |
| 225 | 0.0078 |
| 226 | 0.0059 |
| 227 | 0.003 |
| 228 | 0.0106 |
| 229 | 0.0039 |
| 230 | 0.0353 |
| 231 | 0.0069 |
| 232 | 0.0924 |

Tyrosine-Amino-Transferase Assay

To assess functional agonist or antagonist activities, substances were tested in primary rat hepatocytes for their abilities to modulate tyrosine amino-transferase (TAT) activity. TAT is an enzyme under the control of the glucocorticoid receptor. Binding of an agonist to the glucocorticoid receptor leads to an increase of the TAT activity in primary rat hepatocytes.

To get a primary cell suspension, a Sprague Dawley rat is anesthetized, its liver is cannulated and washed with EDTA and then infused with collagenase. Cells are dissociated by mechanical action and then washed and purified with a Percoll gradient. Cells are plated on 96-well plates coated with collagen type I (50 000 cells/well). To assess a potential agonist activity the substance is given to untreated cells for 24 h. Then the TAT activity is measured as described in Granner et al, *Method in Enyzmology, Vol.* 80, pp 633-637.

To assess a potential antagonist activity, cells are first pretreated with the potential antagonist. Thirty minutes later a challenge with dexamethasone is done (20 nM). The activity of the TAT is also measured 24 h later.

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable salts into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 0.5 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner.

EXAMPLES

Abbreviations: DCM=dichloromethane, DMAP=N,N-Dimethyl-4-aminopyridine, DMF=N,N-dimethylformamide, DMSO=dimethyl sulfoxide, EDC=1-ethyl-3-(3-dimethylaminopropyl)carbodiimide hydrochloride, EI=electron impact (ionization), HPLC=high performance liquid chromatography, ISP=ion spray positive (mode), NMR=nuclear magnetic resonance, MS=mass spectrum, LCMS=liquid chromatography mass spectrometry, THF=tetrahydrofurane, TLC=thin layer chromatography.

Example 1

4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxymethyl}-benzoic acid ethyl ester

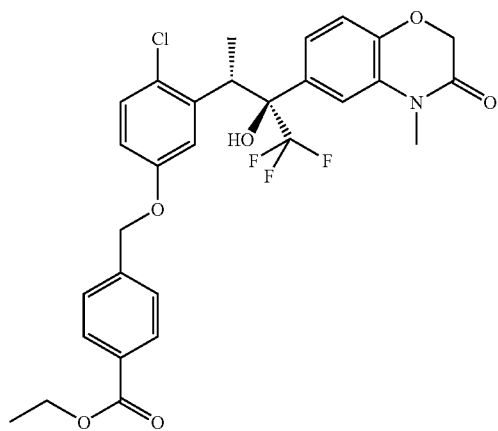

Step 1: 6-[2-(2-Chloro-5-methoxy-phenyl)-acetyl]-4-methyl-4H-benzo[1,4]oxazin-3-one To a solution of (2-chloro-5-methoxy-phenyl)-acetic acid (1 g) in tetrahydrofuran (20 ml) were added N,N-dimethylformamide (2 drops) and oxalylchloride (1.03 g). The mixture was stirred overnight at room temperature. The solvent was evaporated; toluene was added and again evaporated. The residue was dried under high vacuum to give the crude acid chloride. To a cooled solution (ice bath) of 4-methyl-2H-1,4-benzoxazin-3(4H)-one (830 mg) in 1,2-dichloroethane (5 ml) was added AlCl$_3$ (1.99 g). The mixture was stirred for 10 min and a solution of the acid chloride in 1,2-dichloroethane (5 ml) was added dropwise. The mixture was stirred at 0° C. for 4.5 h. The mixture was poured into ice water and hydrochloric acid and extracted with dichloromethane. The organic phase was dried (MgSO$_4$), filtered and concentrated. The product was purified by chromatography (SiO$_2$, cyclohexane/EtOAc 1:0=>0:1) to give the title compound (1.6 g) as an off-white solid. MS (m/e)=346.1 [M+H$^+$].

Step 2: 6-[2-(2-Chloro-5-methoxy-phenyl)-propionyl]-4-methyl-4H-benzo[1,4]oxazin-3-one To a solution of 6-[2-(2-chloro-5-methoxy-phenyl)-acetyl]-4-methyl-4H-benzo[1,4]oxazin-3-one (1.57 g) in tetrahydrofuran (50 ml) was added sodium hydride (55% dispersion in mineral oil, 208 mg). The mixture was stirred at room temperature for 3.5 h and then placed in an ice bath. A solution of methyl iodide (0.677 g) in tetrahydrofuran (1 ml) was added dropwise. The ice bath was removed and the mixture was stirred at room temperature for 1.5 h. The solvent was evaporated and the residue was dissolved in EtOAc. The organic phase was washed with water, dried (MgSO$_4$), filtered and concentrated. The product was purified by chromatography (SiO$_2$, cyclohexane/EtOAc 1:0=>1:1) to give the title compound (1.09 g) as a colorless gum. MS (m/e)=360.0 [M+H$^+$].

Step 3: 6-[2-(2-Chloro-5-methoxy-phenyl)-1-hydroxy-1-trifluoromethyl-propyl]-4-methyl-4H-benzo[1,4]oxazin-3-one To a solution of 6-[2-(2-chloro-5-methoxy-phenyl)-propionyl]-4-methyl-4H-benzo[1,4]oxazin-3-one (1.17 g) in tetrahydrofuran (60 ml) was added a solution of (trifluoromethyl)trimethylsilane (703 mg) in tetrahydrofuran (10 ml) at 0° C. Tetramethylammonium fluoride (30 mg) was added and the mixture was stirred at 0° C. for 30 min and at room temperature for 15 min. A 1 M solution of tetrabutylammonium fluoride in tetrahydrofuran (3.26 ml) was added and the mixture was stirred for 20 min. The solvent was evaporated and the residue was dissolved in dichloromethane. The organic phase was washed with water, dried (MgSO$_4$), filtered and concentrated. The product was purified by chromatography (SiO$_2$, cyclohexane/EtOAc 1:0=>7:3) to give the title compound (1.1 g) as a colorless solid. MS (m/e, ISP neg. ion)=428.4 [M–H$^+$].

Step 4: 6-[2-(2-Chloro-5-hydroxy-phenyl)-1-hydroxy-1-trifluoromethyl-propyl]-4-methyl-4H-benzo[1,4]oxazin-3-one A solution of 6-[2-(2-chloro-5-methoxy-phenyl)-1-hydroxy-1-trifluoromethyl-propyl]-4-methyl-4H-benzo[1,4]oxazin-3-one (553 mg) in dichloromethane (13 ml) was cooled to –70° C. A 1 M solution of boron tribromide in dichloromethane (5.14 ml) was added and the mixture was stirred at –70° C. for 1.5 h and at 0° C. for 1 h. A mixture of ice water and saturated aqueous NaHCO$_3$ solution was added and the mixture was extracted with dichloromethane. The organic phase was washed with water and dried (MgSO$_4$). The product was purified by chromatography (SiO$_2$, cyclohexane/EtOAc 9:1=>2:3) to give the title compound (542 mg) as off-white foam. MS (m/e, ISP neg. ion)=414.0 [M–H$^+$].

Step 5: 4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxymethyl}-benzoic acid ethyl ester To a solution of 6-[2-(2-chloro-5-hydroxy-phenyl)-1-hydroxy-1-trifluoromethyl-propyl]-4-methyl-4H-benzo[1,4]oxazin-3-one (83 mg) in N,N-dimethylacetamide (1.6 ml) were added ethyl-4-(bromomethyl)benzoate (56 mg) and cesium carbonate (72 mg). The mixture was stirred for 4 h at room temperature. Ice water was added and the mixture was extracted with EtOAc. The organic phase was washed with water and dried (MgSO$_4$). The product was purified by chromatography (SiO$_2$, cyclohexane/EtOAc 1:0=>3:2) to give the title compound (96 mg) as colorless foam. MS (m/e, ISP neg. ion)=578.3 [M–H$^+$].

Example 2

4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxymethyl}-benzoic acid

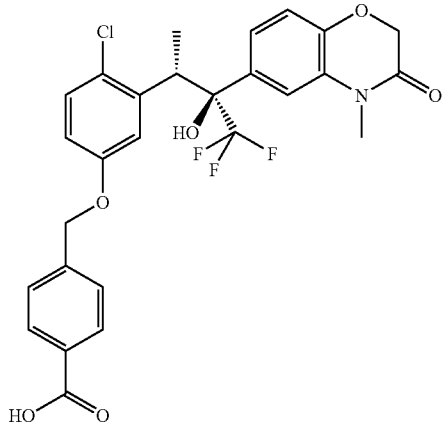

To a solution of 4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxymethyl}-benzoic acid ethyl ester (Example 1, 83 mg) in tetrahydrofuran (0.3 ml) and methanol (0.3 ml) was added a 1 M aqueous LiOH solution (0.29 ml) at 0° C. The mixture was stirred at 0° C. for 30 min and at room temperature for 5.5 h. The mixture was cooled in an ice bath and acidified using 1 M aqueous HCl. The mixture was concentrated to dryness. The product was purified by chromatography (SiO$_2$, CH$_2$Cl$_2$/MeOH 1:0=>85:15) to give the title compound (49 mg) as colorless foam. MS (m/e, ISP neg. ion)=548.2 [M–H$^+$].

Example 3

{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-acetic acid ethyl ester

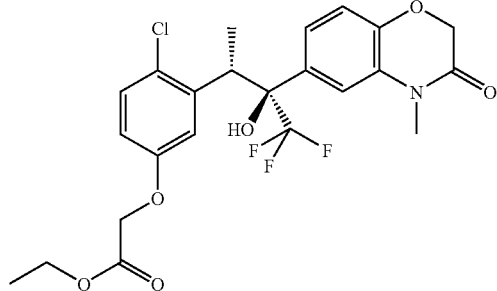

In analogy to Example 1, step 5, 6-[2-(2-chloro-5-hydroxy-phenyl)-1-hydroxy-1-trifluoromethyl-propyl]-4-methyl-4H-benzo[1,4]oxazin-3-one (Example 1, step 4) was reacted with ethylbromoacetate and cesium carbonate to give the title compound as a colorless solid. MS (m/e, ISP neg. ion)=500.2 [M–H$^+$].

Example 4

{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-acetic acid

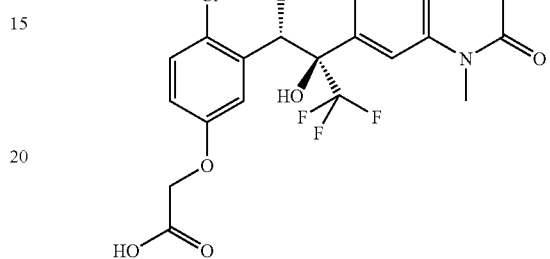

In analogy to Example 2, {4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-acetic acid ethyl ester (Example 3) was hydrolyzed to give the title compound as a colorless foam. MS (m/e, ISP neg. ion)=472.1 [M–H$^+$].

Example 5

3-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid ethyl ester

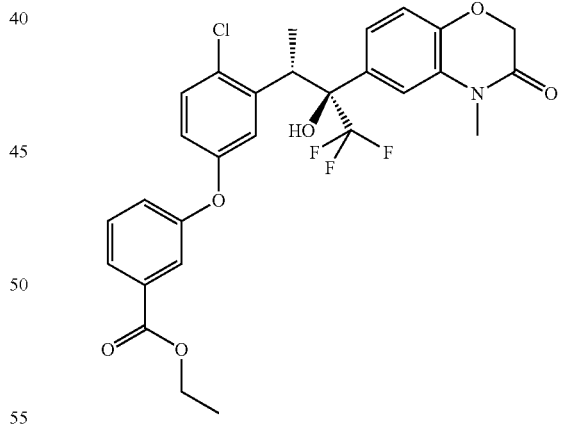

To a solution of 6-[2-(2-chloro-5-hydroxy-phenyl)-1-hydroxy-1-trifluoromethyl-propyl]-4-methyl-4H-benzo[1,4]oxazin-3-one (Example 1, step 4, 150 mg) in CH$_2$Cl$_2$ (3 ml) were added 3-ethoxycarbonylphenylboronic acid (210 mg), copper-(II)-acetate (197 mg), molecular sieve and pyridine (143 mg). The mixture was stirred at room temperature under an air atmosphere with exclusion of moisture for 18 hours. The mixture was filtered, diluted with CH$_2$Cl$_2$ and washed with 1 M aqueous HCl. The organic phase was dried (MgSO$_4$), filtered and concentrated to dryness. The product was purified by chromatography (SiO$_2$, cyclohexane/EtOAc 1:0=>1:1) to give the title compound (195 mg) as a colorless foam. MS (m/e)=564.2 [M+H⁺].

Example 6

3-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid

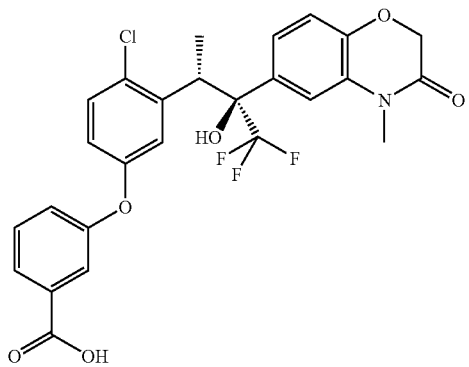

In analogy to Example 2, 3-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid ethyl ester (Example 5) was hydrolyzed to give the title compound as a colorless foam. MS (m/e, ISP neg. ion)=534.1 [M−H⁺].

Example 7

4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester

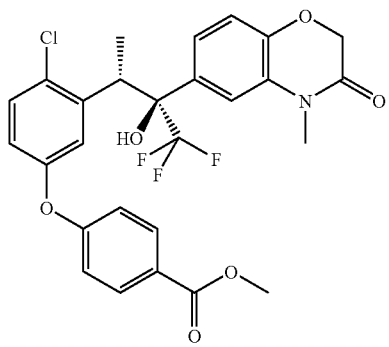

In analogy to Example 5, 6-[2-(2-chloro-5-hydroxy-phenyl)-1-hydroxy-1-trifluoromethyl-propyl]-4-methyl-4H-benzo[1,4]oxazin-3-one (Example 1, step 4) was reacted with 4-methoxycarbonylphenylboronic acid, copper-(II)-acetate and pyridine to give the title compound as a colorless solid. MS (m/e)=550.2 [M+H⁺].

Example 8

4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid

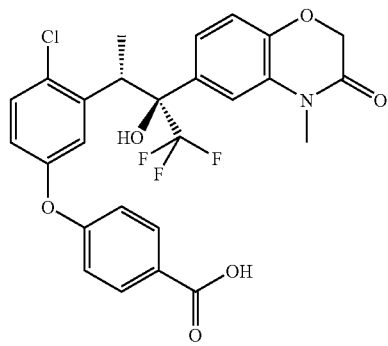

In analogy to Example 2, 4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester (Example 7) was hydrolyzed to give the title compound as a colorless solid. MS (m/e, ISP neg. ion)=534.1 [M−H⁺].

Example 9

2-Chloro-4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester

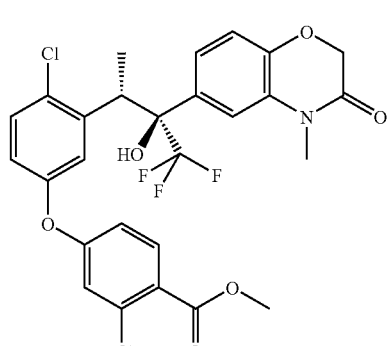

In analogy to Example 5, 6-[2-(2-chloro-5-hydroxy-phenyl)-1-hydroxy-1-trifluoromethyl-propyl]-4-methyl-4H-benzo[1,4]oxazin-3-one (Example 1, step 4) was reacted with 3-chloro-4-methoxycarbonylphenylboronic acid, copper- (II)-acetate and pyridine to give the title compound as a colorless foam. MS (m/e)=585.9 [M+H⁺].

Example 10

2-Chloro-4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid

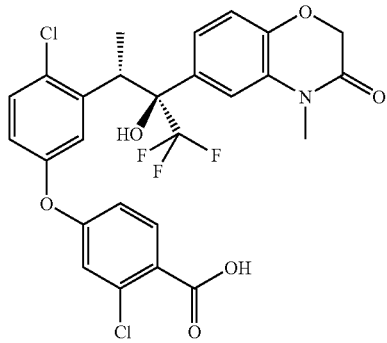

In analogy to Example 2, 2-chloro-4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester (Example 9) was hydrolyzed to give the title compound as a colorless solid. MS (m/e, ISP neg. ion)=568.4 [M−H⁺].

Example 11

5-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid

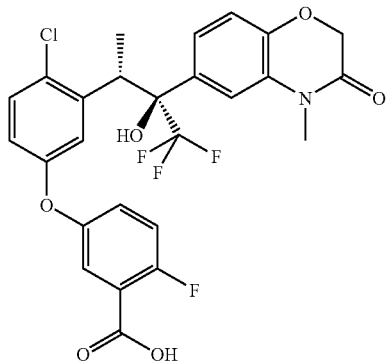

Step 1: 5-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzonitrile In analogy to Example 5, 6-[2-(2-chloro-5-hydroxy-phenyl)-1-hydroxy-1-trifluoromethyl-propyl]-4-methyl-4H-benzo[1,4]oxazin-3-one (Example 1, step 4) was reacted with 3-cyano-4-fluorophenylboronic acid, copper-(II)-acetate and pyridine to give the title compound as an off-white solid. MS (m/e)=535.2 [M+H⁺].

Step 2: 5-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid To a suspension of 5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzonitrile (132 mg) in 2 M aqueous KOH solution (7.4 ml) was added dioxane (0.9 ml). The mixture was stirred at 95° C. for 9 hours and at room temperature for 2 days. The mixture was filtered and the filtrate was washed with diethyl ether. The aqueous phase was acidified with 2 M aqueous HCl (7.6 ml) and extracted with EtOAc. The organic phase was dried (MgSO₄), filtered and concentrated to dryness. The product was purified by chromatography (SiO₂, dichloromethane/MeOH 1:0=>4:1) to give the title compound (41 mg) as an off-white solid. MS (m/e, ISP neg. ion)=552.2 [M−H⁺].

Example 12

(3-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid

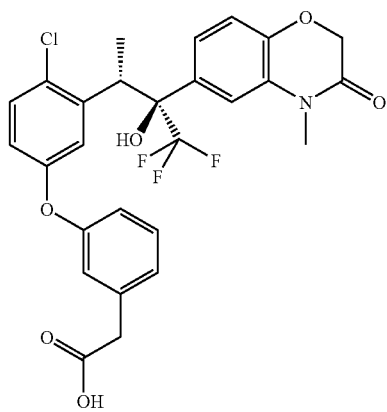

Step 1: (3-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetonitrile In analogy to Example 5, 6-[2-(2-chloro-5-hydroxy-phenyl)-1-hydroxy-1-trifluoromethyl-propyl]-4-methyl-4H-benzo[1,4]oxazin-3-one (Example 1, step 4) was reacted with 3-cyanomethylphenylboronic acid, copper-(II)-acetate and pyridine to give the title compound as an off-white solid. MS (m/e)=531.1 [M+H⁺].

Step 2: (3-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid In analogy to Example 11, step 2, (3-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)- acetonitrile was hydrolyzed with aqueous KOH to give the title compound as an off-white solid. MS (m/e, ISP neg. ion)=548.2 [M−H$^+$].

Example 13

4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid methyl ester

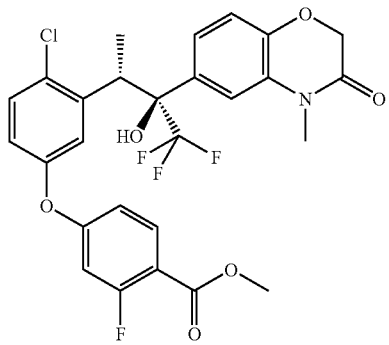

In analogy to Example 5, 6-[2-(2-chloro-5-hydroxy-phenyl)-1-hydroxy-1-trifluoromethyl-propyl]-4-methyl-4H-benzo[1,4]oxazin-3-one (Example 1, step 4) was reacted with 3-fluoro-4-methoxycarbonylphenylboronic acid, copper-(II)-acetate and pyridine to give the title compound as a colorless foam. MS (m/e)=568.3 [M+H$^+$].

Example 14

4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid

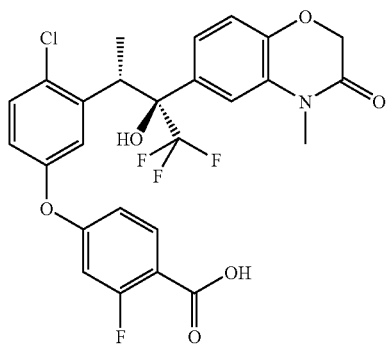

In analogy to Example 2, 4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid methyl ester (Example 13) was hydrolyzed to give the title compound as a colorless solid. MS (m/e, ISP neg. ion)= 552.2 [M−H$^+$].

Example 15

2-Chloro-5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid

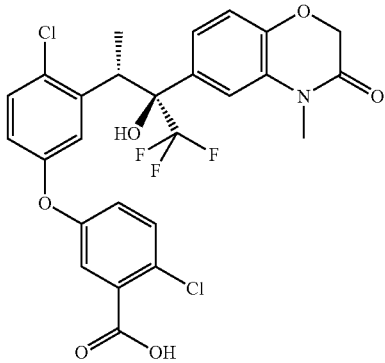

Step 1: 2-Chloro-5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzonitrile In analogy to Example 5, 6-[2-(2-chloro-5-hydroxy-phenyl)-1-hydroxy-1-trifluoromethyl-propyl]-4-methyl-4H-benzo[1,4]oxazin-3-one (Example 1, step 4) was reacted with 4-chloro-3-cyanophenylboronic acid, copper-(II)-acetate and pyridine to give the title compound as a colorless foam. MS (m/e)=551.1 [M+H$^+$].

Step 2: 2-Chloro-5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid In analogy to Example 11, step 2, 2-chloro-5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzonitrile was hydrolyzed with aqueous KOH to give the title compound as a colorless solid. MS (m/e, ISP neg. ion)= 568.2 [M−H$^+$].

Example 16

4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-3-fluoro-benzoic acid

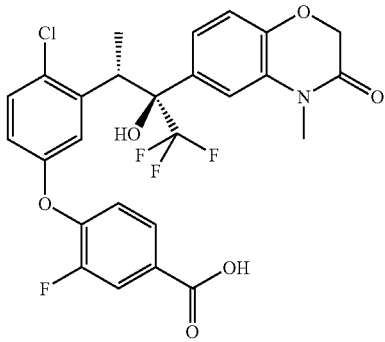

Steps 1 and 2: 4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-3-fluoro-benzonitrile To a solution of 6-[2-(2-chloro-5-hydroxy-phenyl)-1-hydroxy-1-trifluoromethyl-propyl]-4-methyl-4H-benzo[1,4]oxazin-3-one (Example 1, step 4, 100 mg) in N,N-dimethylacetamide (1.8 ml) were added 3,4-difluorobenzonitrile (41 mg) and cesium carbonate (235 mg). The mixture was heated under microwave conditions for 30 min to 120° C. After cooling to room temperature, water was added and the mixture was extracted with EtOAc. The organic phase was dried (MgSO$_4$), filtered and concentrated to dryness. The product was purified by chromatography (SiO$_2$, cyclohexane/EtOAc 1:0=>1:1) to give 4-{4-chloro-3-[1-methyl-2-(4-methyl-3-oxo-3,4-dihydro-2H-benzo[1,4]oxazin-6-yl)-2-oxo-ethyl]-phenoxy}-3-fluoro-benzonitrile (92 mg). In analogy to Example 1, step 3, this compound was reacted with trifluoromethyl trimethylsilane and tetramethylammonium fluoride to give the title compound (89 mg) as a colorless solid. MS (m/e)=535.1 [M+H$^+$].

Step 3: 4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-3-fluoro-benzoic acid In analogy to Example 11, step 2, 4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-3-fluoro-benzonitrile was hydrolyzed with aqueous KOH to give the title compound as a colorless solid. MS (m/e, ISP neg. ion)= 552.2 [M−H$^+$].

Example 17

4'-Chloro-3'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid

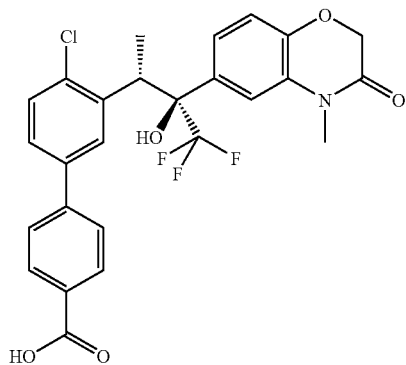

Step 1: Trifluoromethanesulfonic acid 4-chloro-3-[3,3,3-trifluoro-2-hydroxy-1-methyl-2-(4-methyl-3-oxo-3,4-dihydro-2H-benzo[1,4]oxazin-6-yl)-propyl]-phenyl ester To a suspension of 6-[2-(2-chloro-5-hydroxy-phenyl)-1-hydroxy-1-trifluoromethyl-propyl]-4-methyl-4H-benzo[1,4]oxazin-3-one (Example 1, step 4, 394 mg) in dichloromethane (15 ml) was added triethylamine (221 mg). The mixture was cooled to −20° C. and trifluoromethanesulfonic anhydride (327 mg) was added. The mixture was stirred for 20 min at −20° C. and for 1 h at room temperature. The mixture was diluted with dichloromethane and washed with water and brine. The organic phase was dried (MgSO$_4$), filtered and concentrated. The product was purified by chromatography (SiO$_2$, cyclohexane/EtOAc 1:0=>1:1) to give the title compound (484 mg) as a colorless foam. MS (m/e)= 548.1 [M+H$^+$].

Step 2: 4'-Chloro-3'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid To a suspension of trifluoromethanesulfonic acid 4-chloro-3-[3,3,3-trifluoro-2-hydroxy-1-methyl-2-(4-methyl-3-oxo-3,4-dihydro-2H-benzo[1,4]oxazin-6-yl)-propyl]-phenyl ester (100 mg), 4-carboxyphenylboronic acid (48 mg) and dichloro[1,1'-bis(diphenylphosphino)ferrocene]dichloromethane adduct (7.5 mg) in dioxan (0.54 ml) under argon were added water (0.4 ml) and a 2 M aqueous sodium carbonate solution (0.27 ml). The mixture was stirred at 80° C. for 7 h, at 50° C. for 2 days and again at 80° C. for 5 h. The mixture was filtered and to the filtrate was added an aqueous KHSO$_4$ solution. The mixture was extracted with EtOAc. The organic phase was dried (MgSO$_4$), filtered and concentrated. The product was purified by chromatography (SiO$_2$, CH$_2$Cl$_2$/MeOH 1:0=>85:15) to give the title compound (38 mg) as a light brown solid. MS (m/e, ISP neg. ion)=518.2 [M−H$^+$].

Example 18

4'-Chloro-3'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid

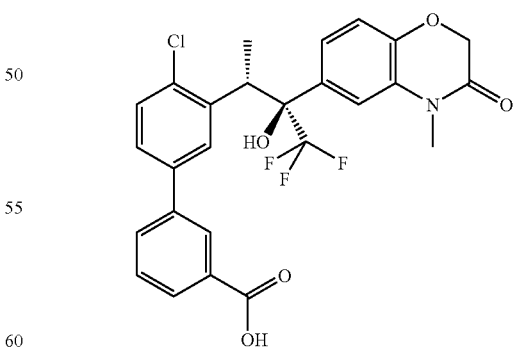

In analogy to Example 17, step 2, trifluoromethanesulfonic acid 4-chloro-3-[3,3,3-trifluoro-2-hydroxy-1-methyl-2-(4-methyl-3-oxo-3,4-dihydro-2H-benzo[1,4]oxazin-6-yl)-propyl]-phenyl ester (Example 17, step 1) was reacted with 3-carboxyphenylboronic acid to give the title compound as a light brown solid. MS (m/e, ISP neg. ion)=518.2 [M−H⁺].

Example 19

(1-{4-Chloro-3-[3,3,3-trifluoro-2-hydroxy-1-methyl-2-(4-methyl-3-oxo-3,4-dihydro-2H-benzo[1,4]oxazin-6-yl)-propyl]-benzoyl}-piperidin-4-yl)-acetic acid methyl ester

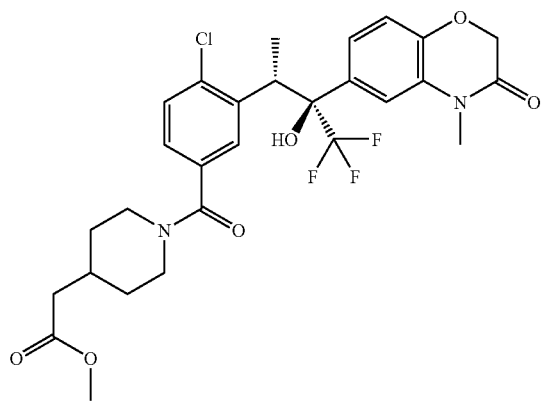

Step 1: 4-Chloro-3-[3,3,3-trifluoro-2-hydroxy-1-methyl-2-(4-methyl-3-oxo-3,4-dihydro-2H-benzo[1,4]oxazin-6-yl)-propyl]-benzoic acid To a suspension of trifluoromethanesulfonic acid 4-chloro-3-[3,3,3-trifluoro-2-hydroxy-1-methyl-2-(4-methyl-3-oxo-3,4-dihydro-2H-benzo[1,4]oxazin-6-yl)-propyl]-phenyl ester (Example 17, step 1, 100 mg) in water (0.55 ml) were added palladium(II)acetate (4.1 mg), 1,1'-bis(diphenylphosphino)ferrocene (10 mg) and pyridine (0.069 ml). Molybdenum hexacarbonyl was added and the mixture was heated under microwave conditions for 20 min at 150° C. After cooling to room temperature, 25% aqueous HCl (0.4 ml) was added and the mixture was filtered. The filtrate was extracted with diethyl ether. The organic phase was extracted with 2 M aqueous NaOH. The aqueous phase was acidified with 25% aqueous HCl and extracted with diethyl ether. The organic phase was concentrated to dryness. The product was purified by chromatography (SiO₂, dichloromethane/MeOH 1:0=>85:15) to give the title compound (25 mg) as a colorless solid. MS (m/e, ISP neg. ion)=442.1 [M−H⁺].

Step 2: (1-{4-Chloro-3-[3,3,3-trifluoro-2-hydroxy-1-methyl-2-(4-methyl-3-oxo-3,4-dihydro-2H-benzo[1,4]oxazin-6-yl)-propyl]-benzoyl}-piperidin-4-yl)-acetic acid methyl ester To a solution of 4-chloro-3-[3,3,3-trifluoro-2-hydroxy-1-methyl-2-(4-methyl-3-oxo-3,4-dihydro-2H-benzo[1,4]oxazin-6-yl)-propyl]-benzoic acid (74 mg) in tetrahydrofuran (0.63 ml) were added 4-piperidine acetic acid methyl ester (32 mg), N-ethyldiisopropylamine (65 mg) and benzotriazol-1-yl-oxy-tris-(dimethylamino)-phosphonium hexafluorophosphate (BOP, 113 mg). The mixture was stirred at room temperature for 18 h and then concentrated to dryness. The product was purified by chromatography (SiO₂, CH₂Cl₂/ MeOH 1:0=>9:1) to give the title compound (82 mg) as colorless foam. MS (m/e)=583.2 [M+H⁺].

Example 20

(1-{4-Chloro-3-[3,3,3-trifluoro-2-hydroxy-1-methyl-2-(4-methyl-3-oxo-3,4-dihydro-2H-benzo[1,4]oxazin-6-yl)-propyl]-benzoyl}-piperidin-4-yl)-acetic acid

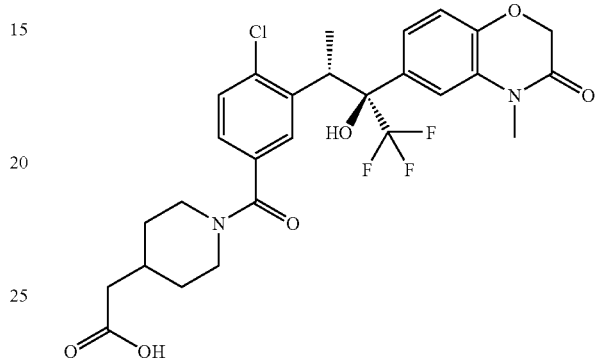

In analogy to Example 2, (1-{4-chloro-3-[3,3,3-trifluoro-2-hydroxy-1-methyl-2-(4-methyl-3-oxo-3,4-dihydro-2H-benzo[1,4]oxazin-6-yl)-propyl]-benzoyl}-piperidin-4-yl)-acetic acid methyl ester (Example 19) was hydrolyzed to give the title compound as a colorless foam. MS (m/e, ISP neg. ion)=567.3 [M−H⁺].

Example 21

4-{4-Chloro-3-[3,3,3-trifluoro-2-hydroxy-1-methyl-2-(4-methyl-3-oxo-3,4-dihydro-2H-benzo[1,4]oxazin-6-yl)-propyl]-benzoylamino}-butyric acid

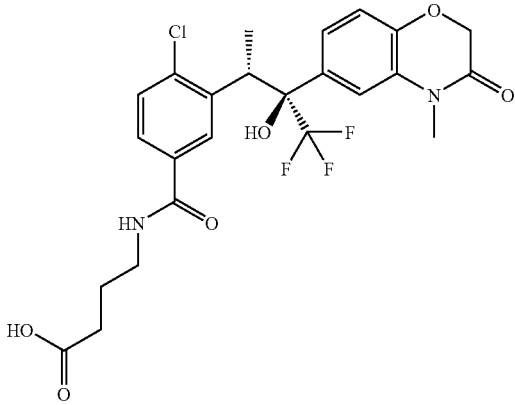

In analogy to Example 19, step 2, 4-chloro-3-[3,3,3-trifluoro-2-hydroxy-1-methyl-2-(4-methyl-3-oxo-3,4-dihydro-2H-benzo[1,4]oxazin-6-yl)-propyl]-benzoic acid (Example 19, step 1) was coupled with methyl-4-aminobutyrate hydrochloride. The product of this reaction was hydrolyzed in analogy to Example 2, to give the title compound as a colorless solid. MS (m/e, ISP neg. ion)=527.2 [M–H⁺].

Example 22

3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid

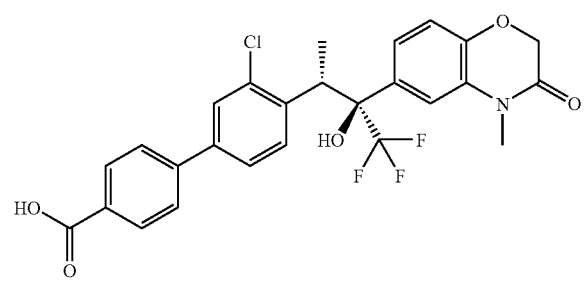

Step 1: 6-[2-(4-Bromo-2-chloro-phenyl)-acetyl]-4-methyl-4H-benzo[1,4]oxazin-3-one In analogy to Example 1, step 1, (4-bromo-2-chloro-phenyl)-acetic acid was converted to the acid chloride and subsequently reacted with 4-methyl-2H-1,4-benzoxazin-3(4H)-one in the presence of AlCl₃ to give the title compound as a light brown solid. MS (m/e, ISP neg. ion)=392.1 [M–H⁺].

Step 2: 6-[2-(4-Bromo-2-chloro-phenyl)-propionyl]-4-methyl-4H-benzo[1,4]oxazin-3-one In analogy to Example 1, step 2, 6-[2-(4-bromo-2-chloro-phenyl)-acetyl]-4-methyl-4H-benzo[1,4]oxazin-3-one was reacted with sodium hydride and methyl iodide to give the title compound as an off-white solid. MS (m/e, ISP neg. ion)=406.1 [M–H⁺].

Step 3: 6-[2-(4-Bromo-2-chloro-phenyl)-1-hydroxy-1-trifluoromethyl-propyl]-4-methyl-4H-benzo[1,4]oxazin-3-one In analogy to Example 1, step 3, 6-[2-(4-bromo-2-chloro-phenyl)-propionyl]-4-methyl-4H-benzo[1,4]oxazin-3-one was reacted with (trifluoromethyl)trimethylsilane and tetramethylammonium fluoride to give the title compound as an off-white solid. MS (m/e, ISP neg. ion)=475.9 [M–H⁺].

Step 4: 3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid In analogy to Example 17, step 2, 6-[2-(4-bromo-2-chloro-phenyl)-1-hydroxy-1-trifluoromethyl-propyl]-4-methyl-4H-benzo[1,4]oxazin-3-one was reacted with 4-carboxyphenylboronic acid to give the title compound as a colorless solid. MS (m/e, ISP neg. ion)=518.2 [M–H⁺].

Example 23

3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid

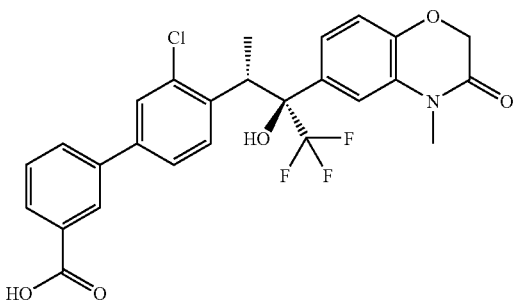

In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 3-carboxyphenylboronic acid to give the title compound as an off-white solid. MS (m/e, ISP neg. ion)=518.2 [M–H⁺].

Example 24

3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-2-carboxylic acid

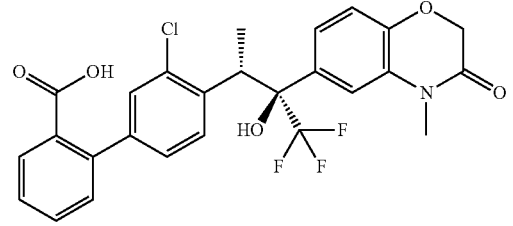

In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 2-carboxyphenylboronic acid to give the title compound as an off-white solid. MS (m/e, ISP neg. ion)=518.2 [M–H⁺].

Example 25

3'-Chloro-3-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester

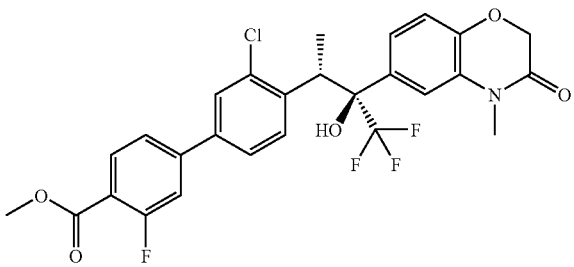

In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 3-fluoro-4-methoxycarbonylphenylboronic acid to give the title compound as an off-white solid. MS (m/e)=552.2 [M+H⁺].

Example 26

3'-Chloro-3-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid

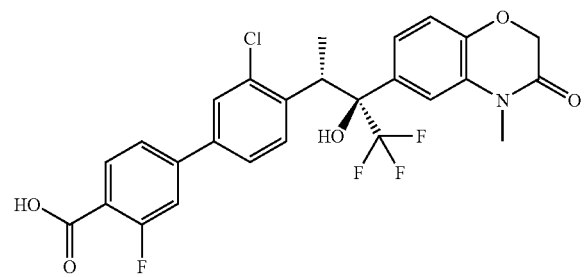

In analogy to Example 2, 3'-chloro-3-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester (Example 25) was hydrolyzed to give the title compound as a colorless solid. MS (m/e, ISP neg. ion)= 536.1 [M−H⁺].

Examples 27 and 28

3'-Chloro-3-fluoro-4'-[(1S,2S)-3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid and 3'-Chloro-3-fluoro-4'-[(1R,2R)-3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid

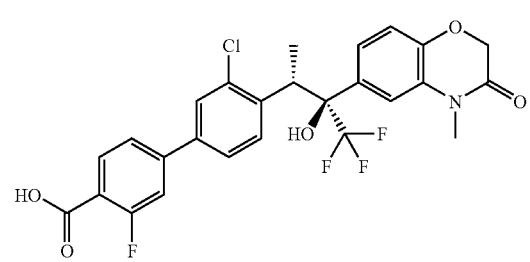

and

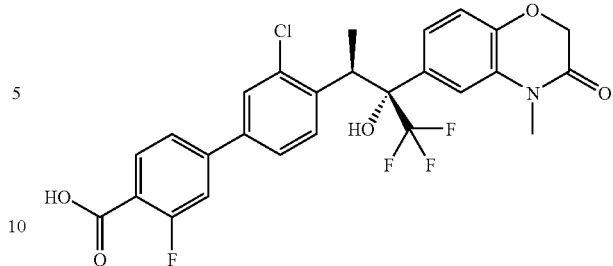

3'-Chloro-3-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid (Example 26) was separated into the enantiomers by chiral HPLC on a Chiralpak AD column using 15% (ethanol+0.5% HCOOH) in heptane as the mobile phase to give the title compounds as colorless amorphous solids.

Example 29

3-{3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-propionic acid

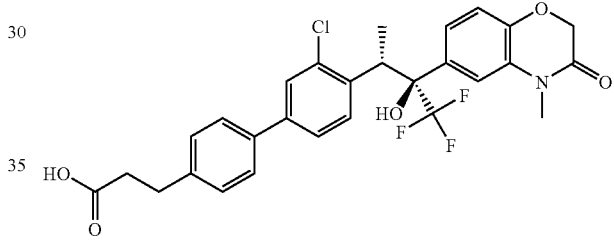

In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 4-(2-carboxyethyl)benzeneboronic acid to give the title compound as a colorless solid. MS (m/e)=548.2 [M+H⁺].

Example 30

3,3'-Dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester

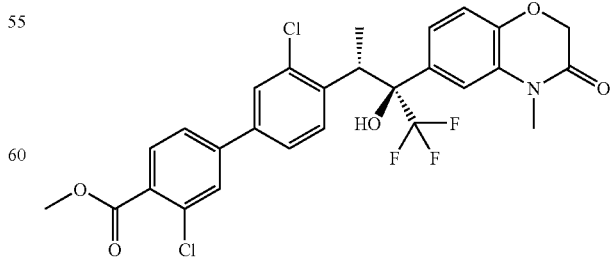

In analogy to Example 17, step 2, 6-[2-(4-bromo-2-chlorophenyl)-1-hydroxy-1-trifluoromethyl-propyl]-4-methyl-4H- benzo[1,4]oxazin-3-one (Example 22, step 3) was reacted with 3-chloro-4-methoxycarbonylphenylboronic acid to give the title compound as an off-white solid. MS (m/e)=568.3 [M+H$^+$].

Example 31

3,3'-Dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid

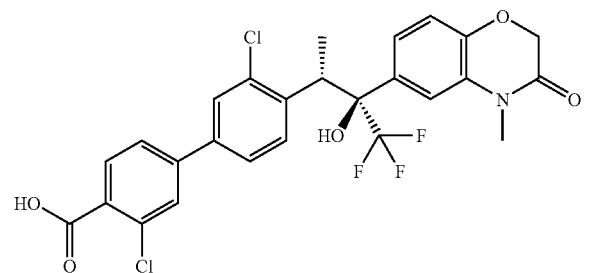

In analogy to Example 2, 3,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester (Example 30) was hydrolyzed to give the title compound as a colorless solid. MS (m/e, ISP neg. ion)=552.2 [M−H$^+$].

Example 32

3'-Chloro-4-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid

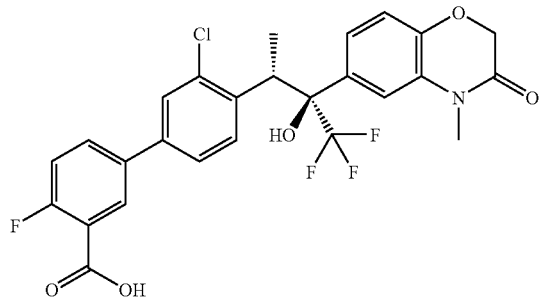

Step 1: 3'-Chloro-4-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carbonitrile In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 3-cyano-4-fluorophenylboronic acid to give the title compound as a colorless solid. MS (m/e)=519.2 [M+H$^+$].

Step 2: 3'-Chloro-4-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid In analogy to Example 11, step 2, 3'-chloro-4-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carbonitrile was hydrolyzed with aqueous KOH to give the title compound as a colorless solid. MS (m/e, ISP neg. ion)=536.1 [M−H$^+$].

Example 33

3'-Chloro-2-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 2-fluoro-4-methoxycarbonylphenylboronic acid to give the title compound as a colorless solid. MS (m/e)=552.2 [M+H$^+$].

Example 34

3'-Chloro-2-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid In analogy to Example 2, 3'-chloro-2-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester (Example 33) was hydrolyzed to give the title compound as a colorless solid. MS (m/e, ISP neg. ion)= 536.1 [M−H⁺].

Example 35

3'-Chloro-3-methoxy-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester

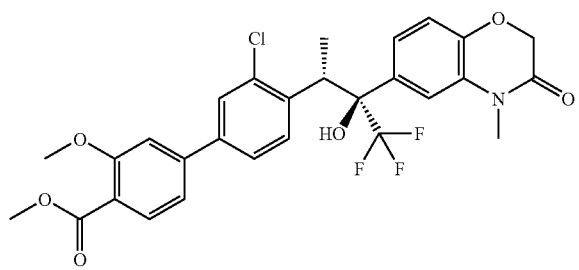

In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 3-methoxy-4-methoxycarbonylphenylboronic acid to give the title compound as an off-white solid. MS (m/e, ISP neg. ion)=562.2 [M−H⁺].

Example 36

3'-Chloro-3-methoxy-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid

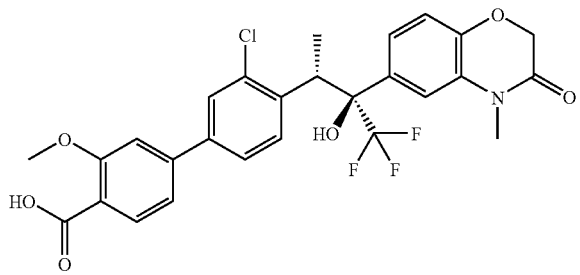

In analogy to Example 2, 3'-chloro-3-methoxy-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester (Example 35) was hydrolyzed to give the title compound as a colorless solid. MS (m/e, ISP neg. ion)=548.2 [M−H⁺].

Example 37

{3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-acetic acid

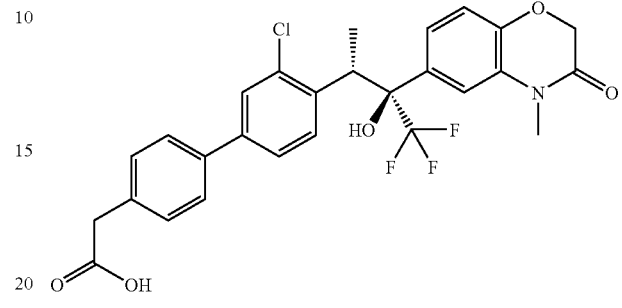

Step 1: {3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-acetonitrile In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 4-cyanomethylphenylboronic acid to give the title compound as a colorless solid. MS (m/e)=515.4 [M+H⁺].

Step 2: {3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-acetic acid In analogy to Example 11, step 2, {3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-acetonitrile was hydrolyzed with aqueous KOH to give the title compound as an off-white solid. MS (m/e)=534.2 [M+H⁺].

Example 38

3'-Chloro-6-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid

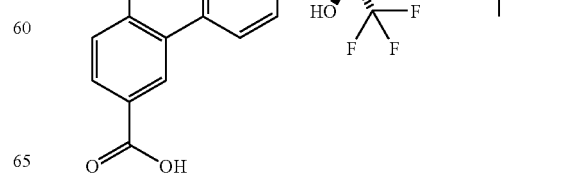

Step 1: 3'-Chloro-6-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carbonitrile In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 5-cyano-2-fluorophenylboronic acid to give the title compound as a colorless solid. MS (m/e)=519.2 [M+H$^+$].

Step 2: 3'-Chloro-6-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid In analogy to Example 11, step 2, 3'-chloro-6-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carbonitrile was hydrolyzed with aqueous KOH to give the title compound as a colorless solid. MS (m/e, ISP neg. ion)= 536.1 [M−H$^+$].

Example 39

4,3'-Dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid ethyl ester

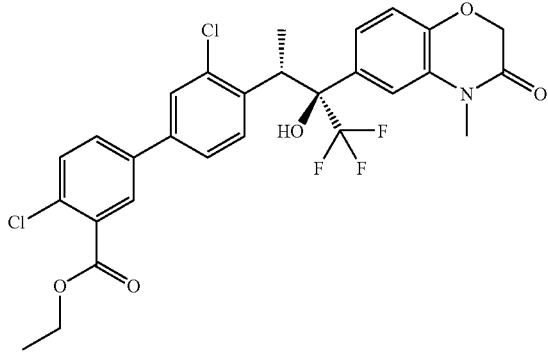

In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 4-chloro-3-ethoxycarbonylphenylboronic acid to give the title compound as a colorless solid. MS (m/e)=582.3 [M+H$^+$].

Example 40

4,3'-Dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid

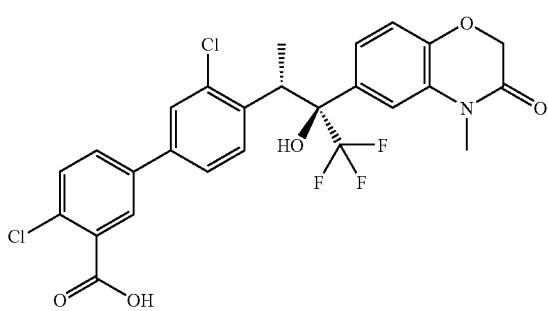

In analogy to Example 2, 4,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid ethyl ester (Example 39) was hydrolyzed to give the title compound as an off-white solid. MS (m/e, ISP neg. ion)= 552.2 [M−H$^+$].

Example 41

{3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-yl}-acetic acid

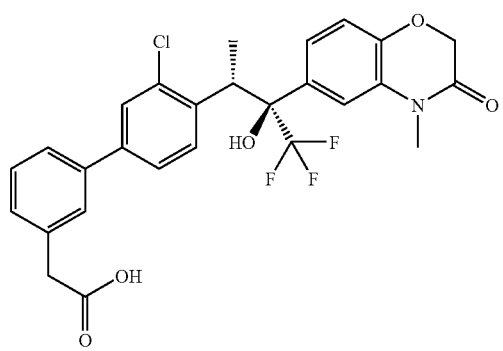

Step 1: {3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-yl}-acetonitrile In analogy to Example 17, step 2, 6-[2-(4-bromo-2-chlorophenyl)-1-hydroxy-1-trifluoromethyl-propyl]-4-methyl-4H-benzo[1,4]oxazin-3-one (Example 22, step 3) was reacted with 3-cyanomethylphenylboronic acid to give the title compound as a colorless solid. MS (m/e)=515.4 [M+H$^+$].

Step 2: {3'-Chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-yl}-acetic acid In analogy to Example 11, step 2, {3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-yl}-acetonitrile was hydrolyzed with aqueous KOH to give the title compound as a colorless solid. MS (m/e, ISP neg. ion)=532.1 [M−H$^+$].

Example 42

1-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenyl}-piperidine-4-carboxylic acid ethyl ester

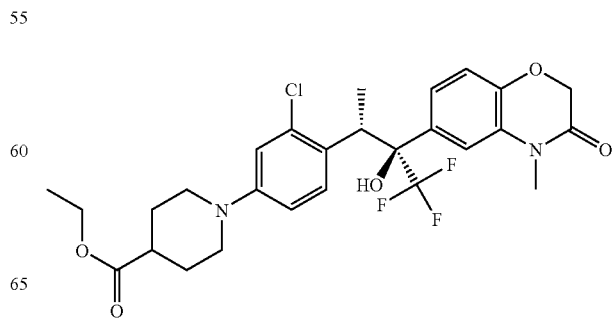

To a suspension of 2,2'-bis(diphenylphosphino)-1,1'binaphthyl (3.1 mg), tris(dibenzylideneacetone)dipalladium (0) (1.5 mg) and sodium-tert.-butylate (19 mg) in toluene (15 ml) were added 6-[2-(4-bromo-2-chloro-phenyl)-1-hydroxy-1-trifluoromethyl-propyl]-4-methyl-4H-benzo[1,4]oxazin-3-one (Example 22, step 3, 80 mg) and ethyl piperidine-4-carboxylate (29 mg). The mixture was stirred at room temperature overnight. 2,2'-Bis(diphenylphosphino)-1,1'binaphthyl (3.1 mg), ethyl piperidine-4-carboxylate (29 mg) and tris(dibenzylideneacetone)dipalladium (0) (1.5 mg) were added and the mixture was stirred at 80° C. for 4 h. After cooling to room temperature, the mixture was diluted with EtOAc. The organic phase was washed with water, dried (MgSO$_4$), filtered and concentrated to dryness. The product was purified by chromatography (SiO$_2$, cyclohexane/EtOAc 1:0=>4:1) to give the title compound (3 mg) as light yellow oil. MS (m/e)=555.3 [M+H$^+$].

Example 43

3-Chloro-4-[3,3,3-trifluoro-2-hydroxy-1-methyl-2-(4-methyl-3-oxo-3,4-dihydro-2H-benzo[1,4]oxazin-6-yl)-propyl]-benzoic acid

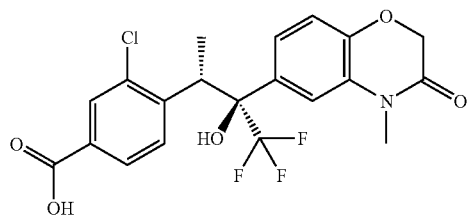

In analogy to Example 19, step 1, 6-[2-(4-bromo-2-chlorophenyl)-1-hydroxy-1-trifluoromethyl-propyl]-4-methyl-4H-benzo[1,4]oxazin-3-one (Example 22, step 3) was reacted with molybdenum hexacarbonyl in the presence of palladium (II)acetate, 1,1'-bis(diphenylphosphino)ferrocene and pyridine to give the title compound as a light brown solid. MS (m/e, ISP neg. ion)=442.1 [M−H$^+$].

Example 44

(4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid

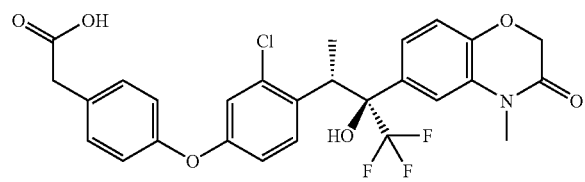

Step 1: (4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid methyl ester A suspension of 6-[2-(4-bromo-2-chloro-phenyl)-1-hydroxy-1-trifluoromethyl-propyl]-4-methyl-4H-benzo[1,4] oxazin-3-one (Example 22, step 3, 50 mg), methyl-4-hydroxyphenylacetate (26 mg), cesium carbonate (68 mg), copper (I)iodide (2 mg) and N,N-dimethylglycine hydrochloride (4.5 mg) in dioxane (0.5 ml) was heated to 120° C. for 10 min under microwave conditions. The reaction was not finished. The reaction mixture was placed in a heating bath and stirred at 70° C. for 16 h and at 90° C. for 4 h. After cooling to room temperature, water was added and the mixture was extracted with EtOAc. The organic phase was washed with water, filtered and concentrated to dryness. The product was purified by chromatography (SiO$_2$, cyclohexane/EtOAc 1:0=>0:1) to give the title compound (23 mg) as an off-white solid. MS (m/e)=564 [M+H$^+$].

Step 2: (4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid In analogy to Example 2, (4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid methyl ester was hydrolyzed to give the title compound as a colorless solid. MS (m/e, ISP neg. ion)=548.2 [M−H$^+$].

Example 45

3'-Chloro-3-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-4-carboxylic acid methyl ester

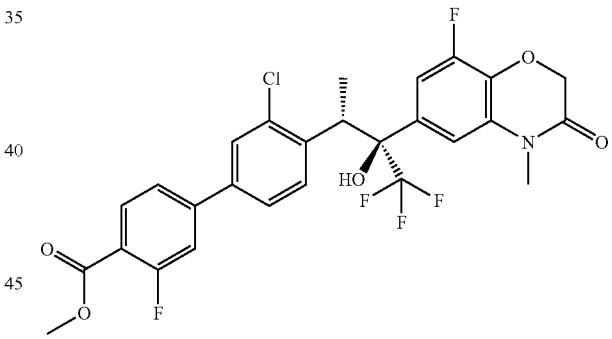

Step 1: 6-[2-(4-Bromo-2-chloro-phenyl)-acetyl]-8-fluoro-4-methyl-4H-benzo[1,4]oxazin-3-one In analogy to Example 1, step 1, (4-bromo-2-chloro-phenyl)-acetic acid was converted to the acid chloride and reacted with 8-fluoro-4-methyl-4H-benzo[1,4]oxazin-3-one in the presence of AlCl$_3$ to give the title compound as a light-brown solid. MS (m/e, ISP neg. ion)=411.9 [M−H$^+$].

Step 2: 6-[2-(4-Bromo-2-chloro-phenyl)-propionyl]-8-fluoro-4-methyl-4H-benzo[1,4]oxazin-3-one In analogy to Example 1, step 2, 6-[2-(4-bromo-2-chlorophenyl)-acetyl]-8-fluoro-4-methyl-4H-benzo[1,4]oxazin-3-one was reacted with sodium hydride and methyl iodide to give the title compound as a light yellow foam. MS (m/e, ISP neg. ion)=423.9 [M−H$^+$].

Step 3: 6-[2-(4-Bromo-2-chloro-phenyl)-1-hydroxy-1-trifluoromethyl-propyl]-8-fluoro-4-methyl-4H-benzo[1,4]oxazin-3-one In analogy to Example 1, step 3, 6-[2-(4-bromo-2-chloro-phenyl)-propionyl]-8-fluoro-4-methyl-4H-benzo[1,4]oxazin-3-one was reacted with trifluoromethyl)trimethylsilane and tetramethylammonium fluoride to give the title compound as a light yellow foam. MS (m/e)=496.0 [M+H$^+$].

Step 4: 3'-Chloro-3-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-4-carboxylic acid methyl ester In analogy to Example 17, step 2, 6-[2-(4-bromo-2-chloro-phenyl)-1-hydroxy-1-trifluoromethyl-propyl]-8-fluoro-4-methyl-4H-benzo[1,4]oxazin-3-one was reacted with 3-fluoro-4-methoxycarbonylphenylboronic acid to give the title compound as a colorless foam. MS (m/e)=570.3 [M+H$^+$].

Example 46

3'-Chloro-3-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-4-carboxylic acid

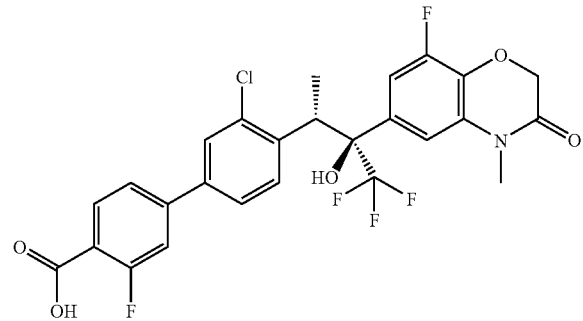

In analogy to Example 2, 3'-chloro-3-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-4-carboxylic acid methyl ester (Example 45) was hydrolyzed to give the title compound as a colorless solid. MS (m/e, ISP neg. ion)=554.2 [M–H$^+$].

Example 47

{3'-Chloro-4-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-3-yloxy}-acetic acid ethyl ester

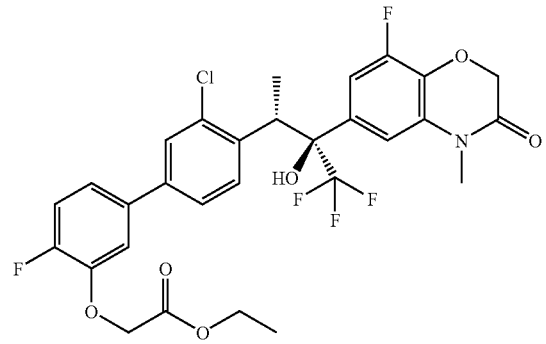

Step 1: 6-[2-(3-Chloro-4'-fluoro-3'-methoxy-biphenyl-4-yl)-1-hydroxy-1-trifluoromethyl-propyl]-8-fluoro-4-methyl-4H-benzo[1,4]oxazin-3-one In analogy to Example 17, step 2, 6-[2-(4-bromo-2-chloro-phenyl)-1-hydroxy-1-trifluoromethyl-propyl]-8-fluoro-4-methyl-4H-benzo[1,4]oxazin-3-one (Example 45, step 3) was reacted with 4-fluoro-3-methoxyphenylboronic acid to give the title compound as a colorless foam. MS (m/e, ISP neg. ion)=540.3 [M–H$^+$].

Step 2: 6-[2-(3-Chloro-4'-fluoro-3'-hydroxy-biphenyl-4-yl)-1-hydroxy-1-trifluoromethyl-propyl]-8-fluoro-4-methyl-4H-benzo[1,4]oxazin-3-one In analogy to Example 1, step 4, 6-[2-(3-chloro-4'-fluoro-3'-methoxy-biphenyl-4-yl)-1-hydroxy-1-trifluoromethyl-propyl]-8-fluoro-4-methyl-4H-benzo[1,4]oxazin-3-one was reacted with BBr$_3$ to give the title compound as a light yellow oil. MS (m/e, ISP neg. ion)=526.2 [M–H$^+$].

Step 3: {3'-Chloro-4-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-3-yloxy}-acetic acid ethyl ester In analogy to Example 1, step 5, 6-[2-(3-chloro-4'-fluoro-3'-hydroxy-biphenyl-4-yl)-1-hydroxy-1-trifluoromethyl-propyl]-8-fluoro-4-methyl-4H-benzo[1,4]oxazin-3-one was reacted with ethylbromoacetate and cesium carbonate to give the title compound as a colorless foam. MS (m/e)=614.2 [M+H$^+$].

Example 48

{3'-Chloro-4-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-3-yloxy}-acetic acid

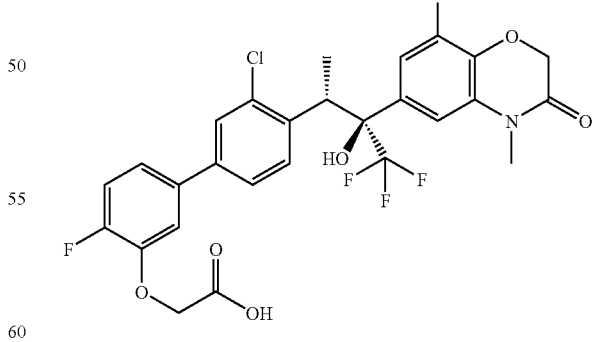

In analogy to Example 2, {3'-chloro-4-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-3-yloxy}-acetic acid ethyl ester (Example 47) was hydrolyzed to give the title compound as a colorless solid. MS (m/e, ISP neg. ion)=584.2 [M–H$^+$].

Example 49

3'-Chloro-3-fluoro-4'-[3,3,3-trifluoro-2-hydroxy-1-methyl-2-(4-oxo-4H-quinolizin-1-yl)-propyl]-biphenyl-4-carboxylic acid methyl ester

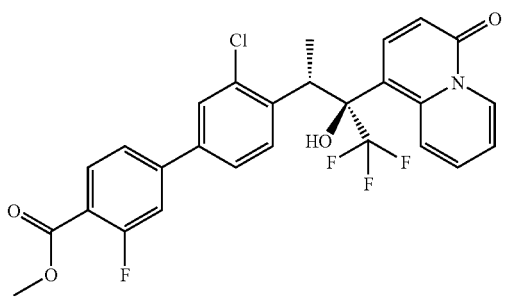

Steps 1 and 2: 1-[2-(4-Bromo-2-chloro-phenyl)-propionyl]-quinolizin-4-one

To a suspension of 4-oxo-4H-quinolizine-1-carboxylic acid (1 g) in CH$_2$Cl$_2$ (6.9 ml) were added two drops of N,N-dimethylformamide and oxalylchloride (1.095 g). The mixture was stirred at room temperature for 2 h and was then concentrated to dryness. 1,2-Dimethoxyethane was added and the solvent was evaporated again to give the crude acid chloride. To a suspension of zinc powder (691 mg) in 1,2-dimethoxyethane (7 ml) was added tetrakis(triphenylphosphine) palladium(0) (61 mg). A suspension of the acid chloride in 1,2-dimethoxyethane (7 ml) was added. The mixture was cooled in an ice bath and a solution of 4-bromo-1-bromomethyl-2-chloro-benzene (1.50 g) in 1,2-dimethoxyethane (7 ml) was slowly added over 45 min. The mixture was stirred for 30 min at 0° C. and overnight at room temperature. The mixture was filtered and the filtrate was concentrated. The product was purified by chromatography (SiO$_2$, CH$_2$Cl$_2$/MeOH 1:0=>9:1) to give a colorless solid (263 mg). The product of this reaction was alkylated with iodomethane in analogy to Example 1, step 2 to give the title compound as a yellow amorphous solid. MS (m/e)=391.9 [M+H$^+$].

Step 3: 1-[2-(4-Bromo-2-chloro-phenyl)-1-hydroxy-1-trifluoromethyl-propyl]-quinolizin-4-one In analogy to Example 1, step 3, 1-[2-(4-bromo-2-chlorophenyl)-propionyl]-quinolizin-4-one was reacted with (trifluoromethyl)trimethylsilane and tetramethylammonium fluoride to give the title compound as a light yellow solid. MS (m/e)=460.2 [M+H$^+$].

Step 4: 3'-Chloro-3-fluoro-4'-[3,3,3-trifluoro-2-hydroxy-1-methyl-2-(4-oxo-4H-quinolizin-1-yl)-propyl]-biphenyl-4-carboxylic acid methyl ester In analogy to Example 17, step 2, 1-[2-(4-bromo-2-chlorophenyl)-1-hydroxy-1-trifluoromethyl-propyl]-quinolizin-4-one was reacted with 3-fluoro-4-methoxycarbonylphenylboronic acid to give the title compound as a light yellow solid. MS (m/e)=534.2 [M+H$^+$].

Example 50

3'-Chloro-3-fluoro-4'-[3,3,3-trifluoro-2-hydroxy-1-methyl-2-(4-oxo-4H-quinolizin-1-yl)-propyl]-biphenyl-4-carboxylic acid

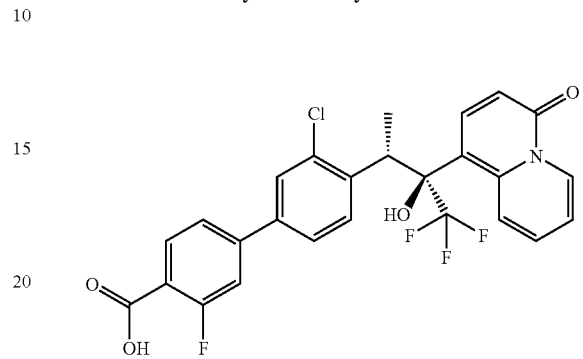

In analogy to Example 2, 3'-chloro-3-fluoro-4'-[3,3,3-trifluoro-2-hydroxy-1-methyl-2-(4-oxo-4H-quinolizin-1-yl)-propyl]-biphenyl-4-carboxylic acid methyl ester (Example 49) was hydrolyzed to give the title compound as an off-white solid. MS (m/e, ISP neg. ion)=518.1 [M−H$^+$].

Example 51

3'-Chloro-3-fluoro-4'-[3,3,3-trifluoro-2-hydroxy-1-methyl-2-(1-methyl-2-oxo-2,3-dihydro-1H-pyrido[2,3-b][1,4]oxazin-7-yl)-propyl]-biphenyl-4-carboxylic acid methyl ester

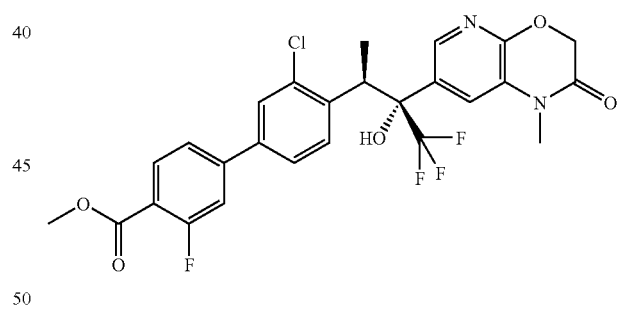

Step 1: 6-Methoxycarbonylmethoxy-5-nitro-nicotinic acid ethyl ester

To a solution of 6-chloro-5-nitro-nicotinic acid ethyl ester (10.5 g, prepared from 6-hydroxy-nicotinic acid with a) fuming nitric acid, b) PCl$_5$, POCl$_3$, c) EtOH, see WO2005012288) in dioxan (100 ml) was added methylglycolate (4.92 g). Sodium hydride (55% dispersion in mineral oil, 2.19 g) was added portion wise at 0° C. The mixture was stirred at room temperature for 24 h. Water was added and the mixture was extracted with EtOAc. The organic phase was dried (MgSO$_4$), filtered and concentrated to dryness. The product was purified by chromatography (SiO$_2$, cyclohexane/EtOAc 1:0=>7:3) to give the title compound (3.026 g) as yellow oil. MS (m/e)=285.2 [M+H$^+$].

Step 2: 2-Oxo-2,3-dihydro-1H-pyrido[2,3-b][1,4]oxazine-7-carboxylic acid ethyl ester To a solution of 6-methoxycarbonylmethoxy-5-nitro-nicotinic acid ethyl ester (3.271 g) in acetic acid (25 ml) was added iron powder (9.64 g). The mixture was stirred for 2 h at 60° C. The mixture was filtered and the filter cake was washed with acetic acid, EtOAc, EtOH, dichloromethane and with MeOH. The filtrate was concentrated. The residue was suspended in $CH_2Cl_2$/MeOH 9:1 and passed with more of the same solvent mixture over silica gel to give the title compound (1.52 g) as a light brown solid. MS (m/e)=223.1 [M+H$^+$].

Step 3: 1-Methyl-2-oxo-2,3-dihydro-1H-pyrido[2,3-b][1,4]oxazine-7-carboxylic acid ethyl ester To a solution of 2-oxo-2,3-dihydro-1H-pyrido[2,3-b][1,4]oxazine-7-carboxylic acid ethyl ester (1.518 g) in N,N-dimethylacetamide (15 ml) were added KOtBu (0.843 g) and methyl iodide (1.067 g). The mixture was stirred at room temperature for 2 h. Water was added and the mixture was extracted with EtOAc. The organic phase was dried (MgSO$_4$), filtered and concentrated to dryness. The product was purified by chromatography (SiO$_2$, $CH_2Cl_2$/MeOH 1:0=>9:1) to give the title compound (0.936 g) as a brown solid.

Step 4: 1-Methyl-2-oxo-2,3-dihydro-1H-pyrido[2,3-b][1,4]oxazine-7-carboxylic acid In analogy to Example 2, 1-methyl-2-oxo-2,3-dihydro-1H-pyrido[2,3-b][1,4]oxazine-7-carboxylic acid ethyl ester was hydrolyzed to give the title compound as a brown solid.

Step 5: 7-[2-(4-Bromo-2-chloro-phenyl)-acetyl]-1-methyl-1H-pyrido[2,3-b][1,4]oxazin-2-one In analogy to Example 49, step 1, 1-methyl-2-oxo-2,3-dihydro-1H-pyrido[2,3-b][1,4]oxazine-7-carboxylic acid was converted to the acid chloride and subsequently reacted with 4-bromo-1-bromomethyl-2-chloro-benzene in the presence of zinc and tetrakis(triphenylphosphine)palladium(0) to give the title compound as a light yellow solid. MS (m/e, ISP neg. ion)=392.9 [M−H$^+$].

Step 6: 7-[2-(4-Bromo-2-chloro-phenyl)-propionyl]-1-methyl-1H-pyrido[2,3-b][1,4]oxazin-2-one In analogy to Example 1, step 2, 7-[2-(4-bromo-2-chloro-phenyl)-acetyl]-1-methyl-1H-pyrido[2,3-b][1,4]oxazin-2-one was reacted with sodium hydride and methyl iodide to give the title compound as a light yellow oil. MS (m/e, ISP neg. ion)=407.2 [M−H$^+$].

Step 7: 7-[2-(4-Bromo-2-chloro-phenyl)-1-hydroxy-1-trifluoromethyl-propyl]-1-methyl-1H-pyrido[2,3-b][1,4]oxazin-2-one In analogy to Example 1, step 3, 7-[2-(4-bromo-2-chloro-phenyl)-propionyl]-1-methyl-1H-pyrido[2,3-b][1,4]oxazin-2-one was reacted with (trifluoromethyl)trimethylsilane and tetramethylammonium fluoride to give the title compound as a colorless solid. MS (m/e, ISP neg. ion)=477.0 [M−H$^+$].

Step 8: 3'-Chloro-3-fluoro-4'-[3,3,3-trifluoro-2-hydroxy-1-methyl-2-(1-methyl-2-oxo-2,3-dihydro-1H-pyrido[2,3-b][1,4]oxazin-7-yl)-propyl]-biphenyl-4-carboxylic acid methyl ester In analogy to Example 17, step 2, 7-[2-(4-bromo-2-chloro-phenyl)-1-hydroxy-1-trifluoromethyl-propyl]-1-methyl-1H-pyrido[2,3-b][1,4]oxazin-2-one was reacted with 3-fluoro-4-methoxycarbonylphenylboronic acid to give the title compound as a colorless solid. MS (m/e)=553.4 [M+H$^+$].

Example 52

3'-Chloro-3-fluoro-4'-[3,3,3-trifluoro-2-hydroxy-1-methyl-2-(1-methyl-2-oxo-2,3-dihydro-1H-pyrido[2,3-b][1,4]oxazin-7-yl)-propyl]-biphenyl-4-carboxylic acid

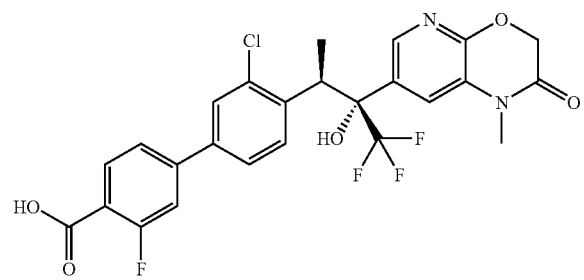

In analogy to Example 2, 3'-chloro-3-fluoro-4'-[3,3,3-trifluoro-2-hydroxy-1-methyl-2-(1-methyl-2-oxo-2,3-dihydro-1H-pyrido[2,3-b][1,4]oxazin-7-yl)-propyl]-biphenyl-4-carboxylic acid methyl ester (Example 51) was hydrolyzed to give the title compound as an off-white solid. MS (m/e, ISP neg. ion)=537.2 [M−H$^+$].

Example 53

3'-Chloro-3-fluoro-4'-[3,3,3-trifluoro-2-hydroxy-1-methyl-2-(4-methyl-3-oxo-3,4-dihydro-2H-benzo[1,4]oxazin-8-yl)-propyl]-biphenyl-4-carboxylic acid methyl ester

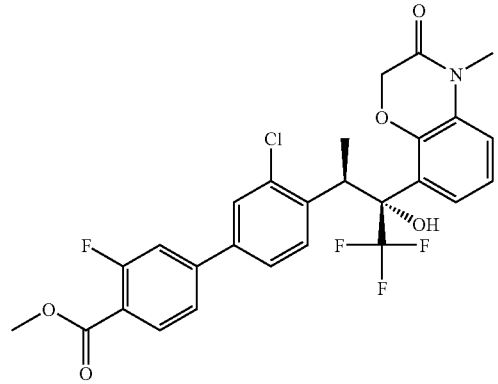

Step 1: 8-[2-(4-Bromo-2-chloro-phenyl)-acetyl]-4-methyl-4H-benzo[1,4]oxazin-3-one In analogy to Example 49, step 1, 4-methyl-3-oxo-3,4-dihydro-2H-benzo[1,4]oxazine-8-carboxylic acid (CAS Reg. No. 1017273-27-6) was converted to the acid chloride and subsequently reacted with 4-bromo-1-bromomethyl-2-chloro-benzene in the presence of zinc and tetrakis(triphenylphosphine)palladium(0) to give the title compound as a colorless solid. MS (m/e, ISP neg. ion)=392.1 [M–H⁺].

Step 2: 8-[2-(4-Bromo-2-chloro-phenyl)-propionyl]-4-methyl-4H-benzo[1,4]oxazin-3-one In analogy to Example 1, step 2, 8-[2-(4-bromo-2-chloro-phenyl)-acetyl]-4-methyl-4H-benzo[1,4]oxazin-3-one was reacted with sodium hydride and methyl iodide to give the title compound as an orange oil. MS (m/e)=408.3 [M+H⁺].

Step 3: 8-[2-(4-Bromo-2-chloro-phenyl)-1-hydroxy-1-trifluoromethyl-propyl]-4-methyl-4H-benzo[1,4]oxazin-3-one In analogy to Example 1, step 3, 8-[2-(4-bromo-2-chloro-phenyl)-propionyl]-4-methyl-4H-benzo[1,4]oxazin-3-one was reacted with (trifluoromethyl)trimethylsilane and tetramethylammonium fluoride to give the title compound as a colorless foam. MS (m/e, ISP neg. ion)=476 [M–H⁺].

Step 4: 3'-Chloro-3-fluoro-4'-[3,3,3-trifluoro-2-hydroxy-1-methyl-2-(4-methyl-3-oxo-3,4-dihydro-2H-benzo[1,4]oxazin-8-yl)-propyl]-biphenyl-4-carboxylic acid methyl ester In analogy to Example 17, step 2, 8-[2-(4-bromo-2-chloro-phenyl)-1-hydroxy-1-trifluoromethyl-propyl]-4-methyl-4H-benzo[1,4]oxazin-3-one was reacted with 3-fluoro-4-methoxycarbonylphenylboronic acid to give the title compound as a light yellow oil. MS (m/e)=552.3 [M+H⁺].

Example 54

3'-Chloro-3-fluoro-4'-[3,3,3-trifluoro-2-hydroxy-1-methyl-2-(4-methyl-3-oxo-3,4-dihydro-2H-benzo[1,4]oxazin-8-yl)-propyl]-biphenyl-4-carboxylic acid

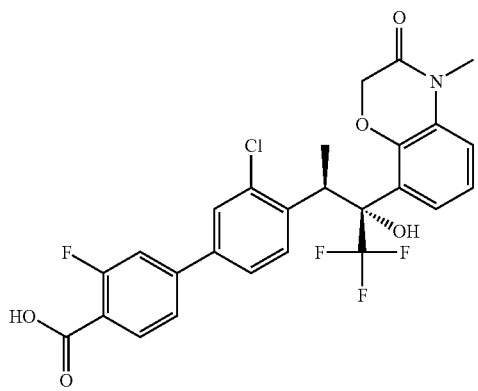

In analogy to Example 2, 3'-chloro-3-fluoro-4'-[3,3,3-trifluoro-2-hydroxy-1-methyl-2-(4-methyl-3-oxo-3,4-dihydro-2H-benzo[1,4]oxazin-8-yl)-propyl]-biphenyl-4-carboxylic acid methyl ester (Example 53) was hydrolyzed to give the title compound as a colorless solid. MS (m/e, ISP neg. ion)=536.1 [M–H⁺].

Example 56

5-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid

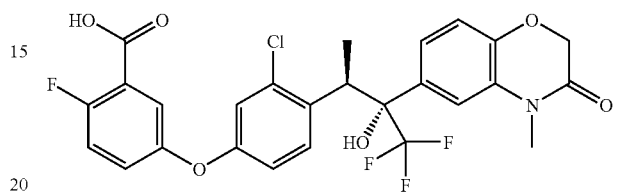

Step 1: 6-[2-(2-Chloro-4-methoxy-phenyl)-acetyl]-4-methyl-4H-benzo[1,4]oxazin-3-one To a solution of (2-chloro-4-methoxy-phenyl)-acetic acid (CAS Reg. No. 91367-09-8) (20 g, 100 mmol) in tetrahydrofuran (400 ml) were added N,N-dimethylformamide (1 ml) and oxalylchloride (20.2 g, 160 mmol) dropwise (15 min). The mixture was stirred overnight at room temperature. The solvent was evaporated; toluene was added and again evaporated. The residue was dried under high vacuum to give the crude acid chloride. To a cooled solution (ice bath) of 4-methyl-2H-1,4-benzoxazin-3(4H)-one (16.6 g, 100 mmol) in 1,2-dichloroethane (110 ml) was added AlCl₃ (39.9 g, 300 mmol). The mixture was stirred for 30 min and a solution of the acid chloride in 1, 2-dichloroethane (110 ml) was added dropwise during 1.2 h at 2° C. The mixture was stirred at 0° C. for 4.5 h. The mixture was poured into ice water and hydrochloric acid and extracted three times with dichloromethane. The organic phases were dried (MgSO₄), filtered and concentrated. The residue was dried under high vacuum for 17 h. The solid product was stirred with ethanol (180 ml) for 1.5 h at r.t., filtered off and dried under high vacuum to give the title compound (26.1 g) as an off-white solid. MS (m/e)=346.1 [M+H⁺].

Step 2: (RS)-6-[2-(2-Chloro-4-methoxy-phenyl)-propionyl]-4-methyl-4H-benzo[1,4]oxazin-3-one To a solution of 6-[2-(2-chloro-4-methoxy-phenyl)-acetyl]-4-methyl-4H-benzo[1,4]oxazin-3-one (5.9 g, 17 mmol) in tetrahydrofuran (380 ml) was added sodium hydride (60% dispersion in mineral oil, 0.72 g, 17.9 mmol). The mixture was stirred at room temperature for 1.5 h and then placed in an ice bath. A solution of methyl iodide (2.54 g, 17.9 mmol) in tetrahydrofuran (15 ml) was added dropwise (5 min) The ice bath was removed and the mixture was stirred at 35° C. for 3.5 h. The reaction mixture was poured on ice-water and extracted twice with AcOEt. The organic phases were washed with water and brine, dried (MgSO₄), filtered and concentrated. The product was purified by column chromatography (SiO₂, heptane/EtOAc 2:1) to give the title compound (3.3 g) as a light yellow foam. MS (m/e)=360.2 [M+H⁺].

Step 3: 6-[2-(2-Chloro-4-methoxy-phenyl)-1-hydroxy-1-trifluoromethyl-propyl]-4-methyl-4H-benzo[1,4]oxazin-3-one To a solution of (RS)-6-[2-(2-chloro-4-methoxy-phenyl)-propionyl]-4-methyl-4H-benzo[1,4]oxazin-3-one (5.56 g, 15.45 mmol) in tetrahydrofuran (280 ml) was added a solution of (trifluoromethyl)trimethylsilane (3.36 g, 23.2 mmol) in tetrahydrofuran (55 ml) dropwise (15 min) at 0° C. Tetramethylammonium fluoride (0.148 g, 1.55 mmol) was added and the mixture was stirred at 0° C. for 30 min. A 1 M solution of tetrabutylammonium fluoride in tetrahydrofuran (13.9 ml) was added dropwise and the mixture was stirred for 45 min at r.t. The reaction mixture was poured on ice-water and extracted twice with AcOEt. The organic phases were washed with water and brine, dried (MgSO$_4$), filtered and concentrated. The product was purified by column chromatography (SiO$_2$, heptane/EtOAc 4:1) to give the title compound (4.9 g) as a white semisolid. MS (m/e)=430.2 [M+H$^+$].

Step 4: 6-[2-(2-Chloro-4-hydroxy-phenyl)-1-hydroxy-1-trifluoromethyl-propyl]-4-methyl-4H-benzo[1,4]oxazin-3-one A solution of 6-[2-(2-chloro-4-methoxy-phenyl)-1-hydroxy-1-trifluoromethyl-propyl]-4-methyl-4H-benzo[1,4]oxazin-3-one (4.9 g, 11.4 mmol) in dichloromethane (130 ml) was cooled to −70° C. A 1 M solution of boron tribromide in dichloromethane (45.6 ml) was added dropwise (25 min) and the mixture was stirred at −70° C. for 1.5 h. The ice bath was removed and the mixture was stirred at r.t. for 3 h. The reaction mixture was poured on a mixture of ice water and sat aq NaHCO$_3$ solution, extracted three times with dichloromethane. The organic phases were washed with water and dried (MgSO$_4$) and concentrated. The product was dried under high vacuum to give the title compound (4.9 g) as an off-white solid. MS (m/e)=416.1 [M+H$^+$].

Step 5: 5-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid ethyl ester In analogy to Example 5, 6-[(2-chloro-4-hydroxy-phenyl)-1-hydroxy-1-trifluoromethyl-propyl]-4-methyl-4H-benzo[1,4]oxazin-3-one (63 mg) was reacted with 3-ethoxycarbonyl-4-fluorophenylboronic acid, copper-(II)-acetate and pyridine to give the title compound (25 mg) as a white solid. MS (m/e)=582.0 [M+H$^+$].

Step 6: 5-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid To a solution of 5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid ethyl ester (23 mg, 0.04 mmol) in tetrahydrofuran (0.085 ml) and methanol (0.085 ml) was added a 1 M aqueous LiOH solution (0.08 ml, 0.08 mmol) at 0° C. The mixture was stirred at 0° C. for 30 min and at room temperature for 2.5 h. The mixture was cooled in an ice bath and acidified using 1 M aqueous HCl. The mixture was concentrated. To the residue, water was added, extracted twice with AcOEt, the organic phases were washed with water, dried (MgSO$_4$) and concentrated to give the title compound (18 mg) as a white solid. MS (m/e, ISP neg. ion)=552.2 [M−H$^+$].

Example 57

4-{3-Chloro-4-[(3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid

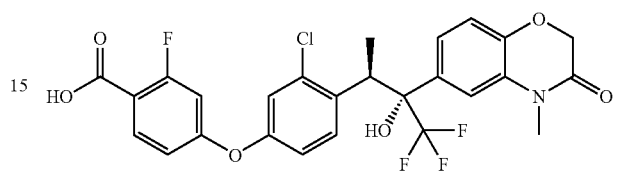

Step 1: 4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid methyl ester In analogy to Example 5, 6-[2-(2-chloro-4-hydroxy-phenyl)-1-hydroxy-1-trifluoromethyl-propyl]-4-methyl-4H-benzo[1,4]oxazin-3-one (Example 56, step 4) was reacted with 3-fluoro-4-methoxycarbonylphenylboronic acid, copper-(II)-acetate and pyridine to give the title compound as a white solid. MS (m/e, ISP neg. ion)=566.2 [M−H$^+$]

Step 2: 4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid In analogy to Example 56, step 6, 4-{3-chloro-4-[(3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid methyl ester was hydrolyzed to give the title compound as a white solid. MS (m/e)=554.3 [M+H$^+$].

Example 58

2-Chloro-5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid

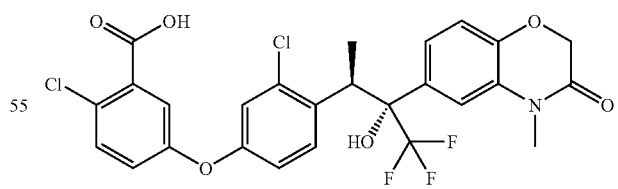

Step 1: 2-Chloro-5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid ethyl ester In analogy to Example 5, 6-[2-(2-chloro-4-hydroxy-phenyl)-1-hydroxy-1-trifluoromethyl-propyl]-4-methyl-4H- benzo[1,4]oxazin-3-one (Example 56, step 4) was reacted with 4-chloro-3-(ethoxycarbonyl)benzeneboronic acid, copper-(II)-acetate and pyridine to give the title compound as a off-white solid. MS (m/e, ISP neg. ion)=596.3 [M−H⁺]

Step 2: 2-Chloro-5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid In analogy to Example 56, step 6, 2-chloro-5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid ethyl ester was hydrolyzed to give the title compound as an off-white solid. MS (m/e)=570.2 [M+H⁺].

Example 59

2-Chloro-4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid

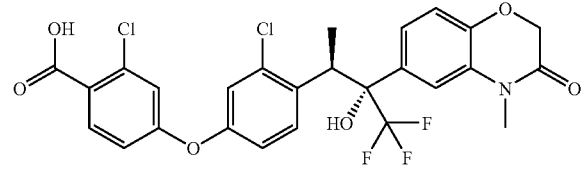

Step 1: 2-Chloro-4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester In analogy to Example 5, 6-[2-(2-chloro-4-hydroxy-phenyl)-1-hydroxy-1-trifluoromethyl-propyl]-4-methyl-4H-benzo[1,4]oxazin-3-one (Example 56, step 4) was reacted with 3-chloro-4-(methoxycarbonyl)phenylboronic acid, copper-(II)-acetate and pyridine to give the title compound as a white solid. MS (m/e, ISP neg. ion)=582.2 [M−H⁺]

Step 2: 2-Chloro-4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid In analogy to Example 56, step 6, 2-chloro-4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester was hydrolyzed to give the title compound as an off-white solid. MS (m/e, ISP neg. ion)=568.3 [M−H⁺].

Example 60

4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid

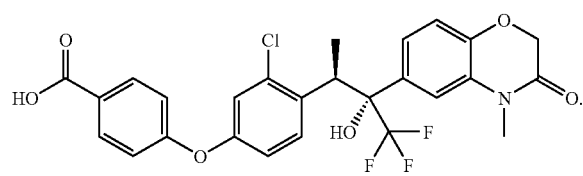

Step 1: 4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester In analogy to Example 5, 6-[2-(2-chloro-4-hydroxy-phenyl)-1-hydroxy-1-trifluoromethyl-propyl]-4-methyl-4H-benzo[1,4]oxazin-3-one (Example 56, step 4) was reacted with 4-methoxycarbonyl-phenylboronic acid, copper-(II)-acetate and pyridine to give the title compound as a white solid. MS (m/e, ISP neg. ion)=548.2 [M−H⁺]

Step 2: 4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid In analogy to Example 56, step 6, 4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester was hydrolyzed (21 h, r.t.) to give the title compound as a white solid. MS (m/e, ISP neg. ion)=534.1 [M−H⁺].

Example 61

3-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid

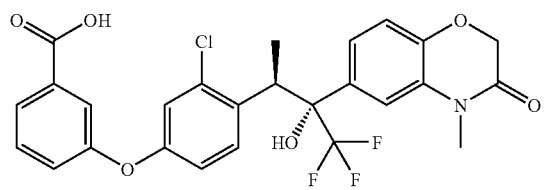

Step 1: 3-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester In analogy to Example 5, 6-[2-(2-chloro-4-hydroxy-phenyl)-1-hydroxy-1-trifluoromethyl-propyl]-4-methyl-4H-benzo[1,4]oxazin-3-one (Example 56, step 4) was reacted with 3-methoxycarbonyl-phenylboronic acid, copper-(II)-acetate and pyridine to give the title compound as a white solid. MS (m/e, ISP neg. ion)=548.2 [M−H⁺]

Step 2: 3-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid In analogy to Example 56, step 6, 3-{3-chloro-4-[-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester was hydrolyzed (5 h, r.t.) to give the title compound as a white solid. MS (m/e, ISP neg. ion)=534.1 [M–H⁺].

Example 62

6-{3-Chloro-4-[(3,3,3-trifluoro-2-hydroxy-1-methyl-2-(4-methyl-3-oxo-3,4-dihydro-2H-benzo[1,4]oxazin-6-yl)-propyl]-phenoxy}-4-trifluoromethyl-nicotinic acid

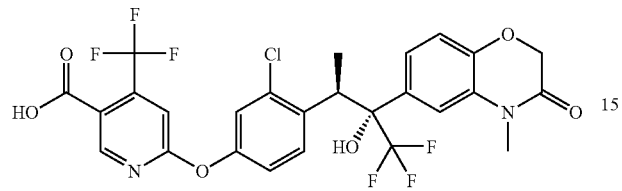

Step 1: 6-{3-Chloro-4-[(3,3,3-trifluoro-2-hydroxy-1-methyl-2-(4-methyl-3-oxo-3,4-dihydro-2H-benzo[1,4]oxazin-6-yl)-propyl]-phenoxy}-4-trifluoromethyl-nicotinic acid methyl ester To a solution of methyl-6-chloro-4-(trifluoromethyl)nicotinate (24 mg, 0.1 mmol) in N,N-dimethylformamide (0.5 ml) were added 6-[2-(2-chloro-4-hydroxy-phenyl)-1-hydroxy-1-trifluoromethyl-propyl]-4-methyl-4H-benzo[1,4]oxazin-3-one (Example 56, step 4, 42 mg, 0.1 mmol) and triethylamine (13 mg, 0.13 mmol). The solution was stirred at r.t. for 10 min. To the solution 1,4-diazabicyclo[2.2.2]octan (2 mg, 0.02 mmol) was added and the mixture was stirred for additional 4 h at r.t. The reaction mixture was poured in water and extracted twice with AcOEt. The combined organic phases were washed with brine, dried over MgSO₄ and concentrated. The crude product was purified by flash chromatography (silica gel, heptane/AcOEt 4:1) to give the title compound (58 mg) as a light yellow solid. MS (m/e)=619.2 [M+H⁺].

Step 2: 6-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-4-trifluoromethyl-nicotinic acid In analogy to Example 56, step 6, 6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-4-trifluoromethyl-nicotinic acid methyl ester was hydrolyzed (6 h, r.t.) and purified by column chromatography (silica gel, AcOEt) to give the title compound as a white solid. MS (m/e, ISP neg. ion)=605.2 [M–H⁺].

Example 63

2-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid

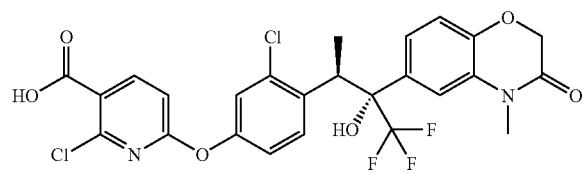

Step 1: 2-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester In analogy to Example 62, step 1, 6-[2-(2-chloro-4-hydroxy-phenyl)-1-hydroxy-1-trifluoromethyl-propyl]-4-methyl-4H-benzo[1,4]oxazin-3-one (Example 56, step 4) was reacted with methyl-2,6-dichloro-pyridine-3-carboxylate and DABCO to give the title compound as a white solid. MS (m/e)=585.2 [M+H⁺]

Step 2: 2-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid In analogy to Example 56, step 6, 2-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester was hydrolyzed (2.5 h, r.t.) to give the title compound as a white solid. MS (m/e)=571.2 [M+H⁺].

Example 64

3,3'-Dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-4-carboxylic acid

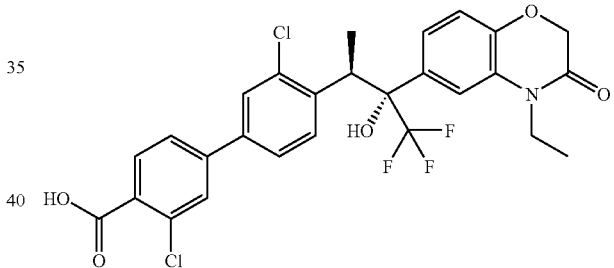

Step 1: 4-Ethyl-4H-benzo[1,4]oxazin-3-one

To a cooled solution of 2H-1,4-benzoxazin-3(4H)-one (11.93 g, 80 mmol) in N,N-dimethylformamide (120 ml) was added sodium hydride (60% dispersion in mineral oil, 3.2 g, 80 mmol) in portions between 0° C. and 5° C. (1 h). The mixture was stirred 1 h at 0° C. To the cooled mixture was added ethyl iodide (13.7 g, 88 mmol) dropwise. The ice bath was removed and the mixture was stirred at r.t. for 17 h. The mixture was poured on water and extracted twice with AcOEt. The organic layers were washed with brine and water, dried (MgSO₄) and concentrated. The crude product was purified by column chromatography (silica gel, heptane/AcOEt 9:1) to give the title compound (13.3 g) as colorless oil.

Step 2: 6-[2-(2-Chloro-4-methoxy-phenyl)-acetyl]-4-ethyl-4H-benzo[1,4]oxazin-3-one In analogy to Example 56, step 1, 4-ethyl-4H-benzo[1,4]oxazin-3-one (10.2 g) was reacted with (2-chloro-4-methoxy-phenyl)-acetyl chloride and AlCl₃ in 1,2-dichloroethane 3 h at 0° C. The crude product was purified by column chromatography (silica gel, heptane/AcOEt 2:1) to give the title compound (12.3 g) as a white solid. MS (m/e)=360.1 [M+H⁺]

Step 3: 6-[2-(2-Chloro-4-methoxy-phenyl)-propionyl]-4-ethyl-4H-benzo[1,4]oxazin-3-one In analogy to Example 56, step 2, 6-[2-(2-chloro-4-methoxy-phenyl)-acetyl]-4-ethyl-4H-benzo[1,4]oxazin-3-one (7.7 g) was reacted with methyl iodide at r.t. for 5.5 h. The product was purified by column chromatography (silica gel, heptane/AcOEt 2:1) to give the title compound (5.1 g) as a white solid. MS (m/e)=374.1 [M+H⁺]

Step 4: 6-[2-(2-Chloro-4-methoxy-phenyl)-1-hydroxy-1-trifluoromethyl-propyl]-4-ethyl-4H-benzo[1,4]oxazin-3-one In analogy to Example 56, step 3, 6-[2-(2-chloro-4-methoxy-phenyl)-propionyl]-4-ethyl-4H-benzo[1,4]oxazin-3-one (1.58 g) was reacted with (trifluoromethyl)-trimethylsilane. The product was purified by flash chromatography (silica gel, heptane/AcOEt 2:1) to give the title compound (1.58 g) as a white solid. MS (m/e)=444.3 [M+H⁺]

Step 5: 6-[2-(2-Chloro-4-hydroxy-phenyl)-1-hydroxy-1-trifluoromethyl-propyl]-4-ethyl-4H-benzo[1,4]oxazin-3-one In analogy to Example 56, step 4, 6-[2-(2-chloro-4-methoxy-phenyl)-1-hydroxy-1-trifluoromethyl-propyl]-4-ethyl-4H-benzo[1,4]oxazin-3-one (1.58 g) was reacted with 1M solution boron tribromide in dichloromethane, to give the title compound (1.57 g) as a light yellow solid. MS (m/e)=430.2 [M+H⁺].

Step 6: Trifluoromethanesulfonic acid 3-chloro-4-[2-(4-ethyl-3-oxo-3,4-dihydro-2H-benzo[1,4]oxazin-6-yl)-3,3,3-trifluoro-2-hydroxy-1-methyl-propyl]-phenyl ester 6-[2-(2-Chloro-4-hydroxy-phenyl)-1-hydroxy-1-trifluoromethyl-propyl]-4-ethyl-4H-benzo[1,4]oxazin-3-one (1.97 g, 4.59 mmol) in dichloromethane (75 ml) was treated with triethyl amine (1.07 g, 10.5 mmol), cooled down to −20° C. and treated with trifluoromethanesulfonic anhydride (1.55 g, 5.5 mmol) in 10 minutes. The reaction mixture was stirred at −20° C. for 15 min. and 3 h at r.t., followed by dilution with dichloromethane (75 ml). The organic phase was washed with 1M aq HCl, water and brine, dried over MgSO₄ and concentrated under vacuum. The solid residue was dried under high vacuum leading to the title compound (2.45 g) as a light yellow solid. MS (m/e)=562.1 (M+H⁺)

Step 7: 3,3'-Dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-4-carboxylic acid methyl ester Trifluoromethanesulfonic acid 3-chloro-4-[2-(4-ethyl-3-oxo-3,4-dihydro-2H-benzo[1,4]oxazin-6-yl)-3,3,3-trifluoro-2-hydroxy-1-methyl-propyl]-phenyl ester (150 mg, 0.27 mmol), 3-chloro-4-(methoxycarbonyl)phenylboronic acid (86 mg, 0.4 mmol) and 1,1, bis(diphenylphosphino)-ferrocenpalladium(II)dichloromethane (11 mg, 0.05% mol) in dioxane (0.8 ml) was treated with water (0.6 ml) and 1M-Na₂CO₃ (0.4 ml, 0.4 mmol) and stirred at 70° C. under argon for 6.5 h. The reaction mixture was cooled down to r.t.,
diluted with ethyl acetate, washed with water and brine, dried over MgSO₄ and concentrated under vacuum. The residue was purified by column chromatography (10 g silica gel, heptane/AcOEt 4:1) to give the title compound (112 mg) as a white solid. MS (m/e)=582.3 [M+H⁺]

Step 8: 3,3'-Dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-4-carboxylic acid In analogy to Example 56, Step 6, 3,3'-dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-4-carboxylic acid methyl ester (110 mg, 0.19 mmol) was hydrolyzed (3 h, 65° C.). The product was treated with heptane for 17 h, filtered and dried to give the title compound as a white solid. MS (m/e, ISP neg. ion)=566.2 [M−H⁺].

Example 65

3'-Chloro-4'-[2-(4-ethyl-3-oxo-3,4-dihydro-2H-benzo[1,4]oxazin-6-yl)-3,3,3-trifluoro-2-hydroxy-1-methyl-propyl]-3-fluoro-biphenyl-4-carboxylic acid

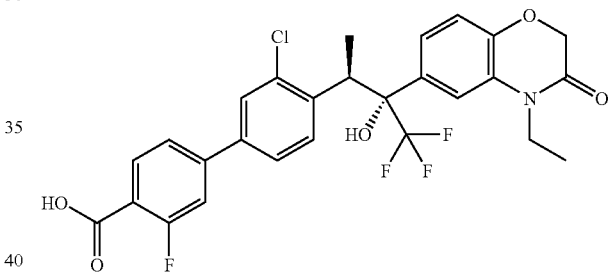

Step 1: 3'-Chloro-4'-[2-(4-ethyl-3-oxo-3,4-dihydro-2H-benzo[1,4]oxazin-6-yl)-3,3,3-trifluoro-2-hydroxy-1-methyl-propyl]-3-fluoro-biphenyl-4-carboxylic acid methyl ester In analogy to Example 64, step 7, trifluoromethanesulfonic acid 3-chloro-4-[2-(4-ethyl-3-oxo-3,4-dihydro-2H-benzo[1,4]oxazin-6-yl)-3,3,3-trifluoro-2-hydroxy-1-methyl-propyl]-phenyl ester (Example 64, step 6) was reacted with 3-fluoro-4-(methoxycarbonyl)phenylboronic acid (70° C., 5.5 h) to give the title compound as a white solid. MS (m/e)=566.3 [M+H⁺].

Step 2: 3'-Chloro-4'-[2-(4-ethyl-3-oxo-3,4-dihydro-2H-benzo[1,4]oxazin-6-yl)-3,3,3-trifluoro-2-hydroxy-1-methyl-propyl]-3-fluoro-biphenyl-4-carboxylic acid In analogy to Example 56, step 6, 3'-chloro-4'-[2-(4-ethyl-3-oxo-3,4-dihydro-2H-benzo[1,4]oxazin-6-yl)-3,3,3-trifluoro-2-hydroxy-1-methyl-propyl]-3-fluoro-biphenyl-4-carboxylic acid methyl ester was hydrolyzed (3 h, 65° C.). The

Example 66

4,3'-Dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-3-carboxylic acid

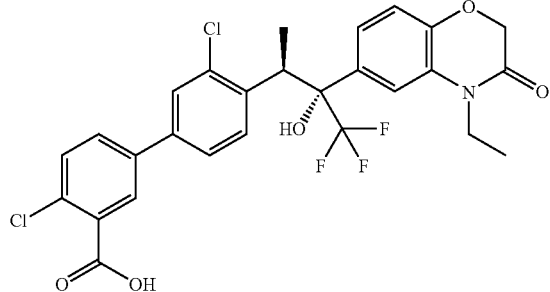

Step 1: 4,3'-Dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-3-carboxylic acid methyl ester In analogy to Example 64, step 7, trifluoromethanesulfonic acid 3-chloro-4-[2-(4-ethyl-3-oxo-3,4-dihydro-2H-benzo[1,4]oxazin-6-yl)-3,3,3-trifluoro-2-hydroxy-1-methyl-propyl]-phenyl ester (Example 64, step 6) was reacted with 4-chloro-3-(ethoxycarbonyl)phenylboronic acid (70° C., 5.5 h) to give title compound as a white solid. MS (m/e)=596.3 [M+H⁺].

Step 2: 4,3'-Dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-3-carboxylic acid In analogy to Example 56, step 6, 4,3'-Dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-3-carboxylic acid methyl ester was hydrolyzed (3 h, 65° C.). The product was treated with heptane for 17 h, filtered and dried to give the title compound as a white solid. MS (m/e, ISP neg. ion)=566.2 [M−H⁺].

Example 67

3'-Chloro-4'-[2-(4-ethyl-3-oxo-3,4-dihydro-2H-benzo[1,4]oxazin-6-yl)-3,3,3-trifluoro-2-hydroxy-1-methyl-propyl]-4-fluoro-biphenyl-3-carboxylic acid

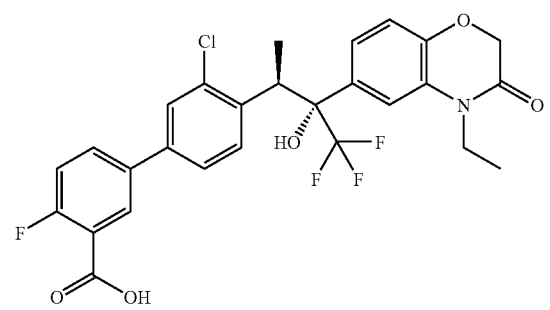

Step 1: 3'-Chloro-4'-[2-(4-ethyl-3-oxo-3,4-dihydro-2H-benzo[1,4]oxazin-6-yl)-3,3,3-trifluoro-2-hydroxy-1-methyl-propyl]-4-fluoro-biphenyl-3-carboxylic acid ethyl ester In analogy to Example 64, step 7, trifluoromethanesulfonic acid 3-chloro-4-[2-(4-ethyl-3-oxo-3,4-dihydro-2H-benzo[1,4]oxazin-6-yl)-3,3,3-trifluoro-2-hydroxy-1-methyl-propyl]-phenyl ester (Example 64, step 6) was reacted with 4-fluoro-3-(ethoxycarbonyl)phenylboronic acid (70° C., 5 h) to give title compound as a white solid. MS (m/e)=580.3 [M+H⁺].

Step 2: 3'-Chloro-4'-[2-(4-ethyl-3-oxo-3,4-dihydro-2H-benzo[1,4]oxazin-6-yl)-3,3,3-trifluoro-2-hydroxy-1-methyl-propyl]-4-fluoro-biphenyl-3-carboxylic acid In analogy to Example 56, step 6, 3'-chloro-4'-[2-(4-ethyl-3-oxo-3,4-dihydro-2H-benzo[1,4]oxazin-6-yl)-3,3,3-trifluoro-2-hydroxy-1-methyl-propyl]-4-fluoro-biphenyl-3-carboxylic acid ethyl ester was hydrolyzed (3 h, 65° C.) to give the title compound as an off-white solid. MS (m/e, ISP neg. ion)=550.2 [M−H⁺].

Example 68

6-{3-Chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-4-trifluoromethyl-nicotinic acid

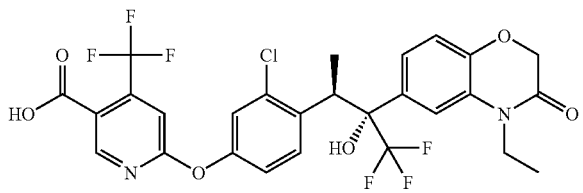

Step 1: 6-{3-Chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-4-trifluoromethyl-nicotinic acid methyl ester In analogy to Example 62, step 1, 6-[2-(2-chloro-4-hydroxy-phenyl)-1-hydroxy-1-trifluoromethyl-propyl]-4-ethyl-4H-benzo[1,4]oxazin-3-one (Example 64, step 5) was reacted with methyl-6-chloro-4-(trifluoromethyl)nicotinate and DABCO to give the title compound as a white solid. MS (m/e)=633.4 [M+H⁺].

Step 2: 6-{3-Chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-4-trifluoromethyl-nicotinic acid In analogy to Example 56, step 6, 6-{3-chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-4-trifluoromethyl-nicotinic acid methyl ester was hydrolyzed (2.5 h, 0° C. and 1 h r.t.). The crude product was purified by chromatography (silica gel, heptane/AcOEt 1:1) to give the title compound as a white solid. MS (m/e)=619.3 [M+H⁺].

Example 69

2-Chloro-6-{3-chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-nicotinic acid

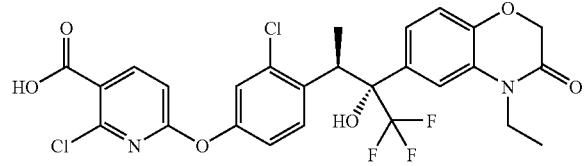

Step 1: 2-Chloro-6-{3-chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-nicotinic acid methyl ester In analogy to Example 62 step 1, 6-[2-(2-chloro-4-hydroxy-phenyl)-1-hydroxy-1-trifluoromethyl-propyl]-4-ethyl-4H-benzo[1,4]oxazin-3-one (Example 64, step 5) was reacted with methyl-2,6-dichloro-pyridine-3-carboxylate and DABCO (21 h, r.t.) to give the title compound as a white solid. MS (m/e)=599.3 [M+H⁺].

Step 2: 2-Chloro-6-{3-chloro-4-[-2-(4-ethyl-3-oxo-3,4-dihydro-2H-benzo[1,4]oxazin-6-yl)-3,3,3-trifluoro-2-hydroxy-1-methyl-propyl]-phenoxy}-nicotinic acid In analogy to Example 56, step 6, 2-chloro-6-{3-chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-nicotinic acid methyl ester was hydrolyzed (2.5 h, r.t.) to give the title compound as a white solid. MS (m/e)=585.2 [M+H⁺].

Example 70

4'-[2-(4-Allyl-3-oxo-3,4-dihydro-2H-benzo[1,4]oxazin-6-yl)-3,3,3-trifluoro-2-hydroxy-1-methyl-propyl]-3'-chloro-3-fluoro-biphenyl-4-carboxylic acid methyl ester

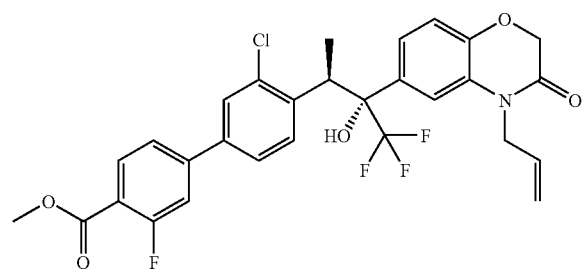

Step 1: 4-Allyl-4H-benzo[1,4]oxazin-3-one

In analogy to Example 64, step 1, 2H-1,4-benzoxazin-3(4H)-one (15 g) was reacted with 3-bromo-propene to give the title compound (17.4 g) as a colorless oil. MS (m/e)=190.3 [M+H⁺].

Step 2: 4-Allyl-6-[2-(2-chloro-4-methoxy-phenyl)-acetyl]-4H-benzo[1,4]oxazin-3-one In analogy to Example 56, step 1, 4-allyl-4H-benzo[1,4]oxazin-3-one (18.8 g) was reacted with (2-chloro-4-methoxy-phenyl)-acetyl chloride and AlCl₃ in 1,2-dichloroethane 3 h at 0° C. The crude product was purified by column chromatography (silica gel, heptane/AcOEt 6:1) to give the title compound (10.6 g) as a white solid. MS (m/e)=372.2 [M+H⁺].

Step 3: 4-Allyl-6-[2-(2-chloro-4-methoxy-phenyl)-propionyl]-4H-benzo[1,4]oxazin-3-one In analogy to Example 56, step 2, 4-allyl-6-[2-(2-chloro-4-methoxy-phenyl)-acetyl]-4H-benzo[1,4]oxazin-3-one (8.9 g) was reacted with methyl iodide at r.t. for 2 h. The crude product was treated with ethanol (25 ml), filtered and dried under high vacuum to give the title compound (7.2 g) as a light yellow solid. MS (m/e)=386.2 [M+H⁺].

Step 4: 4-Allyl-6-[2-(2-chloro-4-methoxy-phenyl)-1-hydroxy-1-trifluoromethyl-propyl]-4H-benzo[1,4]oxazin-3-one In analogy to Example 56, step 3, 4-allyl-6-[2-(2-chloro-4-methoxy-phenyl)-propionyl]-4H-benzo[1,4]oxazin-3-one (7.2 g) was reacted with (trifluoromethyl)-trimethylsilane. The product was purified by crystallization with heptane/AcOEt (4:1) to give the title compound (4.45 g) as an off-white solid. MS (m/e)=456.3 [M+H⁺].

Step 5: 4-Allyl-6-[2-(2-chloro-4-hydroxy-phenyl)-1-hydroxy-1-trifluoromethyl-propyl]-4H-benzo[1,4]oxazin-3-one In analogy to Example 56, step 4, 4-allyl-6-[2-(2-chloro-4-methoxy-phenyl)-1-hydroxy-1-trifluoromethyl-propyl]-4H-benzo[1,4]oxazin-3-one (2.5 g) was reacted with a 1M of solution boron tribromide in dichloromethane, to give the title compound (2.3 g) as a light yellow foam. MS (m/e)=442.3 [M+H⁺].

Step 6: Trifluoromethanesulfonic acid 4-[2-(4-allyl-3-oxo-3,4-dihydro-2H-benzo[1,4]oxazin-6-yl)-3,3,3-trifluoro-2-hydroxy-1-methyl-propyl]-3-chloro-phenyl ester In analogy to Example 64, step 6, 4-allyl-6-[2-(2-chloro-4-hydroxy-phenyl)-1-hydroxy-1-trifluoromethyl-propyl]-4H-benzo[1,4]oxazin-3-one (2.53 g) was reacted with trifluoromethansulfonic anhydride in dichloromethane. The product was treated with heptane, filtered and dried under high vacuum to give the title compound (2.65 g) as an off-white solid. MS (m/e)=574.2 [M+H⁺].

Step 7: 4'-[2-(4-Allyl-3-oxo-3,4-dihydro-2H-benzo[1,4]oxazin-6-yl)-3,3,3-trifluoro-2-hydroxy-1-methyl-propyl]-3'-chloro-3-fluoro-biphenyl-4-carboxylic acid methyl ester In analogy to Example 64, step 7, trifluoromethanesulfonic acid 4-[2-(4-allyl-3-oxo-3,4-dihydro-2H-benzo[1,4]oxazin- 6-yl)-3,3,3-trifluoro-2-hydroxy-1-methyl-propyl]-3-chlorophenyl ester (58 mg) was reacted with (3-fluoro-4-methoxycarbonyl)boronic acid (80° C., 17 h) to give title compound (19 mg) as a colorless amorphous solid. MS (m/e)=578.1 [M+H$^+$].

Example 71

3'-Chloro-3-fluoro-4'-[3,3,3-trifluoro-2-hydroxy-1-methyl-2-(3-oxo-3,4-dihydro-2H-benzo[1,4]oxazin-6-yl)-propyl]-biphenyl-4-carboxylic acid methyl ester

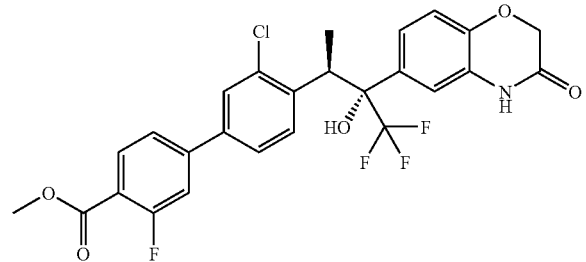

To a suspension of 3'-chloro-3-fluoro-4'-[3,3,3-trifluoro-2-hydroxy-1-methyl-2-(3-oxo-3,4-dihydro-2H-benzo[1,4]oxazin-6-yl)-propyl]-biphenyl-4-carboxylic acid methyl ester (255 mg, 0.44 mmol, Example 70, step 7) in n-propanol (5 ml) was added rhodium(III)chloride (10 mg, 0.04 mmol). The mixture was stirred under reflux for 18 h. The reaction mixture was concentrated. The crude product was purified by flash chromatography (silica gel, heptane/AcOEt 8:2=>7:3) to give the title compound (68 mg) as a white solid. MS (m/e)=538.3 [M+H$^+$].

Example 72

3'-Chloro-3-fluoro-4'-[3,3,3-trifluoro-2-hydroxy-1-methyl-2-(3-oxo-3,4-dihydro-2H-benzo[1,4]oxazin-6-yl)-propyl]-biphenyl-4-carboxylic acid

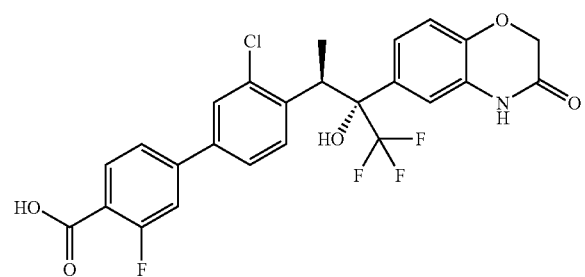

In analogy to Example 56, step 6, 3'-chloro-3-fluoro-4'-[3,3,3-trifluoro-2-hydroxy-1-methyl-2-(3-oxo-3,4-dihydro-2H-benzo[1,4]oxazin-6-yl)-propyl]-biphenyl-4-carboxylic acid methyl ester was hydrolyzed (2 h, 55° C.) to give the title compound as a white solid. MS (m/e)=522.4 [M+H$^+$].

Example 73

3'-Chloro-4'-[2-(1,3-dimethyl-2-oxo-2,3-dihydro-1H-benzoimidazol-5-yl)-3,3,3-trifluoro-2-hydroxy-1-methyl-propyl]-3-fluoro-biphenyl-4-carboxylic acid

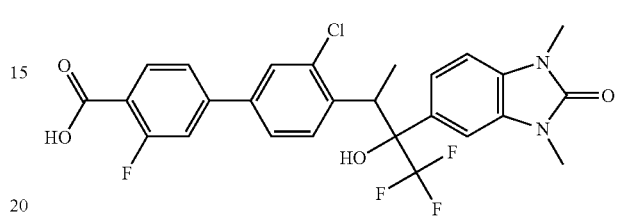

Step 1: 2-(4-Bromo-2-chloro-phenyl)-propionaldehyde

Potassium tert-butoxide (7.53 g) was added to a solution 2-chloro-4-bromoacetophenone (CAS Reg. No. 252561-81-2, 10.45 g) and (methoxymethyl)-triphenylphosphosium chloride (21.48 g) in THF (100 ml) at room temperature. The mixture was stirred for 1 h at room temperature. 25% aqueous HCl (90 ml) was added. The resulting mixture was stirred 1 h at room temperature and poured then carefully to a saturated aqueous NaHCO$_3$ solution. After neutralization, the mixture was extracted with EtOAc. The combined organic layers were dried over Na$_2$SO$_4$ and then concentrated to an oil. The residue was purified by flash chromatography (SiO$_2$, EtOAc/heptane 1:4) to give the title compound (8.1 g) as a yellow oil. MS (m/e, ISP neg. ion)=247.2 [M–H$^+$].

Step 2: 5-Bromo-1,3-dihydro-benzoimidazol-2-one 1,1'-Carbonyldiimidazole (2.1 g) in NMP (5 ml) was added to a solution of 4-bromo-o-phenylenediamine (CAS Reg. No. 1575-37-7, 2 g) in NMP (5 ml). The mixture was heated to 100° C. for 2 h and then allowed to cool to 60° C. MeOH (3 ml) was added, and the mixture was allowed to cool to room temperature. Water (50 ml) was added. The mixture was filtered. The residue was washed with isopropanol and then dried in vacuo to give the title compound (1.65 g) as a dark brown solid. MS (m/e, ISP neg. ion)=213.1 [M–H$^+$].

Step 3: 5-Bromo-1,3-dimethyl-1,3-dihydro-benzoimidazol-2-one

Iodomethane (2.41 g) was added to a suspension of 5-bromo-1,3-dihydro-benzoimidazol-2-one (1.65 g) and potassium tert-butoxide (1.91 g) in DMA (20 ml). The mixture was stirred overnight at room temperature. The mixture was poured to 2.5N aqueous HCl (80 ml) and extracted with EtOAc. The combined organic layers were dried over Na$_2$SO$_4$ and then concentrated in vacuo. Heptane (50 ml) was added to the residue and the mixture was filtered. The residue was washed with diethyl ether and dried in vacuo to give the title compound (1.1 g) as a light brown solid. MS (m/e)=241.1 [M+H$^+$].

Step 4: 5-[2-(4-Bromo-2-chloro-phenyl)-1-hydroxy-propyl]-1,3-dimethyl-1,3-dihydro-benzoimidazol-2-one A 1.6M solution of n-BuLi in hexanes (0.62 ml) was added at −78° C. to a solution of 5-bromo-1,3-dimethyl-1,3-dihydro-benzoimidazol-2-one (241 mg) in THF at (10 ml). The gray suspension was stirred for 10 min, then a solution of 2-(4-bromo-2-chloro-phenyl)-propionaldehyde (248 mg) in THF (2 ml) was added. The mixture was stirred for 10 min at −78° C. and then warmed to room temperature. Water (25 ml) was added and extracted with DCM. The combined organic layers were dried over $Na_2SO_4$ and concentrated to an oil. The residue was purified by flash chromatography ($SiO_2$, 0 to 100% EtOAc/heptane) to give the title compound (194 mg) as a colorless oil. MS (m/e)=409.1 [M+H$^+$].

Step 5: 5-[2-(4-Bromo-2-chloro-phenyl)-propionyl]-1,3-dimethyl-1,3-dihydro-benzoimidazol-2-one 4-Methyl-morpholine-4-oxide (280 mg) and tetrapropylammonium perruthenate (36 mg) were added to a solution of 5-[2-(4-bromo-2-chloro-phenyl)-1-hydroxy-propyl]-1,3-dimethyl-1,3-dihydro-benzoimidazol-2-one (424 mg) in DCM (5 ml) with 3A molecular sieves. The mixture was stirred for 3 h at room temperature, filtered over $SiO_2$ (10 g) and concentrated to give the title compound (410 mg) as a white foam. MS (m/e)=409.1 [M+H$^+$].

Step 6: 5-[2-(4-Bromo-2-chloro-phenyl)-1-hydroxy-1-trifluoromethyl-propyl]-1,3-dimethyl-1,3-dihydro-benzoimidazol-2-one Tetrabutylammonium fluoride trihydrate (31 mg) was added to a solution of (trifluoromethyl)trimethylsilane (1 ml of a 2M solution in THF) and 5-[2-(4-bromo-2-chloro-phenyl)-propionyl]-1,3-dimethyl-1,3-dihydro-benzoimidazol-2-one (410 mg) in THF (20 ml) at room temperature. The mixture was stirred for 30 min at room temperature. MeOH (1 ml) and 1M tetrabutylammonium fluoride in THF (1 ml) were added and the mixture was stirred 1 h at room temperature. Water (50 ml) was added and extracted with EtOAc. The combined organic layers were dried over $Na_2SO_4$ and concentrated to an oil. The residue was purified by flash chromatography ($SiO_2$, 0 to 100% EtOAc/heptane) to give the title compound (400 mg) as a colorless oil. MS (m/e)=479.0 [M+H$^+$].

Step 7: 3′-Chloro-4′-[2-(1,3-dimethyl-2-oxo-2,3-dihydro-1H-benzoimidazol-5-yl)-3,3,3-trifluoro-2-hydroxy-1-methyl-propyl]-3-fluoro-biphenyl-4-carboxylic acid A mixture of 5-[2-(4-bromo-2-chloro-phenyl)-1-hydroxy-1-trifluoromethyl-propyl]-1,3-dimethyl-1,3-dihydro-benzoimidazol-2-one (40 mg), dichloro[1,1′-bis(diphenylphosphino)ferrocene]palladium(II) (7 mg), $Cs_2CO_3$ (82 mg) and 3-fluoro-4-methoxycarbonylphenylboronic acid (CAS Reg. No. 505083-04-5, 33 mg) in dioxane (2 ml) was heated at 80° C. for 20 min in a sealed tube. 1N aqueous LiOH solution (1 ml) was added and stirred for 20 min at room temperature. The mixture was acidified with HCOOH and then purified by prep. HPLC (C18-column, solvent gradient 30-98% $CH_3CN$ in 0.1% HCOOH[aq]) to give the title compound (32 mg) as a yellow solid. MS (m/e)=537.2[M+H$^+$].

Example 74

3′-Chloro-4′-[2-(1,3-dimethyl-2-oxo-2,3-dihydro-1H-benzoimidazol-5-yl)-3,3,3-trifluoro-2-hydroxy-1-methyl-propyl]-4-fluoro-biphenyl-3-carboxylic acid

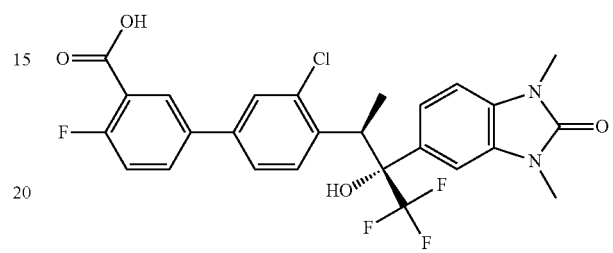

The title compound was prepared in analogy to Example 73 step 7 from 3-ethoxycarbonyl-4-fluorophenylboronic acid (CAS Reg. No. 874219-36-0). MS (m/e)=537.2 [M+H$^+$].

Example 75

{3′-Chloro-4′-[2-(1,3-dimethyl-2-oxo-2,3-dihydro-1H-benzoimidazol-5-yl)-3,3,3-trifluoro-2-hydroxy-1-methyl-propyl]-biphenyl-4-yloxy}-acetic acid

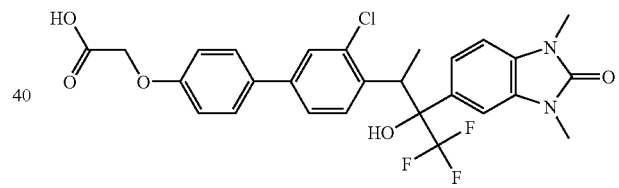

The title compound was prepared in analogy to Example 73 step 7 from ethylphenoxyacetate-4-boronic acid pinacol ester (CAS Reg. No. 269410-28-8). MS (m/e)=549.2 [M+H$^+$]

Example 76

3,3′-Dichloro-4′-[2-(1,3-dimethyl-2-oxo-2,3-dihydro-1H-benzoimidazol-5-yl)-3,3,3-trifluoro-2-hydroxy-1-methyl-propyl]-biphenyl-4-carboxylic acid

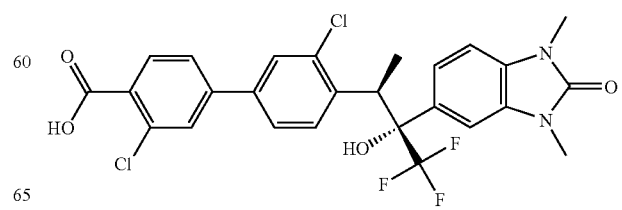

The title compound was prepared in analogy to Example 73 step 7 from (3-chloro-4-methoxycarbonyl)benzeneboronic acid (CAS Reg. No. 603122-82-3). MS (m/e)=553.1 [M+H⁺].

Example 77

3'-Chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-carboxylic acid

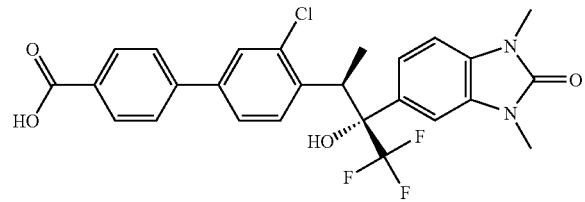

The title compound was prepared in analogy to Example 73 step 7 from (4-methoxycarbonylphenyl)boronic acid (CAS Reg. No. 99768-12-4). MS (m/e)=519.2 [M+H⁺].

Example 78

3'-Chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-3-carboxylic acid

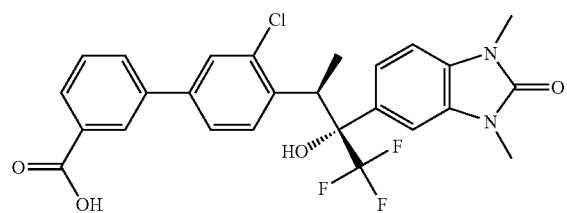

The title compound was prepared in analogy to Example 73 step 7 from 3-methoxycarbonylphenylboronic acid (CAS Reg. No. 99769-19-4). MS (m/e)=519.2 [M+H⁺].

Example 79

4,3'-Dichloro-4'-[2-(1,3-dimethyl-2-oxo-2,3-dihydro-1H-benzoimidazol-5-yl)-3,3,3-trifluoro-2-hydroxy-1-methyl-propyl]-biphenyl-3-carboxylic acid

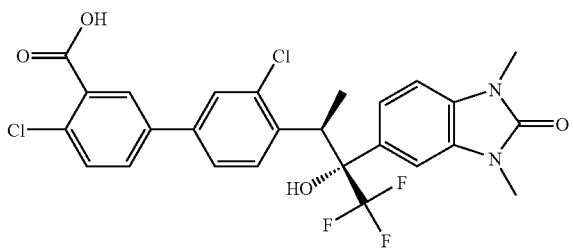

The title compound was prepared in analogy to Example 73 step 7 from 4-chloro-3-(ethoxycarbonyl)benzeneboronic acid (CAS Reg. No. 874219-46-2). MS (m/e)=553.2 [M+H⁺].

Example 80

3'-Chloro-4'-[2-(1,3-dimethyl-2-oxo-2,3-dihydro-1H-benzoimidazol-5-yl)-3,3,3-trifluoro-2-hydroxy-1-methyl-propyl]-3-methoxy-biphenyl-4-carboxylic acid

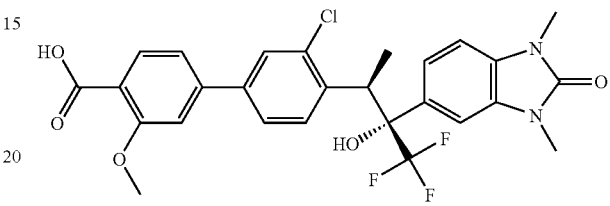

The title compound was prepared in analogy to Example 73 step 7 from 3-methoxy-4-methoxycarbonylphenylboronic acid (CAS Reg. No. 603122-41-4). MS (m/e)=549.2 [M+H⁺].

Example 81

2,3'-Dichloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-carboxylic acid

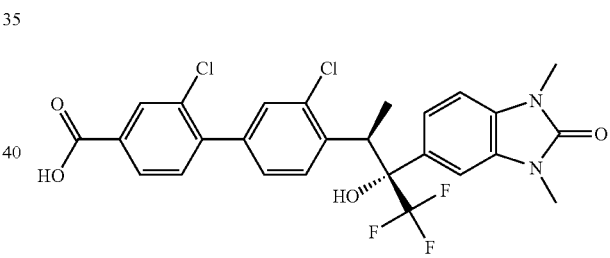

The title compound was prepared in analogy to Example 73 step 7 from 2-chloro-4-(methoxycarbonyl)benzeneboronic acid (CAS Reg. No. 603122-80-1). MS (m/e)=553.1 [M+H⁺].

Example 82

{3'-Chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-yl}-acetic acid

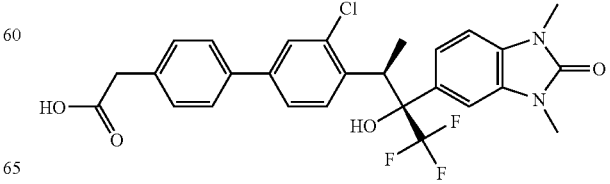

Step 1: {3'-Chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-yl}-acetonitrile A mixture of 5-[2-(4-bromo-2-chloro-phenyl)-1-hydroxy-1-trifluoromethyl-propyl]-1,3-dimethyl-1,3-dihydro-benzoimidazol-2-one (Example 73 step 6, 40 mg), dichloro[1,1'-bis(diphenylphosphino)ferrocene]palladium(II) (10 mg), $Cs_2CO_3$ (84 mg) and (4-cyanomethylphenyl)boronic acid (CAS Reg. No. 91983-26-5, 27 mg) in dioxane (1 ml) and water (0.1 ml) was heated at 80° C. for 20 min in a sealed tube. The mixture was acidified with HCOOH and then purified by prep. HPLC (C18-column, solvent gradient 30-98%) to give the title compound (27 mg). MS (m/e)=514.2 [M+H$^+$].

Step 2: {3'-Chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-yl}-acetic acid A solution of {3'-chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-4-yl}-acetonitrile (27 mg) in saturated ethanolic HCl (10 ml) was stirred overnight at room temperature. The mixture was concentrated to dryness. Ethanol (1 ml), THF (2 ml) and water (1 ml) were added. The mixture was stirred for 1 h at room temperature. Aqueous 1N LiOH solution (1 ml) was added and the mixture stirred for 1 h at room temperature. Organic solvents were evaporated. The remaining aqueous phase was diluted with water (10 ml), washed with diethyl ether (10 ml), and then acidified with concentrated aqueous HCl. The mixture was extracted with EtOAc. The combined organic layers were dried over $Na_2SO_4$ and concentrated to give the title compound (26 mg). MS (m/e)=533.2 [M+H$^+$].

Example 83

{3'-Chloro-4'-[2-(1,3-dimethyl-2-oxo-2,3-dihydro-1H-benzoimidazol-5-yl)-3,3,3-trifluoro-2-hydroxy-1-methyl-propyl]-biphenyl-3-yl}-acetic acid

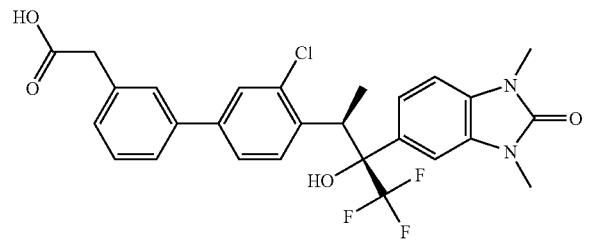

The title compound was prepared in analogy to Example 82 from 3-cyanomethylphenyl-boronic acid (CAS Reg. No. 220616-39-7). MS (m/e)=533.3 [M+H$^+$].

Example 84

5-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenyl}-pyridine-2-carboxylic acid

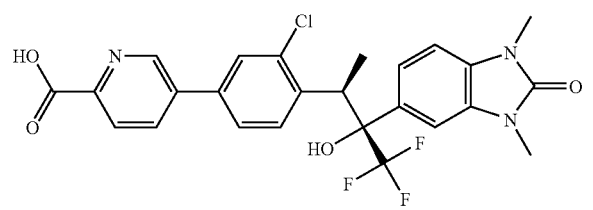

The title compound was prepared in analogy to Example 82 from 2-cyanopyridine-5-boronic acid pinacol ester (CAS Reg. No. 741709-63-7). MS (m/e)=520.2 [M+H$^+$].

Example 85

5-[2-(2-Chloro-4-hydroxy-phenyl)-1-hydroxy-1-trifluoromethyl-propyl]-1,3-dimethyl-1,3-dihydro-benzoimidazol-2-one

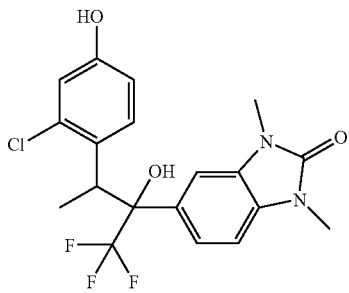

Step 1: 5-[2-(2-Chloro-4-methoxy-phenyl)-acetyl]-1,3-dimethyl-1,3-dihydro-benzoimidazol-2-one 1 Drop DMF was added to a solution of (2-chloro-4-methoxy-phenyl)-acetic acid (CAS 91367-09-8) (800 mg) and oxalyl chloride (0.55 ml) in THF (15 ml). The mixture was stirred for 30 min at room temperature and then concentrated to dryness to give the corresponding acid chloride. Aluminum chloride (1.6 g) was added to a solution of 1,3-dimethyl-1,3-dihydro-benzoimidazol-2-one (CAS Reg. No. 3097-21-0, 647 mg) in DCE (9 ml) at 0° C. After stirring for 5 min, a solution of the acid chloride obtained above in DCE (4 ml) was added and the mixture was stirred 1 h at room temperature. The mixture was poured onto ice water and extracted with DCM and EtOAc. The combined organic layers were dried over $Na_2SO_4$ and concentrated to an oil. The residue was purified by flash chromatography ($SiO_2$, 0 to 100% EtOAc/DCM) to give the title compound (1 g) as a white solid. MS (m/e)=345.0 [M+H$^+$].

Step 2: 5-[2-(2-Chloro-4-methoxy-phenyl)-propionyl]-1,3-dimethyl-1,3-dihydro-benzoimidazol-2-one Sodium hydride (55% in mineral oil, 139 mg) was added to a solution of 5-[2-(2-chloro-4-methoxy-phenyl)-acetyl]-1,3-dimethyl-1,3-dihydro-benzoimidazol-2-one (1 g) in DMF (16 ml) at 0° C. The mixture was stirred for 30 min, then methyl iodide (0.2 ml) was added at 0° C. Water was added to the mixture and extracted with DCM. The combined organic layers were dried over $Na_2SO_4$ and concentrated to an oil. The residue was purified by flash chromatography ($SiO_2$, 0 to 60% EtOAc/DCM) to give the title compound (830 mg) as light yellow oil. MS (m/e)=359.0 [M+H$^+$].

Step 3: 5-[2-(2-Chloro-4-methoxy-phenyl)-1-hydroxy-1-trifluoromethyl-propyl]-1,3-dimethyl-1,3-dihydro-benzoimidazol-2-one The title compound was obtained in analogy to Example 73 step 6 from 5-[2-(2-chloro-4-methoxy-phenyl)-propionyl]-1,3-dimethyl-1,3-dihydro-benzoimidazol-2-one. White foam. MS (m/e)=429.2 [M+H$^+$].

Step 4: 5-[2-(2-Chloro-4-hydroxy-phenyl)-1-hydroxy-1-trifluoromethyl-propyl]-1,3-dimethyl-1,3-dihydro-benzoimidazol-2-one A 1M solution of boron tribromide in DCM (3.7 ml) was added to a solution of 5-[2-(2-chloro-4-methoxy-phenyl)-1-hydroxy-1-trifluoromethyl-propyl]-1,3-dimethyl-1,3-dihydro-benzoimidazol-2-one (300 mg) in DCM (10 ml). at −65° C. The mixture was allowed to warm to room temperature and then stirred for 4 h. MeOH (1.4 ml) and saturated aqueous NaHCO$_3$ solution were added and stirred for 30 min. The mixture was extracted with DCM. The combined organic layers were dried over Na$_2$SO$_4$ and concentrated to an oil. The residue was purified by flash chromatography (SiO$_2$, 30 to 100% EtOAc/heptane) to give the title compound (259 mg) as a light yellow oil. MS (m/e)=415.3 [M+H$^+$].

Example 86

4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-3-fluoro-benzoic acid

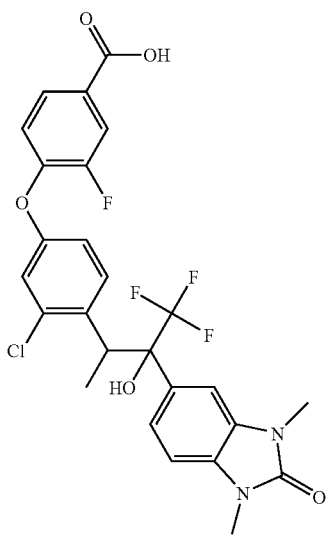

Step 1: 4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-3-fluoro-benzonitrile A mixture of 5-[2-(2-chloro-4-hydroxy-phenyl)-1-hydroxy-1-trifluoromethyl-propyl]-1,3-dimethyl-1,3-dihydro-benzoimidazol-2-one (Example 85, 25 mg), 3,4-difluorobenzonitrile (CAS Reg. No. 64248-62-0, 10 mg), and Cs$_2$CO$_3$ (59 mg) in DMF (1 ml) was heated in a microwave oven at 120° C. for 30 min. The mixture was acidified with HCOOH and then purified by prep. HPLC (C18-column, solvent gradient 30-98%) to give the title compound (19 mg) as a colorless oil. MS (m/e)=534.1 [M+H$^+$].

Step 2: 4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-3-fluoro-benzoic acid A 2N aqueous KOH solution (4 ml) was added to a solution of 4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-3-fluoro-benzonitrile (19 mg) in dioxane (2 ml). The mixture was heated to 100° C. for 20 h. The mixture was diluted with 1N aqueous KOH (15 ml), washed with diethyl ether, acidified with 25% aqueous HCl and extracted with EtOAc. The combined organic layers were dried over Na$_2$SO$_4$ and concentrated to an oil. The residue was purified by prep. HPLC (C18-column, solvent gradient 30-98%) to give the title compound (11 mg) as colorless oil. MS (m/e)=553.0 [M+H$^+$].

Example 87

3-Chloro-4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid

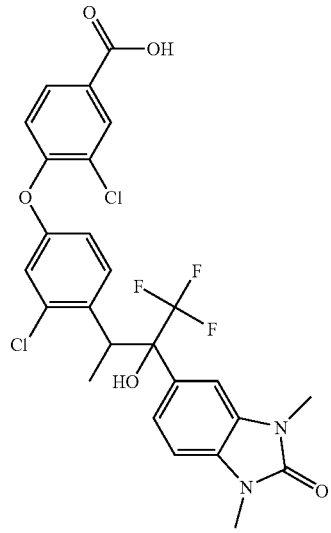

The title compound was obtained in analogy to Example 86 from 3-chloro-4-fluorobenzonitrile (CAS Reg. No. 117482-84-5) as a colorless oil. MS (m/e)=569.1 [M+H$^+$].

Example 88

4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-fluoro-benzoic acid

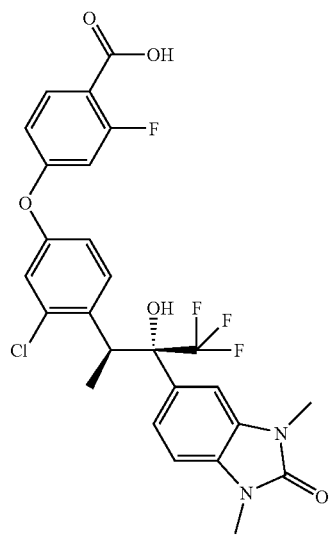

Step 1: 4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-fluoro-benzoic acid methyl ester Copper(II)acetate (657 mg), 3-fluoro-4-methoxycarbonylphenylboronic acid (CAS Reg. 505083-04-5, 716 mg), and pyridine (0.3 ml) were added to a solution of 5-[2-(2-chloro-4-hydroxy-phenyl)-1-hydroxy-1-trifluoromethyl-propyl]-1,3-dimethyl-1,3-dihydro-benzoimidazol-2-one (Example 85, 500 mg) in DCM (20 ml). The mixture was stirred with molecular sieves under air atmosphere for 4 days and then concentrated to an oil. The residue was purified by flash chromatography (SiO$_2$, 2:1 EtOAc/heptane) to give the title compound (400 mg) as a light yellow oil. MS (m/e)=567.1 [M+H$^+$].

Step 2: 4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-fluoro-benzoic acid To 4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-fluoro-benzoic acid methyl ester (400 mg) aqueous 1N LiOH (1.5 ml), MeOH (5 ml) and THF (10 ml) were added. The resulting solution was stirred for 1 h at room temperature. Volatile solvents were removed in vacuo. The residual aqueous solution was diluted with water (10 ml) and then acidified to pH 6 with 1 N aqueous HCl and extracted with EtOAc. The combined EtOAc layers were dried over Na$_2$SO$_4$ and concentrated to give the title compound (300 mg) as a white foam. MS (m/e)=551.2 [M+H$^+$].

Example 89

(4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenyl)-acetic acid

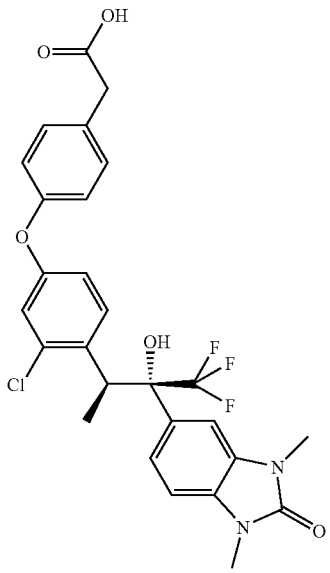

Step 1: (4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenyl)-acetonitrile The title compound was prepared in analogy to Example 88 step 1 from (4-cyanomethylphenyl)boronic acid (CAS Reg. No. 91983-26-5, 70 mg). Light yellow oil. MS (m/e)=530.1 [M+H$^+$].

Step 2: (4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenyl)-acetic acid The title compound was prepared in analogy to Example 86, step 2, from (4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenyl)-acetonitrile. Colorless oil. MS (m/e)=549.2 [M+H$^+$].

Example 90

2-Chloro-4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid

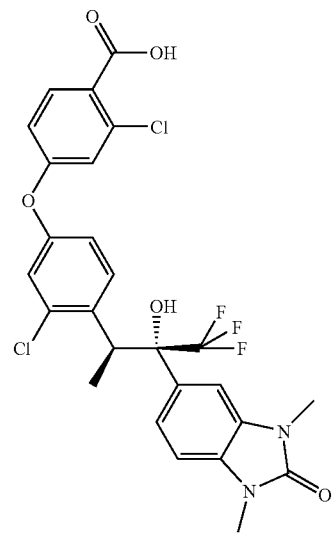

The title compound was prepared in analogy to Example 88 from 3-chloro-4-methoxycarbonyl)benzeneboronic acid (CAS Reg. No. 603122-82-3). White solid. MS (m/e)=569.1 [M+H$^+$].

Example 91

5-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-fluoro-benzoic acid

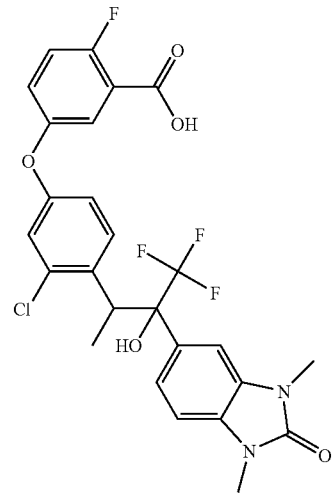

The title compound was prepared in analogy to Example 88 from 3-3-ethoxycarbonyl-4-fluorophenylboronic acid (CAS Reg. No. 874219-36-0). White foam. MS (m/e)=553.1 [M+H$^+$].

Example 92

2-Chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid

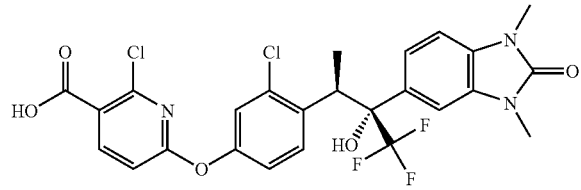

Step 1: 2-Chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid methyl ester To a solution of methyl 2,6-dichloronicotinate (CAS Reg. No. 65515-28-8, 20 mg) in DMF (0.5 ml) was added 5-[2-(2-chloro-4-hydroxy-phenyl)-1-hydroxy-1-trifluoromethyl-propyl]-1,3-dimethyl-1,3-dihydro-benzoimidazol-2-one (Example 85, 40 mg), followed by triethyl amine (0.02 ml). The mixture was stirred for 10 min, then DABCO (2 mg) was added. The mixture was stirred at room temperature over night. Water was added to the mixture and extracted with EtOAc. The combined organic layers were dried over Na$_2$SO$_4$ and concentrated to an oil. The residue was purified by flash chromatography (SiO$_2$, 1:2 EtOAc/heptane) to give the title compound (55 mg) as white foam. MS (m/e)=585.9 [M+H$^+$].

Step 2: 2-Chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid The title compound was prepared in analogy to Example 88 step 2 from 2-chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid methyl ester. White foam. MS (m/e)=570.1 [M+H$^+$].

Example 93

(4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenoxy)-acetic acid

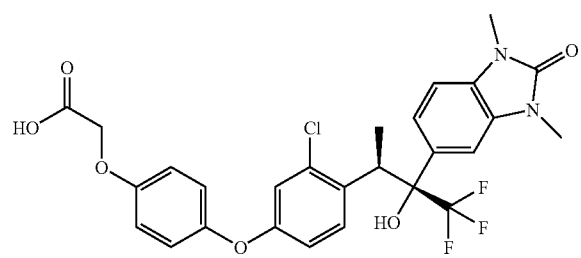

Step 1: (4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenoxy)-acetonitrile Copper(II)acetate (26 mg), 4-cyanomethoxy-phenylboronic acid pinacol ester (CAS Reg. No. 475272-13-0, 38 mg), and DMAP (30 mg) were added to a solution of 5-[2-(2-chloro-4-hydroxy-phenyl)-1-hydroxy-1-trifluoromethyl-propyl]-1,3-dimethyl-1,3-dihydro-benzoimidazol-2-one (Example 85, 20 mg) in acetonitrile (3 ml). The mixture was stirred with molecular sieves under air atmosphere for 4 h at 80° C., and then filtered over Celite concentrated to an oil. The residue was purified by prep. HPLC (C18-column, solvent gradient 20-98% CH$_3$CN in 0.1% HCOOH[aq]) to give the title compound (24 mg) as a white solid. MS (m/e)=546.1 [M+H$^+$].

Step 2: (4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenoxy)-acetic acid The title compound was prepared in analogy to Example 82 step 2 from (4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenoxy)-acetonitrile. White solid. MS (m/e)=565.2 [M+H$^+$].

Example 94

(3-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-phenoxy)-acetic acid

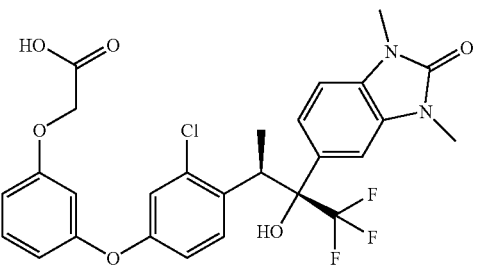

Copper(II)acetate (39 mg), 3-(4,4,5,5-tetramethyl-[1,3,2]dioxaborolan-2-yl)-phenoxy]-acetic acid ethyl ester (CAS Reg. No. 850411-07-3, 66 mg), and DMAP (44 mg) were added to a solution of 5-[2-(2-chloro-4-hydroxy-phenyl)-1-hydroxy-1-trifluoromethyl-propyl]-1,3-dimethyl-1,3-dihydro-benzoimidazol-2-one (Example 85, 30 mg) in acetonitrile (3 ml). The mixture was stirred with molecular sieves under air atmosphere for 5 h at 80° C. Aqueous 1N LiOH solution was added, and the mixture stirred for 1 h. The mixture was acidified with HCOOH and purified by prep. HPLC (C18-column, solvent gradient 20-98% CH$_3$CN in 0.1% HCOOH[aq]) to give the title compound (32 mg) as a white solid. MS (m/e)=565.2 [M+H$^+$].

Example 95
5-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-pyridine-2-carboxylic acid

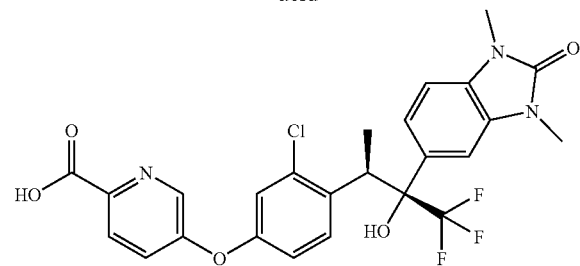

The title compound was prepared in analogy to Example 93 from 2-cyanopyridine-5-boronic acid pinacol ester (CAS Reg. No. 741709-63-7). Colorless oil. MS (m/e)=536.3 [M+H$^+$].

Example 96
2-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid

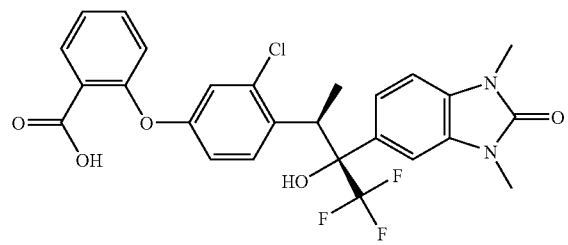

The title compound was prepared in analogy to Example 94 from (2-methoxycarbonyl-phenyl)boronic acid (CAS Reg. No. 374538-03-1). MS (m/e)=535.2 [M+H$^+$].

Example 97
4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-methoxy-benzoic acid

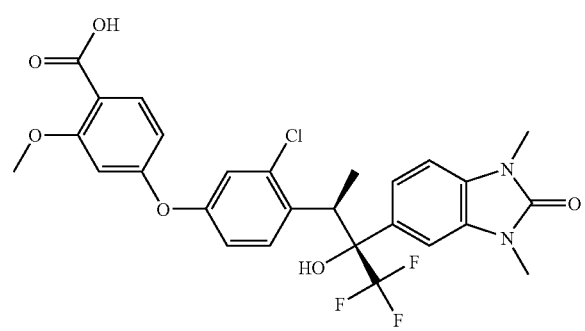

The title compound was prepared in analogy to Example 94 from 3-methoxy-4-methoxycarbonylphenylboronic acid pinacol ester (CAS Reg. No. 603122-40-3). MS (m/e)=565.2 [M+H$^+$].

Example 98
4-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid

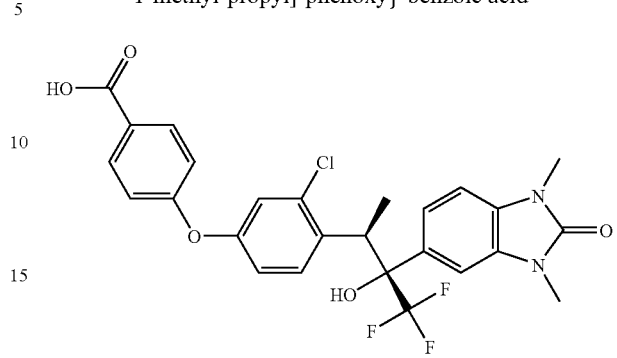

The title compound was prepared in analogy to Example 94 from (4-methoxycarbonyl-phenyl)boronic acid (CAS Reg. No. 99768-12-4). MS (m/e)=535.2 [M+H$^+$].

Example 99
3-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid

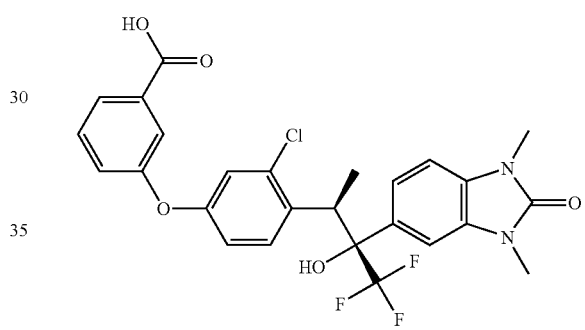

The title compound was prepared in analogy to Example 94 from 3-methoxycarbonyl-phenylboronic acid (CAS Reg. No. 99769-19-4). MS (m/e)=535.2 [M+H$^+$].

Example 100
5-Chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid

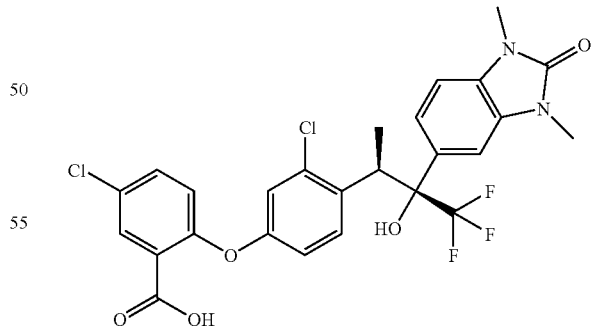

Step 1: 5-Chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid ethyl ester The title compound was prepared in analogy to Example 93 step 1 from (4-chloro-2-ethoxycarbonylphenyl)boronic acid (CAS Reg. No. 850568-61-5). Light yellow oil. MS (m/e)=597.3 [M+H$^+$].

Step 2: 5-Chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid The title compound was prepared in analogy to Example 88 step 2 from 5-chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-benzoic acid ethyl ester. White solid. MS (m/e)=569.3 [M+H$^+$].

Example 101

6-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid

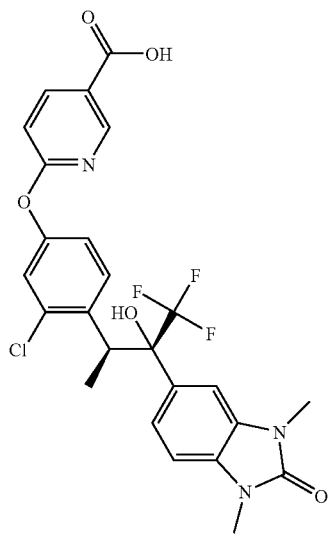

The title compound was prepared in analogy to Example 92 from ethyl 6-chloronicotinate (CAS Reg. No. 49608-01-7). Colorless oil. MS (m/e)=536.3 [M+H$^+$].

Example 102

6-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-4-trifluoromethyl-nicotinic acid

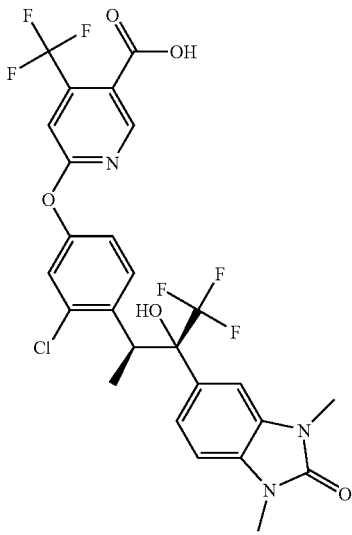

The title compound was prepared in analogy to Example 92 from methyl 6-chloro-4-(trifluoromethyl)nicotinate (CAS Reg. No. 261635-79-4). Colorless oil. MS (m/e)=604.4 [M+H$^+$].

Example 103

4-[4-(2-Benzo[1,3]dioxol-5-yl-3,3,3-trifluoro-2-hydroxy-1-methyl-propyl)-3-chloro-phenoxy]-2-chloro-benzoic acid

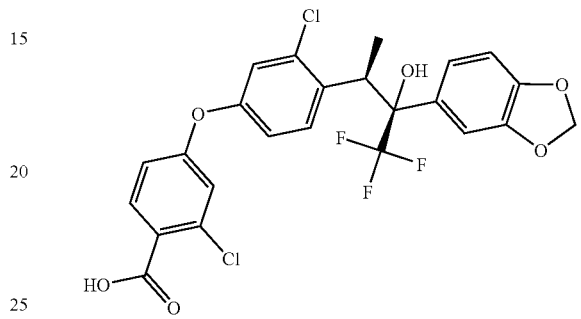

Step 1: 4-(4-Acetyl-3-chloro-phenoxy)-2-chloro-benzonitrile

To a solution 2-chloro-4-hydroxybenzonitrile (CAS Reg. No. 3336-16-1, 1 g), 2-chloro-4-fluoroacetophenone (CAS Reg. No. 700-35-6, 1.12 g) in DMA (10 ml) was added K$_2$CO$_3$ (1.08 g). The mixture is heated to 110° C. for 2 h and at 130° C. for 1 h. Water was added and the mixture was extracted with EtOAc. The combined organic layers were dried over Na$_2$SO$_4$ and then concentrated to an oil. The residue was purified by flash chromatography (SiO$_2$, 0 to 30% EtOAc/heptane) to give the title compound (780 mg) as light yellow oil. MS (m/e)=306.0 [M+H$^+$].

Step 2: 2-Chloro-4-[3-chloro-4-(1-methyl-2-oxo-ethyl)-phenoxy]-benzonitrile The title compound was prepared in analogy to Example 73 step 1 from 4-(4-acetyl-3-chloro-phenoxy)-2-chloro-benzonitrile. Light yellow oil. MS (m/e, ISP neg. ion)=318.1 [M−H$^+$].

Step 3: 4-[4-(2-Benzo[1,3]dioxol-5-yl-3,3,3-trifluoro-2-hydroxy-1-methyl-propyl)-3-chloro-phenoxy]-2-chloro-benzonitrile The title compound was prepared in analogy to Example 73 steps 4-6 from 2-chloro-4-[3-chloro-4-(1-methyl-2-oxo-ethyl)-phenoxy]-benzonitrile and 4-bromo-1,2-methylenedioxy-benzene (CAS Reg. No. 2635-13-4). Colorless oil. $^1$H NMR (300 MHz, CDCl$_3$) δ 7.6 (2H, dd), 6.7-7.0 (6H, m), 5.9 (1H, s), 4.3 (1H, q), 3.0 (1H, br. s), 1.5 (3H, d).

Step 4: 4-[4-(2-Benzo[1,3]dioxol-5-yl-3,3,3-trifluoro-2-hydroxy-1-methyl-propyl)-3-chloro-phenoxy]-2-chloro-benzoic acid The title compound was prepared in analogy to Example 86 step 2 from 4-[4-(2-benzo[1,3]dioxol-5-yl-3,3,3-trifluoro-2- hydroxy-1-methyl-propyl)-3-chloro-phenoxy]-2-chloro-benzonitrile. Light yellow oil. MS (m/e, ISP neg. ion)=527.0 [M−H⁺].

Example 104

5-Chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid

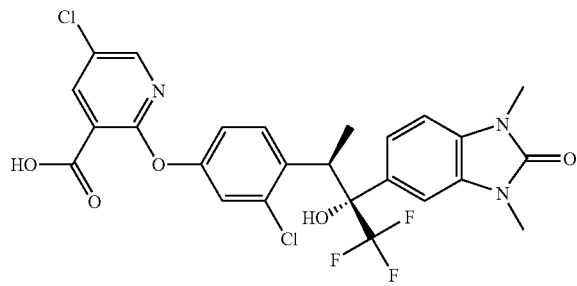

Step 1: 5-Chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid methyl ester Potassium tert-butoxide (6 mg) was added to a solution of 5-[2-(2-chloro-4-hydroxy-phenyl)-1-hydroxy-1-trifluoromethyl-propyl]-1,3-dimethyl-1,3-dihydro-benzoimidazol-2-one (Example 85, 20 mg) in DMF (3.6 ml). The solution was added to methyl 2,5-dichloronicotinate (CAS Reg. No. 67754-03-4, 20 mg). The resulting mixture was stirred overnight at room temperature. The mixture was acidified with HCOOH and purified by prep. HPLC (C18-column, solvent gradient 20-98% CH₃CN in 0.1% HCOOH[aq]) to give the title compound (10 mg). MS (m/e)=584.3 [M+H⁺].

Step 2: 5-Chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid The title compound was prepared in analogy to Example 88 step 2 from 5-chloro-2-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid methyl ester. MS (m/e)=570.3 [M+H⁺].

Example 105

2-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid

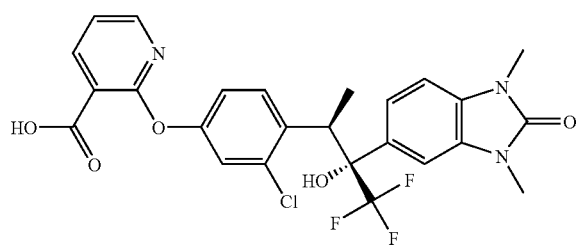

The title compound was prepared in analogy to Example 104 from ethyl 2-chloronicotinate (CAS Reg. No. 1452-94-4). MS (m/e)=536.3 [M+H⁺].

Example 106

5-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-pyrazine-2-carboxylic acid

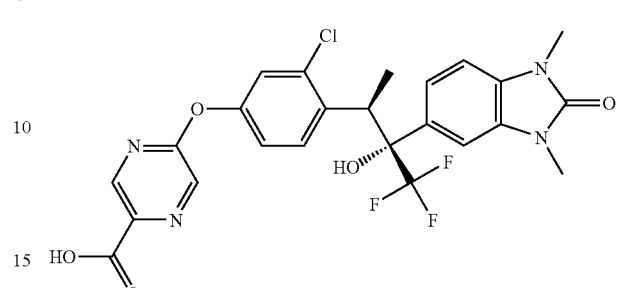

The title compound was prepared in analogy to Example 104 from methyl 5-chloropyrazine-2-carboxylate (CAS Reg. No. 33332-25-1). MS (m/e)=537.3 [M+H⁺].

Example 107

5-Chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid

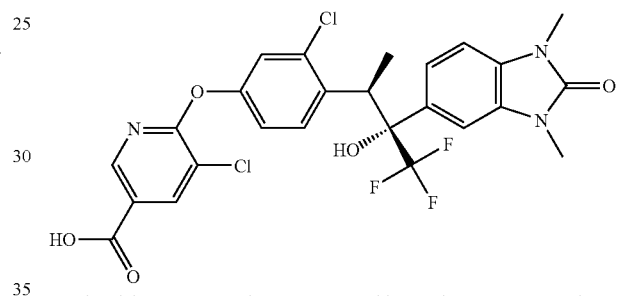

The title compound was prepared in analogy to Example 92 from methyl 5,6-dichloronicotinate (CAS Reg. No. 56055-54-0). White solid. MS (m/e)=570.1 [M+H⁺].

Example 108 and Example 109

6-Chloro-4-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid (Example 108)

4-Chloro-6-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-nicotinic acid (Example 109)

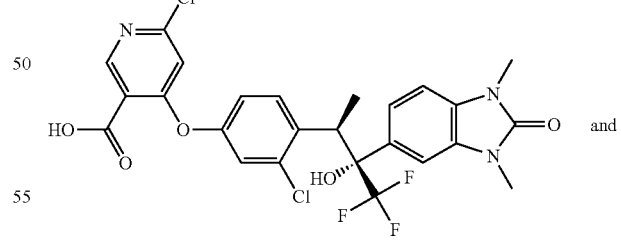

and

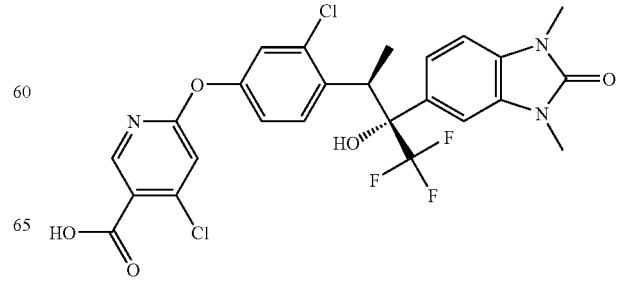

The title compounds were formed as a mixture in analogy to Example 104 from methyl 2,6-dichloronicotinate (CAS Reg. No. 65515-28-8) and separated by prep. HPLC (C18-column, solvent gradient 20-98% CH₃CN in 0.1% HCOOH [aq]). Example 108: MS (m/e)=570.4 [M+H⁺]. Example 109: MS (m/e)=570.4 [M+H⁺].

Example 110

2-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-5-trifluoromethyl-isonicotinic acid

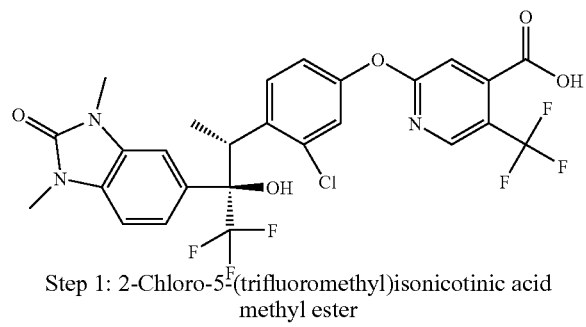

Step 1: 2-Chloro-5-(trifluoromethyl)isonicotinic acid methyl ester

Oxalyl chloride (0.5 ml) was added to a solution of 2-chloro-5-(trifluoromethyl)isonicotinic acid (CAS Reg. No. 505084-58-2, 68 mg) in DCM (5 ml). DMF (1 drop) was added and the resulting mixture was stirred overnight at room temperature. Methanol (5 ml) was added and the mixture was concentrated to dryness. The crude product was used in the next step without further purification.

Step 2: 2-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-5-trifluoromethyl-isonicotinic acid The title compound was prepared in analogy to Example 104 from 2-chloro-5-(trifluoromethyl)isonicotinic acid methyl ester. MS (m/e)=604.5 [M+H⁺].

Example 111

2-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-6-trifluoromethyl-nicotinic acid

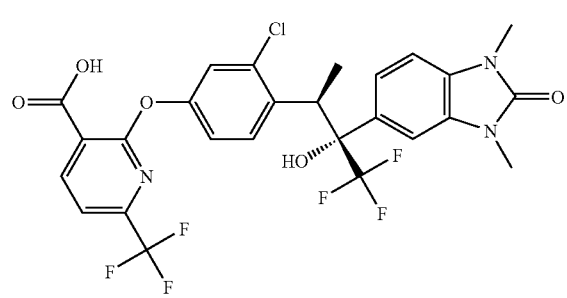

The title compound was prepared in analogy to Example 110 from 2-chloro-6-(trifluoromethyl)nicotinic acid (CAS Reg. No. 280566-45-2). MS (m/e)=604.5 [M+H⁺].

Example 112

6-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-3-trifluoromethyl-pyridine-2-carboxylic acid

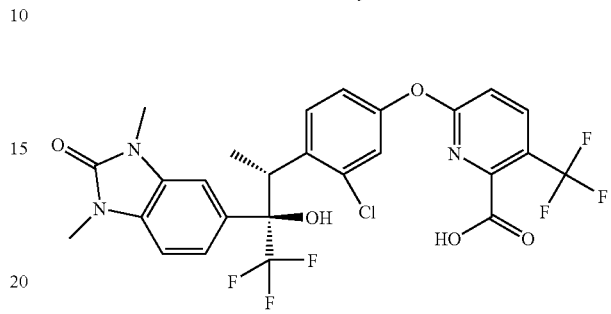

The title compound was prepared in analogy to Example 110 from 6-chloro-3-(trifluoromethyl)pyridine-2-carboxylic acid (CAS Reg. No. 796090-24-9). MS (m/e)=604.5 [M+H⁺].

Example 113

2-Chloro-3-{3-chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-isonicotinic acid

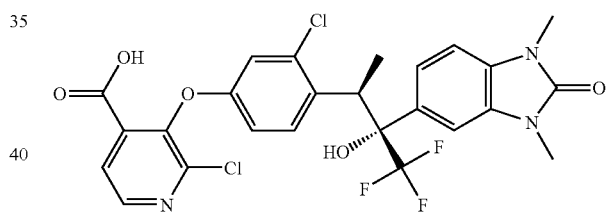

The title compound was prepared in analogy to Example 110 from 2-chloro-3-fluoroisonicotinic acid (CAS Reg. No. 628691-93-0). MS (m/e)=570.4 [M+H⁺].

Example 114

3'-Chloro-3-fluoro-4'-[3,3,3-trifluoro-2-hydroxy-1-methyl-2-(2-oxo-2,3-dihydro-1H-benzoimidazol-5-yl)-propyl]-biphenyl-4-carboxylic acid

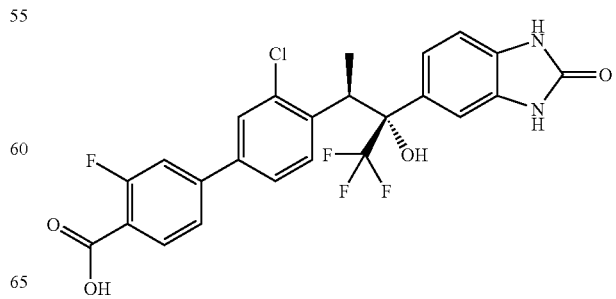

Step 1: 1-(2-Chloro-4-methoxy-phenyl)-ethanol

A 1.6M solution of n-butyllithium in hexane (4 ml) was added to a solution of 4-bromo-3-chloroanisole (CAS Reg. No. 50638-46-5, 1.3 g) in THF (20 ml) at −78° C. The mixture was stirred for 30 min at −78° C. Acetaldehyde (0.7 ml) was added to the mixture. The mixture was allowed to warm to room temperature. Water (50 ml) was added and extracted with DCM. The combined organic layers were dried over $Na_2SO_4$ and concentrated to an oil to give the title compound (983 mg) as colorless oil. MS (m/e)=186 [M+].

Step 2: 2-Chloro-1-(1-chloro-ethyl)-4-methoxy-benzene

Thionyl chloride (0.9 ml) was added to a solution of 1-(2-chloro-4-methoxy-phenyl)-ethanol (2 g) in DCM (5 ml) at 0° C. The mixture was allowed to warm to room temperature and then stirred for 1 h. The mixture was concentrated to an oil and filtered over $SiO_2$ (1 g) to give the title compound (2 g) as a light brown oil. $^1H$ NMR (300 MHz, $CDCl_3$) δ 7.5 (1H, d), 6.8-6.9 (2H, m), 5.5 (1H, q), 3.8 (3H, s), 1.8 (3H, d).

Step 3: 2-Oxo-2,3-dihydro-1H-benzoimidazole-5-carboxylic acid methyl ester

A solution of 1,1'-carbonyldiimidazole (5 g) in THF (20 ml) was added to a solution of methyl 3,4-diaminobenzoate (CAS Reg. No. 36692-49-6, 5 g) in THF (50 ml). The mixture was stirred at room temperature for 2 h. Water (150 ml) was added. The mixture was filtered and the residue dried to give the title compound (5.6 g) as a light yellow powder. MS (m/e, ISP neg. ion)=191.2 [M−H+].

Step 4: 1,3-Diallyl-2-oxo-2,3-dihydro-1H-benzoimidazole-5-carboxylic acid methyl ester Potassium tert-butoxide (2.57 g) was added to a solution of 2-oxo-2,3-dihydro-1H-benzoimidazole-5-carboxylic acid methyl ester (2 g) in DMA (30 ml). Allyl bromide (2 ml) was added, and the mixture was stirred for 2 h at room temperature. The mixture was acidified with 2N aqueous HCl and then extracted with EtOAc. The combined organic layers were dried over $Na_2SO_4$ and then concentrated to an oil. The residue was purified by flash chromatography ($SiO_2$, EtOAc/heptane 1:2) to give the title compound (2.2 g) as a yellow oil. MS (m/e)=273.2 [M+H+].

Step 5: 1,3-Diallyl-2-oxo-2,3-dihydro-1H-benzoimidazole-5-carboxylic acid

The title compound was prepared in analogy to Example 88 step 2 from 1,3-diallyl-2-oxo-2,3-dihydro-1H-benzoimidazole-5-carboxylic acid methyl ester. Light yellow solid. MS (m/e)=259.1 [M+H+].

Step 6: 1,3-Diallyl-2-oxo-2,3-dihydro-1H-benzoimidazole-5-carboxylic acid methoxy-methyl-amide Oxalyl chloride (0.9 ml) and DMF (2 drops) were added to a solution of 1,3-diallyl-2-oxo-2,3-dihydro-1H-benzoimidazole-5-carboxylic acid (1.5 g) in DCM (100 ml). The mixture was stirred for 1 h at room temperature and then concentrated to an oil. The residue was dissolved in DCM (100 ml). N,O-dimethylhydroxylamine HCl (0.8 g) and N,N-diisopropyl-ethylamine (2.9 ml) were added. The mixture was stirred for 30 min at room temperature, and then washed with 3N aqueous HCl. The combined organic layers were dried over $Na_2SO_4$ and then concentrated to an oil. The residue was purified by flash chromatography ($SiO_2$, EtOAc/heptane 2:1) to give the title compound (1.6 g) as a light yellow oil. MS (m/e)=302.2 [M+H+].

Step 7: 1,3-Diallyl-5-[2-(2-chloro-4-methoxy-phenyl)-propionyl]-1,3-dihydro-benzoimidazol-2-one A 1M suspension of Rieke magnesium in THF (1.3 ml) was added to THF (2 ml). The mixture was cooled to −10° C., and a solution of 2-chloro-1-(1-chloro-ethyl)-4-methoxy-benzene (136 mg) in THF (2 ml) was added. The mixture was stirred for 15 min. A solution of 1,3-diallyl-2-oxo-2,3-dihydro-1H-benzoimidazole-5-carboxylic acid methoxy-methyl-amide (100 mg) in THF (2 ml) was added at −10° C. The mixture was stirred overnight at room temperature. Water was added and extracted with EtOAc. The combined organic layers were dried over $Na_2SO_4$ and then concentrated to an oil. The residue was purified by flash chromatography ($SiO_2$, 0 to 100% EtOAc/heptane) to give the title compound (72 mg) as a light yellow foam. MS (m/e)=411.2 [M+H+].

Step 8: 1,3-Diallyl-5-[2-(2-chloro-4-hydroxy-phenyl)-1-hydroxy-1-trifluoromethyl-propyl]-1,3-dihydro-benzoimidazol-2-one The title compound was prepared in analogy to Example 85, steps 3 and 4 from 1,3-diallyl-5-[2-(2-chloro-4-methoxy-phenyl)-propionyl]-1,3-dihydro-benzoimidazol-2-one. Light brown solid. MS (m/e)=467.2 [M+H+].

Step 9: 3'-Chloro-4'-[2-(1,3-diallyl-2-oxo-2,3-dihydro-1H-benzoimidazol-5-yl)-3,3,3-trifluoro-2-hydroxy-1-methyl-propyl]-3-fluoro-biphenyl-4-carboxylic acid methyl ester Trifluoromethanesulfonic anhydride (0.052 ml) and triethylamine (0.11 ml) were added to a solution of 1,3-diallyl-5-[2-(2-chloro-4-hydroxy-phenyl)-1-hydroxy-1-trifluoromethyl-propyl]-1,3-dihydro-benzoimidazol-2-one (74 mg) in DCM (10 ml). The mixture was stirred for 3 h at room temperature, and then washed with 10% aqueous citric acid and saturated aqueous $NaHCO_3$ solution. The organic layer was dried over $Na_2SO_4$ and then concentrated to an oil. The residue was converted in analogy to Example 82 step 1 with 3-fluoro-4-methoxycarbonyl-phenylboronic acid (CAS Reg. No. 505083-04-5, 46 mg) to the title compound (57 mg). Light yellow oil. MS (m/e)=603.4 [M+H+]

Step 10: 3'-Chloro-3-fluoro-4'-[3,3,3-trifluoro-2-hydroxy-1-methyl-2-(2-oxo-2,3-dihydro-1H-benzoimidazol-5-yl)-propyl]-biphenyl-4-carboxylic acid A mixture of $RhCl_3$ trihydrate (2.5 mg) and 3'-chloro-4'-[2-(1,3-diallyl-2-oxo-2,3-dihydro-1H-benzoimidazol-5-yl)-3,3,3-trifluoro-2-hydroxy-1-methyl-propyl]-3-fluoro-biphenyl-4-carboxylic acid methyl ester (57 mg) in n-PrOH (2 ml) was heated for 2 h to 100° C. in a sealed tube. 25% aqueous HCl (1 ml) was added and heating continued for 2 h at 100° C. The mixture was alkalized by addition of LiOH and stirred for 30 min at room temperature. Volatile solvents were evaporated and the residue dissolved in 1N aqueous NaOH (10 ml). The aqueous phase was washed with ether, acidified with 25% aqueous HCl and then extracted with EtOAc. The combined org. phases were dried over $Na_2SO_4$ and then concentrated to an oil. The residue was purified by prep. HPLC (C18-column, solvent gradient 20-98% CH₃CN in 0.1% HCOOH[aq]) to give the title compound (12 mg) as a white solid. MS (m/e)=509.3 [M+H⁺].

Example 115

6-{3-Chloro-4-[2-(1,3-dimethyl-2-oxo-2,3-dihydro-1H-benzoimidazol-5-yl)-3,3,3-trifluoro-2-hydroxy-1-methyl-propyl]-phenoxy}-2-trifluoromethyl-nicotinic acid

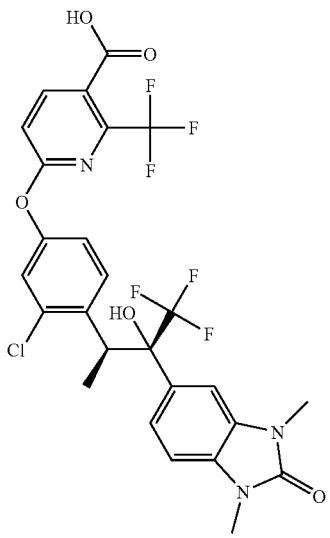

The title compound was prepared in analogy to Example 110 from 2-chloro-3-fluoroisonicotinic acid 6-chloro-2-trifluoromethylnicotinic acid ethyl ester (CAS Reg. No. 261635-82-9, prepared according to WO2000015615). White foam. MS (m/e)=604.4 [M+H⁺].

Example 116

5-[2-(4-Bromo-2-chloro-phenyl)-1-hydroxy-1-trifluoromethyl-propyl]-3-methyl-3H-benzooxazol-2-one

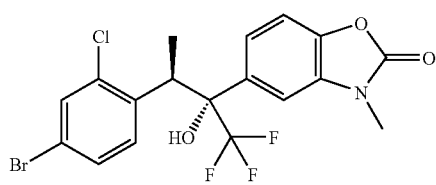

Step 1: 5-Nitro-3H-benzooxazol-2-one

2-Amino-4-nitrophenol (30.0 g) and 1,1'-carbonyldiimidazole (47.34 g) were dissolved in THF (300 mL). The mixture was refluxed over night. The reaction mixture was cooled, poured into ice/water and acidified with 1M aqueous HCl to pH 2. The aqueous layer was extracted two times with ethyl acetate. The combined organic layers were washed with brine, dried over Na₂SO₄, filtered and the solvent was evaporated. Methanol (150 mL) was added to the resulting precipitate and the mixture was stirred for 30 minutes at r.t. The resulting solid was filtered off and dried in vacuo. The title compound was obtained as a yellow solid (32.32 g, 88%). MS (neg. ion, m/e)=179.0 [(M−H)⁻].

Step 2: 3-Methyl-5-nitro-3H-benzooxazol-2-one

A solution of 5-nitro-3H-benzooxazol-2-one (26 g) in DMF (100 mL) was added to a suspension of NaH (60% in mineral oil, 10.71 g) in DMF (100 mL) over a period of 1 hour. Stirring was continued for 45 minutes at r.t. The mixture was cooled to 0° C. and methyl iodide dissolved in DMF (20 mL) was added dropwise over a period of 30 minutes. The mixture was stirred over night at r.t. The reaction mixture was poured into ice/water and extracted two times with ethyl acetate. The combined organic layers were washed with brine, dried over Na₂SO₄, filtered and the solvent was evaporated. CH₂Cl₂:methanol=4:1 (150 mL) was added to the resulting precipitate and the suspension was stirred for 1 hour at r.t. The solid was filtered off and dried in vacuo. The title compound was obtained as a orange solid (18.33 g, 62%). MS (EI)=194.0 [M⁺].

Step 3: 5-Amino-3-methyl-3H-benzooxazol-2-one

3-Methyl-5-nitro-3H-benzooxazol-2-one (22.87 g) was dissolved in acetic acid (350 mL). Palladium on activated charcoal 10% (6.27 g) was added and an atmosphere of hydrogen was introduced at r.t. The mixture was stirred over night. The reaction mixture was filtered over dicalite speed plus (Acros) and the solvent was evaporated. The residue was dissolved in 2M aqueous HCl (500 mL) and stirred for 10 minutes. The resulting solution was basified with conc. aqueous NaOH (200 mL) to pH 11 and stirred for 20 minutes at r.t. The resulting precipitate was filtered off and washed with cold water. Residual water was removed by co-evaporation with toluene. The resulting solid was dried in vacuo. The title compound was obtained as a brown solid (18.72 g, 92%). MS (m/e)=165.2 [M+H⁺].

Step 4: 5-Iodo-3-methyl-3H-benzooxazol-2-one

A solution of sodium nitrite (4.62 g) in water (40 mL) was added dropwise over a period of 15 minutes at 0° C. to a solution of 5-amino-3-methyl-3H-benzooxazol-2-one (10 g) in acetic acid (400 mL). Stirring was continued for 10 minutes at 0° C. A solution of potassium iodide (11.12 g) in water (40 mL) was added dropwise over a period of 15 minutes. Stirring was continued for 1 hour at 0° C. Sodium pyrosulfite (1.0 g) was added to the reaction mixture. Stirring was continued for 10 minutes. The reaction mixture was then evaporated to dryness. The residue was dissolved in CH₂Cl₂ and the solution was poured into sat. Na₂CO₃ (pH 9) and 0.2 M sodium pyrosulfite solution and extracted two times with CH₂Cl₂. The combined organic layers were washed with brine, dried over Na₂SO₄, filtered and the solvent was evaporated. The residue was purified by flash chromatography (silica gel, gradient of heptane in ethyl acetate) to give the title compound as a colorless solid (9.35 g, 55%). MS (m/e)=275.9 [M+H⁺].

Step 5: 3-Methyl-2-oxo-2,3-dihydro-benzooxazole-5-carboxylic acid

5-Iodo-3-methyl-3H-benzooxazol-2-one (3.03 g) in DMSO (100 mL) and water (20 mL) was treated with palladium(II)-acetate (124 mg) and 1,3-bis(diphenyl-phosphino)-propane (DPPP) (227 mg) and triethylamine (4.58 mL). Carbon monoxide was introduced into the reaction mixture for 30 minutes under agitation and the stirring was continued under CO atmosphere over night at 70° C. (bath-temperature). The dark reaction mixture was cooled, poured into ice/water and 1M aqueous HCl to pH 1 and extracted two times with ethyl acetate. The combined organic layers were washed with brine, dried over $Na_2SO_4$, filtered and the solvent was evaporated. Ethyl acetate:heptane=1:1 (20 mL) was added to the resulting precipitate. Stirring was continued for 30 minutes at r.t. The resulting solid was filtered off and dried in vacuo. The title compound was obtained as a brown solid (2.2 g, 93%). MS (neg. ion, m/e)=192.2 [(M−H)−].

Step 6: 5-[2-(4-Bromo-2-chloro-phenyl)-acetyl]-3-methyl-3H-benzooxazol-2-one

To a suspension of 3-methyl-2-oxo-2,3-dihydro-benzooxazole-5-carboxylic acid (2.20 g) in $CH_2Cl_2$ (30 mL) were added five drops of DMF and oxalylchloride (1.57 mL). The mixture was stirred at room temperature for 1.5 hours and was then concentrated to dryness. 1,2-Dimethoxyethane (150 mL) was added and the solvent was evaporated again to give the crude acid chloride (3-methyl-2-oxo-2,3-dihydro-benzooxazole-5-carbonyl chloride). To a suspension of zinc powder (1.49 g) in 1,2-dimethoxyethane (15 mL) was added tetrakis(triphenylphosphine)palladium(0) (132 mg). A suspension of the acid chloride in 1,2-dimethoxyethane (20 mL) was added. The mixture was cooled in an ice bath and a solution of 4-bromo-1-bromomethyl-2-chloro-benzene (3.25 g, [CAS Reg. No. 89720-77-4]) in 1,2-dimethoxyethane (15 mL) was slowly added over a period of 30 minutes. The mixture was stirred for 10 minutes at 0° C. and then for 2 hours at r.t. The reaction mixture was poured into ice and basified with sat. $NaHCO_3$. The aqueous phase was then extracted two times with ethyl acetate and the organic layers were washed with brine, dried over $Na_2SO_4$, filtered and the solvent was evaporated. Ethyl acetate (50 mL) was added to the resulting precipitate and the suspension was stirred for 30 minutes at r.t. The solid was filtered off and dried in vacuo. The title compound was obtained as a light yellow solid (1.95 g, 40%). MS (neg. ion, m/e)=378.0 [(M−H)−].

Step 7: 5-[2-(4-Bromo-2-chloro-phenyl)-propionyl]-3-methyl-3H-benzooxazol-2-one

5-[2-(4-Bromo-2-chloro-phenyl)-acetyl]-3-methyl-3H-benzooxazol-2-one (304 mg) was dissolved in DMF (8 mL). The mixture was cooled to 0° C. To this solution was added sodium hydride (60% in mineral oil, 37 mg). The mixture was stirred for 10 minutes at 0° C. and then for 1 hour at r.t. The mixture was cooled to 0° C. and methyl iodide (119 mg) was added dropwise over a period of 10 minutes. Stirring was continued over night at r.t. The reaction mixture was poured into ice/water and extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title compound as a colorless foam (238 mg, 76%). MS (neg. ion, m/e)=394.2 [(M−H)+].

Step 8: 5-[2-(4-Bromo-2-chloro-phenyl)-1-hydroxy-1-trifluoromethyl-propyl]-3-methyl-3H-benzooxazol-2-one Trifluoromethyltrimethylsilane (2M in THF, 1.13 mL) was added at 0° C. to a solution of 5-[2-(4-bromo-2-chloro-phenyl)-propionyl]-3-methyl-3H-benzooxazol-2-one (404 mg) in THF (8 mL) followed by the addition of tetrabutylammonium fluoride trihydrate (65 mg). Stirring was continued for 2 hours at 0° C. More tetrabutylammonium fluoride (1M in THF, 0.82 mL) was added to the reaction mixture and stirring was continued for 1 hour at 0° C. The reaction mixture was poured into ice/water and extracted two times with ethyl acetate. The combined organic layers were washed with brine, dried over $Na_2SO_4$, filtered and the solvent was evaporated. The residue was purified by flash chromatography (silica gel, $CH_2Cl_2$:MeOH=100:0 to 96:4) to give the title compound as a colorless foam (320 mg, 67%). MS (m/e)= 466.1 [M+H+].

Example 117

3'-Chloro-3-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester

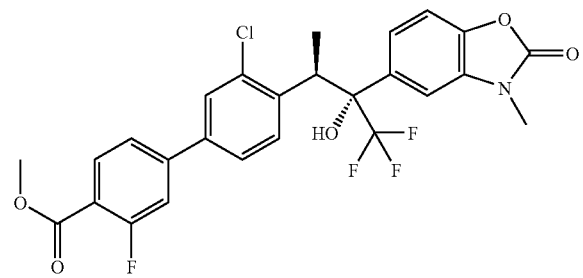

5-[2-(4-Bromo-2-chloro-phenyl)-1-hydroxy-1-trifluoromethyl-propyl]-3-methyl-3H-benzooxazol-2-one (500 mg, obtained in Example 116, step 8), 3-fluoro-4-methoxycarbonyl-phenylboronic acid (320 mg, [CAS Reg. No. 505083-04-5]) and dichloro(1,1'-bis(diphenyl-phosphino)ferrocene)palladium(II)dichloromethane adduct (39 mg) were dissolved in dioxane (9 mL) and water (5 mL). To the reaction mixture was added 2.0 M aqueous $Na_2CO_3$ (0.81 mL). The mixture was heated to 80° C. for 2 hours. The reaction mixture was cooled, poured into ice/water and extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title compound as a colorless foam (440 mg, 76%). MS (m/e)=555.2 [(M+$NH_4^+$)+], MS (m/e)=506.1 [(M−$CH_3O^-$)+].

Example 118

3'-Chloro-3-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid

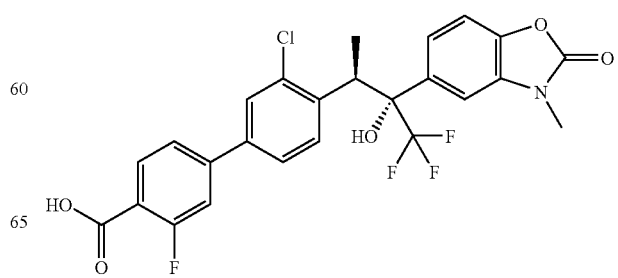

3'-Chloro-3-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester (435 mg, obtained in Example 117) was dissolved in THF (15 mL) followed by the addition of aqueous LiOH solution (1.0M, 1.21 mL). The mixture was stirred at r.t. for 6 hours. The reaction mixture was poured into ice/water and acified with 1M aqueous HCl to pH 1. The aqueous layer was extracted two times with ethylacetate. The combined organic layers were washed with brine, dried over Na$_2$SO$_4$, filtered and the solvent was evaporated. The residue was purified by flash chromatography (silica gel, CH$_2$Cl$_2$:MeOH:CH$_3$COOH=100:0:0 to 97:3:0.5) to give the title compound as a white solid. The residual acetic acid was removed by co-evaporation with toluene (250 mg, 59%). MS (neg. ion, m/e)=522.4 [(M−H)⁻].

Example 119

3'-Chloro-3-fluoro-4'-[(1S,2S)-3,3,3-trifluoro-2-hydroxy-1-methyl-2-(3-methyl-2-oxo-2,3-dihydro-benzooxazol-5-yl)-propyl]-biphenyl-4-carboxylic acid or (1R,2R) enantiomer

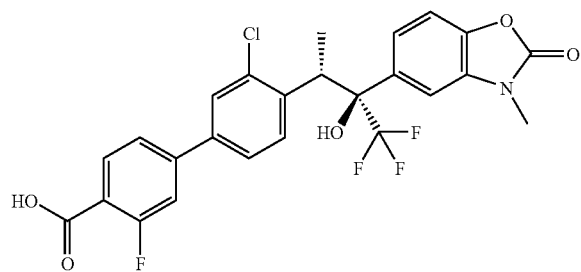

The racemic mixture 3'-chloro-3-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid (205 mg, obtained in Example 118) was separated by chiral prep. HPLC to get the title compound as a colorless solid (79 mg, 39%). MS (neg. ion, m/e)=522.2 [(M−H)⁻].

Example 120

3'-Chloro-3-fluoro-4'-[(1R,2R)-3,3,3-trifluoro-2-hydroxy-1-methyl-2-(3-methyl-2-oxo-2,3-dihydro-benzooxazol-5-yl)-propyl]-biphenyl-4-carboxylic acid or (1S,2S) enantiomer

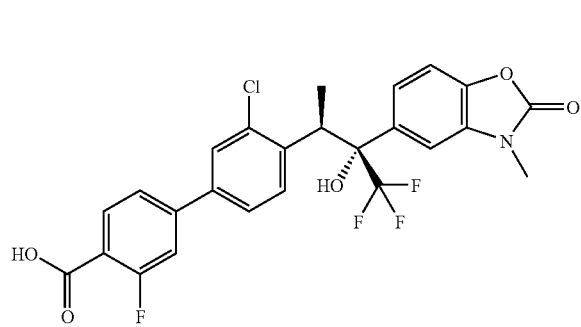

The racemic mixture 3'-chloro-3-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid (205 mg, obtained in Example 118) was separated by chiral preparative HPLC to obtain the title compound as a colorless solid (75 mg, 37%). MS (neg. ion, m/e)=522.3 [(M−H)⁻].

Example 121

3'-Chloro-4-fluoro-4'-[3,3,3-trifluoro-2-hydroxy-1-methyl-2-(3-methyl-2-oxo-2,3-dihydro-benzooxazol-5-yl)-propyl]-biphenyl-3-carboxylic acid ethyl ester

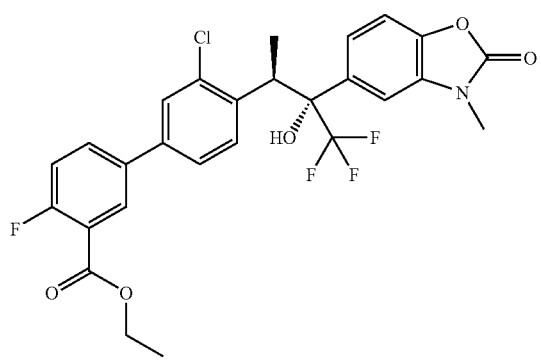

The title compound was prepared in analogy to Example 117 from 5-[2-(4-bromo-2-chloro-phenyl)-1-hydroxy-1-trifluoromethyl-propyl]-3-methyl-3H-benzooxazol-2-one (obtained in Example 116, step 8) by Suzuki coupling with 3-ethoxycarbonyl-4-fluoro-phenylboronic acid [CAS Reg. No. 874219-36-0]. MS (m/e)=552.3 [M+H⁺], MS (m/e)=506.1 [(M−CH$_3$CH$_2$O⁻)⁺].

Example 122

3'-Chloro-4-fluoro-4'-[3,3,3-trifluoro-2-hydroxy-1-methyl-2-(3-methyl-2-oxo-2,3-dihydro-benzooxazol-5-yl)-propyl]-biphenyl-3-carboxylic acid

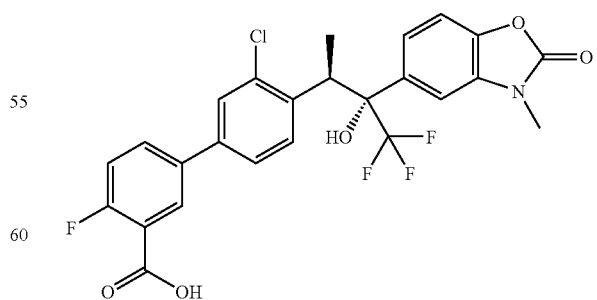

The title compound was prepared in analogy to Example 118 from 3'-chloro-4-fluoro-4'-[3,3,3-trifluoro-2-hydroxy-1-methyl-2-(3-methyl-2-oxo-2,3-dihydro-benzooxazol-5-yl)- propyl]-biphenyl-3-carboxylic acid ethyl ester (obtained in Example 121). MS (m/e)=524.2 [M+H⁺].

Example 123

3,3'-Dichloro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester

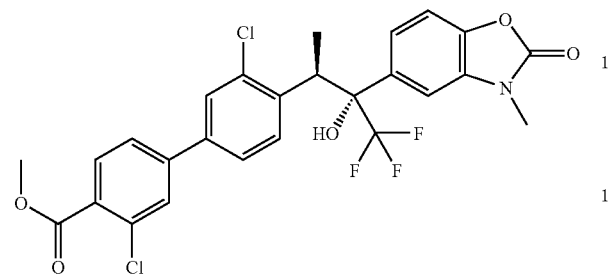

The title compound was prepared in analogy to Example 117 from 5-[2-(4-bromo-2-chloro-phenyl)-1-hydroxy-1-trifluoromethyl-propyl]-3-methyl-3H-benzooxazol-2-one (obtained in Example 116, step 8) by Suzuki coupling with (3-chloro-4-methoxycarbonyl)-benzeneboronic acid [CAS Reg. No. 603122-82-3]. MS (m/e)=571.1 [(M+NH$_4^+$)$^+$], MS (m/e)=522.2 [(M−CH$_3$O$^-$)$^+$].

Example 124

3,3'-Dichloro-4'-[3,3,3-trifluoro-2-hydroxy-1-methyl-2-(3-methyl-2-oxo-2,3-dihydro-benzooxazol-5-yl)-propyl]-biphenyl-4-carboxylic acid

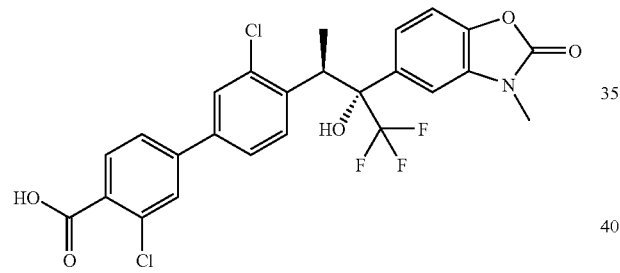

The title compound was prepared in analogy to Example 118 from 3,3'-dichloro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester (obtained in Example 123). MS (neg. ion, m/e)=538.5 [(M−H)$^-$].

Example 125

3'-Chloro-2-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester

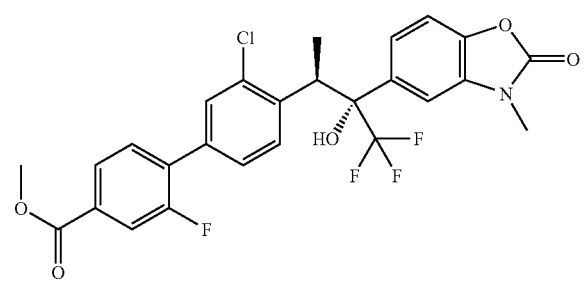

The title compound was prepared in analogy to Example 117 from 5-[2-(4-bromo-2-chloro-phenyl)-1-hydroxy-1-trifluoromethyl-propyl]-3-methyl-3H-benzooxazol-2-one (obtained in Example 116, step 8) by Suzuki coupling with 2-fluoro-4-methoxycarbonylphenylboronic acid [CAS Reg. No. 603122-84-5]. MS (m/e)=538.3 [M+H⁺].

Example 126

3'-Chloro-2-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid

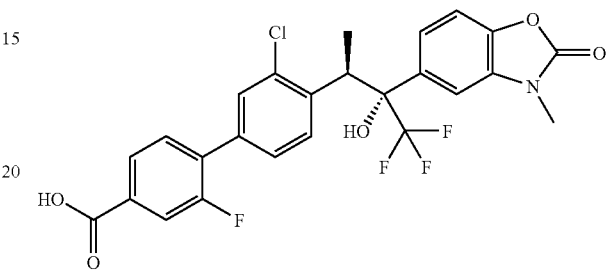

The title compound was prepared in analogy to Example 118 from 3'-chloro-2-fluoro-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester (obtained in Example 125). MS (neg. ion, m/e)=522.4 [(M−H)$^-$].

Example 127

6-{3-Chloro-4-[3,3,3-trifluoro-2-hydroxy-1-methyl-2-(3-methyl-2-oxo-2,3-dihydro-benzooxazol-5-yl)-propyl]-phenyl}-nicotinic acid methyl ester

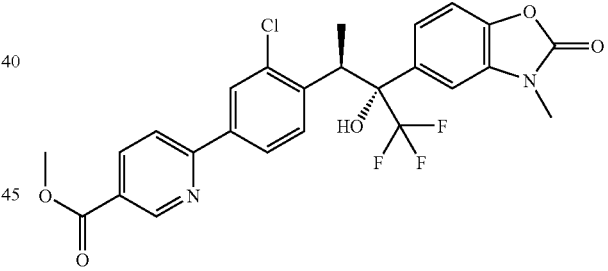

5-[2-(4-Bromo-2-chloro-phenyl)-1-hydroxy-1-trifluoromethyl-propyl]-3-methyl-3H-benzooxazol-2-one (130 mg, obtained in Example 116, step 8), bis-(pinacolato)-diboron (78 mg), potassium acetate (82 mg) and bis-(triphenylphosphine)-palladium(II)-dichloride (6 mg) was dissolved in dioxane (6 mL). The reaction mixture was heated to 100° C. for 2.5 hours. The reaction mixture was cooled to r.t. and water (1 mL), methyl-6-chloronicotinate (96 mg, [CAS Reg. No. 73781-91-6]), dichloro(1,1'-bis(diphenylphosphino)ferrocene)palladium (II) dichloromethane adduct (20 mg) and 2.0 M aqueous Na$_2$CO$_3$ (0.21 mL) were added and the mixture was heated to 65° C. over night. The reaction mixture was cooled, poured into ice/water and extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless foam (35 mg, 24%). MS (m/e)=521.3 [M+H⁺].

Example 128

6-{3-Chloro-4-[3,3,3-trifluoro-2-hydroxy-1-methyl-2-(3-methyl-2-oxo-2,3-dihydro-benzooxazol-5-yl)-propyl]-phenyl}-nicotinic acid

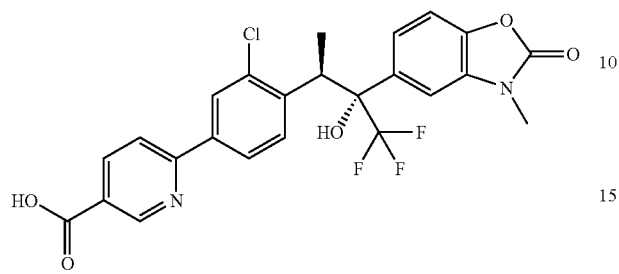

The title compound was prepared in analogy to Example 118 from 6-{3-chloro-4-[3,3,3-trifluoro-2-hydroxy-1-methyl-2-(3-methyl-2-oxo-2,3-dihydro-benzooxazol-5-yl)-propyl]-phenyl}-nicotinic acid methyl ester (obtained in Example 127). MS (neg. ion, m/e)=505.1 [(M−H)⁻].

Example 129

{3'-Chloro-4'-[3,3,3-trifluoro-2-hydroxy-1-methyl-2-(3-methyl-2-oxo-2,3-dihydro-benzooxazol-5-yl)-propyl]-biphenyl-4-yloxy}-acetic acid ethyl ester

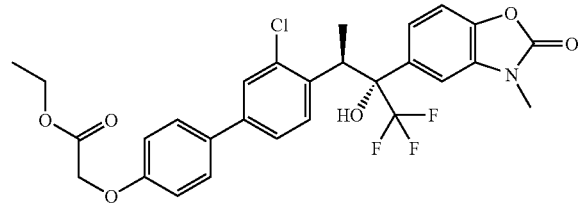

The title compound was prepared in analogy to Example 117 from 5-[2-(4-bromo-2-chloro-phenyl)-1-hydroxy-1-trifluoromethyl-propyl]-3-methyl-3H-benzooxazol-2-one (obtained in Example 116, step 8) by Suzuki coupling with ethylphenoxyacetate-4-boronic acid pinacol ester [CAS Reg. No. 269410-28-8]. MS (m/e)=564.2 [M+H⁺].

Example 130

{3'-Chloro-4'-[3,3,3-trifluoro-2-hydroxy-1-methyl-2-(3-methyl-2-oxo-2,3-dihydro-benzooxazol-5-yl)-propyl]-biphenyl-4-yloxy}-acetic acid

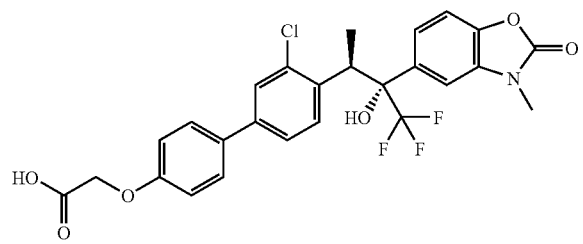

The title compound was prepared in analogy to Example 118 from {3'-chloro-4'-[3,3,3-trifluoro-2-hydroxy-1-methyl-2-(3-methyl-2-oxo-2,3-dihydro-benzooxazol-5-yl)-propyl]-biphenyl-4-yloxy}-acetic acid ethyl ester (obtained in Example 129). MS (neg. ion, m/e)=534.4 [(M−H)⁻].

Example 131

3'-Chloro-3-methoxy-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester

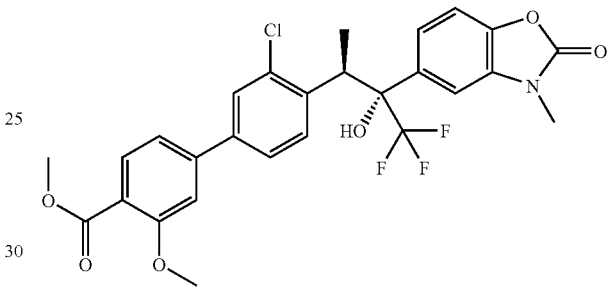

The title compound was prepared in analogy to Example 117 from 5-[2-(4-bromo-2-chloro-phenyl)-1-hydroxy-1-trifluoromethyl-propyl]-3-methyl-3H-benzooxazol-2-one (obtained in Example 116, step 8) by Suzuki coupling with 3-methoxy-4-methoxycarbonylphenylboronic acid [CAS Reg. No. 603122-41-4]. MS (m/e)=550.3 [M+H⁺].

Example 132

3'-Chloro-3-methoxy-4'-[3,3,3-trifluoro-2-hydroxy-1-methyl-2-(3-methyl-2-oxo-2,3-dihydro-benzooxazol-5-yl)-propyl]-biphenyl-4-carboxylic acid

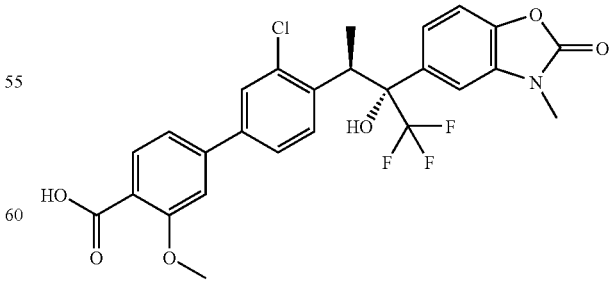

The title compound was prepared in analogy to Example 118 from 3'-chloro-3-methoxy-4'-[3,3,3-trifluoro-2-hydroxy-1-methyl-2-(3-methyl-2-oxo-2,3-dihydro-benzooxazol-5-yl)-propyl]-biphenyl-4-carboxylic acid methyl ester (obtained in Example 131). MS (neg. ion, m/e)=534.3 [(M–H)⁻].

Example 133

6-[2-(4-Bromo-2-chloro-phenyl)-1-hydroxy-1-trifluoromethyl-propyl]-3-methyl-3H-benzooxazol-2-one

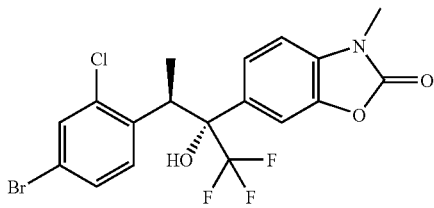

Step 1: 6-[2-(4-Bromo-2-chloro-phenyl)-acetyl]-3-methyl-3H-benzooxazol-2-one

To a suspension of 3-methyl-2-oxo-2,3-dihydro-benzooxazole-6-carboxylic acid (1.0 g, [CAS Reg. No. 140934-94-7]) in CH$_2$Cl$_2$ (14 mL) were added two drops of DMF and oxalylchloride (0.71 mL). The mixture was stirred at room temperature for 1 hour and was then concentrated to dryness. 1,2-Dimethoxyethane (20 mL) was added and the solvent was evaporated again to give the crude acid chloride (3-methyl-2-oxo-2,3-dihydro-benzooxazole-6-carbonyl chloride). To a suspension of zinc powder (677 mg) in 1,2-dimethoxyethane (8 mL) was added tetrakis(triphenylphosphine)palladium(0) (60 mg). A suspension of the acid chloride in 1,2-dimethoxyethane (8 mL) was added. The mixture was cooled in an ice bath and a solution of 4-bromo-1-bromomethyl-2-chlorobenzene (1.47 g, [CAS Reg. No. 89720-77-4]) in 1,2-dimethoxyethane (10 mL) was slowly added over a period of 15 minutes. The mixture was stirred for 10 minutes at 0° C. and then for 2 hours at r.t. The reaction mixture was poured into ice and basified with sat. NaHCO$_3$. The aqueous phase was then extracted two times with ethyl acetate and the organic layers were washed with brine, dried over Na$_2$SO$_4$, filtered and the solvent was evaporated. Ethyl acetate (20 mL) was added to the resulting precipitate and the suspension was stirred for 1 hour at r.t. The solid was filtered off and dried in vacuo. The title compound was obtained as an off-white solid (747 mg, 38%). MS (neg. ion, m/e)=380.2 [(M–H)⁻].

Step 2: 6-[2-(4-Bromo-2-chloro-phenyl)-propionyl]-3-methyl-3H-benzooxazol-2-one

6-[2-(4-Bromo-2-chloro-phenyl)-acetyl]-3-methyl-3H-benzooxazol-2-one (747 mg) was dissolved in DMF (20 mL). The mixture was cooled to 0° C. To this solution was added sodium hydride (55% in mineral oil, 90 mg). The mixture was stirred for 10 minutes at 0° C. and then for 1 hour at r.t. The mixture was cooled to 0° C. and methyl iodide (292 mg) was added dropwise over a period of 10 minutes. Stirring was continued over night at r.t. The reaction mixture was poured into ice/water and extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a brown foam (531 mg, 69%). MS (neg. ion, m/e)=394.2 [(M–H)⁻].

Step 3: 6-[2-(4-Bromo-2-chloro-phenyl)-1-hydroxy-1-trifluoromethyl-propyl]-3-methyl-3H-benzooxazol-2-one Trifluoromethyltrimethylsilane (2M in THF, 1.48 mL) was added at 0° C. to a solution of 6-[2-(4-bromo-2-chloro-phenyl)-propionyl]-3-methyl-3H-benzooxazol-2-one (531 mg) in THF (15 mL) followed by the addition of tetrabutylammonium fluoride trihydrate (424 mg). Stirring was continued for 48 hours at r.t. The reaction mixture was poured into ice/water and extracted two times with ethyl acetate. The combined organic layers were washed with brine, dried over Na$_2$SO$_4$, filtered and the solvent was evaporated. The residue was purified by flash chromatography (silica gel, heptane:ethyl acetate=7:3) to give the title compound as a orange amorphous foam (440 mg, 70%). MS (neg. ion, m/e)=464.0 [(M–H)⁻].

Example 134

3'-Chloro-3-fluoro-4'-[3,3,3-trifluoro-2-hydroxy-1-methyl-2-(3-methyl-2-oxo-2,3-dihydro-benzooxazol-6-yl)-propyl]-biphenyl-4-carboxylic acid

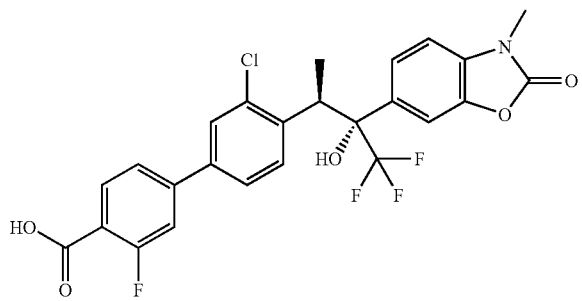

Step 1: 3'-Chloro-3-fluoro-4'-[3,3,3-trifluoro-2-hydroxy-1-methyl-2-(3-methyl-2-oxo-2,3-dihydro-benzooxazol-6-yl)-propyl]-biphenyl-4-carboxylic acid methyl ester The title compound was prepared in analogy to Example 117 from 6-[2-(4-bromo-2-chloro-phenyl)-1-hydroxy-1-trifluoromethyl-propyl]-3-methyl-3H-benzooxazol-2-one (obtained in Example 133, step 3) by Suzuki coupling with 3-fluoro-4-methoxycarbonylphenylboronic acid [CAS Reg. No. 505083-04-5]. MS (neg. ion, m/e)=536.3 [(M–H)⁻].

Step 2: 3'-Chloro-3-fluoro-4'-[3,3,3-trifluoro-2-hydroxy-1-methyl-2-(3-methyl-2-oxo-2,3-dihydro-benzooxazol-6-yl)-propyl]-biphenyl-4-carboxylic acid 3'-Chloro-3-fluoro-4'-[3,3,3-trifluoro-2-hydroxy-1-methyl-2-(3-methyl-2-oxo-2,3-dihydro-benzooxazol-6-yl)-propyl]-biphenyl-4-carboxylic acid methyl ester (60 mg, obtained in Example 134, step 1) was dissolved in THF (4 mL) followed by the addition of aqueous LiOH solution (1.0M, 0.145 mL). The mixture was stirred over night at r.t. The reaction mixture was poured into water and extracted with ethyl acetate. The aqueous phase was acidified with 2 M aqueous HCl to pH 1 and extracted three times with ethyl acetate. The combined organic layers were washed with brine, dried over $Na_2SO_4$ and the solvent was evaporated. The residue was purified by flash chromatography (silica gel, $CH_2Cl_2$:MeOH=7:3 to 1:1) to give the title compound as a brown solid (13 mg, 22%). MS (neg. ion, m/e)=522.2 [(M−H)⁻].

Example 135

3,3'-Dichloro-4'-[3,3,3-trifluoro-2-hydroxy-1-methyl-2-(3-methyl-2-oxo-2,3-dihydro-benzooxazol-6-yl)-propyl]-biphenyl-4-carboxylic acid

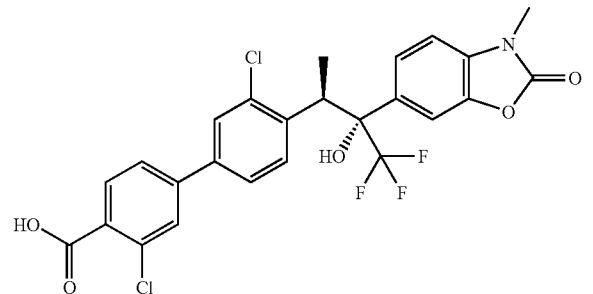

Step 1: 3,3'-Dichloro-4'-[3,3,3-trifluoro-2-hydroxy-1-methyl-2-(3-methyl-2-oxo-2,3-dihydro-benzooxazol-6-yl)-propyl]-biphenyl-4-carboxylic acid methyl ester The title compound was prepared in analogy to Example 117 from 6-[2-(4-bromo-2-chloro-phenyl)-1-hydroxy-1-trifluoromethyl-propyl]-3-methyl-3H-benzooxazol-2-one (obtained in Example 133, step 3) by Suzuki coupling with (3-chloro-4-methoxycarbonyl)-benzeneboronic acid [CAS Reg. No. 603122-82-3]. MS (m/e)=571.2 [(M+NH₄⁺)⁺].

Step 2: 3,3'-Dichloro-4'-[3,3,3-trifluoro-2-hydroxy-1-methyl-2-(3-methyl-2-oxo-2,3-dihydro-benzooxazol-6-yl)-propyl]-biphenyl-4-carboxylic acid The title compound was prepared in analogy to Example 134, step 2 from 3,3'-dichloro-4'-[3,3,3-trifluoro-2-hydroxy-1-methyl-2-(3-methyl-2-oxo-2,3-dihydro-benzooxazol-6-yl)-propyl]-biphenyl-4-carboxylic acid methyl ester (obtained in Example 135, step 1). MS (neg. ion, m/e)=538.2 [(M−H)⁻].

Example 136

3'-Chloro-3-fluoro-4'-[3,3,3-trifluoro-2-(7-fluoro-4-methyl-3-oxo-3,4-dihydro-2H-benzo[1,4]oxazin-6-yl)-2-hydroxy-1-methyl-propyl]-biphenyl-4-carboxylic acid methyl ester

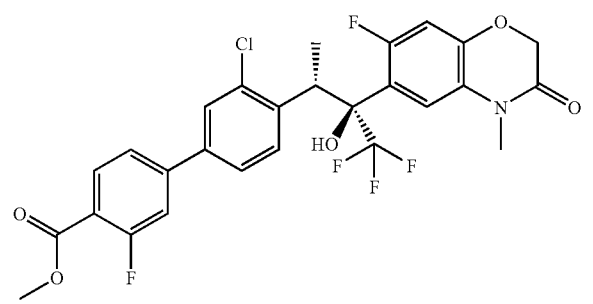

Step 1: 7-Fluoro-4-methyl-3-oxo-3,4-dihydro-2H-benzo[1,4]oxazine-6-carbonitrile

To a stirred solution of 7-fluoro-3-oxo-3,4-dihydro-2H-benzo[1,4]oxazine-6-carbonitrile (CAS Reg. No. [151982-49-9], 4.71 g) in N,N-dimethylacetamide (108 ml) were added KOtBu (3.08 g) and methyl iodide (3.83 g). The mixture was stirred at room temperature for 3.5 h. Ice water was added. The suspension was filtered and the solid was washed with water and dried to give the title compound (4.07 g) as an off-white solid.

Step 2: 7-Fluoro-4-methyl-3-oxo-3,4-dihydro-2H-benzo[1,4]oxazine-6-carboxylic acid In analogy to Example 11, step 2, 7-fluoro-4-methyl-3-oxo-3,4-dihydro-2H-benzo[1,4]oxazine-6-carbonitrile was hydrolyzed with aqueous KOH to give the title compound as a light brown solid. MS (m/e, ISP neg. ion)=223.9 [M−H⁺].

Step 3: 6-[2-(4-Bromo-2-chloro-phenyl)-acetyl]-7-fluoro-4-methyl-4H-benzo[1,4]oxazin-3-one In analogy to Example 49, step 1, 7-fluoro-4-methyl-3-oxo-3,4-dihydro-2H-benzo[1,4]oxazine-6-carboxylic acid was converted to the acid chloride and subsequently reacted with 4-bromo-1-bromomethyl-2-chloro-benzene in the presence of zinc and tetrakis(triphenylphosphine)palladium(0) to give the title compound as an off-white solid. MS (m/e)=412.2 [M+H⁺].

Step 4: 6-[2-(4-Bromo-2-chloro-phenyl)-propionyl]-7-fluoro-4-methyl-4H-benzo[1,4]oxazin-3-one In analogy to Example 1, step 2, 6-[2-(4-bromo-2-chloro-phenyl)-acetyl]-7-fluoro-4-methyl-4H-benzo[1,4]oxazin-3-one was reacted with sodium hydride and methyl iodide to give the title compound as a light brown foam. MS (m/e, ISP neg. ion)=426.0 [M+H⁺].

Step 5: 6-[2-(4-Bromo-2-chloro-phenyl)-1-hydroxy-1-trifluoromethyl-propyl]-7-fluoro-4-methyl-4H-benzo[1,4]oxazin-3-one In analogy to Example 1, step 3, 6-[2-(4-bromo-2-chloro-phenyl)-propionyl]-7-fluoro-4-methyl-4H-benzo[1,4]oxazin-3-one was reacted with (trifluoromethyl)trimethylsilane and tetramethylammonium fluoride to give the title compound as a colorless solid. MS (m/e, ISP neg. ion)=496.0 [M−H⁺].

Step 6: 3'-Chloro-3-fluoro-4'-[3,3,3-trifluoro-2-(7-fluoro-4-methyl-3-oxo-3,4-dihydro-2H-benzo[1,4]oxazin-6-yl)-2-hydroxy-1-methyl-propyl]-biphenyl-4-carboxylic acid methyl ester In analogy to Example 17, step 2, 6-[2-(4-bromo-2-chloro-phenyl)-1-hydroxy-1-trifluoromethyl-propyl]-7-fluoro-4-methyl-4H-benzo[1,4]oxazin-3-one was reacted with 3-fluoro-4-methoxycarbonylphenylboronic acid to give the title compound as a colorless solid. MS (m/e)=570.3 [M+H⁺].

Example 137

3'-Chloro-3-fluoro-4'-[3,3,3-trifluoro-2-(7-fluoro-4-methyl-3-oxo-3,4-dihydro-2H-benzo[1,4]oxazin-6-yl)-2-hydroxy-1-methyl-propyl]-biphenyl-4-carboxylic acid

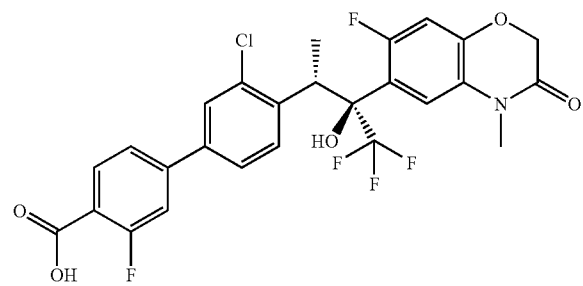

In analogy to Example 2,3'-chloro-3-fluoro-4'-[3,3,3-trifluoro-2-(7-fluoro-4-methyl-3-oxo-3,4-dihydro-2H-benzo[1,4]oxazin-6-yl)-2-hydroxy-1-methyl-propyl]-biphenyl-4-carboxylic acid methyl ester (Example 136) was hydrolyzed to give the title compound as a colorless solid. MS (m/e, ISP neg. ion)=554.2 [M−H⁺].

Example 138

2-Chloro-4-{3-chloro-4-[3,3,3-trifluoro-2-(7-fluoro-4-methyl-3-oxo-3,4-dihydro-2H-benzo[1,4]oxazin-6-yl)-2-hydroxy-1-methyl-propyl]-phenoxy}-benzoic acid methyl ester

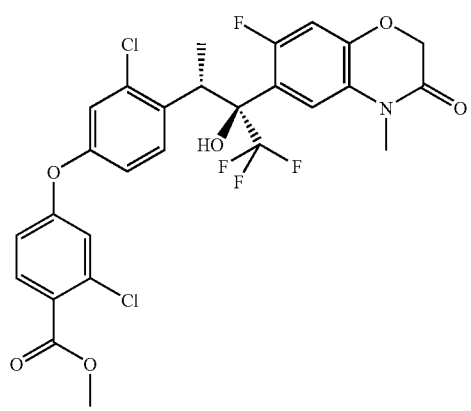

Steps 1 and 2: 6-[2-(2-Chloro-4-methoxy-phenyl)-acetyl]-7-fluoro-4-methyl-4H-benzo[1,4]oxazin-3-one To a solution of 7-fluoro-4-methyl-3-oxo-3,4-dihydro-2H-benzo[1,4]oxazine-6-carboxylic acid (Example 136, step 2, 1.98 g) in N,N-dimethylformamide (66 ml) was added 1,1'-carbonyldiimidazole (1.43 g). The mixture was stirred at 50° C. for 90 min. The mixture was cooled to −10° C. and (2-chloro-5-methoxy-phenyl)-acetic acid methyl ester (1.8 g) was added. Sodium hydride (60% dispersion in mineral oil, 1.12 g) was added portionwise over 30 min. The mixture was slowly warmed to room temperature and stirred for 4 h. The mixture was poured into ice water (135 ml) and saturated aqueous ammonium chloride solution (42 ml) and was extracted with ethyl acetate (5×). The organic phase was washed with brine, dried (MgSO₄), filtered and concentrated to dryness. The residue was dissolved in dimethylsulfoxide (18 ml). NaCl (0.54 g) and water (0.23 ml) were added and the mixture was heated to 140° C. for 40 h. After cooling to room temperature, water was added and the mixture was extracted with ethyl acetate. The organic phase was washed with brine, dried (MgSO₄), filtered and concentrated to dryness to give a light brown solid. The product was purified by chromatography (SiO₂, CH₂Cl₂/MeOH 1:0=>95:5) to give the title compound as a light yellow solid (318 mg). MS (m/e)=364.1 [M+H⁺].

Step 3: 6-[2-(2-Chloro-4-methoxy-phenyl)-propionyl]-7-fluoro-4-methyl-4H-benzo[1,4]oxazin-3-one In analogy to Example 1, step 2, 6-[2-(2-chloro-4-methoxy-phenyl)-acetyl]-7-fluoro-4-methyl-4H-benzo[1,4]oxazin-3-one was reacted with sodium hydride and methyl iodide to give the title compound as an off-white oil. MS (m/e, ISP neg. ion)=376.2 [M−H⁺].

Step 4: 6-[2-(2-Chloro-4-methoxy-phenyl)-1-hydroxy-1-trifluoromethyl-propyl]-7-fluoro-4-methyl-4H-benzo[1,4]oxazin-3-one In analogy to Example 1, step 3, 6-[2-(2-chloro-4-methoxy-phenyl)-propionyl]-7-fluoro-4-methyl-4H-benzo[1,4]oxazin-3-one was reacted with (trifluoromethyl)trimethylsilane and tetramethylammonium fluoride to give the title compound as a colorless solid. MS (m/e)=448.1 [M+H⁺].

Step 5: 6-[2-(2-Chloro-4-hydroxy-phenyl)-1-hydroxy-1-trifluoromethyl-propyl]-7-fluoro-4-methyl-4H-benzo[1,4]oxazin-3-one In analogy to Example 1, step 4, 6-[2-(2-chloro-4-methoxy-phenyl)-1-hydroxy-1-trifluoromethyl-propyl]-7-fluoro-4-methyl-4H-benzo[1,4]oxazin-3-one was reacted with BBr₃ to give the title compound as a colorless foam. MS (m/e, ISP neg. ion)=432.1 [M−H⁺].

Step 6: 2-Chloro-4-{3-chloro-4-[3,3,3-trifluoro-2-(7-fluoro-4-methyl-3-oxo-3,4-dihydro-2H-benzo[1,4]oxazin-6-yl)-2-hydroxy-1-methyl-propyl]-phenoxy}-benzoic acid methyl ester In analogy to Example 5, 6-[2-(2-chloro-4-hydroxy-phenyl)-1-hydroxy-1-trifluoromethyl-propyl]-7-fluoro-4-methyl-4H-benzo[1,4]oxazin-3-one was reacted with 3-chloro-

Example 139

2-Chloro-4-{3-chloro-4-[3,3,3-trifluoro-2-(7-fluoro-4-methyl-3-oxo-3,4-dihydro-2H-benzo[1,4]oxazin-6-yl)-2-hydroxy-1-methyl-propyl]-phenoxy}-benzoic acid

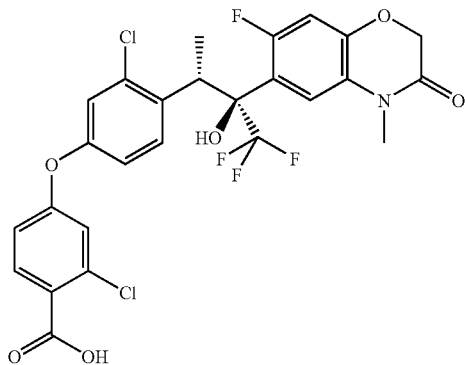

In analogy to Example 2, 2-chloro-4-{3-chloro-4-[3,3,3-trifluoro-2-(7-fluoro-4-methyl-3-oxo-3,4-dihydro-2H-benzo[1,4]oxazin-6-yl)-2-hydroxy-1-methyl-propyl]-phenoxy}-benzoic acid methyl ester (Example 138) was hydrolyzed to give the title compound as a colorless solid. MS (m/e, ISP neg. ion)=586.0 [M−H$^+$].

Example 140

2-Chloro-4-{3-chloro-4-[3,3,3-trifluoro-2-hydroxy-1-methyl-2-(2-oxo-4-trifluoromethyl-1,2-dihydro-quinolin-6-yl)-propyl]-phenoxy}-benzoic acid

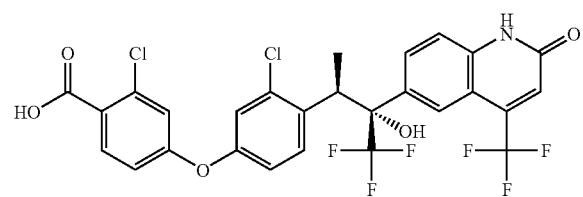

Step 1: 2-Chloro-4-(3-chloro-4-methyl-phenoxy)-benzonitrile

To a solution of 3-chloro-4-methylphenol (7.5 g) and 2-chloro-4-fluorobenzonitrile (8.14 g) in N,N-dimethylacetamide (23 ml) was added potassium carbonate (8.55 g). The mixture was stirred for 5 hours at 120° C. The mixture was poured into ice water and extracted with ethyl acetate. The organic phase was washed with water, dried (MgSO$_4$), filtered and concentrated to dryness to give the title compound (14.42 g) as a colorless solid.

Step 2: 4-(4-Bromomethyl-3-chloro-phenoxy)-2-chloro-benzonitrile

To a stirred solution of 2-chloro-4-(3-chloro-4-methyl-phenoxy)-benzonitrile (14.41 g) in CCl$_4$ (100 ml) under argon were added N-bromosuccinimide (9.5 g) and dibenzoylperoxide (1.38 g). The mixture was heated to reflux for 2.5 h. After cooling to room temperature, the mixture was filtered. The filter cake was washed with cyclohexane. The combined filtrate was concentrated to dryness to give the crude product (19.75 g) as a light orange solid. Part of the product was purified by repeated chromatography (SiO$_2$, cyclohexane/ethyl acetate 1:0=>4:1) to give the title compound as an off-white solid (3.27 g).

Step 3: 2-Isopropoxy-4-trifluoromethyl-quinoline-6-carboxylic acid

The title compound was synthesized by carbonylation of 6-bromo-2-isopropoxy-4-trifluoromethyl-quinoline (CAS [328955-63-1]) in ethyl acetate/water using 50 bar CO, PdCl$_2$ dppf CH$_2$Cl$_2$, 80° C. for 20 h. Light grey solid. MS (m/e, ISP neg. ion)=298.3 [M−H$^+$].

Step 4: 2-Chloro-4-{3-chloro-4-[2-(2-isopropoxy-4-trifluoromethyl-quinolin-6-yl)-2-oxo-ethyl]-phenoxy}-benzonitrile In analogy to Example 49, step 1, 2-isopropoxy-4-trifluoromethyl-quinoline-6-carboxylic acid was converted to the acid chloride and subsequently reacted with 4-(4-bromomethyl-3-chloro-phenoxy)-2-chloro-benzonitrile in the presence of zinc and tetrakis(triphenyl-phosphine)palladium(0) to give the title compound as a yellow oil. MS (m/e, ISP neg. ion)=557.0 [M−H$^+$].

Step 5: 2-Chloro-4-{3-chloro-4-[2-(2-isopropoxy-4-trifluoromethyl-quinolin-6-yl)-1-methyl-2-oxo-ethyl]-phenoxy}-benzonitrile In analogy to Example 1, step 2, 2-chloro-4-{3-chloro-4-[2-(2-isopropoxy-4-trifluoromethyl-quinolin-6-yl)-2-oxo-ethyl]-phenoxy}-benzonitrile was reacted with sodium hydride and methyl iodide to give the title compound as a yellow oil. MS (m/e, ISP neg. ion)=571.1 [M−H$^+$].

Step 6: 2-Chloro-4-{3-chloro-4-[3,3,3-trifluoro-2-hydroxy-2-(2-isopropoxy-4-trifluoromethyl-quinolin-6-yl)-1-methyl-propyl]-phenoxy}-benzonitrile In analogy to Example 1, step 3, 2-chloro-4-{3-chloro-4-[2-(2-isopropoxy-4-trifluoromethyl-quinolin-6-yl)-1-methyl-2-oxo-ethyl]-phenoxy}-benzonitrile was reacted with (trifluoromethyl)trimethylsilane and tetramethylammonium fluoride to give the title compound as an off-white gum. MS (m/e, ISP neg. ion)=641.1 [M−H$^+$].

Step 7: 2-Chloro-4-{3-chloro-4-[3,3,3-trifluoro-2-hydroxy-1-methyl-2-(2-oxo-4-trifluoromethyl-1,2-dihydro-quinolin-6-yl)-propyl]-phenoxy}-benzonitrile To 2-chloro-4-{3-chloro-4-[3,3,3-trifluoro-2-hydroxy-2-(2-isopropoxy-4-trifluoromethyl-quinolin-6-yl)-1-methyl-propyl]-phenoxy}-benzonitrile (53 mg) was added acetic acid (270 mg) and aqueous HCl (37%, 92 mg). The mixture was stirred at 60° C. for 24 h. The mixture was neutralized with aqueous NaOH solution and extracted with ethyl acetate. The organic phase was washed with water, dried (MgSO$_4$), filtered and concentrated to dryness to give the title compound (46 mg) as an orange solid. MS (m/e, ISP neg. ion)=599.1 [M−H$^+$].

Step 8: 2-Chloro-4-{3-chloro-4-[3,3,3-trifluoro-2-hydroxy-1-methyl-2-(2-oxo-4-trifluoromethyl-1,2-dihydro-quinolin-6-yl)-propyl]-phenoxy}-benzoic acid In analogy to Example 11, step 2, 2-chloro-4-{3-chloro-4-[3,3,3-trifluoro-2-hydroxy-1-methyl-2-(2-oxo-4-trifluoromethyl-1,2-dihydro-quinolin-6-yl)-propyl]-phenoxy}-benzonitrile was hydrolyzed with aqueous KOH to give the title compound as a colorless solid. MS (m/e, ISP neg. ion)=618.1 [M−H+].

Example 141

4-{3-Chloro-4-[2-(4-cyano-3,5-dimethyl-phenyl)-3,3,3-trifluoro-2-hydroxy-1-methyl-propyl]-phenoxy}-2-fluoro-benzoic acid methyl ester

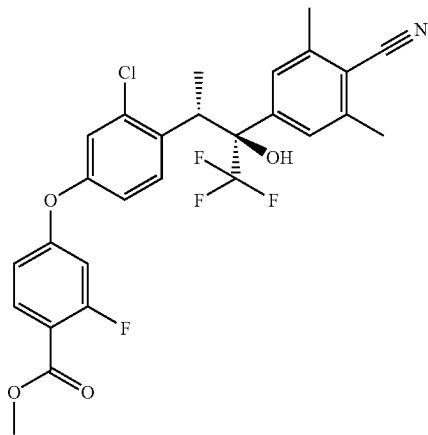

Steps 1 and 2: 4-[2-(2-Chloro-4-methoxy-phenyl)-acetyl]-2,6-dimethyl-benzonitrile The title compound was prepared in analogy to Example 138, steps 1 and 2, from (2-chloro-4-methoxy-phenyl)-acetic acid methyl ester and 4-cyano-3,5-dimethyl-benzoic acid (CAS [90924-01-0]). Orange solid. MS (m/e, ISP neg. ion)= 312.1 [M−H+].

Step 3: 4-[2-(2-Chloro-4-methoxy-phenyl)-propionyl]-2,6-dimethyl-benzonitrile

In analogy to Example 1, step 2, 4-[2-(2-chloro-4-methoxy-phenyl)-acetyl]-2,6-dimethyl-benzonitrile was reacted with sodium hydride and methyl iodide to give the title compound as an orange oil. MS (m/e)=328.3 [M+H+].

Step 4: 4-[2-(2-Chloro-4-methoxy-phenyl)-1-hydroxy-1-trifluoromethyl-propyl]-2,6-dimethyl-benzonitrile In analogy to Example 1, step 3, 4-[2-(2-chloro-4-methoxy-phenyl)-propionyl]-2,6-dimethyl-benzonitrile was reacted with (trifluoromethyl)trimethylsilane and tetramethylammonium fluoride to give the title compound as a colorless solid. MS (m/e, ISP neg. ion)=395.9 [M−H+].

Step 5: 4-[2-(2-Chloro-4-hydroxy-phenyl)-1-hydroxy-1-trifluoromethyl-propyl]-2,6-dimethyl-benzonitrile In analogy to Example 1, step 4, 4-[2-(2-chloro-4-methoxy-phenyl)-1-hydroxy-1-trifluoromethyl-propyl]-2,6-dimethyl-benzonitrile was reacted with $BBr_3$ to give the title compound as a colorless foam. MS (m/e, ISP neg. ion)=382.1 [M−H+].

Step 6: 4-{3-Chloro-4-[2-(4-cyano-3,5-dimethyl-phenyl)-3,3,3-trifluoro-2-hydroxy-1-methyl-propyl]-phenoxy}-2-fluoro-benzoic acid methyl ester In analogy to Example 5, 4-[2-(2-chloro-4-hydroxy-phenyl)-1-hydroxy-1-trifluoromethyl-propyl]-2,6-dimethyl-benzonitrile was reacted with 3-fluoro-4-methoxycarbonylphenylboronic acid, copper-(II)-acetate and pyridine to give the title compound as a colorless foam. MS (m/e)=534.1 [M+H+].

Example 142

4-{3-Chloro-4-[2-(4-cyano-3,5-dimethyl-phenyl)-3,3,3-trifluoro-2-hydroxy-1-methyl-propyl]-phenoxy}-2-fluoro-benzoic acid

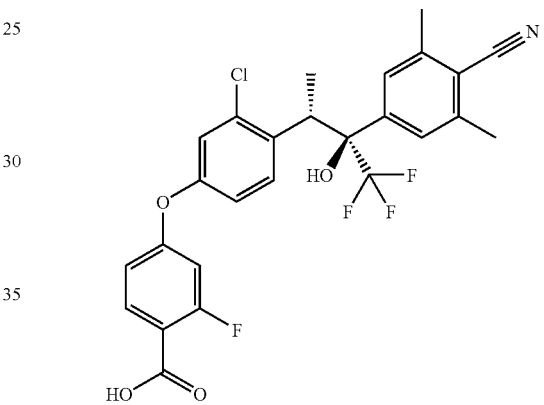

In analogy to Example 2, 4-{3-chloro-4-[2-(4-cyano-3,5-dimethyl-phenyl)-3,3,3-trifluoro-2-hydroxy-1-methyl-propyl]-phenoxy}-2-fluoro-benzoic acid methyl ester (Example 141) was hydrolyzed to give the title compound as a colorless solid. MS (m/e, ISP neg. ion)=520.1 [M−H+].

Example 143

2-Chloro-4-{3-chloro-4-[2-(4-cyano-3,5-dimethyl-phenyl)-3,3,3-trifluoro-2-hydroxy-1-methyl-propyl]-phenoxy}-benzoic acid methyl ester

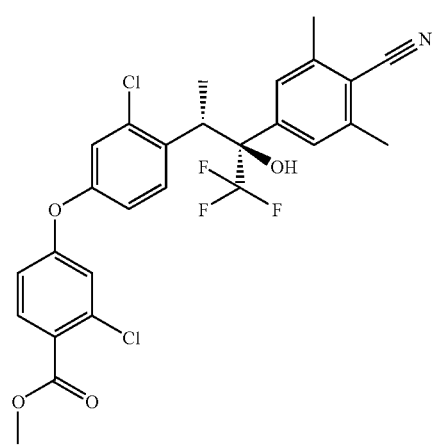

In analogy to Example 5, 4-[2-(2-chloro-4-hydroxy-phenyl)-1-hydroxy-1-trifluoromethyl-propyl]-2,6-dimethyl-benzonitrile (Example 141, step 5) was reacted with 3-chloro-4-methoxycarbonylphenylboronic acid, copper-(II)-acetate and pyridine to give the title compound as a colorless solid. MS (m/e, ISP neg. ion)=550.1 [M−H⁺].

Example 144

2-Chloro-4-{3-chloro-4-[2-(4-cyano-3,5-dimethyl-phenyl)-3,3,3-trifluoro-2-hydroxy-1-methyl-propyl]-phenoxy}-benzoic acid

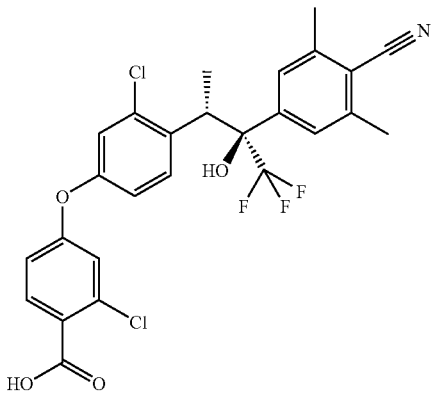

In analogy to Example 2, 2-chloro-4-{3-chloro-4-[2-(4-cyano-3,5-dimethyl-phenyl)-3,3,3-trifluoro-2-hydroxy-1-methyl-propyl]-phenoxy}-benzoic acid methyl ester (Example 143) was hydrolyzed to give the title compound as a colorless solid. MS (m/e, ISP neg. ion)=536.0 [M−H⁺].

Example 145

6-{3-Chloro-4-[2-(4-cyano-3,5-dimethyl-phenyl)-3,3,3-trifluoro-2-hydroxy-1-methyl-propyl]-phenoxy}-4-trifluoromethyl-nicotinic acid methyl ester

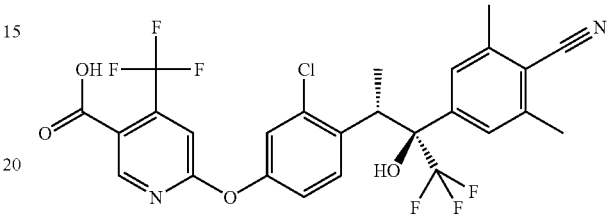

To a solution of 4-[2-(2-chloro-4-hydroxy-phenyl)-1-hydroxy-1-trifluoromethyl-propyl]-2,6-dimethyl-benzonitrile (Example 141, step 5, 100 mg) in N,N-dimethylacetamide (1 ml) were added methyl-6-chloro-4-(trifluoromethyl)-nicotinate (75 mg), triethylamine (34 mg) and 1,4-diazabicyclo[2.2.2]octane (4 mg). The mixture was stirred at room temperature for 6 h and then diluted with EtOAc. Water was added. The mixture was extracted with EtOAc. The organic phase was washed with water, dried (MgSO₄), filtered and concentrated. The product was purified by chromatography (SiO₂, cyclohexane/EtOAc 1:0=>2:3) to give the title compound (132 mg) as a colorless solid. MS (m/e, ISP neg. ion)=585.1 [M−H⁺].

Example 146

6-{3-Chloro-4-[2-(4-cyano-3,5-dimethyl-phenyl)-3,3,3-trifluoro-2-hydroxy-1-methyl-propyl]-phenoxy}-4-trifluoromethyl-nicotinic acid In analogy to Example 2, 6-{3-chloro-4-[2-(4-cyano-3,5-dimethyl-phenyl)-3,3,3-trifluoro-2-hydroxy-1-methyl-propyl]-phenoxy}-4-trifluoromethyl-nicotinic acid methyl ester (Example 145) was hydrolyzed to give the title compound as a colorless solid. MS (m/e)=573.1 [M+H⁺].

Example 147

6-{3-Chloro-4-[2-(4-cyano-3,5-dimethyl-phenyl)-3,3,3-trifluoro-2-hydroxy-1-methyl-propyl]-phenoxy}-nicotinic acid methyl ester

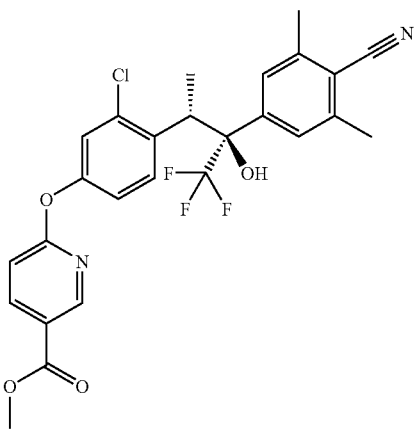

To a solution of 4-[2-(2-chloro-4-hydroxy-phenyl)-1-hydroxy-1-trifluoromethyl-propyl]-2,6-dimethyl-benzonitrile (Example 141, step 5, 100 mg) in N,N-dimethylacetamide (2 ml) were added methyl-6-chloro-nicotinate (68 mg) and cesium carbonate (256 mg). The mixture was stirred at room temperature for 3 h. Methyl-6-chloro-nicotinate (23 mg) was added and the mixture was stirred overnight and then diluted with EtOAc. Water was added. The mixture was extracted with EtOAc. The organic phase was washed with water, dried (MgSO₄), filtered and concentrated. The product was purified by chromatography (SiO₂, cyclohexane/EtOAc 1:0=>2:3) to give the title compound (103 mg) as a colorless solid. MS (m/e)=519.2 [M+H⁺].

Example 148

6-{3-Chloro-4-[2-(4-cyano-3,5-dimethyl-phenyl)-3,3,3-trifluoro-2-hydroxy-1-methyl-propyl]-phenoxy}-nicotinic acid

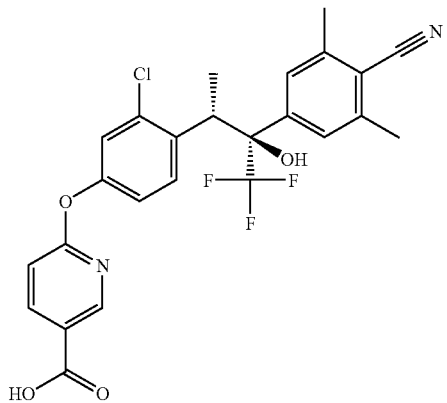

In analogy to Example 2, 6-{3-chloro-4-[2-(4-cyano-3,5-dimethyl-phenyl)-3,3,3-trifluoro-2-hydroxy-1-methyl-propyl]-phenoxy}-nicotinic acid methyl ester (Example 147) was hydrolyzed to give the title compound as a colorless solid. MS (m/e, ISP neg. ion)=503.0 [M−H⁺].

Example 149

5-Chloro-6-{3-chloro-4-[2-(4-cyano-3,5-dimethyl-phenyl)-3,3,3-trifluoro-2-hydroxy-1-methyl-propyl]-phenoxy}-nicotinic acid methyl ester

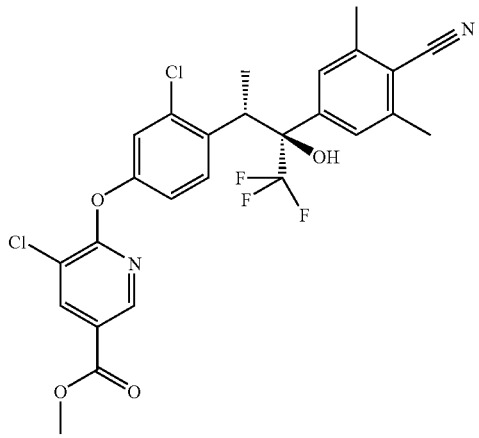

In analogy to Example 147, 4-[2-(2-chloro-4-hydroxy-phenyl)-1-hydroxy-1-trifluoromethyl-propyl]-2,6-dimethyl-benzonitrile (Example 141, step 5) was reacted with methyl-5,6-dichloro-nicotinate in the presence of cesium carbonate to give the title compound as a colorless solid. MS (m/e)= 553.3 [M+H⁺].

Example 150

5-Chloro-6-{3-chloro-4-[2-(4-cyano-3,5-dimethyl-phenyl)-3,3,3-trifluoro-2-hydroxy-1-methyl-propyl]-phenoxy}-nicotinic acid

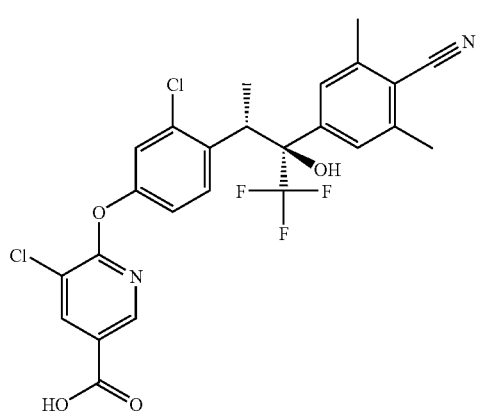

In analogy to Example 2, 5-chloro-6-{3-chloro-4-[2-(4-cyano-3,5-dimethyl-phenyl)-3,3,3-trifluoro-2-hydroxy-1-methyl-propyl]-phenoxy}-nicotinic acid methyl ester (Example 149) was hydrolyzed to give the title compound as a colorless solid. MS (m/e, ISP neg. ion)=537.1 [M−H⁺].

Example 151

3'-Chloro-4'-[2-(4-cyano-phenyl)-3,3,3-trifluoro-2-hydroxy-1-methyl-propyl]-4-fluoro-biphenyl-3-carboxylic acid

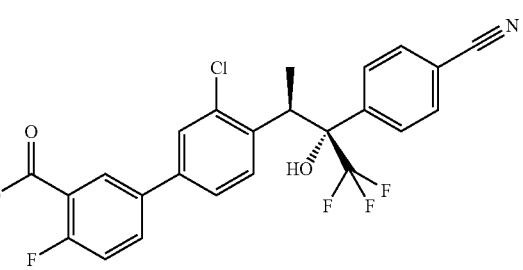

The title compound was prepared in analogy to Example 73, steps 4-7, from 4-iodobenzonitrile (CAS Reg. No. 3058-39-7) using isopropylmagnesium chloride instead of butyl-lithium as metallating agent in step 4, and 3-ethoxycarbonyl-4-fluorophenylboronic acid (CAS Reg. No. 874219-36-0) in step 7. Light brown oil. MS (m/e, ISP neg. ion)=476.1 [M−H⁺].

Example 152

3'-Chloro-4'-[2-(4-cyano-phenyl)-3,3,3-trifluoro-2-hydroxy-1-methyl-propyl]-3-fluoro-biphenyl-4-carboxylic acid

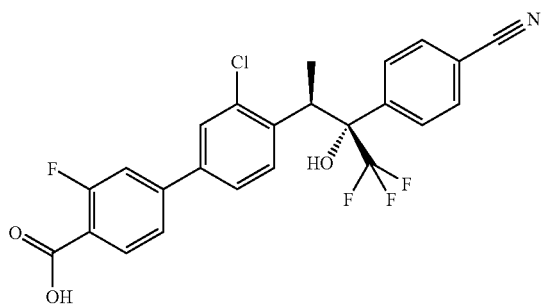

The title compound was prepared in analogy to Example 151 from fluoro-4-methoxycarbonylphenylboronic acid (CAS Reg. No. 505083-04-5). Light brown oil. MS (m/e, ISP neg. ion)=476.1 [M−H⁺].

Example 153

3'-Chloro-4'-[2-(3-cyano-phenyl)-3,3,3-trifluoro-2-hydroxy-1-methyl-propyl]-3-fluoro-biphenyl-4-carboxylic acid

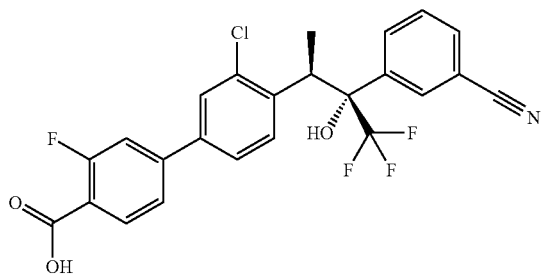

The title compound was prepared in analogy to Example 152 from 3-iodobenzonitrile (CAS Reg. No. 69113-59-3). White foam. MS (m/e, ISP neg. ion)=476.1 [M−H⁺].

Example 154

3'-Chloro-4'-[2-(3-cyano-phenyl)-3,3,3-trifluoro-2-hydroxy-1-methyl-propyl]-4-fluoro-biphenyl-3-carboxylic acid

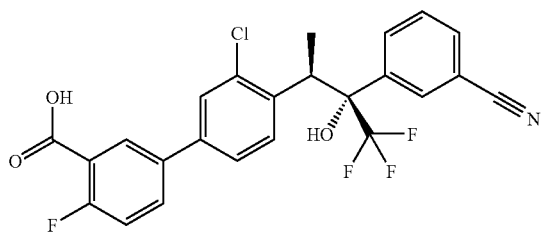

The title compound was prepared in analogy to Example 151 from 3-iodobenzonitrile (CAS Reg. No. 69113-59-3). White foam. MS (m/e, ISP neg. ion)=476.1 [M−H⁺].

Example 155

5-Chloro-6-{3-chloro-4-[2-(4-cyano-phenyl)-3,3,3-trifluoro-2-hydroxy-1-methyl-propyl]-phenoxy}-nicotinic acid

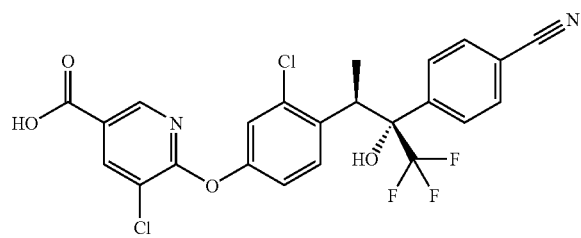

Step 1: 4-[2-(2-Chloro-4-hydroxy-phenyl)-1-hydroxy-1-trifluoromethyl-propyl]-benzonitrile The title compound was prepared in analogy to Example 73, steps 1-6, from 2'-chloro-4'-methoxyacetophenone (CAS Reg. No. 41068-36-4) in step 1 and 4-iodobenzonitrile (CAS Reg. No. 3058-39-7) using isopropylmagnesium chloride instead of butyllithium as metallating agent in step 4. The crude methyl ether was deprotected using boron tribromide in analogy to Example 85 step 4. Brown oil. MS (m/e, ISP neg. ion)=354.2 [M−H⁺].

Step 2: 5-Chloro-6-{3-chloro-4-[2-(4-cyano-phenyl)-3,3,3-trifluoro-2-hydroxy-1-methyl-propyl]-phenoxy}-nicotinic acid The title compound was prepared in analogy to Example 107 from 4-[2-(2-chloro-4-hydroxy-phenyl)-1-hydroxy-1-trifluoromethyl-propyl]-benzonitrile. White foam. MS (m/e)= 513.2 [M+H⁺].

Example 156

2-Chloro-4-{3-chloro-4-[2-(4-cyano-phenyl)-3,3,3-trifluoro-2-hydroxy-1-methyl-propyl]-phenoxy}-benzoic acid

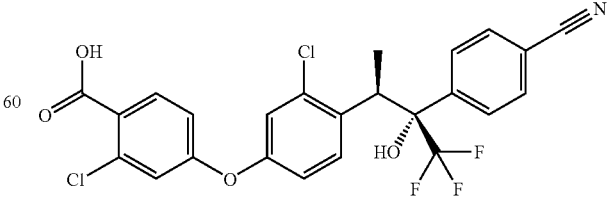

The title compound was prepared in analogy to Example 90 from 4-[2-(2-chloro-4-hydroxy-phenyl)-1-hydroxy-1-trifluoromethyl-propyl]-benzonitrile (Example 155 step 1). White foam. MS (m/e, ISP neg. ion)=508.1 [M−H⁺].

Example 157

6-{3-Chloro-4-[2-(4-cyano-phenyl)-3,3,3-trifluoro-2-hydroxy-1-methyl-propyl]-phenoxy}-nicotinic acid

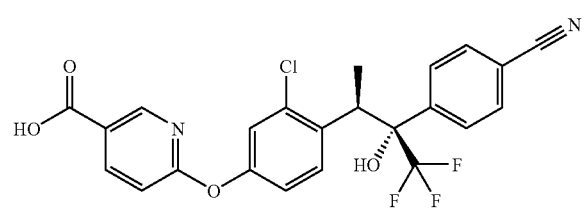

The title compound was prepared in analogy to Example 101 from 4-[2-(2-chloro-4-hydroxy-phenyl)-1-hydroxy-1-trifluoromethyl-propyl]-benzonitrile (Example 155 step 1). White foam. MS (m/e, ISP neg. ion)=475.2 [M−H⁺].

Example 158

2-Chloro-6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid

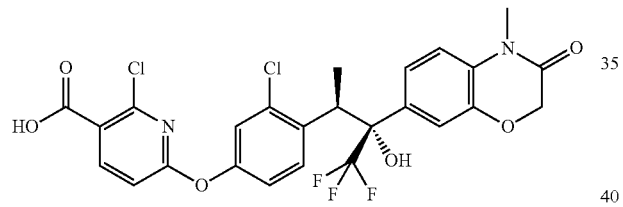

Step 1: 7-[2-(2-Chloro-4-methoxy-phenyl)-acetyl]-4-methyl-4H-benzo[1,4]oxazin-3-one A 1M solution of tert-butylmagnesium chloride (CAS Reg. No. 677-22-5) in diethyl ether (2.1 ml) was added to 2-chloro-4-methoxyphenylacetic acid (CAS 91367-09-8) (200 mg) in THF (5 ml). The mixture was stirred at room temperature for 30 min. A solution of 4-methyl-3-oxo-3,4-dihydro-2H-benzo[1,4]oxazine-7-carboxylic acid methyl ester (200 mg, CAS Reg. No. 201294-27-1) in THF (3 ml) was added and the resulting mixture was stirred overnight. Aqueous HCl (25%, 0.5 ml) and water (10 ml) were added and extracted with EtOAc. The combined organic layers were dried over Na₂SO₄ and then concentrated to an oil. The residue was purified by flash chromatography (SiO₂, 10 to 50% EtOAc/heptane) to give the title compound (100 mg) as a light yellow solid. MS (m/e)=346.1 [M+H⁺].

Step 2: 7-[2-(2-Chloro-4-hydroxy-phenyl)-1-hydroxy-1-trifluoromethyl-propyl]-4-methyl-4H-benzo[1,4]oxazin-3-one The title compound was prepared in analogy to Example 85, steps 2 to 4, from 7-[2-(2-chloro-4-methoxy-phenyl)-acetyl]-4-methyl-4H-benzo[1,4]oxazin-3-one. Light yellow foam. MS (m/e)=416.3 [M+H⁺].

Step 3: 2-Chloro-6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid The title compound was prepared in analogy to Example 92 from 7-[2-(2-chloro-4-hydroxy-phenyl)-1-hydroxy-1-trifluoromethyl-propyl]-4-methyl-4H-benzo[1,4]oxazin-3-one. Light yellow oil. MS (m/e)=571.3 [M+H⁺].

Example 159

2-Chloro-6-{3-chloro-4-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-phenoxy}-nicotinic acid

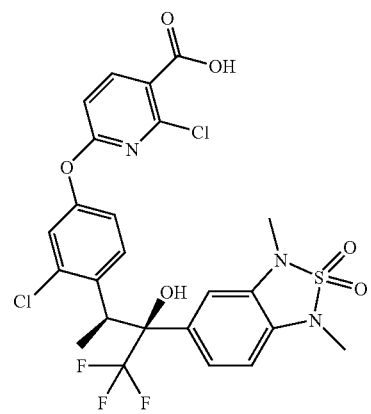

Step 1: 3-Chloro-4-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-phenol The title compound was prepared in analogy to Example 85 from 1,3-dimethyl-1,3-dihydro-benzo[1,2,5]thiadiazole 2,2-dioxide (CAS Reg. No. 31378-12-8). White Foam. MS (m/e, ISP neg. ion)=449.1 [M−H⁺].

Step 2: 2-Chloro-6-{3-chloro-4-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-phenoxy}-nicotinic acid The title compound was prepared in analogy to Example 92 from 3-chloro-4-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-phenol. Colorless foam. MS (m/e, ISP neg. ion)=604.5 [M−H⁺].

Example 160

2-Chloro-4-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-benzoic acid

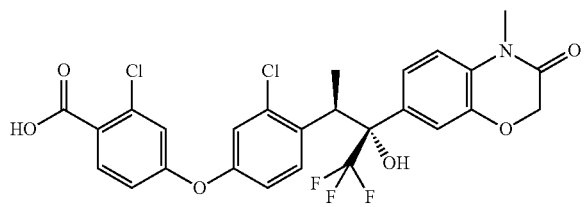

The title compound was prepared in analogy to Example 90 from 7-[2-(2-chloro-4-hydroxy-phenyl)-1-hydroxy-1-trifluoromethyl-propyl]-4-methyl-4H-benzo[1,4]oxazin-3-one (Example 158 step 2). White solid. MS (m/e)=570.2 [M+H⁺].

Example 161

2-Chloro-4-{3-chloro-4-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-phenoxy}-benzoic acid

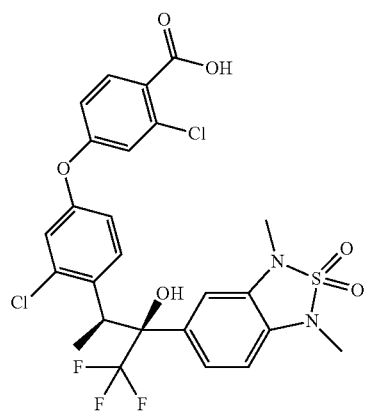

The title compound was prepared in analogy to Example 90 from 3-chloro-4-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-phenol (Example 159 step 1). Light yellow foam. MS (m/e, ISP neg. ion)=603.3 [M–H⁺].

Example 162

3'-Chloro-4'-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-4-fluoro-biphenyl-3-carboxylic acid

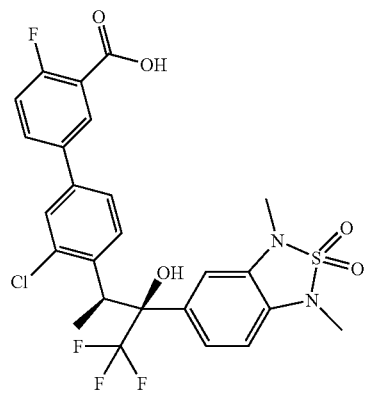

Step 1: 3-(4-Bromo-2-chloro-phenyl)-2-(1,3-dimethyl-2,2-dioxo-2,3-dihydro-1H-2λ6-benzo[1,2,5]thiadiazol-5-yl)-1,1,1-trifluoro-butan-2-ol The title compound was prepared in analogy to Example 85 from 1,3-dimethyl-1,3-dihydro-benzo[1,2,5]thiadiazole 2,2-dioxide (CAS Reg. No. 31378-12-8) and 4-bromo-2-chlorophenylacetic acid (CAS Reg. No. 916516-89-7). White solid. MS (m/e, ISP neg. ion)=429.2 [M–H⁺].

Step 2: 3'-Chloro-4'-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-4-fluoro-biphenyl-3-carboxylic acid The title compound was prepared in analogy to Example 74 from 3-(4-bromo-2-chloro-phenyl)-2-(1,3-dimethyl-2,2-dioxo-2,3-dihydro-1H-2λ6-benzo[1,2,5]thiadiazol-5-yl)-1,1,1-trifluoro-butan-2-ol. Colorless oil. MS (m/e, ISP neg. ion)=571.4 [M–H⁺].

Example 163

3'-Chloro-4'-[2-(1,3-dimethyl-2,2-dioxo-2,3-dihydro-1H-2λ6-benzo[1,2,5]thiadiazol-5-yl)-3,3,3-trifluoro-2-hydroxy-1-methyl-propyl]-3-fluoro-biphenyl-4-carboxylic acid

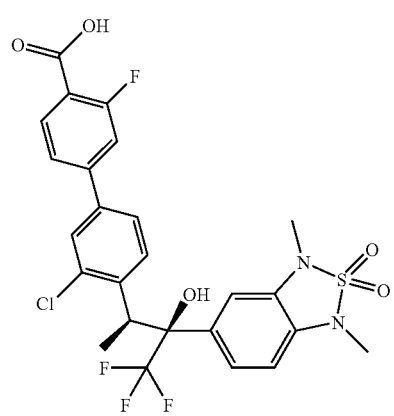

The title compound was prepared in analogy to Example 73 step 7 from 3-(4-bromo-2-chloro-phenyl)-2-(1,3-dimethyl-2,2-dioxo-2,3-dihydro-1H-2λ6-benzo[1,2,5]thiadiazol-5-yl)-1,1,1-trifluoro-butan-2-ol (Example 162 step 1). White foam. MS (m/e, ISP neg. ion)=571.2 [M–H⁺].

Example 164

3'-Chloro-3-fluoro-4'-[3,3,3-trifluoro-2-hydroxy-1-methyl-2-(4-methyl-3-oxo-3,4-dihydro-2H-benzo[1,4]oxazin-7-yl)-propyl]-biphenyl-4-carboxylic acid

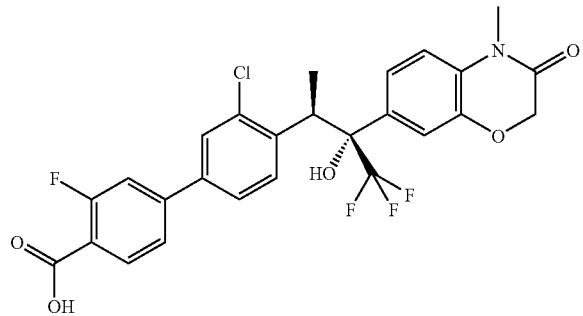

Step 1: Trifluoromethanesulfonic acid 3-chloro-4-[3,3,3-trifluoro-2-hydroxy-1-methyl-2-(4-methyl-3-oxo-3,4-dihydro-2H-benzo[1,4]oxazin-7-yl)-propyl]-phenyl ester Trifluoromethanesulfonic anhydride (0.12 ml) was added to 7-[2-(2-chloro-4-hydroxy-phenyl)-1-hydroxy-1-trifluoromethyl-propyl]-4-methyl-4H-benzo[1,4]oxazin-3-one (150 mg, Example 158 step 2) and triethylamine (0.2 ml) in DCM (5 ml). The mixture was stirred for 2 h at room temperature. 10% aqueous citric acid was added and extracted with DCM. The combined organic layers were dried over Na$_2$SO$_4$ and then concentrated to give the title compound (140 mg) as light yellow foam. MS (m/e, ISP neg. ion)=546.2 [M−H$^+$].

Step 2: 3'-Chloro-3-fluoro-4'-[3,3,3-trifluoro-2-hydroxy-1-methyl-2-(4-methyl-3-oxo-3,4-dihydro-2H-benzo[1,4]oxazin-7-yl)-propyl]-biphenyl-4-carboxylic acid The title compound was prepared in analogy to Example 73 step 7 from trifluoromethanesulfonic acid 3-chloro-4-[3,3,3-trifluoro-2-hydroxy-1-methyl-2-(4-methyl-3-oxo-3,4-dihydro-2H-benzo[1,4]oxazin-7-yl)-propyl]-phenyl ester. White foam. MS (m/e, ISP neg. ion)=536.2 [M−H$^+$].

Example 165

5-Chloro-6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid

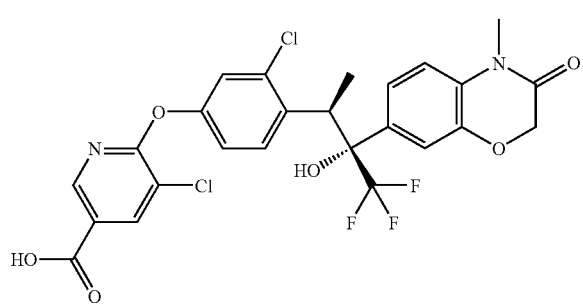

The title compound was prepared in analogy to Example 107 from 7-[2-(2-chloro-4-hydroxy-phenyl)-1-hydroxy-1-trifluoromethyl-propyl]-4-methyl-4H-benzo[1,4]oxazin-3-one (Example 158 step 2). White foam. MS (m/e, ISP neg. ion)=569.0 [M−H$^+$].

Example 166

4-{3-Chloro-4-[3,3,3-trifluoro-2-hydroxy-1-methyl-2-(4-methyl-3-oxo-3,4-dihydro-2H-benzo[1,4]oxazin-7-yl)-propyl]phenoxy}-2-fluoro-benzoic acid

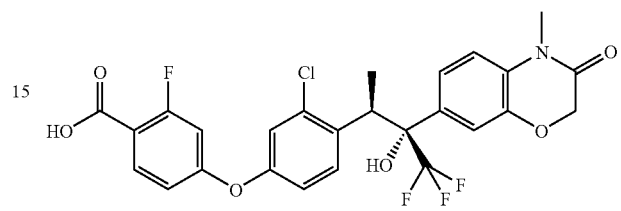

The title compound was prepared in analogy to Example 88 from 7-[2-(2-chloro-4-hydroxy-phenyl)-1-hydroxy-1-trifluoromethyl-propyl]-4-methyl-4H-benzo[1,4]oxazin-3-one (Example 158 step 2). Light yellow foam. MS (m/e, ISP neg. ion)=552.1 [M−H$^+$].

Example 167

5-{3-Chloro-4-[3,3,3-trifluoro-2-hydroxy-1-methyl-2-(4-methyl-3-oxo-3,4-dihydro-2H-benzo[1,4]oxazin-7-yl)-propyl]phenoxy}-2-fluoro-benzoic acid

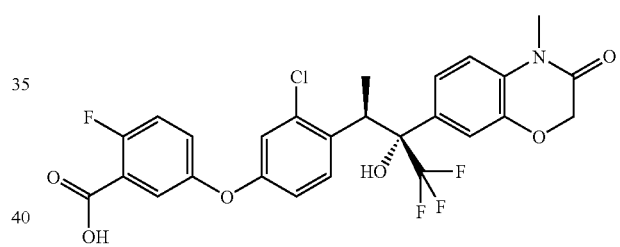

The title compound was prepared in analogy to Example 91 from 7-[2-(2-chloro-4-hydroxy-phenyl)-1-hydroxy-1-trifluoromethyl-propyl]-4-methyl-4H-benzo[1,4]oxazin-3-one (Example 158 step 2). Light yellow foam. MS (m/e, ISP neg. ion)=552.1 [M−H$^+$].

Example 168

3'-Chloro-3-fluoro-4'-[3,3,3-trifluoro-2-hydroxy-1-methyl-2-(2,2,4-trimethyl-3-oxo-3,4-dihydro-2H-benzo[1,4]oxazin-6-yl)-propyl]-biphenyl-4-carboxylic acid

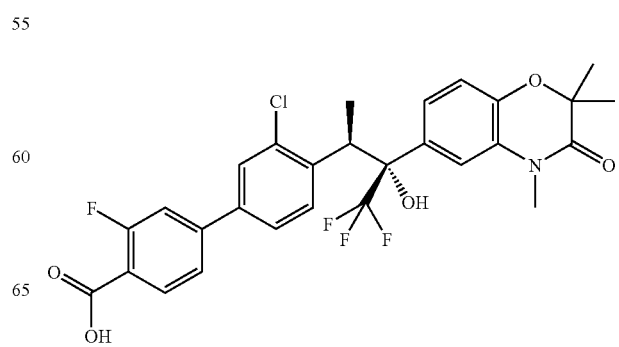

Step 1: 6-[2-(4-Bromo-2-chloro-phenyl)-propionyl]-2,2,4-trimethyl-4H-benzo[1,4]oxazin-3-one A mixture of 5-[2-(4-bromo-2-chloro-phenyl)-propionyl]-3-methyl-3H-benzooxazol-2-one (20 mg, Example 116 step 7) in 1N aqueous NaOH (1 ml) and dioxane (1 ml) was heated for 20 min at 100° C. in a microwave oven. Aqueous 1N HCl solution (1.2 ml) was added, followed by NaHCO$_3$ (100 mg) and EtOAc (10 ml). Bromoisobutyryl bromide (20 mg) was added and the mixture was stirred for 1 h. Water (10 ml) was added and extracted with EtOAc. The combined organic layers were dried over Na$_2$SO$_4$ and then concentrated to an oil. The residue was dissolved in DMF (3 ml), and K$_2$CO$_3$ (100 mg) was added. The mixture was heated to 100° C. for 2 h. The mixture was purified by prep. HPLC (C18-column, solvent gradient 20-98% CH$_3$CN in 0.1% HCOOH[aq]) to give the title compound (11 mg) as a light yellow oil. MS (m/e)=438.0 [M+H$^+$].

Step 2: 6-[2-(4-Bromo-2-chloro-phenyl)-1-hydroxy-1-trifluoromethyl-propyl]-2,2,4-trimethyl-4H-benzo[1,4]oxazin-3-one The title compound was prepared in analogy to Example 73 step 6 from 6-[2-(4-bromo-2-chloro-phenyl)-propionyl]-2,2,4-trimethyl-4H-benzo[1,4]oxazin-3-one. Light yellow oil. MS (m/e, ISP neg. ion)=504.1 [M−H$^+$].

Step 3: 3'-Chloro-3-fluoro-4'-[3,3,3-trifluoro-2-hydroxy-1-methyl-2-(2,2,4-trimethyl-3-oxo-3,4-dihydro-2H-benzo[1,4]oxazin-6-yl)-propyl]-biphenyl-4-carboxylic acid The title compound was prepared in analogy to Example 73 step 7 from 6-[2-(4-bromo-2-chloro-phenyl)-1-hydroxy-1-trifluoromethyl-propyl]-2,2,4-trimethyl-4H-benzo[1,4]oxazin-3-one. Light yellow solid. MS (m/e, ISP neg. ion)=564.3 [M−H$^+$].

Example 169

6-{3-Chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid

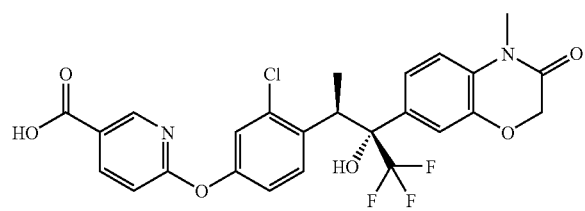

The title compound was prepared in analogy to Example 101 from 7-[2-(2-chloro-4-hydroxy-phenyl)-1-hydroxy-1-trifluoromethyl-propyl]-4-methyl-4H-benzo[1,4]oxazin-3-one (Example 158 step 2). White foam. MS (m/e, ISP neg. ion)=535.2 [M−H$^+$].

Example 170

3'-Chloro-3-fluoro-4'-[3,3,3-trifluoro-2-hydroxy-1-methyl-2-(4-methyl-3,4-dihydro-2H-benzo[1,4]oxazin-6-yl)-propyl]-biphenyl-4-carboxylic acid

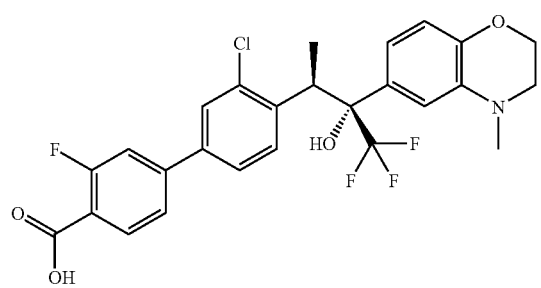

The title compound was prepared in analogy to Example 168 using 1,2 dibromoethane instead of bromoisobutyryl bromide for the ring closure in step 1. Light yellow foam. MS (m/e, ISP neg. ion)=522.2 [M−H$^+$].

Example 171

5-[2-(2-Chloro-4-methoxy-phenyl)-1-hydroxy-1-trifluoromethyl-propyl]-3-methyl-3H-benzooxazol-2-one

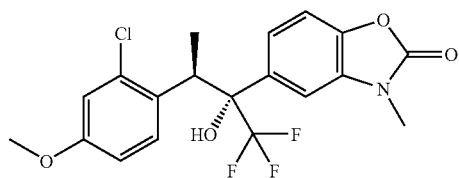

Step 1: 3-Methyl-2-oxo-2,3-dihydro-benzooxazole-5-carbonyl chloride

To a suspension of 3-methyl-2-oxo-2,3-dihydro-benzooxazole-5-carboxylic acid (2.50 g, obtained in Example 116, step 5) in CH$_2$Cl$_2$ (40 mL) were added nine drops of DMF and oxalylchloride (1.78 mL). The mixture was stirred at room temperature for 2 hours and was then concentrated to dryness. The resulting solid was dried at high vacuum over night. The title compound was obtained as a colorless solid (2.85 g, 99%). MS (EI)=211.0 [M$^+$].

Step 2: 5-[2-(2-Chloro-4-methoxy-phenyl)-acetyl]-3-methyl-3H-benzooxazol-2-one To a suspension of zinc powder (1.67 g) in 1,2-dimethoxyethane (60 mL) was added tetrakis(triphenylphosphine)palladium(0) (295 mg). A suspension of the 3-methyl-2-oxo-2,3-dihydro-benzooxazole-5-carbonyl chloride (2.71 g) in 1,2-dimethoxyethane (60 mL) was slowly added over a period of 20 minutes. The mixture was cooled in an ice bath and a solution of 1-bromomethyl-2-chloro-4-methoxy-benzene (3.01 g, [CAS Reg. No. 54788-17-9]) in 1,2-dimethoxyethane (20 mL) was slowly added over a period of 30 minutes. The mixture was stirred for 30 minutes at 0° C. and then for 2 hours at r.t. The reaction mixture was poured into ice and basified with sat. NaHCO$_3$. The aqueous phase was then extracted two times with ethyl acetate and the organic layers were washed with brine, dried over Na$_2$SO$_4$, filtered and the solvent was evaporated. The residue was purified by flash chromatography (silica gel, CH$_2$Cl$_2$) to give the title compound as a light yellow solid (2.45 g, 55%). MS (neg. ion, m/e)=330.3 [(M−H)$^-$].

Step 3: 5-[2-(2-Chloro-4-methoxy-phenyl)-propionyl]-3-methyl-3H-benzooxazol-2-one 5-[2-(2-Chloro-4-methoxy-phenyl)-acetyl]-3-methyl-3H-benzooxazol-2-one (2.45 g) was dissolved in DMF (60 mL). The mixture was cooled to 0° C. To this solution was added sodium hydride (55% in mineral oil, 403 mg) over a period of 10 minutes. The mixture was stirred for 10 minutes at 0° C. and then for 1 hour at r.t. The mixture was cooled to 0° C. and methyl iodide (0.49 mL) was added dropwise over a period of 10 minutes. Stirring was continued for 1.5 hours at r.t. The reaction mixture was poured into ice/water and extracted three times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a light brown foam (1.99 g, 76%). MS (m/e)=346.1 [M+H$^+$].

Step 4: 5-[2-(2-Chloro-4-methoxy-phenyl)-1-hydroxy-1-trifluoromethyl-propyl]-3-methyl-3H-benzooxazol-2-one Trifluoromethyltrimethylsilane (2M in THF, 6.33 mL) was added at 0° C. to a solution of 5-[2-(2-chloro-4-methoxy-phenyl)-propionyl]-3-methyl-3H-benzooxazol-2-one (1.99 g) in THF (30 mL) followed by the addition of tetrabutylammonium fluoride trihydrate (363 mg). Stirring was continued for 2.5 hours at 0° C. More tetrabutylammonium fluoride (1M in THF, 4.60 mL) was added to the reaction mixture and stirring was continued for 30 minutes at r.t. The reaction mixture was poured into ice/water and extracted two times with ethyl acetate. The combined organic layers were washed with brine, dried over Na$_2$SO$_4$, filtered and the solvent was evaporated. The residue was purified by flash chromatography (silica gel, CH$_2$Cl$_2$:MeOH=100:0 to 99:1) to give the title compound as a colorless foam (2.0 g, 80%). MS (m/e)=416.3 [M+H$^+$].

Example 172

5-[2-(2-Chloro-4-hydroxy-phenyl)-1-hydroxy-1-trifluoromethyl-propyl]-3-methyl-3H-benzooxazol-2-one

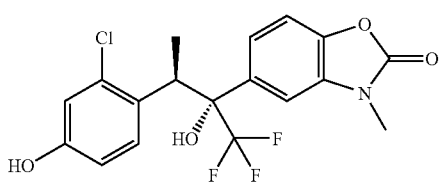

5-[2-(2-Chloro-4-methoxy-phenyl)-1-hydroxy-1-trifluoromethyl-propyl]-3-methyl-3H-benzooxazol-2-one (766 mg) was dissolved in CH$_2$Cl$_2$ (25 mL) and cooled to −78° C. Borontribromide (1M in CH$_2$Cl$_2$, 7.37 mL) was added over a period of 20 minutes. Stirring was continued for 1.5 hours at −78° C. The cooling bath was removed and the mixture was allowed to warm to 0° C. Stirring was continued for 2 hours at 0° C. The reaction mixture was poured into ice and basified with sat. NaHCO$_3$ and extracted three times with CH$_2$Cl$_2$. The combined organic layers were washed with brine, dried over Na$_2$SO$_4$, filtered and the solvent was evaporated. The title compound was obtained as a colorless foam (740 mg, 99%) and was used without further purification. MS (m/e)=402.2 [M+H$^+$].

Example 173

2-Chloro-4-{3-chloro-4-[3,3,3-trifluoro-2-hydroxy-1-methyl-2-(3-methyl-2-oxo-2,3-dihydro-benzooxazol-5-yl)-propyl]-phenoxy}-benzoic acid

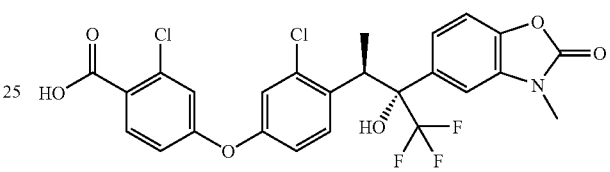

Step 1: 2-Chloro-4-{3-chloro-4-[3,3,3-trifluoro-2-hydroxy-1-methyl-2-(3-methyl-2-oxo-2,3-dihydro-benzooxazol-5-yl)-propyl]-phenoxy}-benzoic acid methyl ester 5-[2-(2-Chloro-4-hydroxy-phenyl)-1-hydroxy-1-trifluoromethyl-propyl]-3-methyl-3H-benzooxazol-2-one (90 mg, obtained in Example 172), 3-chloro-4-methoxycarbonylphenyl-boronic acid (144 mg, [CAS Reg. No. 603122-82-3]), copper(II)-acetate (122 mg) and pyridine (0.090 mL) were dissolved in CH$_2$Cl$_2$ (3 mL). The mixture was stirred over night at r.t. The reaction mixture was poured into ice/water and acified with 1M aqueous HCl. The aqueous layer was extracted three times with ethylacetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless foam (35 mg, 27%). MS (m/e)=570.1 [M+H$^+$].

Step 2: 2-Chloro-4-{3-chloro-4-[3,3,3-trifluoro-2-hydroxy-1-methyl-2-(3-methyl-2-oxo-2,3-dihydro-benzooxazol-5-yl)-propyl]-phenoxy}-benzoic acid 2-Chloro-4-{3-chloro-4-[3,3,3-trifluoro-2-hydroxy-1-methyl-2-(3-methyl-2-oxo-2,3-dihydro-benzooxazol-5-yl)-propyl]-phenoxy}-benzoic acid methyl ester (33 mg, obtained in Example 173, step 1) was dissolved in THF (2 mL) followed by the addition of aqueous LiOH solution (1.0M, 0.14 mL). The mixture was stirred for 5 hours at r.t. The reaction mixture was poured into ice/water and acified with 1M aqueous HCl to pH 1. The aqueous layer was extracted three times with ethylacetate. The combined organic layers were washed with brine, dried over Na$_2$SO$_4$, filtered and the solvent was evaporated. The residue was purified by flash chromatography (silica gel, CH$_2$Cl$_2$:MeOH:CH$_3$COOH=100:0:0 to 98:2:0.5) to give the title compound as a light yellow foam. The residual acetic acid was removed by co-evaporation with toluene (10 mg, 31%). MS (neg. ion, m/e)=554.3 [(M−H)$^-$].

Example 174

6-{3-Chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester

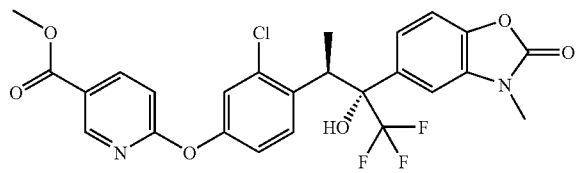

5-[2-(2-Chloro-4-hydroxy-phenyl)-1-hydroxy-1-trifluoromethyl-propyl]-3-methyl-3H-benzooxazol-2-one (150 mg, obtained in Example 172) was added to a solution of methyl-6-chloro-nicotinate (64 mg, [CAS Reg. No. 73781-91-6]) in DMF (1.9 mL) followed by the addition of triethylamine (0.067 mL). Stirring was continued for 10 minutes at r.t. Then 1,4-diazabicyclo[2.2.2]octane (6 mg) was added. The mixture was stirred over night at r.t. and then 4 hours at 60° C. The reaction mixture was poured into water, extracted with ethyl acetate and the organic layer was washed with brine, dried over $Na_2SO_4$ and evaporated. The residue was purified by flash chromatography (silica gel, gradient of heptane in ethyl acetate) to give the desired compound as a colorless foam (33 mg, 16%). MS (m/e)=537.2 [M+H⁺].

Example 175

5-Chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester

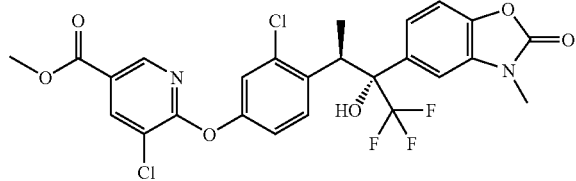

The title compound was prepared in analogy to Example 174 from 5-[2-(2-chloro-4-hydroxy-phenyl)-1-hydroxy-1-trifluoromethyl-propyl]-3-methyl-3H-benzooxazol-2-one (obtained in Example 172) with methyl-5,6-dichloronicotinate [CAS Reg. No. 56055-54-0]. MS (m/e)=571.2 [M+H⁺].

Example 176

4-{3-Chloro-4-[3,3,3-trifluoro-2-hydroxy-1-methyl-2-(3-methyl-2-oxo-2,3-dihydro-benzooxazol-5-yl)-propyl]-phenoxy}-2-fluoro-benzoic acid methyl ester

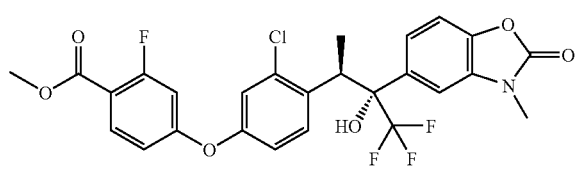

The title compound was prepared in analogy to Example 173, step 1 from 5-[2-(2-chloro-4-hydroxy-phenyl)-1-hydroxy-1-trifluoromethyl-propyl]-3-methyl-3H-benzooxazol-2-one (obtained in Example 172) with 3-fluoro-4-methoxycarbonylphenylboronic acid [CAS Reg. No. 505083-04-5]. MS (neg. ion, m/e)=552.5 [(M−H)⁻].

Example 177

4-{3-Chloro-4-[3,3,3-trifluoro-2-hydroxy-1-methyl-2-(3-methyl-2-oxo-2,3-dihydro-benzooxazol-5-yl)-propyl]-phenoxy}-2-fluoro-benzoic acid

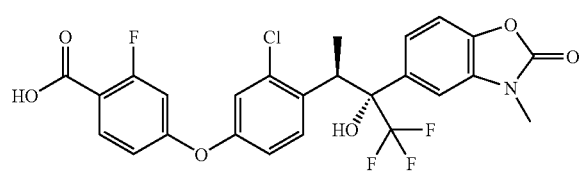

The title compound was prepared in analogy to Example 173, step 2 from 4-{3-chloro-4-[3,3,3-trifluoro-2-hydroxy-1-methyl-2-(3-methyl-2-oxo-2,3-dihydro-benzooxazol-5-yl)-propyl]-phenoxy}-2-fluoro-benzoic acid methyl ester (obtained in Example 176). MS (neg. ion, m/e)=538.2 [(M−H)⁻].

Example 178

3'-Chloro-4-fluoro-4'-[3,3,3-trifluoro-2-hydroxy-1-methyl-2-(3-methyl-2-oxo-2,3-dihydro-benzooxazol-6-yl)-propyl]-biphenyl-3-carboxylic acid

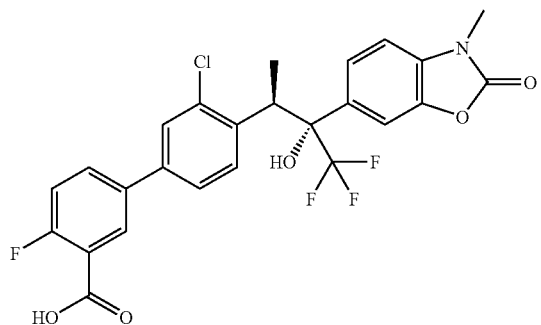

Step 1: 3'-Chloro-4-fluoro-4'-[3,3,3-trifluoro-2-hydroxy-1-methyl-2-(3-methyl-2-oxo-2,3-dihydro-benzooxazol-6-yl)-propyl]-biphenyl-3-carboxylic acid ethyl ester The title compound was prepared in analogy to Example 117 from 6-[2-(4-bromo-2-chloro-phenyl)-1-hydroxy-1-trifluoromethyl-propyl]-3-methyl-3H-benzooxazol-2-one (obtained in Example 133, step 3) by Suzuki coupling with 4-fluoro-3-ethoxycarbonylphenylboronic acid [CAS Reg. No. 874219-36-0]. The title compound was used without further analysis.

Step 2: 3'-Chloro-4-fluoro-4'-[3,3,3-trifluoro-2-hydroxy-1-methyl-2-(3-methyl-2-oxo-2,3-dihydro-benzooxazol-6-yl)-propyl]-biphenyl-3-carboxylic acid The title compound was prepared in analogy to Example 134, step 2 from 3'-chloro-4-fluoro-4'-[3,3,3-trifluoro-2-hydroxy-1-methyl-2-(3-methyl-2-oxo-2,3-dihydro-benzooxazol-6-yl)-propyl]-biphenyl-3-carboxylic acid ethyl ester (obtained in Example 178, step 1). MS (neg. ion, m/e)=522.0 [(M−H)⁻].

Example 179

3'-Chloro-4'-[3,3,3-trifluoro-2-hydroxy-1-methyl-2-(3-methyl-2-oxo-2,3-dihydro-benzooxazol-6-yl)-propyl]-biphenyl-3-carboxylic acid

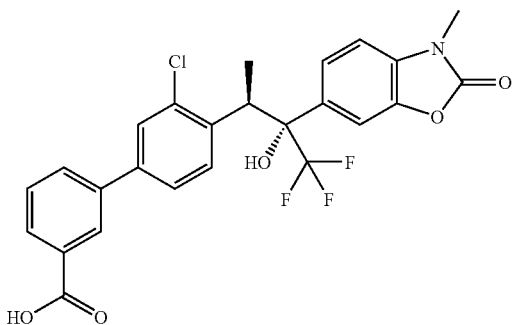

Step 1: 3'-Chloro-4'-[3,3,3-trifluoro-2-hydroxy-1-methyl-2-(3-methyl-2-oxo-2,3-dihydro-benzooxazol-6-yl)-propyl]-1-biphenyl-3-carboxylic acid methyl ester The title compound was prepared in analogy to Example 117 from 6-[2-(4-bromo-2-chloro-phenyl)-1-hydroxy-1-trifluoromethyl-propyl]-3-methyl-3H-benzooxazol-2-one (obtained in Example 133, step 3) by Suzuki coupling with 3-methoxycarbonylphenyl-boronic acid [CAS Reg. No. 99769-19-4]. ¹H-NMR (, CDCl₃): 8.13 (m, 1H), 8.00 (m, 1H), 7.63 (m, 1H), 7.60 (d, 1H), 7.48 (t, 1H), 7.41 (d, 1H), 7.36 (s(br), 1H), 7.31-7.25 (m, 2H), 6.77 (d, 1H), 4.42 (q, 1H), 3.93 (s, 3H), 3.31 (s, 3H), 3.08 (s, 1H), 1.52 (d, 3H).

Step 2: 3'-Chloro-4'-[3,3,3-trifluoro-2-hydroxy-1-methyl-2-(3-methyl-2-oxo-2,3-dihydro-benzooxazol-6-yl)-propyl]-1-biphenyl-3-carboxylic acid The title compound was prepared in analogy to Example 134, step 2 from 3'-chloro-4'-[3,3,3-trifluoro-2-hydroxy-1-methyl-2-(3-methyl-2-oxo-2,3-dihydro-benzooxazol-6-yl)-propyl]-biphenyl-3-carboxylic acid methyl ester (obtained in Example 179, step 1). MS (neg. ion, m/e)=504.0 [(M−H)⁻].

Example 180

5-Chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid

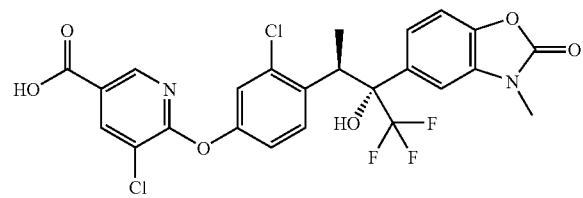

The title compound was prepared in analogy to Example 173, step 2 from 5-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester (obtained in Example 175). MS (neg. ion, m/e)=555.0 [(M−H)⁻].

Example 181

6-{3-Chloro-4-[3,3,3-trifluoro-2-hydroxy-1-methyl-2-(3-methyl-2-oxo-2,3-dihydro-benzooxazol-5-yl)-propyl]-phenoxy}-nicotinic acid

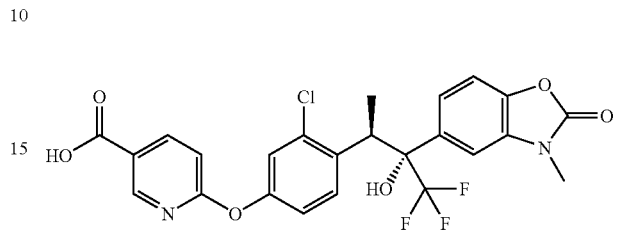

The title compound was prepared in analogy to Example 173, step 2 from 6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester (obtained in Example 174). MS (neg. ion, m/e)=521.1 [(M−H)⁻].

Example 182

2-Chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester

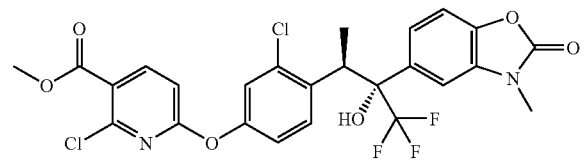

5-[2-(2-Chloro-4-hydroxy-phenyl)-1-hydroxy-1-trifluoromethyl-propyl]-3-methyl-3H-benzooxazol-2-one (157 mg, obtained in Example 172) was added to a solution of methyl-2,6-dichloropyridine-3-carboxylate (81 mg, [CAS Reg. No. 65515-28-8]) in DMF (3 mL) followed by the addition of triethylamine (0.071 mL). Stirring was continued for 10 minutes at r.t. Then 1,4-diazabicyclo[2.2.2]octane (7 mg) was added. The mixture was stirred over night at r.t. The reaction mixture was poured into water, extracted with ethyl acetate and the organic layer was washed with brine, dried over Na₂SO₄ and evaporated. The residue was purified by flash chromatography (silica gel, gradient of heptane in ethyl acetate) to give the desired compound as a colorless foam (195 mg, 87%). MS (neg. ion, m/e)=569.2 [(M−H)⁻].

Example 183

4-Chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester

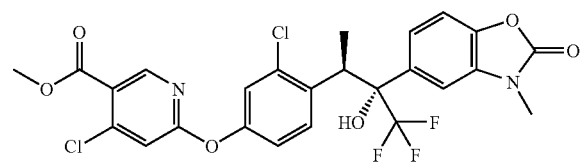

The title compound was prepared in analogy to Example 182 from 5-[2-(2-chloro-4-hydroxy-phenyl)-1-hydroxy-1-trifluoromethyl-propyl]-3-methyl-3H-benzooxazol-2-one (obtained in Example 172) with methyl-4,6-dichloronicotinate [CAS Reg. No. 65973-52-6]. MS (m/e)=571.0 [M+H⁺].

Example 184

2-Chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid

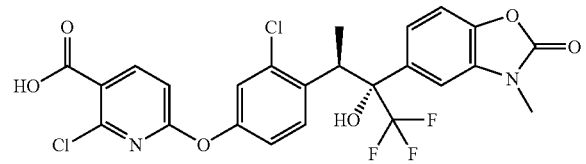

The title compound was prepared in analogy to Example 173, step 2 from 2-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester (obtained in Example 182). MS (neg. ion, m/e)=555.1 [(M−H)⁻].

Example 185

4-Chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid

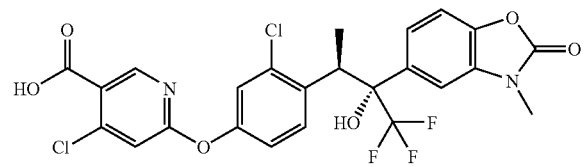

The title compound was prepared in analogy to Example 173, step 2 from 4-chloro-6-{3-chloro-4-[3,3,3-trifluoro-2-hydroxy-1-methyl-2-(3-methyl-2-oxo-2,3-dihydro-benzooxazol-5-yl)-propyl]-phenoxy}-nicotinic acid methyl ester (obtained in Example 183). MS (neg. ion, m/e)=555.3 [(M−H)⁻].

Example 186

5-{3-Chloro-4-[3,3,3-trifluoro-2-hydroxy-1-methyl-2-(3-methyl-2-oxo-2,3-dihydro-benzooxazol-5-yl)-propyl]-phenyl}-nicotinic acid methyl ester

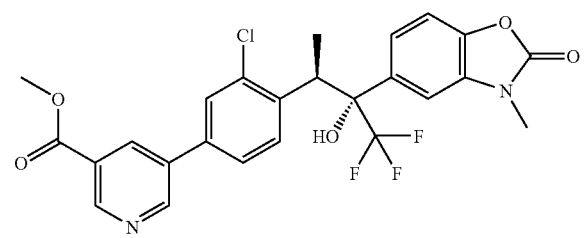

Step 1: 5-{2-[2-Chloro-4-(4,4,5,5-tetramethyl-[1,3,2]dioxaborolan-2-yl)-phenyl]-1-hydroxy-1-trifluoromethyl-propyl}-3-methyl-3H-benzooxazol-2-one 5-[2-(4-Bromo-2-chloro-phenyl)-1-hydroxy-1-trifluoromethyl-propyl]-3-methyl-3H-benzooxazol-2-one (2.0 g, obtained in Example 116, step 8), bis-(pinacolato)-diboron (2.73 g), potassium acetate (1.27 g) and bis-(triphenylphosphine)-palladium(II)-dichloride (211 mg) was dissolved in DMF (40 mL). The mixture was heated to 90° C. over night. The reaction mixture was cooled, poured into ice/water and extracted three times with ethyl acetate. The combined organic layers were washed with brine, dried over Na₂SO₄, filtered and the solvent was evaporated. The residue was purified by flash chromatography (silica gel, CH₂Cl₂:MeOH=100:0 to 95:5) to give the title compound as a colorless foam (2.45 g, 89%). MS (neg. ion, m/e)=510.2 [(M−H)⁻].

Step 2: 5-{3-Chloro-4-[3,3,3-trifluoro-2-hydroxy-1-methyl-2-(3-methyl-2-oxo-2,3-dihydro-benzooxazol-5-yl)-propyl]-phenyl}-nicotinic acid methyl ester 5-{2-[2-Chloro-4-(4,4,5,5-tetramethyl-[1,3,2]dioxaborolan-2-yl)-phenyl]-1-hydroxy-1-trifluoromethyl-propyl}-3-methyl-3H-benzooxazol-2-one (200 mg, obtained in Example 186, step 1), methyl-5-bromopyridine-3-carboxylate (169 mg, [CAS Reg. No. 29681-44-5]) and dichloro(1,1'-bis(diphenylphosphino)ferrocene)palladium(II)dichloromethane adduct (29 mg) were dissolved in dioxane (5 mL) and water (1.7 mL). To the reaction mixture was added 2.0 M aqueous Na₂CO₃ (0.29 mL). The mixture was heated to 65° C. over night. The reaction mixture was cooled, poured into ice/water and extracted three times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a colorless foam (110 mg, 52%). MS (m/e)=521.1 [M+H⁺].

Example 187

5-{3-Chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid methyl ester

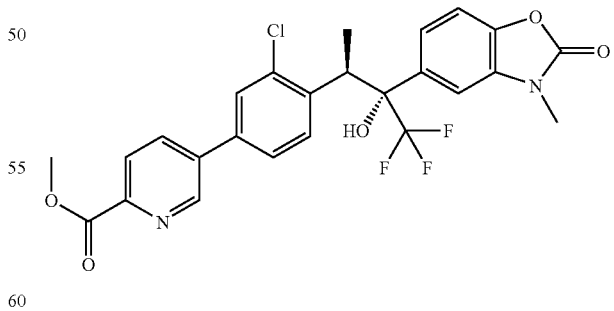

The title compound was prepared in analogy to Example 186, step 2 from 5-{2-[2-chloro-4-(4,4,5,5-tetramethyl-[1,3,2]dioxaborolan-2-yl)-phenyl]-1-hydroxy-1-trifluoromethyl-propyl}-3-methyl-3H-benzooxazol-2-one (obtained in Example 186, step 1) with methyl-5-bromopyridine-2-carboxylate [CAS Reg. No. 29682-15-3]. MS (m/e)=521.2 [M+H⁺].

Example 188

6-{3-Chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid ethyl ester

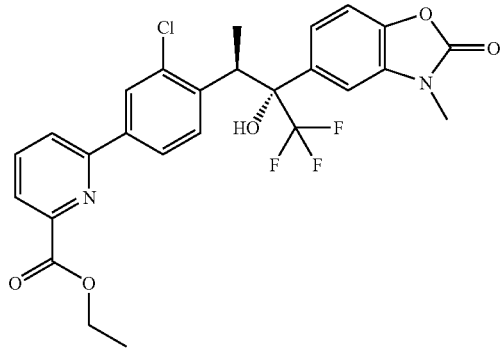

The title compound was prepared in analogy to Example 186, step 2 from 5-{2-[2-chloro-4-(4,4,5,5-tetramethyl-[1,3,2]dioxaborolan-2-yl)-phenyl]-1-hydroxy-1-trifluoromethyl-propyl}-3-methyl-3H-benzooxazol-2-one (obtained in Example 186, step 1) with ethyl-6-bromopyridine-2-carboxylate [CAS Reg. No. 21190-88-5]. MS (m/e)=535.2 [M+H⁺].

Example 189

5-{3-Chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid

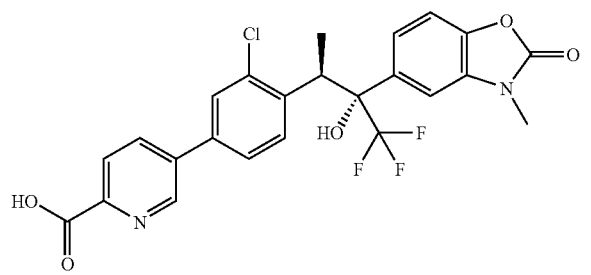

The title compound was prepared in analogy to Example 173, step 2 from 5-{3-chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid methyl ester (obtained in Example 187). MS (m/e)=507.2 [M+H⁺].

Example 190

6-{3-Chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid

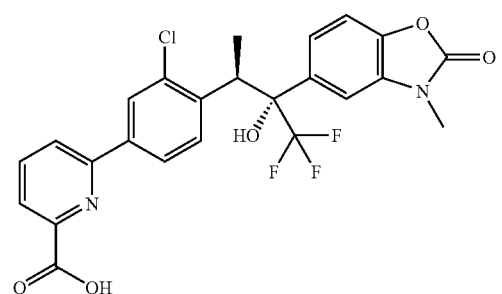

The title compound was prepared in analogy to Example 173, step 2 from 6-{3-chloro-4-[3,3,3-trifluoro-2-hydroxy-1-methyl-2-(3-methyl-2-oxo-2,3-dihydro-benzooxazol-5-yl)-propyl]-phenyl}-pyridine-2-carboxylic acid ethyl ester (obtained in Example 188). MS (m/e)=507.1 [M+H⁺].

Example 191

5-{3-Chloro-4-[3,3,3-trifluoro-2-hydroxy-1-methyl-2-(3-methyl-2-oxo-2,3-dihydro-benzooxazol-5-yl)-propyl]-phenyl}-nicotinic acid

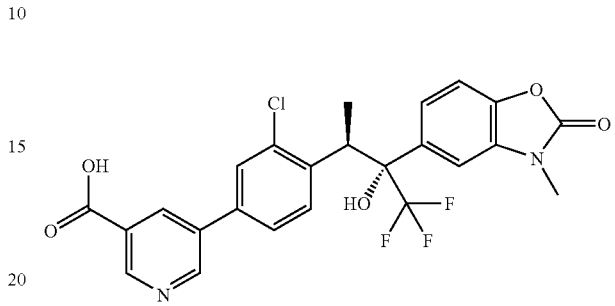

The title compound was prepared in analogy to Example 173, step 2 from 5-{3-chloro-4-[3,3,3-trifluoro-2-hydroxy-1-methyl-2-(3-methyl-2-oxo-2,3-dihydro-benzooxazol-5-yl)-propyl]-phenyl }-nicotinic acid methyl ester (obtained in Example 186, step 2). MS (neg. ion, m/e)=505.3 [(M−H)⁻].

Example 192

5-[2-(2-Chloro-5-methoxy-phenyl)-1-hydroxy-1-trifluoromethyl-propyl]-3-methyl-3H-benzooxazol-2-one

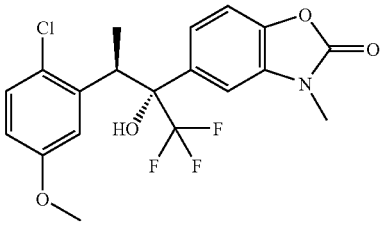

Step 1: 5-[2-(2-Chloro-5-methoxy-phenyl)-acetyl]-3-methyl-3H-benzooxazol-2-one

To a suspension of 3-methyl-2-oxo-2,3-dihydro-benzooxazole-5-carboxylic acid (820 mg, obtained in Example 116, step 5) in CH₂Cl₂ (10 mL) were added two drops of DMF and oxalylchloride (0.58 mL). The mixture was stirred at room temperature for 1 hour and was then concentrated to dryness. 1,2-Dimethoxyethane (20 mL) was added and the solvent was evaporated again to give the crude acid chloride (3-methyl-2-oxo-2,3-dihydro-benzooxazole-5-carbonyl chloride). To a suspension of zinc powder (555 mg) in 1,2-dimethoxyethane (10 mL) was added tetrakis(triphenylphosphine)palladium (0) (49 mg). A suspension of the acid chloride in 1,2-dimethoxyethane (5 mL) was added. The mixture was cooled in an ice bath and a solution of 2-bromomethyl-1-chloro-4-methoxy-benzene (1.0 g, [CAS Reg. No. 3771-13-9]) in 1,2-dimethoxyethane (5 mL) was slowly added over a period of 15 minutes. The mixture was stirred for 10 minutes at 0° C. and then for 2 hours at r.t. The reaction mixture was poured into ice and basified with sat. NaHCO₃. The aqueous phase was then extracted two times with ethyl acetate and the organic layers were washed with brine, dried over Na₂SO₄, filtered and the solvent was evaporated. The residue was purified by flash chromatography (silica gel, heptane:ethyl acetate=6:4) to give the title compound as a colorless solid (510 mg, 36%). MS (neg. ion, m/e)=330.3 [(M−H)⁻].

Step 2: 5-[2-(2-Chloro-5-methoxy-phenyl)-propionyl]-3-methyl-3H-benzooxazol-2-one 5-[2-(2-Chloro-5-methoxy-phenyl)-acetyl]-3-methyl-3H-benzooxazol-2-one (500 mg, obtained in Example 192, step 1) was dissolved in DMF (15 mL). The mixture was cooled to 0° C. To this solution was added sodium hydride (55% in mineral oil, 72 mg). The mixture was stirred for 50 minutes at 0° C. Methyl iodide (0.104 mL) was added dropwise over a period of 10 minutes. Stirring was continued at 0° C. for 1.5 hours. The reaction mixture was poured into ice/water and extracted two times with ethyl acetate. The combined organic layers were washed with brine, dried over $Na_2SO_4$, filtered and the solvent was evaporated. The residue was purified by flash chromatography (silica gel, heptane:ethyl acetate=7:3) to give the title compound as a colorless gum (312 mg, 60%). MS (m/e)=346.1 [M+H$^+$].

Step 3: 5-[2-(2-Chloro-5-methoxy-phenyl)-1-hydroxy-1-trifluoromethyl-propyl]-3-methyl-3H-benzooxazol-2-one Trifluoromethyltrimethylsilane (2M in THF, 0.80 mL) was added at 0° C. to a solution of 5-[2-(2-chloro-5-methoxy-phenyl)-propionyl]-3-methyl-3H-benzooxazol-2-one (312 mg, obtained in Example 192, step 2) in THF (20 mL) followed by the addition of tetrabutylammonium fluoride trihydrate (253 mg). Stirring was continued for 72 hours at r.t. The reaction mixture was poured into ice/water and extracted two times with ethyl acetate. The combined organic layers were washed with brine, dried over $Na_2SO_4$, filtered and the solvent was evaporated. The residue was purified by flash chromatography (silica gel, heptane:ethyl acetate=7:3 to 6:4) to give the title compound as a orange amorphous foam (43 mg, 14%). MS (neg. ion, m/e)=414.3 [(M−H)$^−$].

Example 193

5-[2-(4-Bromo-2-trifluoromethyl-phenyl)-1-hydroxy-1-trifluoromethyl-propyl]-3-methyl-3H-benzooxazol-2-one

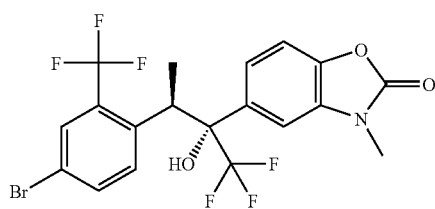

Step 1: 5-[2-(4-Bromo-2-trifluoromethyl-phenyl)-acetyl]-3-methyl-3H-benzooxazol-2-one To a suspension of 3-methyl-2-oxo-2,3-dihydro-benzooxazole-5-carboxylic acid (935 mg, obtained in Example 116, step 5) in $CH_2Cl_2$ (15 mL) were added two drops of DMF and oxalylchloride (0.66 mL). The mixture was stirred at room temperature for 1 hour and was then concentrated to dryness. 1,2-Dimethoxyethane (20 mL) was added and the solvent was evaporated again. The resulting solid was dried at high vacuum over night to give the crude acid chloride (3-methyl-2-oxo-2,3-dihydro-benzooxazole-5-carbonyl chloride). To a suspension of zinc powder (633 mg) in 1,2-dimethoxyethane (10 mL) was added tetrakis(triphenyl-phosphine)palladium (0) (56 mg). A suspension of the acid chloride in 1,2-dimethoxyethane (10 mL) was added. The mixture was cooled in an ice bath and a solution of 4-bromo-1-bromomethyl-2-trifluoromethyl-benzene (1.54 g, [CAS Reg. No. 335013-18-8]) in 1,2-dimethoxyethane (10 mL) was slowly added over a period of 15 minutes. The mixture was stirred for 10 minutes at 0° C. and then for 18 hours at r.t. The reaction mixture was poured into ice and basified with sat. $NaHCO_3$. The aqueous phase was then extracted two times with ethyl acetate and the organic layers were washed with brine, dried over $Na_2SO_4$, filtered and the solvent was evaporated. The residue was purified by flash chromatography (silica gel, heptane:ethyl acetate=1:1) to give the title compound as a yellow oil (944 mg, 47%). MS (neg. ion, m/e)=414.1 [(M−H)$^−$].

Step 2: 5-[2-(4-Bromo-2-trifluoromethyl-phenyl)-propionyl]-3-methyl-3H-benzooxazol-2-one The title compound was prepared in analogy to Example 171, step 3 from 5-[2-(4-bromo-2-trifluoromethyl-phenyl)-acetyl]-3-methyl-3H-benzooxazol-2-one (obtained in Example 193, step 1). MS (neg. ion, m/e)=426.2 [(M−H)$^−$].

Step 3: 5-[2-(4-Bromo-2-trifluoromethyl-phenyl)-1-hydroxy-1-trifluoromethyl-propyl]-3-methyl-3H-benzooxazol-2-one The title compound was prepared in analogy to Example 192, step 3 from 5-[2-(4-bromo-2-trifluoromethyl-phenyl)-propionyl]-3-methyl-3H-benzooxazol-2-one (obtained in Example 193, step 2). MS (neg. ion, m/e)=496.1 [(M−H)$^−$].

Example 194

5-[2-(2-Chloro-4-pyrimidin-5-yl-phenyl)-1-hydroxy-1-trifluoromethyl-propyl]-3-methyl-3H-benzooxazol-2-one

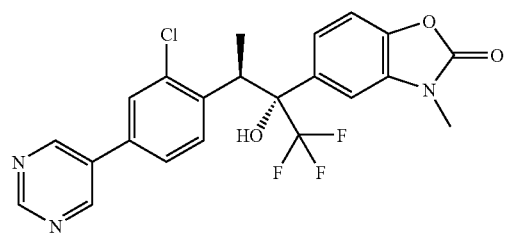

The title compound was prepared in analogy to Example 186, step 2 from 5-{2-[2-chloro-4-(4,4,5,5-tetramethyl-[1,3,2]dioxaborolan-2-yl)-phenyl]-1-hydroxy-1-trifluoromethyl-propyl}-3-methyl-3H-benzooxazol-2-one (obtained in Example 186, step 1) with 5-bromopyrimidine [CAS Reg. No. 4595-59-9]. MS (m/e)=464.1 [M+H⁺].

Example 195

5-[2-(2-Chloro-4-pyridazin-4-yl-phenyl)-1-hydroxy-1-trifluoromethyl-propyl]-3-methyl-3H-benzooxazol-2-one

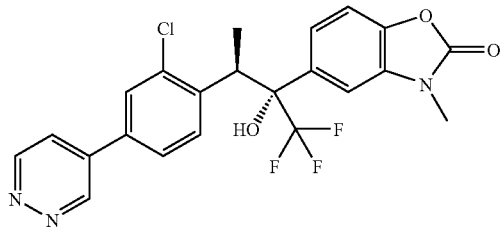

The title compound was prepared in analogy to Example 186, step 2 from 5-{2-[2-chloro-4-(4,4,5,5-tetramethyl-[1,3,2]dioxaborolan-2-yl)-phenyl]-1-hydroxy-1-trifluoromethyl-propyl}-3-methyl-3H-benzooxazol-2-one (obtained in Example 186, step 1) with 4-bromopyridazine [CAS Reg. No. 115514-66-4]. MS (m/e)=464.1 [M+H⁺].

Example 196

5-{2-[2-Chloro-4-(pyrimidin-2-yloxy)-phenyl]-1-hydroxy-1-trifluoromethyl-propyl}-3-methyl-3H-benzooxazol-2-one

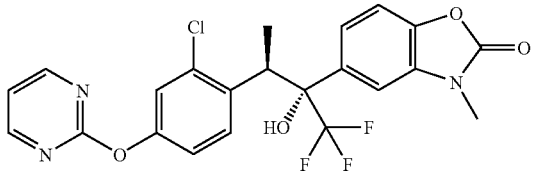

5-[2-(2-Chloro-4-hydroxy-phenyl)-1-hydroxy-1-trifluoromethyl-propyl]-3-methyl-3H-benzooxazol-2-one (100 mg, obtained in Example 172) was added to a suspension of NaH (60% in mineral oil, 20 mg) in DMF (4 mL). Stirring was continued for 30 minutes at r.t. The mixture was cooled to 0° C. and 2-bromopyrimidine (59 mg, [CAS Reg. No. 4595-60-2]) was added. Stirring was continued for 4 hours at r.t. The reaction mixture was poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a light yellow solid (35 mg, 30%). MS (m/e)=480.1 [M+H⁺].

Example 197

5-[2-(2-Chloro-5-hydroxy-phenyl)-1-hydroxy-1-trifluoromethyl-propyl]-3-methyl-3H-benzooxazol-2-one

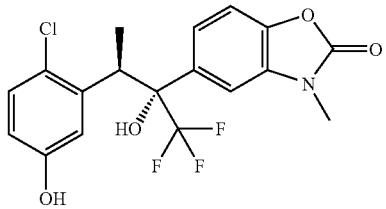

5-[2-(2-Chloro-5-methoxy-phenyl)-1-hydroxy-1-trifluoromethyl-propyl]-3-methyl-3H-benzooxazol-2-one (34 mg, obtained in Example 192, step 3) was dissolved in CH₂Cl₂ (5 mL) and cooled to 0° C. Borontribromide (1M in CH₂Cl₂, 0.33 mL) was added over a period of 10 minutes. Stirring was continued for 1 hour at 0° C. The reaction mixture was poured into ice and basified with sat. NaHCO₃ and extracted three times with CH₂Cl₂. The combined organic layers were washed with brine, dried over Na₂SO₄, filtered and the solvent was evaporated. The residue was purified by flash chromatography (silica gel, heptane:ethyl acetate=6:4) to give the title compound as a colorless amorphous foam (22 mg, 67%). MS (neg. ion, m/e)=400.1 [(M−H)⁻].

Example 198

3-Fluoro-4'-[3,3,3-trifluoro-2-hydroxy-1-methyl-2-(3-methyl-2-oxo-2,3-dihydro-benzooxazol-5-yl)-propyl]-3'-trifluoromethyl-biphenyl-4-carboxylic acid methyl ester

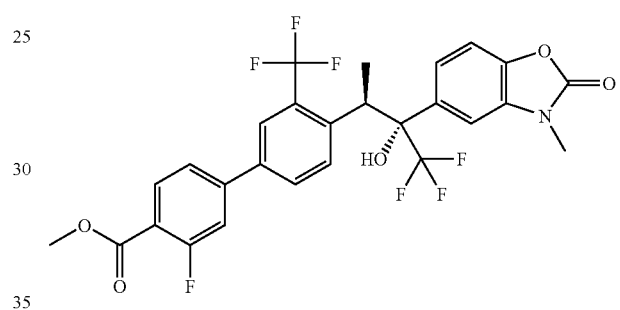

The title compound was prepared in analogy to Example 117 from 5-[2-(4-bromo-2-trifluoromethyl-phenyl)-1-hydroxy-1-trifluoromethyl-propyl]-3-methyl-3H-benzooxazol-2-one (obtained in Example 193, step 3) by Suzuki coupling with 3-fluoro-4-methoxycarbonyl-benzeneboronic acid [CAS Reg. No. 505083-04-5]. MS (m/e)=572.1 [M+H⁺].

Example 199

6-{3-Chloro-4-[3,3,3-trifluoro-2-hydroxy-1-methyl-2-(3-methyl-2-oxo-2,3-dihydro-benzooxazol-5-yl)-propyl]-phenoxy}-pyridazine-3-carboxylic acid methyl ester

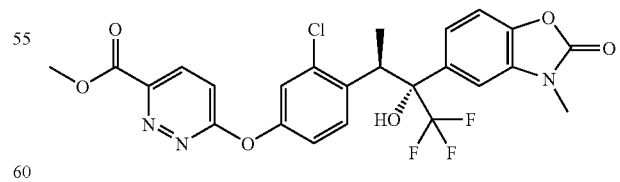

The title compound was prepared in analogy to Example 196 from 5-[2-(2-chloro-4-hydroxy-phenyl)-1-hydroxy-1-trifluoromethyl-propyl]-3-methyl-3H-benzooxazol-2-one (obtained in Example 172) by alkylation with methyl-6-chloropyridazine-3-carboxylate [CAS Reg. No. 65202-50-8]. MS (m/e)=538.2 [M+H⁺].

Example 200

3-Fluoro-4'-[3,3,3-trifluoro-2-hydroxy-1-methyl-2-(3-methyl-2-oxo-2,3-dihydro-benzooxazol-5-yl)-propyl]-3'-trifluoromethyl-biphenyl-4-carboxylic acid

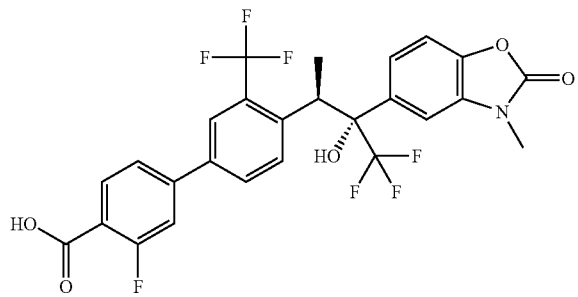

The title compound was prepared in analogy to Example 134, step 2 from 3-fluoro-4'-[3,3,3-trifluoro-2-hydroxy-1-methyl-2-(3-methyl-2-oxo-2,3-dihydro-benzooxazol-5-yl)-propyl]-3'-trifluoromethyl-biphenyl-4-carboxylic acid methyl ester (obtained in Example 198). MS (neg. ion, m/e)=556.2 [(M−H)⁻].

Example 201

6-{3-Chloro-4-[3,3,3-trifluoro-2-hydroxy-1-methyl-2-(3-methyl-2-oxo-2,3-dihydro-benzooxazol-5-yl)-propyl]-phenoxy}-pyridazine-3-carboxylic acid

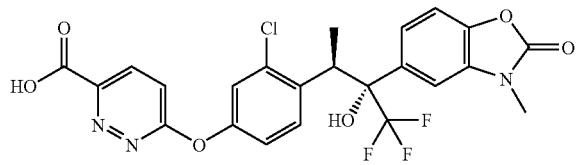

The title compound was prepared in analogy to Example 173, step 2 from 6-{3-chloro-4-[3,3,3-trifluoro-2-hydroxy-1-methyl-2-(3-methyl-2-oxo-2,3-dihydro-benzooxazol-5-yl)-propyl]-phenoxy}-pyridazine-3-carboxylic acid methyl ester (obtained in Example 199). MS (neg. ion, m/e)=522.2 [(M−H)⁻].

Example 202

2-{3-Chloro-4-[3,3,3-trifluoro-2-hydroxy-1-methyl-2-(3-methyl-2-oxo-2,3-dihydro-benzooxazol-5-yl)-propyl]-phenoxy}-pyrimidine-5-carboxylic acid methyl ester

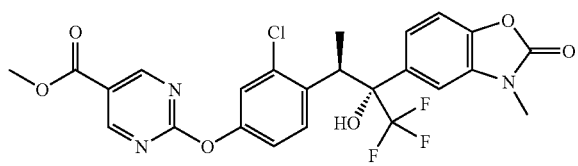

The title compound was prepared in analogy to Example 196 from 5-[2-(2-chloro-4-hydroxy-phenyl)-1-hydroxy-1-trifluoromethyl-propyl]-3-methyl-3H-benzooxazol-2-one (obtained in Example 172) by alkylation with methyl-2-chloropyrimidine-5-carboxylate [CAS Reg. No. 287714-35-6]. MS (m/e)=538.2 [M+H⁺].

Example 203

2-{3-Chloro-4-[3,3,3-trifluoro-2-hydroxy-1-methyl-2-(3-methyl-2-oxo-2,3-dihydro-benzooxazol-5-yl)-propyl]-phenoxy}-pyrimidine-5-carboxylic acid

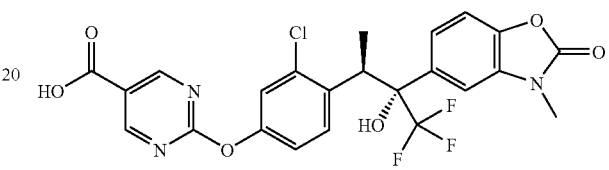

The title compound was prepared in analogy to Example 173, step 2 from 2-{3-chloro-4-[3,3,3-trifluoro-2-hydroxy-1-methyl-2-(3-methyl-2-oxo-2,3-dihydro-benzooxazol-5-yl)-propyl]-phenoxy}-pyrimidine-5-carboxylic acid methyl ester (obtained in Example 202). MS (neg. ion, m/e)=522.4 [(M−H)⁻].

Example 204

6-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester

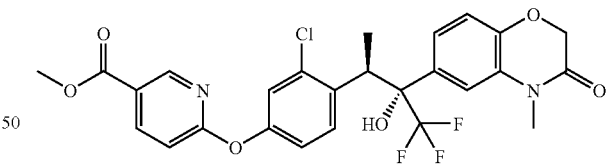

To a solution of 6-[2-(2-chloro-4-hydroxy-phenyl)-1-hydroxy-1-trifluoromethyl-propyl]-4-methyl-4H-benzo[1,4]oxazin-3-one (200 mg, 0.48 mmol, Example 56, step 4) in N'N-dimethylformamide (2.0 ml) were added methyl 6-chloropyridine-3-carboxylate (93 mg, 0.53 mmol) and potassium carbonate (199 mg, 1.44 mmol). The mixture was stirred for 4 h at 110° C. After cooling to r.t. water was added and the mixture was extracted twice with AcOEt. The organic phases were washed with water and brine, dried (MgSO₄) and concentrated. The product was purified by column chromatography (silica gel, heptane/AcOEt 4:1) to give the title compound (24 mg) as light yellow solid. MS (m/e)=551.2 [M+H⁺].

Example 205

6-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid

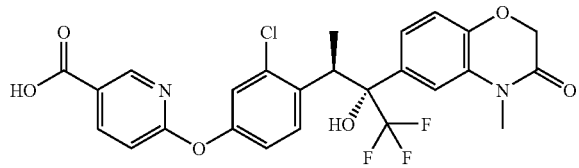

In analogy to Example 228, 6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester (Example 229) was hydrolyzed with 1 M aqueous LiOH solution (4 h, r.t.) to give the title compound as a white solid. MS (m/e, ISP neg. ion)=535.1 [M−H⁺].

Example 206

2-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-methyl-propionic acid ethyl ester

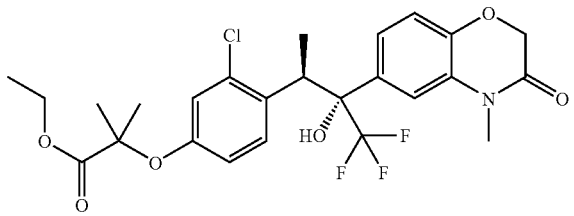

A suspension of 6-[2-(2-chloro-4-hydroxy-phenyl)-1-hydroxy-1-trifluoromethyl-propyl]-4-methyl-4H-benzo[1,4]oxazin-3-one (208 mg, 0.5 mmol, Example 56, step 4), 2-bromo-2-methyl propionic acid (117 mg, 0.6 mmol) and silver carbonate (138 mg, 0.5 mmol) was stirred for 18 h at 145° C. After cooling to r.t. the suspension was filtered (Dicalit) and concentrated in vacuum. The residue was purified by column chromatography (silica gel, heptane/acetone 4:1) to give the title compound (115 mg) as a white solid. MS (m/e)=530.2 [M+H⁺].

Example 207

2-{3-Chloro-4-[3,3,3-trifluoro-2-hydroxy-1-methyl-2-(4-methyl-3-oxo-3,4-dihydro-2H-benzo[1,4]oxazin-6-yl)-propyl]phenoxy}-2-methyl-propionic acid

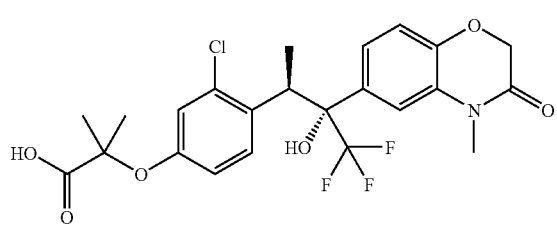

In analogy to Example 56, step 6, 2-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-methyl-propionic acid ethyl ester (Example 231) was hydrolyzed (6 h, 50° C.) to give the title compound as a white solid. MS (m/e, ISP neg. ion)=500.1 [M−H⁺].

Example 208

2-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester

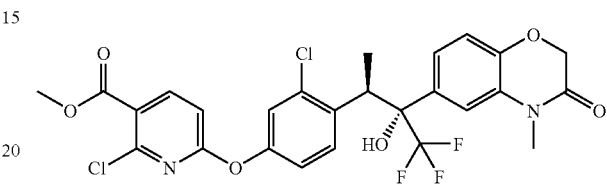

In analogy to Example 62, step 1, 6-[2-(2-chloro-4-hydroxy-phenyl)-1-hydroxy-1-trifluoromethyl-propyl]-4-methyl-4H-benzo[1,4]oxazin-3-one (Example 56, step 4) was reacted with methyl-2,6-dichloro-pyridine-3-carboxylate and DABCO (21 h, r.t.) to give the title compound as a white solid. MS (m/e)=585.2 [M+H⁺].

Example 209

2-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid

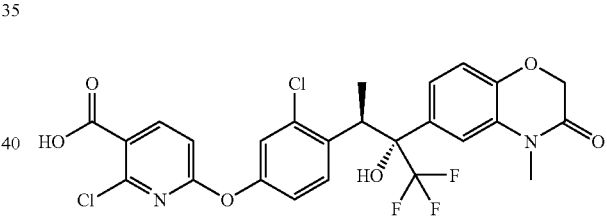

In analogy to Example 56, step 6, 2-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester (Example 208) was hydrolyzed (2.5 h, r.t.) to give the title compound as a white solid. MS (m/e)=571.2 [M+H⁺].

Example 210

4-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester

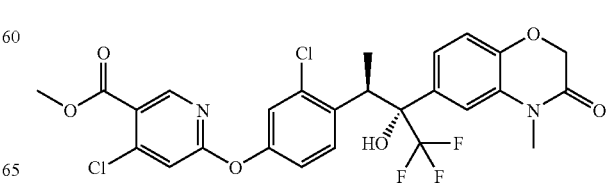

In analogy to Example 62, step 1, 6-[2-(2-chloro-4-hydroxy-phenyl)-1-hydroxy-1-trifluoromethyl-propyl]-4-methyl-4H-benzo[1,4]oxazin-3-one (Example 56, Step 4) was reacted with methyl-4,6-dichloronicotinate and DABCO (5 h, r.t.) to give the title compound as a white solid. MS (m/e)= 585.1 [M+H⁺].

Example 211

4-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid

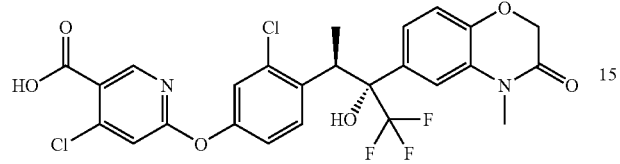

In analogy to Example 56, step 6, 4-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester (Example 210) was hydrolyzed (2 h, 50° C.) to give the title compound as a white solid. MS (m/e, ISP neg. ion)=569.1 [M−H⁺].

Example 212

5-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester

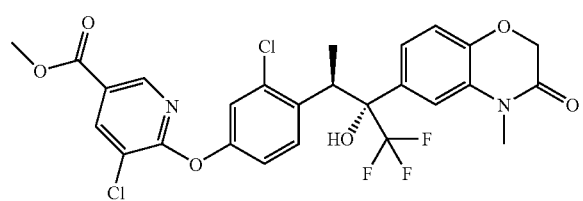

In analogy to Example 62, step 1, 6-[2-(2-chloro-4-hydroxy-phenyl)-1-hydroxy-1-trifluoromethyl-propyl]-4-methyl-4H-benzo[1,4]oxazin-3-one (Example 56, step 4) was reacted with methyl 5,6-dichloronicotinate and DABCO (17 h, r.t.) to give the title compound as a white solid. MS (m/e)= 585.0 [M+H⁺].

Example 213

5-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid

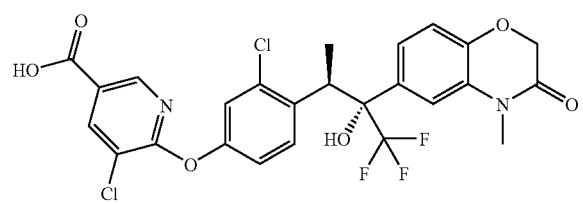

In analogy to Example 56, step 6, 5-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic methyl ester (Example 212) was hydrolyzed (2 h, 50° C.) to give the title compound as a white solid. MS (m/e, ISP neg. ion)=569.1 [M−H⁺].

Example 214

6-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-nicotinic acid ethyl ester In analogy to Example 62, step 1, 6-[2-(2-chloro-4-hydroxy-phenyl)-1-hydroxy-1-trifluoromethyl-propyl]-4-methyl-4H-benzo[1,4]oxazin-3-one (Example 56, Step 4) was reacted with 6-chloro-2-trifluoromethyl-nicotinic acid ethyl-ester and DABCO (17 h, r.t.) to give the title compound as a white solid. MS (m/e)=633.2 [M+H⁺].

Example 215

6-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-nicotinic acid In analogy to Example 56, step 6, 6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-nicotinic acid ethyl ester (Example 214) was hydrolyzed (2 h, 50° C.) to give the title compound as a white solid. MS (m/e,)=605.0 [M+H+].

Examples 216 and 217

2-Chloro-4-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester or (1S,2S) enantiomer and 2-Chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester or (1R,2R) enantiomer

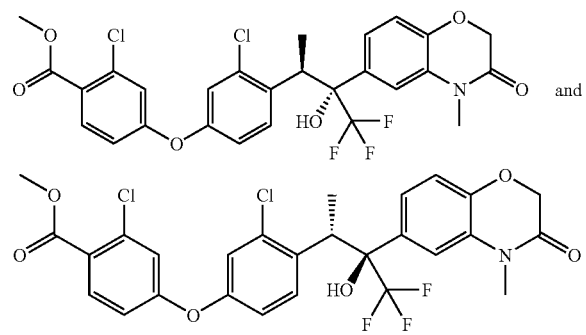

2-Chloro-4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester (Example 59, step 1) was separated into the enantiomers by chiral HPLC Chiralpak AD column using 10% 2-propanol in heptane as the mobile phase to give the title compounds as a white solid. MS (m/e, ISP neg. ion)=582.1 [M−H+].

Example 218

2-Chloro-4-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid or (1S,2S) enantiomer

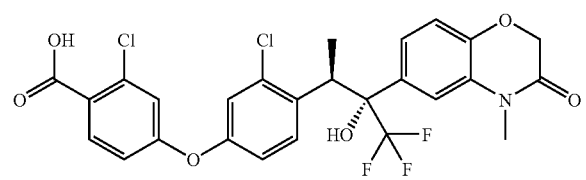

In analogy to Example 56, step 6, 2-Chloro-4-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester or (1S,2S) enantiomer (Example 216) was hydrolyzed (3 h, 40° C.) to give the title compound as a white solid. MS (m/e, ISP neg. ion)=568.3 [M−H+].

Example 219

2-Chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid or (1R,2R) enantiomer

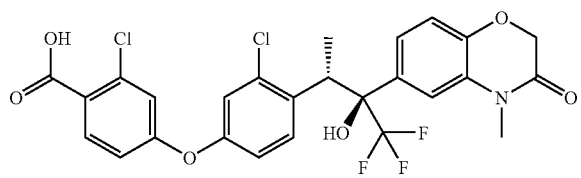

In analogy to Example 56, step 6, 2-Chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester or (1R,RS) enantiomer (Example 217) was hydrolyzed (2.5 h, 40° C.) to give the title compound as a white solid. MS (m/e, ISP neg. ion)=568.3 [M−H+].

Example 220

4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-benzoic acid

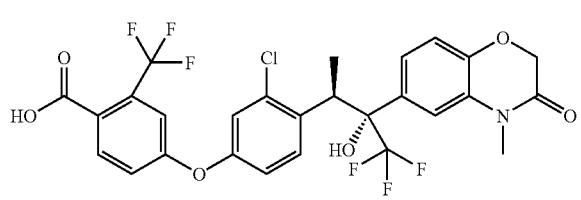

Step 1: 4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-benzaldehyde To a solution of 6-[2-(2-chloro-4-hydroxy-phenyl)-1-hydroxy-1-trifluoromethyl-propyl]-4-methyl-4H-benzo[1,4]oxazin-3-one (100 mg, 0.24 mmol, Example 56, step 4) in N'N-dimethylacetamide (1.5 ml) were added 4-fluoro-2-(trifluoromethyl)benzaldehyde (69 mg, 0.36 mmol) and cesium carbonate (234 mg, 0.72 mmol). The mixture was stirred for 17 h at room temperature. Ice water was added and the mixture was extracted with AcOEt. The organic phase was washed with water, dried (MgSO4) and concentrated. The product was purified by column chromatography (silica gel, heptane/AcOEt 3:1) to give the title compound (91 mg) as white foam. MS (m/e, ISP neg. ion)=586.2 [M−H+].

Step 2: 4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-1-phenoxy}-2-trifluoromethyl-benzoic acid To a suspension of 4-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-benzaldehyde (87 mg, 0.15 mmol) in tert-butanol (0.8 ml) were added 2-methyl-2-butene (52 mg, 0.74 mmol) and a solution of sodium chlorite (17 mg, 0.19 mmol) and sodium dihydrogen phosphate dehydrate (27 mg, 0.19 mmol) in water (0.6 ml) at 2° C. The mixture was stirred for 5 min. at 2° C., 17 h at r.t. and 1.5 h at 40° C. Ice water was added and the mixture was acidified using 1 M aqueous HCl. The mixture was extracted twice with AcOEt. The organic layers were washed with brine, dried (MgSO$_4$) and concentrated. The product was purified by column chromatography (silica gel, dichloromethane/methanol 9:1) to give the title compound (67 mg) as a white solid. MS (m/e, ISP neg. ion)=602.3 [M–H$^+$].

Examples 221 and 222

5-Chloro-6-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester or (1S,2S) enantiomer and 5-Chloro-6-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester or (1R,2R) enantiomer

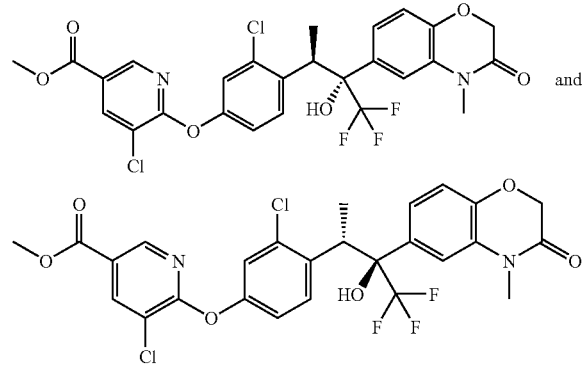

5-Chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester (Example 212) was separated into the enantiomers by chiral HPLC Chiralpak AD column using 8% ethanol in heptane as the mobile phase to give the title compounds as a white solid. MS (m/e)=585.1 [M+H$^+$].

Example 223

5-Chloro-6-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid or (1S,2S) enantiomer

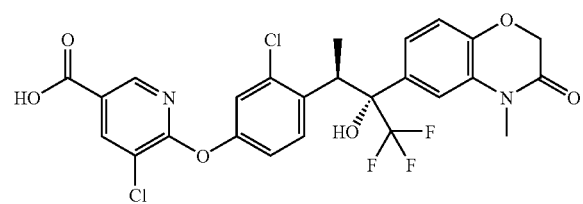

In analogy to Example 56, step 6, 5-Chloro-6-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester or (1S,2S) enantiomer (Example 221) was hydrolyzed (2 h, 40° C.) to give the title compound as a white solid. MS (m/e, ISP neg. ion)=569.2 [M–H$^+$].

Example 224

5-Chloro-6-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]phenoxy}-nicotinic acid or (1R,2R) enantiomer

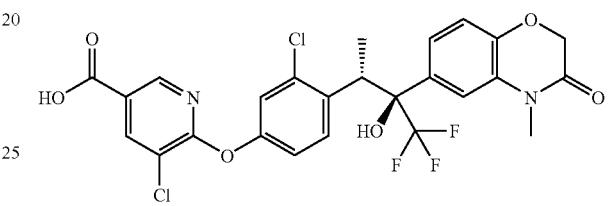

In analogy to Example 56, step 6, 5-Chloro-6-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester or (1R,2R) enantiomer (Example 222) was hydrolyzed (2 h, 40° C.) to give the title compound as a white solid. MS (m/e, ISP neg. ion)=569.2 [M–H$^+$].

Example 225

2-{3-Chloro-4-[3,3,3-trifluoro-2-hydroxy-1-methyl-2-(4-methyl-3-oxo-3,4-dihydro-2H-benzo[1,4]oxazin-6-yl)-propyl]phenoxy}-4-trifluoromethyl-pyrimidine-5-carboxylic acid methyl ester

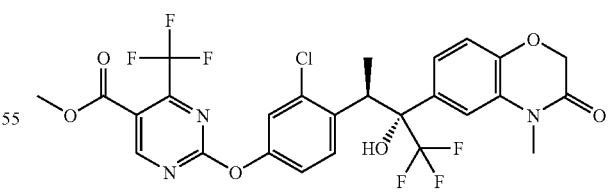

In analogy to Example 62, step 1, 6-[2-(2-chloro-4-hydroxy-phenyl)-1-hydroxy-1-trifluoromethyl-propyl]-4-methyl-4H-benzo[1,4]oxazin-3-one (Example 56, step 4) was reacted with methyl 2-chloro-4-(trifluoromethyl)pyrimidine-5-carboxylate and DABCO (17 h, r.t.) to give the title compound as a white solid. MS (m/e)=620.2 [M+H$^+$].

Example 226

2-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrimidine-5-carboxylic acid methyl ester

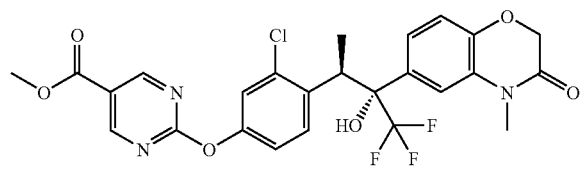

In analogy to Example 62, step 1, 6-[2-(2-chloro-4-hydroxy-phenyl)-1-hydroxy-1-trifluoromethyl-propyl]-4-methyl-4H-benzo[1,4]oxazin-3-one (Example 56, step 4) was react with methyl 2-chloropyrimidine-5-carboxylate and DABCO (1.5 h, r.t.) to give the title compound as a white solid. MS (m/e)=552.2 [M+H$^+$].

Example 227

5-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrazine-2-carboxylic acid methyl ester

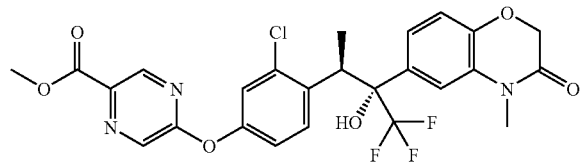

In analogy to Example 62, step 1, 6-[(2-(2-chloro-4-hydroxy-phenyl)-1-hydroxy-1-trifluoromethyl-propyl]-4-methyl-4H-benzo[1,4]oxazin-3-one (Example 56, Step 4) was react with methyl 5-chloro-2-pyrazine carboxylate and DABCO (1.5 h, r.t.) to give the title compound as a white solid. MS (m/e)=552.2 [M+H$^+$].

Example 228

5-{3-Chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrazine-2-carboxylic acid

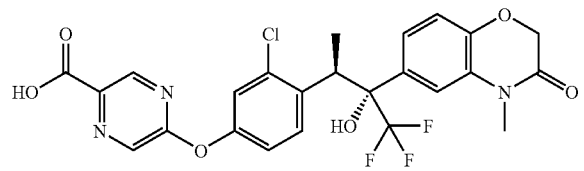

To a solution of 5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrazine-2-carboxylic acid methyl ester (Example 227, 70 mg, 0.13 mmol) in tetrahydrofuran (0.5 ml) was added 1M aqueous NaOH solution (0.25 ml). The mixture was stirred 2 h at r.t. Water was added and the mixture was acidified using 1M aqueous HCl solution. The aqueous phase was extracted twice with AcOEt, dried (MgSO$_4$) and concentrated. The solid residue was dried under high vacuum leading to the title compound (76 mg) as a white solid. MS (m/e, ISP neg. ion)=536.1 [M−H$^+$].

Example 229

2-{3-Chloro-4-[3,3,3-trifluoro-2-hydroxy-1-methyl-2-(3-methyl-2-oxo-2,3-dihydro-benzooxazol-5-yl)-propyl]-phenoxy}-2-methyl-propionic acid ethyl ester

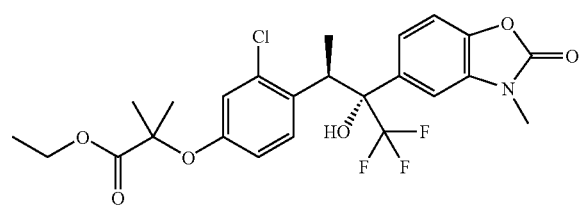

5-[2-(2-Chloro-4-hydroxy-phenyl)-1-hydroxy-1-trifluoromethyl-propyl]-3-methyl-3H-benzooxazol-2-one (80 mg, obtained in Example 172) and ethyl 2-bromoisobutyrate (0.2 mL) were dissolved in dimethylacetamide (2 mL). Powdered sodium hydroxide (54 mg) was added to this solution and the mixture was allowed to stir at r.t. for 12 hours. The mixture was poured into water and ice and was acidified to pH 3 with 2N HCl. The aqueous phase was extracted with ethyl acetate two times and the organic extracts were washed with brine, dried over Na$_2$SO$_4$ and evaporated in vacuo. The residue was purified by flash chromatography (silica gel, ethyl acetate:hexanes=4:1) to provide the title compound 2-{3-chloro-4-[3,3,3-trifluoro-2-hydroxy-1-methyl-2-(3-methyl-2-oxo-2,3-dihydro-benzooxazol-5-yl)-propyl]-phenoxy}-2-methyl-propionic acid ethyl ester as a colorless foam (113 mg). MS (m/e, ISP neg. ion)=514.1 [M−H+].

Example 230

2-{3-Chloro-4-[3,3,3-trifluoro-2-hydroxy-1-methyl-2-(3-methyl-2-oxo-2,3-dihydro-benzooxazol-5-yl)-propyl]-phenoxy}-2-methyl-propionic acid

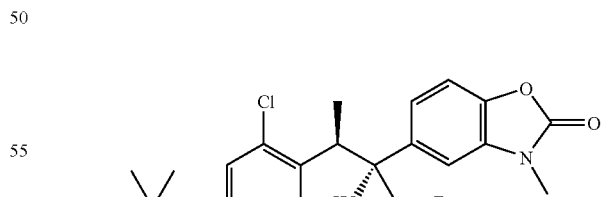

2-{3-Chloro-4-[3,3,3-trifluoro-2-hydroxy-1-methyl-2-(3-methyl-2-oxo-2,3-dihydro-benzooxazol-5-yl)-propyl]-phenoxy}-2-methyl-propionic acid ethyl ester (99 mg, obtained in Example 229) was dissolved in THF (2.3 mL) under argon. LiOH solution (1M, 0.31 mL) was added and the mixture was stirred for 3 hours. Another 0.19 mL of the LiOH solution was added and stirring was continued at r.t. for 48 hours. The reaction mixture was poured into water containing ice and the aqueous solution was acidified with 1M HCl to pH 1. The aqueous mixture was extracted with ethyl acetate and the organic extracts were washed with brine, dried over Na₂SO₄ and evaporated. The residue was purified by flash chromatography (silica gel, ethyl acetate, then ethyl acetate containing 0.25% acetic acid) to provide the title compound 2-{3-chloro-4-[3,3,3-trifluoro-2-hydroxy-1-methyl-2-(3-methyl-2-oxo-2,3-dihydro-benzooxazol-5-yl)-propyl]-phenoxy}-2-methyl-propionic acid as a light brown foam (15 mg). MS (m/e, ISP neg. ion)=486.5 [M−H+].

Example 231

{3-Chloro-4-[3,3,3-trifluoro-2-hydroxy-1-methyl-2-(3-methyl-2-oxo-2,3-dihydrobenzooxazol-5-yl)-propyl]-benzoylamino}-acetic acid tert-butyl ester

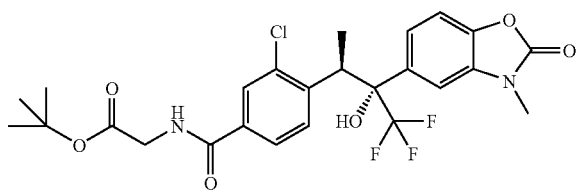

Step 1: Trifluoro-methanesulfonic acid 3-chloro-4-[3,3,3-trifluoro-2-hydroxy-1-methyl-2-(3-methyl-2-oxo-2,3-dihydro-benzooxazol-5-yl)-propyl]-phenyl ester To a solution of 5-[2-(2-chloro-4-hydroxy-phenyl)-1-hydroxy-1-trifluoromethyl-propyl]-3-methyl-3H-benzooxazol-2-one (1.10 g, obtained in Example 172) in dry dichloromethane (35 mL) was added triethylamine (0.88 mL). The mixture was cooled to −15° C. and trifluoromethanesulfonic anhydride (0.55 mL) was added drop by drop over 10 minutes. The solution was stirred for 15 minutes and was then allowed to warm to r.t. where stirring was continued for 1 hour. The reaction mixture was poured into water containing ice and the aqueous phase was extracted with dichloromethane. The organic extracts were washed with brine, dried over Na₂SO₄ and evaporated. The residue was purified by flash chromatography (silica gel, gradient of ethyl acetate in heptane) to provide the title compound trifluoro-methanesulfonic acid 3-chloro-4-[3,3,3-trifluoro-2-hydroxy-1-methyl-2-(3-methyl-2-oxo-2,3-dihydro-benzooxazol-5-yl)-propyl]-phenyl ester as a colorless foam (1.42 g). MS (m/e, ISP neg. ion)=431.9 [M−H+].

Step 2: 3-Chloro-4-[3,3,3-trifluoro-2-hydroxy-1-methyl-2-(3-methyl-2-oxo-2,3-dihydro-benzooxazol-5-yl)-propyl]-1-benzoic acid methyl ester Trifluoro-methanesulfonic acid 3-chloro-4-[3,3,3-trifluoro-2-hydroxy-1-methyl-2-(3-methyl-2-oxo-2,3-dihydrobenzooxazol-5-yl)-propyl]-phenyl ester (1.41 g) was dissolved in dry DMSO (15 mL) and subsequently, dry methanol (5.36 mL), triethylamine (1.10 mL), palladium(II)-acetate (30 mg) and 1,3-bis(diphenylphosphino)propane (54 mg) were added. The flask was evacuated and an argon atmosphere was introduced. Carbonmonoxide was introduced by means of a balloon, first at r.t. for 10 minutes and then at 70° C. for another 2 hours. The reaction mixture was cooled and poured into a mixture of water, ice and 1M HCl (19 mL). The aqueous phase was extracted with ethyl acetate and the organic extracts were washed with brine, dried over Na₂SO₄ and evaporated. The residue was purified by flash chromatography (silica gel, gradient of ethyl acetate in heptane) to provide the title compound 3-chloro-4-[3,3,3-trifluoro-2-hydroxy-1-methyl-2-(3-methyl-2-oxo-2,3-dihydro-benzooxazol-5-yl)-propyl]-benzoic acid methyl ester as a colorless foam (1.06 g). MS (m/e)=444.2 [MH+].

Step 3: 3-Chloro-4-[3,3,3-trifluoro-2-hydroxy-1-methyl-2-(3-methyl-2-oxo-2,3-dihydro-benzooxazol-5-yl)-propyl]-benzoic acid In analogy to Example 230, 3-chloro-4-[3,3,3-trifluoro-2-hydroxy-1-methyl-2-(3-methyl-2-oxo-2,3-dihydro-benzooxazol-5-yl)-propyl]-benzoic acid methyl ester (1.05 g) was saponified with LiOH solution (1M, 6.12 mL) in THF (15 mL) to give the title compound 3-chloro-4-[3,3,3-trifluoro-2-hydroxy-1-methyl-2-(3-methyl-2-oxo-2,3-dihydro-benzooxazol-5-yl)-propyl]-benzoic acid as an off-white foam (0.47 g). MS (m/e, ISP neg. ion)=428.3 [M−H+].

Step 4: {3-Chloro-4-[3,3,3-trifluoro-2-hydroxy-1-methyl-2-(3-methyl-2-oxo-2,3-dihydrobenzooxazol-5-yl)-propyl]-1-benzoylamino}-acetic acid tert-butyl ester 3-Chloro-4-[3,3,3-trifluoro-2-hydroxy-1-methyl-2-(3-methyl-2-oxo-2,3-dihydro-benzooxazol-5-yl)-propyl]-benzoic acid (80 mg) and 1,1-carbonyldiimidazole (45 mg) were dissolved in dry DMF (2.0 mL) and stirred at 50° C. for 1 hour. The mixture was cooled to r.t. and a solution of tert-butylglycinate (391 mg) in DMF (0.7 mL) was added drop by drop. Stirring was then continued for 2 hours. The reaction mixture was poured into a mixture of water and ice and the aqueous phase was extracted with ethyl acetate. The organic extracts were washed with brine, dried over Na₂SO₄ and evaporated. The residue was purified by flash chromatography (silica gel, gradient of ethyl acetate in heptane) to provide the title compound {3-chloro-4-[3,3,3-trifluoro-2-hydroxy-1-methyl-2-(3-methyl-2-oxo-2,3-dihydrobenzooxazol-5-yl)-propyl]-benzoylamino}-acetic acid tert-butyl ester as a colorless solid (101 mg). MS (m/e)=560.3 [m+NH₄⁺].

Example 232

{3-Chloro-4-[3,3,3-trifluoro-2-hydroxy-1-methyl-2-(3-methyl-2-oxo-2,3-dihydrobenzooxazol-5-yl)-propyl]-benzoylamino}-acetic acid

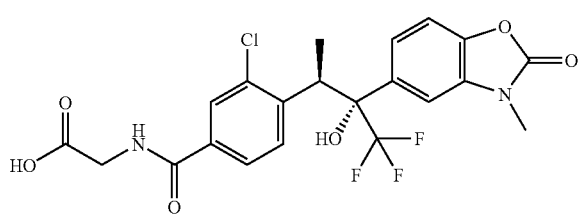

{3-Chloro-4-[3,3,3-trifluoro-2-hydroxy-1-methyl-2-(3-methyl-2-oxo-2,3-dihydrobenzooxazol-5-yl)-propyl]-benzoylamino}-acetic acid tert-butyl ester (20 mg, obtained in Example 231) was dissolved in dry dichloromethane (1.0 mL) and trifluoroacetic acid (0.41 mL) was added. The mixture was then allowed to stir at r.t. for 12 hours. The reaction mixture was concentrated in vacuo and the residue was further purified by repeated evaporation from ether (2 times), methanol (2 times) and again dichloromethane (2 times) to give the title compound {3-chloro-4-[3,3,3-trifluoro-2-hydroxy-1-methyl-2-(3-methyl-2-oxo-2,3-dihydrobenzooxazol-5-yl)-propyl]-benzoylamino}-acetic acid as a colorless solid (18 mg). MS (m/e, ISP neg. ion)=485.1 [M−H+].

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The invention claimed is:

1. A compound of formula I,

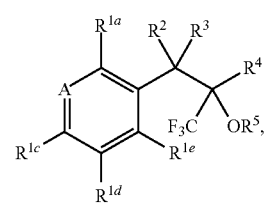

wherein

A is C—$R^{1b}$ or N;

$R^{1a}$, $R^{1b}$, $R^{1c}$, $R^{1d}$ and $R^{1e}$ independently from each other are selected from the group consisting of:

hydrogen; $C_{1-7}$-alkyl; $C_{2-7}$-alkenyl; $C_{3-7}$-cycloalkyl-$C_{1-7}$-alkyl; halogen; halogen-$C_{1-7}$-alkyl; halogen-$C_{1-7}$-alkoxy; halogen-$C_{1-7}$-alkyl-sulfonyloxy; hydroxy; hydroxy-$C_{1-7}$-alkyl; $C_{1-7}$-alkoxy; $C_{1-7}$-alkoxy-$C_{1-7}$-alkoxy; hydroxy-$C_{1-7}$-alkoxy; amino-$C_{1-7}$-alkoxy; cyano; carboxyl; carboxyl-$C_{1-7}$-alkyl; carboxyl-$C_{1-7}$-alkoxy; $C_{1-7}$-alkoxycarbonyl; $C_{1-7}$-alkoxycarbonyl-$C_{1-7}$-alkoxy; $C_{1-7}$-alkoxycarbonylamino-$C_{1-7}$-alkoxy; $C_{1-7}$-alkylcarbonyloxy-$C_{1-7}$-alkoxy; aminocarbonyl-$C_{1-7}$-alkoxy; di-$C_{1-7}$-alkylamino; di-$C_{2-7}$-alkenylamino; $C_{1-7}$-alkylsulfonyl-amino; carboxyl-$C_{1-7}$-alkylaminocarbonyl;

phenyl, said phenyl being substituted by a group selected from carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy;

phenyloxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

heteroaryl selected from the group consisting of pyridyl, pyridazinyl, pyrimidinyl and pyrazinyl, said heteroaryl being unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

heteroaryloxy, wherein heteroaryl is selected from the group consisting of pyridyl, pyridazinyl, pyrimidinyl and pyrazinyl, and is unsubstituted or substituted by one, two or three substituents selected from the group consisting of $C_{1-7}$-alkyl, halogen, halogen-$C_{1-4}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

phenyl-$C_{1-7}$-alkoxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkyl, hydroxy, cyano, $C_{1-7}$-alkylsulfonyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxy-carbonyl, $C_{1-7}$-alkoxycarbonyl-$C_{1-7}$-alkyl and $C_{1-7}$-alkoxycarbonyl-$C_{1-7}$-alkoxy; and heterocyclyl or heterocyclylcarbonyl, wherein heterocyclyl is selected from the group consisting of pyrrolidine, piperidine and azepine and is substituted by carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy;

$R^2$ is selected from the group consisting of $C_{1-7}$-alkyl, $C_{3-7}$-cycloalkyl-$C_{1-7}$-alkyl, carboxyl-$C_{1-4}$-alkyl, $C_{1-4}$-alkoxycarbonyl-$C_{1-7}$-alkyl, triazolyl-$C_{1-7}$-alkyl and phenyl, said phenyl being unsubstituted or substituted by one, two or three halogen groups;

$R^3$ is hydrogen or $C_{1-7}$-alkyl;

or $R^2$ and $R^3$ together with the carbon atom they are attached to form a $C_3$-$C_5$-cycloalkyl ring;

$R^4$ is a heteroaryl ring selected from the group consisting of 3-oxo-3,4-dihydro-2H-benzo[1,4]oxazinyl and 3,4-dihydro-2H-benzo[1,4]oxazinyl, said heteroaryl ring being unsubstituted or substituted by one, two or three substituents selected from the group consisting of $C_{1-7}$-alkyl, $C_{2-7}$-alkenyl and halogen; and $R^5$ is hydrogen or methyl;

or a pharmaceutically acceptable salt thereof.

2. A compound according to claim 1, wherein A is C—$R^{1b}$.

3. A compound according to claim 1, wherein one of $R^{1c}$ and $R^{1d}$ is selected from the group consisting of:

phenyl, said phenyl being substituted by a group selected from carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy;

phenyloxy, wherein the phenyl ring is unsubstituted or substituted by one, two or three substituents selected from the group consisting of $C_{1-7}$-alkyl, halogen, halogen-$C_{1-7}$-alkoxy, halogen-$C_{1-7}$-alkoxy; carboxyl, carboxyl-$C_{1-7}$-alkyl, carboxyl-$C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, heteroaryl selected from the group consisting of pyridyl, pyridazinyl, pyrimidinyl and pyrazinyl, said heteroaryl being unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;

heteroaryloxy, wherein heteroaryl is selected from the group consisting of pyridyl, pyridazinyl, pyrimidinyl and pyrazinyl, and is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, phenyl-$C_{1-7}$-alkoxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkyl, hydroxy, cyano, $C_{1-7}$-alkylsulfonyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxy-carbonyl, $C_{1-7}$-alkoxycarbonyl-$C_{1-7}$-alkyl and $C_{1-7}$-alkoxycarbonyl-$C_{1-7}$-alkoxy; and heterocyclyl or heterocyclylcarbonyl, wherein heterocyclyl is selected from the group consisting of pyrrolidine, piperidine and azepine and is substituted by carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy.

4. A compound according to claim 1, wherein one of $R^{1c}$ and $R^{1d}$ is selected from the group consisting of:
  phenyl, said phenyl being substituted by a group selected from carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and, in addition, optionally substituted by one or two substituents selected from the group consisting of $C_{1-7}$-alkyl, halogen, halogen-$C_{1-7}$-alkyl, $C_{1-7}$-alkoxy and halogen-$C_{1-7}$-alkoxy;
  phenyloxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy; carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl; and
  phenyl-$C_{1-7}$-alkoxy, wherein the phenyl ring is unsubstituted or substituted by one, two or three substituents selected from the group consisting of $C_{1-7}$-alkyl, halogen, halogen-$C_{1-7}$-alkyl, $C_{1-7}$-alkyl, hydroxy, cyano, $C_{1-7}$-alkylsulfonyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxy-carbonyl, $C_{1-7}$-alkoxycarbonyl-$C_{1-7}$-alkyl and $C_{1-7}$-alkoxycarbonyl-$C_{1-7}$-alkoxy.

5. A compound according to claim 1, wherein one of $R^{1c}$ and $R^{1d}$ is selected from the group consisting of
  heteroaryl selected from the group consisting of pyridyl, pyridazinyl, pyrimidinyl and pyrazinyl, said heteroaryl being unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl;
  heteroaryloxy, wherein heteroaryl is selected from the group consisting of pyridyl, pyridazinyl, pyrimidinyl and pyrazinyl, and is unsubstituted or substituted by one, two or three substituents selected from the group consisting of $C_{1-7}$-alkyl, halogen, halogen-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and aminocarbonyl, and heterocyclyl or heterocyclylcarbonyl, wherein heterocyclyl is selected from the group consisting of pyrrolidine, piperidine and azepine and is substituted by carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy.

6. A compound according to claim 1, wherein one of $R^{1c}$ and $R^{1d}$ is selected from the group consisting of hydroxy, $C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy and carboxyl-$C_{1-7}$-alkylaminocarbonyl.

7. A compound according to claim 1, wherein $R^{1a}$ is halogen or halogen-$C_{1-7}$-alkyl.

8. A compound according to claim 1, wherein three of $R^{1a}$, $R^{1b}$, $R^{1c}$, $R^{1d}$ and $R^{1e}$ are hydrogen.

9. A compound according to claim 1, wherein $R^2$ is $C_{1-7}$-alkyl.

10. A compound according to claim 1, wherein $R^3$ is hydrogen.

11. A compound according to claim 1, wherein $R^5$ is hydrogen.

12. A compound according to claim 1, selected from the group consisting of:
  4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxymethyl}-benzoic acid ethyl ester,
  4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxymethyl}-benzoic acid,
  {4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-acetic acid ethyl ester,
  {4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-acetic acid,
  3-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid ethyl ester,
  3-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
  4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester,
  4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
  2-chloro-4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester,
  and pharmaceutically acceptable salts thereof.

13. A compound according to claim 1, selected from the group consisting of
  4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid,
  3'-chloro-3-fluoro-4'-[(1R,2R)-3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid or (1S,2S) enantiomer,
  2-chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid or (1R,2R) enantiomer,
  and pharmaceutically acceptable salts thereof.

14. A pharmaceutical composition comprising a compound according to claim 1 and a pharmaceutically acceptable carrier and/or adjuvant.

15. A compound according to claim 1, selected from the group consisting of:
  5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid,
  (3-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid,
  4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid methyl ester,
  4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid,
  2-chloro-5-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
  4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-3-fluoro-benzoic acid, 4'-chloro-3'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid, 4'-chloro-3'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid, (1-{4-chloro-3-[3,3,3-trifluoro-2-hydroxy-1-methyl-2-(4-methyl-3-oxo-3,4-dihydro-2H-benzo[1,4]oxazin-6-yl)-propyl]-benzoyl}-piperidin-4-yl)-acetic acid methyl ester, (1-{4-chloro-3-[3,3,3-trifluoro-2-hydroxy-1-methyl-2-(4-methyl-3-oxo-3,4-dihydro-2H-benzo[1,4]oxazin-6-yl)-propyl]-benzoyl}-piperidin-4-yl)-acetic acid, and pharmaceutically-acceptable salts thereof.

16. A compound according to claim 1, selected from the group consisting of:

4-{4-chloro-3-[3,3,3-trifluoro-2-hydroxy-1-methyl-2-(4-methyl-3-oxo-3,4-dihydro-2H-benzo[1,4]oxazin-6-yl)-propyl]-benzoylamino}-butyric acid, 3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid, 3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid, 3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-2-carboxylic acid, 3'-chloro-3-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester, 3'-chloro-3-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid, 3'-chloro-3-fluoro-4'(1S,2S)-3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid or (1R,2R) enantiomer, 3'-chloro-3-fluoro-4'-[(1R,2R)-3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid or (1S,2S) enantiomer, 3-{3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-propionic acid, 3,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester, and pharmaceutically-acceptable salts thereof.

17. A compound according to claim 1, selected from the group consisting of:

3,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid, 3'-chloro-4-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid, 3'-chloro-2-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester, 3'-chloro-2-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid, 3'-chloro-3-methoxy-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid methyl ester, 3'-chloro-3-methoxy-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-carboxylic acid, {3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-4-yl}-acetic acid, 3'-chloro-6-fluoro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid, 4,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid ethyl ester, 4,3'-dichloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-carboxylic acid, and pharmaceutically-acceptable salts thereof.

18. A compound according to claim 1, selected from the group consisting of:

{3'-chloro-4'-[3,3,3-trifluoro-2-hydroxy-1-methyl-2-(4-methyl-3-oxo-3,4-dihydro-2H-benzo[1,4]oxazin-6-yl)-propyl]-biphenyl-3-yl}-acetic acid, 1-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenyl}-piperidine-4-carboxylic acid ethyl ester, 3-chloro-4-[3,3,3-trifluoro-2-hydroxy-1-methyl-2-(4-methyl-3-oxo-3,4-dihydro-2H-benzo[1,4]oxazin-6-yl)-propyl]-benzoic acid, (4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-phenyl)-acetic acid, 3'-chloro-3-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-4-carboxylic acid methyl ester, 3'-chloro-3-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-4-carboxylic acid, {3'-chloro-4-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-3-yloxy}-acetic acid ethyl ester, {3'-chloro-4-fluoro-4'-[3,3,3-trifluoro-2-(8-fluoro-4-methyl-3-oxo-3,4-dihydro-2H-benzo[1,4]oxazin-6-yl)-2-hydroxy-1-methyl-propyl]-biphenyl-3-yloxy}-acetic acid, 3'-chloro-3-fluoro-4'-[3,3,3-trifluoro-2-hydroxy-1-methyl-2-(4-methyl-3-oxo-3,4-dihydro-2H-benzo[1,4]oxazin-8-yl)-propyl]-biphenyl-4-carboxylic acid methyl ester, 3'-chloro-3-fluoro-4'-[3,3,3-trifluoro-2-hydroxy-1-methyl-2-(4-methyl-3-oxo-3,4-dihydro-2H-benzo[1,4]oxazin-8-yl)-propyl]-biphenyl-4-carboxylic acid, and pharmaceutically-acceptable salts thereof.

19. A compound according to claim 1, selected from the group consisting of:

5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid, 4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-fluoro-benzoic acid, 2-chloro-5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
2-chloro-4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
3-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid,
6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-4-trifluoromethyl-nicotinic acid,
2-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
3,3'-dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-4-carboxylic acid,
3'-chloro-4'-[2-(4-ethyl-3-oxo-3,4-dihydro-2H-benzo[1,4]oxazin-6-yl)-3,3,3-trifluoro-2-hydroxy-1-methyl-propyl]-3-fluoro-biphenyl-4-carboxylic acid,
and pharmaceutically-acceptable salts thereof.

20. A compound according to claim 1, selected from the group consisting of:
4,3'-dichloro-4'-[2-(4-ethyl-3-oxo-3,4-dihydro-2H-benzo[1,4]oxazin-6-yl)-3,3,3-trifluoro-2-hydroxy-1-methyl-propyl]-biphenyl-3-carboxylic acid,
3'-chloro-4'-[2-(4-ethyl-3-oxo-3,4-dihydro-2H-benzo[1,4]oxazin-6-yl)-3,3,3-trifluoro-2-hydroxy-1-methyl-propyl]-4-fluoro-biphenyl-3-carboxylic acid,
6-{3-chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-4-trifluoromethyl-nicotinic acid,
2-chloro-6-{3-chloro-4-[2-(4-ethyl-3-oxo-3,4-dihydro-2H-benzo[1,4]oxazin-6-yl)-3,3,3-trifluoro-2-hydroxy-1-methyl-propyl]-phenoxy}-nicotinic acid,
4'-[2-(4-allyl-3-oxo-3,4-dihydro-2H-benzo[1,4]oxazin-6-yl)-3,3,3-trifluoro-2-hydroxy-1-methyl-propyl]-3'-chloro-3-fluoro-biphenyl-4-carboxylic acid methyl ester,
3'-chloro-3-fluoro-4'-[3,3,3-trifluoro-2-hydroxy-1-methyl-2-(3-oxo-3,4-dihydro-2H-benzo[1,4]oxazin-6-yl)-propyl]-biphenyl-4-carboxylic acid methyl ester,
3'-chloro-3-fluoro-4'-[3,3,3-trifluoro-2-hydroxy-1-methyl-2-(3-oxo-3,4-dihydro-2H-benzo[1,4]oxazin-6-yl)-propyl]-biphenyl-4-carboxylic acid,
3'-chloro-3-fluoro-4'-[3,3,3-trifluoro-2-(7-fluoro-4-methyl-3-oxo-3,4-dihydro-2H-benzo[1,4]oxazin-6-yl)-2-hydroxy-1-methyl-propyl]-biphenyl-4-carboxylic acid methyl ester,
3'-chloro-3-fluoro-4'-[3,3,3-trifluoro-2-(7-fluoro-4-methyl-3-oxo-3,4-dihydro-2H-benzo[1,4]oxazin-6-yl)-2-hydroxy-1-methyl-propyl]-biphenyl-4-carboxylic acid,
2-chloro-4-{3-chloro-4-[3,3,3-trifluoro-2-(7-fluoro-4-methyl-3-oxo-3,4-dihydro-2H-benzo[1,4]oxazin-6-yl)-2-hydroxy-1-methyl-propyl]-phenoxy}-benzoic acid methyl ester,
and pharmaceutically-acceptable salts thereof.

21. A compound according to claim 1, selected from the group consisting of:
2-chloro-4-{3-chloro-4-[3,3,3-trifluoro-2-(7-fluoro-4-methyl-3-oxo-3,4-dihydro-2H-benzo[1,4]oxazin-6-yl)-2-hydroxy-1-methyl-propyl]-phenoxy}-benzoic acid,
2-chloro-6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid,
2-chloro-4-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-benzoic acid,
3'-chloro-3-fluoro-4'-[3,3,3-trifluoro-2-hydroxy-1-methyl-2-(4-methyl-3-oxo-3,4-dihydro-2H-benzo[1,4]oxazin-7-yl)-propyl]-biphenyl-4-carboxylic acid,
5-chloro-6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid,
4-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-2-fluoro-benzoic acid,
5-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-2-fluoro-benzoic acid,
3'-chloro-3-fluoro-4'-[3,3,3-trifluoro-2-hydroxy-1-methyl-2-(2,2,4-trimethyl-3-oxo-3,4-dihydro-2H-benzo[1,4]oxazin-6-yl)-propyl]-biphenyl-4-carboxylic acid,
6-{3-chloro-4-[3,3,3-trifluoro-2-hydroxy-1-methyl-2-(4-methyl-3-oxo-3,4-dihydro-2H-benzo[1,4]oxazin-7-yl)-propyl]-phenoxy}-nicotinic acid,
3'-chloro-3-fluoro-4'-[3,3,3-trifluoro-2-hydroxy-1-methyl-2-(4-methyl-3,4-dihydro-2H-benzo[1,4]oxazin-6-yl)-propyl]-biphenyl-4-carboxylic acid,
and pharmaceutically-acceptable salts thereof.

22. A compound according to claim 1, selected from the group consisting of:
6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester,
6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
2-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-methyl-propionic acid ethyl ester,
2-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-methyl-propionic acid,
2-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester,
2-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
4-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester,
4-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
5-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester,
5-chloro-6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid,
and pharmaceutically-acceptable salts thereof.

23. A compound according to claim 1, selected from the group consisting of:
- 6-{3-chloro-4-[3,3,3-trifluoro-2-hydroxy-1-methyl-2-(4-methyl-3-oxo-3,4-dihydro-2H!-benzo[1,4]oxazin-6-yl)-propyl]-phenoxy}-2-trifluoromethyl-nicotinic acid ethyl ester,
- 6-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-nicotinic acid,
- 2-chloro-4-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester or (1S,2S) enantiomer,
- 2-chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid methyl ester or (1R,2R) enantiomer,
- 2-chloro-4-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid or (1S,2S) enantiomer,
- 2-chloro-4-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid or (1R,2R) enantiomer,
- 4-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-2-trifluoromethyl-benzoic acid,
- 5-chloro-6-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid methyl ester or (1S,2S) enantiomer,
- 5-chloro-6-{3-chloro-4-[(1S,2S)-3,3,3-trifluoro-2-hydroxy-1 methyl-2-(4-methyl-3-oxo-3,4-dihydro-2H-benzo[1,4]oxazin-6-yl)-propyl]-phenoxy}-nicotinic acid methyl ester or (1R,2R) enantiomer,
- 5-chloro-6-{3-chloro-4-[(1R,2R)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid or (1S,2S) enantiomer, and pharmaceutically-acceptable salts thereof.

24. A compound according to claim 1, selected from the group consisting of:
- 5-chloro-6-{3-chloro-4-[(1S,2S)-3,3,3-trifluoro-2-hydroxy-1-methyl-2-(4-methyl-3-oxo-3,4-dihydro-2H-benzo[1,4]oxazin-6-yl)-propyl]-phenoxy}-nicotinic acid or (1R,2R) enantiomer,
- 2-{3-chloro-4-[,3,3-trifluoro-2-hydroxy-1-methyl-2-(4-methyl-3-oxo-3,4-dihydro-2H-benzo[1,4]oxazin-6-yl)-propyl]-phenoxy}-4-trifluoromethyl-pyrimidine-5-carboxylic acid methyl ester,
- 2-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrimidine-5-carboxylic acid methyl ester,
- 5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrazine-2-carboxylic acid methyl ester,
- 5-{3-chloro-4-[3,3,3-trifluoro-2-hydroxy-1-methyl-2-(4-methyl-3-oxo-3,4-dihydro-2H-benzo[1,4]oxazin-6-yl)-propyl]-phenoxy}-pyrazine-2-carboxylic acid, and pharmaceutically acceptable salts thereof.

* * * * *

UNITED STATES PATENT AND TRADEMARK OFFICE
CERTIFICATE OF CORRECTION

PATENT NO. : 8,268,820 B2
APPLICATION NO. : 12/727271
DATED : September 18, 2012
INVENTOR(S) : Hunziker et al.

Page 1 of 2

It is certified that error appears in the above-identified patent and that said Letters Patent is hereby corrected as shown below:

Cover page, column 1, under (75) Inventors:
Delete "Chrisitan Lerner" and insert -- Christian Lerner --

Claim 1, column 183, line 47, delete "halogen-$C_{1-4}$-alkyl,"
and insert -- halogen-$C_{1-7}$-alkyl, --

Claim 1, column 184, line 2, delete "carboxyl-$C_{1-4}$-alkyl, $C_{1-4}$-"
and insert -- carboxyl-$C_{1-7}$-alkyl, $C_{1-7}$- --

Claim 3, column 184, line 31, delete "halogen, halo-"
and insert -- halogen, halogen-$C_{1-7}$-alkyl, $C_{1-7}$-alkoxy, --

Claim 3, column 184, line 32, delete "gen-$C_{1-7}$-alkoxy,"

Claim 3, column 184, line 33, delete "carboxyl $C_{1-7}$-alkoxycarbonyl,"
and insert -- carboxyl-$C_{1-7}$-alkoxy, $C_{1-7}$-alkoxycarbonyl, --

Claim 12, column 186, beginning of line 30, insert -- 2-chloro-4-{4-chloro-3-[3,3,3-trifluoro-2-hydroxy-1-methyl-2-(4-methyl-3-oxo-3,4-dihydro-2H-benzo[1,4]oxazin-6-yl)-propyl]-phenoxy}-benzoic acid, --

Signed and Sealed this
Twelfth Day of February, 2013

Teresa Stanek Rea
*Acting Director of the United States Patent and Trademark Office*

CERTIFICATE OF CORRECTION (continued)
U.S. Pat. No. 8,268,820 B2

*Claim 23, column 191, line 4, delete "2H!-" and insert -- 2H- --

*Claim 24, column 192, line 16, delete "[,3,3-trifluoro-" and insert -- [3,3,3-trifluoro- --